(12) United States Patent
Shelton, IV et al.

(10) Patent No.: US 12,205,712 B2
(45) Date of Patent: Jan. 21, 2025

(54) METHOD OF SURGICAL SYSTEM POWER MANAGEMENT, COMMUNICATION, PROCESSING, STORAGE AND DISPLAY

(71) Applicant: Cilag GmbH International, Zug (CH)

(72) Inventors: Frederick E. Shelton, IV, Hillsboro, OH (US); Shane R. Adams, Lebanon, OH (US); Kevin Fiebig, Cincinnati, OH (US); Jeffrey D. Messerly, Cincinnati, OH (US); Taylor Aronhalt, Loveland, OH (US); Bernhard Adolf Fuerst, Sunnyvale, CA (US); Matjaž Jogan, Philadelphia, PA (US); Gregory J. Bakos, Mason, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/384,274

(22) Filed: Jul. 23, 2021

(65) Prior Publication Data

US 2023/0023083 A1 Jan. 26, 2023

Related U.S. Application Data

(60) Provisional application No. 63/224,813, filed on Jul. 22, 2021.

(51) Int. Cl.
*G16H 40/20* (2018.01)
*A61B 17/00* (2006.01)
(Continued)

(52) U.S. Cl.
CPC ............. *G16H 40/20* (2018.01); *A61B 17/00* (2013.01); *A61B 18/1206* (2013.01);
(Continued)

(58) Field of Classification Search
CPC ........ G16H 40/20; G16H 40/67; A61B 17/00; A61B 2017/00221; H04L 41/12; H04L 67/12
See application file for complete search history.

(56) References Cited

U.S. PATENT DOCUMENTS 5,652,866 A 7/1997 Aldred et al.
6,766,373 B1 7/2004 Beadle et al.
(Continued)

FOREIGN PATENT DOCUMENTS

EP 1010230 B1 10/2003
EP 3506287 A1 7/2019
(Continued)

OTHER PUBLICATIONS

Jagannath, et al., "An Analysis of Speech as a Modality for Activity Recognition during Complex Medical Teamwork", Pervasive Computing Technologies for Healthcare, May 2018, pp. 1-10.
(Continued)

*Primary Examiner* — Mohamed A. Wasel
(74) *Attorney, Agent, or Firm* — Condo Roccia Koptiw LLP

(57) ABSTRACT

Examples described herein may include a surgical computing device that directs data communications to surgical networks. The surgical computing device may include a processor that is configured to determine a present network locus, wherein the present network locus is any of a first surgical network or a second surgical network; identify a data communications session; determine a surgical data type of the data communication session, wherein the surgical data type is any of a first type of surgical data or a second type of surgical data, and direct the data communications session to the first surgical network if the surgical data type is the
(Continued)

first type of surgical data or to the second surgical network if the surgical data type is the second type of surgical data.

20 Claims, 81 Drawing Sheets

(51) Int. Cl.

| | | |
|---|---|---|
| *A61B 18/12* | (2006.01) | |
| *A61B 34/00* | (2016.01) | |
| *A61B 34/10* | (2016.01) | |
| *A61B 34/20* | (2016.01) | |
| *A61B 34/30* | (2016.01) | |
| *A61B 34/32* | (2016.01) | |
| *A61B 90/00* | (2016.01) | |
| *G05B 13/02* | (2006.01) | |
| *G06F 3/14* | (2006.01) | |
| *G06F 3/16* | (2006.01) | |
| *G06F 9/48* | (2006.01) | |
| *G06F 9/54* | (2006.01) | |
| *G06F 13/40* | (2006.01) | |
| *G06F 16/21* | (2019.01) | |
| *G06F 16/28* | (2019.01) | |
| *G06N 20/00* | (2019.01) | |
| *G06Q 10/30* | (2023.01) | |
| *G06T 11/60* | (2006.01) | |
| *G08B 5/22* | (2006.01) | |
| *G10L 15/22* | (2006.01) | |
| *G16H 10/60* | (2018.01) | |
| *G16H 15/00* | (2018.01) | |
| *G16H 20/40* | (2018.01) | |
| *G16H 30/40* | (2018.01) | |
| *G16H 40/40* | (2018.01) | |
| *G16H 40/63* | (2018.01) | |
| *G16H 40/67* | (2018.01) | |
| *G16H 50/20* | (2018.01) | |
| *G16H 50/70* | (2018.01) | |
| *H04L 1/22* | (2006.01) | |
| *H04L 41/12* | (2022.01) | |
| *H04L 65/80* | (2022.01) | |
| *H04L 67/12* | (2022.01) | |
| *H04L 67/125* | (2022.01) | |
| *H04N 5/272* | (2006.01) | |
| *H04N 7/15* | (2006.01) | |
| *A61B 8/06* | (2006.01) | |
| *A61B 18/00* | (2006.01) | |
| *G06F 21/62* | (2013.01) | |
| *G06F 40/169* | (2020.01) | |
| *G16H 30/20* | (2018.01) | |
| *H02J 7/00* | (2006.01) | |

(52) U.S. Cl.
CPC .............. *A61B 34/10* (2016.02); *A61B 34/20* (2016.02); *A61B 34/25* (2016.02); *A61B 34/30* (2016.02); *A61B 34/32* (2016.02); *A61B 90/08* (2016.02); *A61B 90/37* (2016.02); *G05B 13/0265* (2013.01); *G06F 3/14* (2013.01); *G06F 3/1423* (2013.01); *G06F 3/167* (2013.01); *G06F 9/4881* (2013.01); *G06F 9/542* (2013.01); *G06F 13/4068* (2013.01); *G06F 16/211* (2019.01); *G06F 16/284* (2019.01); *G06F 16/285* (2019.01); *G06N 20/00* (2019.01); *G06Q 10/30* (2013.01); *G06T 11/60* (2013.01); *G08B 5/22* (2013.01); *G10L 15/22* (2013.01); *G16H 10/60* (2018.01); *G16H 15/00* (2018.01); *G16H 20/40* (2018.01); *G16H 30/40* (2018.01); *G16H 40/40* (2018.01); *G16H 40/63* (2018.01); *G16H 40/67* (2018.01); *G16H 50/20* (2018.01); *G16H 50/70* (2018.01); *H04L 1/22* (2013.01); *H04L 41/12* (2013.01); *H04L 65/80* (2013.01); *H04L 67/12* (2013.01); *H04L 67/125* (2013.01); *H04N 5/272* (2013.01); *H04N 7/15* (2013.01); *A61B 8/06* (2013.01); *A61B 2017/00221* (2013.01); *A61B 2018/00702* (2013.01); *A61B 2018/00994* (2013.01); *A61B 2034/2072* (2016.02); *A61B 2034/254* (2016.02); *A61B 2090/364* (2016.02); *A61B 2090/365* (2016.02); *A61B 2090/373* (2016.02); *G06F 21/6245* (2013.01); *G06F 40/169* (2020.01); *G10L 2015/223* (2013.01); *G16H 30/20* (2018.01); *H02J 7/0063* (2013.01)

(56) References Cited

U.S. PATENT DOCUMENTS

| | | | | |
|---|---|---|---|---|
| 8,565,073 | B2* | 10/2013 | Rahman | .................. H04L 45/28 |
| | | | | 370/329 |
| 8,908,678 | B1* | 12/2014 | McGonigal | ........... H04L 67/303 |
| | | | | 370/352 |
| 9,011,427 | B2 | 4/2015 | Price et al. | |
| 9,283,054 | B2 | 3/2016 | Morgan et al. | |
| 9,345,481 | B2 | 5/2016 | Hall et al. | |
| 9,404,870 | B2 | 8/2016 | Butte et al. | |
| 9,788,907 | B1 | 10/2017 | Alvi et al. | |
| 10,656,089 | B2 | 5/2020 | Butte et al. | |
| 10,758,309 | B1 | 9/2020 | Chow et al. | |
| 11,146,690 | B2* | 10/2021 | Minert | ................ H04M 7/0084 |
| 11,166,765 | B1 | 11/2021 | Fuerst et al. | |
| 11,232,556 | B2 | 1/2022 | Jin et al. | |
| 11,232,868 | B1 | 1/2022 | Sutherland et al. | |
| 11,304,699 | B2 | 4/2022 | Shelton, IV et al. | |
| 11,304,763 | B2 | 4/2022 | Shelton, IV et al. | |
| 11,428,636 | B2 | 8/2022 | Butte et al. | |
| 11,564,573 | B2 | 1/2023 | Hirst | |
| 11,601,232 | B2 | 3/2023 | Shelton, IV et al. | |
| 11,630,061 | B2 | 4/2023 | Butte et al. | |
| 11,678,881 | B2 | 6/2023 | Yates et al. | |
| 2002/0000464 | A1 | 1/2002 | Ramberg et al. | |
| 2005/0210070 | A1* | 9/2005 | Macneil | .................. H04L 67/12 |
| 2007/0140235 | A1 | 6/2007 | Aysan et al. | |
| 2008/0030345 | A1 | 2/2008 | Austin et al. | |
| 2013/0051220 | A1 | 2/2013 | Ryshakov | |
| 2013/0092727 | A1 | 4/2013 | Edwards et al. | |
| 2013/0149967 | A1 | 6/2013 | Ma et al. | |
| 2014/0160259 | A1 | 6/2014 | Blanquart et al. | |
| 2014/0160260 | A1 | 6/2014 | Blanquart et al. | |
| 2014/0263552 | A1 | 9/2014 | Hall et al. | |
| 2014/0267655 | A1 | 9/2014 | Richardson et al. | |
| 2015/0119035 | A1* | 4/2015 | Ganu | .............. H04W 36/00837 |
| | | | | 455/436 |
| 2015/0128274 | A1 | 5/2015 | Giokas | |
| 2015/0182118 | A1 | 7/2015 | Bradbury et al. | |
| 2015/0215159 | A1 | 7/2015 | Liao et al. | |
| 2017/0296213 | A1 | 10/2017 | Swensgard et al. | |
| 2018/0122506 | A1 | 5/2018 | Grantcharov et al. | |
| 2018/0344308 | A1 | 12/2018 | Nawana et al. | |
| 2018/0360452 | A1 | 12/2018 | Shelton, IV et al. | |
| 2019/0104919 | A1 | 4/2019 | Shelton, IV et al. | |
| 2019/0019163 | A1 | 6/2019 | Kuhn et al. | |
| 2019/0191963 | A1 | 6/2019 | Kuhn et al. | |
| 2019/0200844 | A1 | 7/2019 | Shelton, IV et al. | |
| 2019/0200906 | A1 | 7/2019 | Shelton, IV et al. | |
| 2019/0200980 | A1 | 7/2019 | Shelton, IV et al. | |
| 2019/0200988 | A1 | 7/2019 | Shelton, IV | |
| 2019/0201033 | A1 | 7/2019 | Yates et al. | |
| 2019/0201102 | A1 | 7/2019 | Shelton, IV et al. | |
| 2019/0201104 | A1 | 7/2019 | Shelton, IV et al. | |
| 2019/0201115 | A1 | 7/2019 | Shelton, IV et al. | |

(56) References Cited

U.S. PATENT DOCUMENTS

| | | |
|---|---|---|
| 2019/0201116 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201129 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201140 A1 | 7/2019 | Yates et al. |
| 2019/0204201 A1 | 7/2019 | Shelton, IV et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1* | 7/2019 | Shelton, IV ............ H04L 47/24 |
| 2019/0207911 A1 | 7/2019 | Wiener et al. |
| 2019/0279765 A1 | 9/2019 | Giataganas et al. |
| 2019/0333626 A1 | 10/2019 | Mansi et al. |
| 2020/0008044 A1 | 1/2020 | Poornachandran et al. |
| 2020/0188047 A1 | 6/2020 | Itkowitz et al. |
| 2020/0244734 A1 | 7/2020 | Mendiola et al. |
| 2020/0285771 A1 | 9/2020 | Dey et al. |
| 2020/0405403 A1 | 12/2020 | Shelton, IV et al. |
| 2021/0005321 A1 | 1/2021 | Hwang |
| 2021/0076966 A1 | 3/2021 | Grantcharov et al. |
| 2021/0145523 A1 | 5/2021 | Xing et al. |
| 2021/0205030 A1 | 7/2021 | Shelton, IV et al. |
| 2021/0205031 A1 | 7/2021 | Shelton, IV et al. |
| 2021/0212670 A1 | 7/2021 | Babaris et al. |
| 2021/0212717 A1 | 7/2021 | Yates et al. |
| 2021/0236227 A1 | 8/2021 | Kumar et al. |
| 2021/0290046 A1 | 9/2021 | Nazareth et al. |
| 2021/0313051 A1 | 10/2021 | Asselmann et al. |
| 2021/0313077 A1 | 10/2021 | Smurro |
| 2021/0346094 A1 | 11/2021 | Fuerst et al. |
| 2022/0020476 A1* | 1/2022 | Souissi ................ G16H 40/20 |
| 2022/0020486 A1 | 1/2022 | Giataganas et al. |
| 2022/0046292 A1* | 2/2022 | Nair .................. H04N 21/4312 |
| 2022/0079675 A1 | 3/2022 | Lang |
| 2022/0104713 A1 | 4/2022 | Shelton, IV |
| 2022/0104807 A1 | 4/2022 | Shelton, IV et al. |
| 2022/0104822 A1 | 4/2022 | Shelton, IV et al. |
| 2022/0104896 A1 | 4/2022 | Shelton, IV et al. |
| 2022/0104910 A1* | 4/2022 | Shelton, IV ....... A61B 1/00045 |
| 2022/0104912 A1 | 4/2022 | Shelton, IV et al. |
| 2022/0108789 A1 | 4/2022 | Shelton, IV et al. |
| 2022/0202508 A1 | 6/2022 | Hiranandani et al. |
| 2022/0233119 A1 | 7/2022 | Shelton, IV et al. |
| 2022/0233135 A1 | 7/2022 | Shelton, IV et al. |
| 2022/0233136 A1 | 7/2022 | Shelton, IV et al. |
| 2022/0233151 A1 | 7/2022 | Shelton, IV et al. |
| 2022/0233191 A1 | 7/2022 | Shelton, IV et al. |
| 2022/0233252 A1 | 7/2022 | Shelton, IV et al. |
| 2022/0233254 A1 | 7/2022 | Shelton, IV et al. |
| 2022/0238216 A1 | 7/2022 | Shelton, IV et al. |
| 2022/0240869 A1 | 8/2022 | Shelton, IV et al. |
| 2022/0241028 A1 | 8/2022 | Shelton, IV et al. |
| 2022/0241474 A1 | 8/2022 | Shelton, IV et al. |
| 2022/0265357 A1 | 8/2022 | Morvan et al. |
| 2022/0303945 A1* | 9/2022 | Tsuda .................... H04W 76/20 |
| 2022/0375605 A1 | 11/2022 | Lipton et al. |
| 2022/0387116 A1 | 12/2022 | Hashimoto |
| 2023/0005266 A1 | 1/2023 | Quist et al. |
| 2023/0021832 A1 | 1/2023 | Shelton, IV et al. |
| 2023/0021920 A1 | 1/2023 | Shelton, IV et al. |
| 2023/0022604 A1 | 1/2023 | Shelton, IV |
| 2023/0023083 A1 | 1/2023 | Shelton, IV et al. |
| 2023/0023635 A1 | 1/2023 | Shelton, IV et al. |
| 2023/0025061 A1 | 1/2023 | Shelton, IV et al. |
| 2023/0025790 A1 | 1/2023 | Shelton, IV et al. |
| 2023/0025827 A1 | 1/2023 | Shelton, IV et al. |
| 2023/0026634 A1 | 1/2023 | Shelton, IV et al. |
| 2023/0026893 A1 | 1/2023 | Shelton, IV et al. |
| 2023/0027210 A1 | 1/2023 | Shelton, IV et al. |
| 2023/0027543 A1 | 1/2023 | Shelton, IV et al. |
| 2023/0028059 A1 | 1/2023 | Shelton, IV et al. |
| 2023/0028633 A1 | 1/2023 | Shelton, IV et al. |
| 2023/0028677 A1 | 1/2023 | Shelton, IV et al. |
| 2023/0035775 A1* | 2/2023 | Kohada ................. G06Q 10/00 |
| 2023/0057639 A1 | 2/2023 | Foelsch et al. |
| 2023/0254257 A1 | 8/2023 | Shelton, IV et al. |

FOREIGN PATENT DOCUMENTS

| | | |
|---|---|---|
| JP | 2017504019 A5 | 12/2017 |
| WO | 2013174327 A1 | 11/2013 |
| WO | 2017089479 A1 | 6/2017 |
| WO | 2017089910 A1 | 6/2017 |
| WO | 2019119130 A1 | 6/2019 |
| WO | 2020159978 A1 | 8/2020 |
| WO | 2021048326 A1 | 3/2021 |

OTHER PUBLICATIONS

Hashimoto, Daniel A., "Artificial Intelligence in Surgery: Promises and Perils", Annals of Surgery, vol. 268, No. 1, Jul. 2018, 7 pages.

Hutchins, Andrew R., "Machine Learning Applications for Objectively Assessing Surgical Skill and Instrument Dynamics", Department of Mechanical Engineering & Materials Science, Duke University; Available from ProQuest Dissertations and Theses Professional, 2019, 151 pages.

Orhub (Orhb), , "Enhances Leading Data Analytics Platform with Integration of Sterilization Process Module", Internet, May 9, 2017, 3 pages.

Kum, Sang-Uok , "Encoding of Multiple Depth Streams", 2008, 162 pages.

* cited by examiner

| 45206 | 45208 | 45210 | 45212 | 45213 | 45214 |
|---|---|---|---|---|---|
| Standard format ID | Classification parameter | Source | Payload type | Timing element | Payload |

Data source =
Visualization
Biomarker
Surgical instrument
Capital Equipment

Payload type =
Image/frame
Heartrate
Energy level
Actuation
Sensor data
Tunnel
Operational Status Timing element =
Frame number
Time stamp (local, global, offset)
Milestone + offset
Latency

FIG. 43

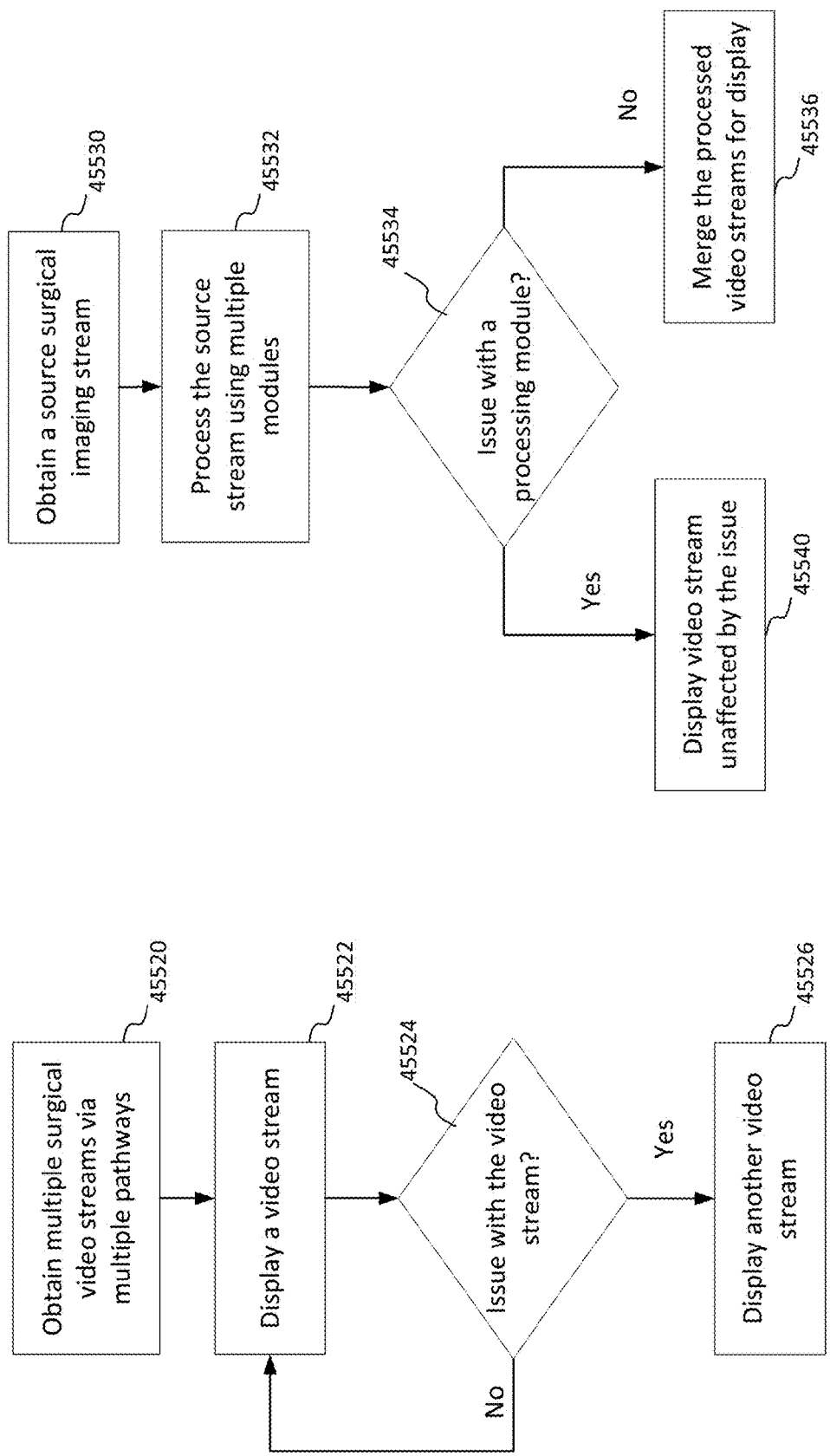

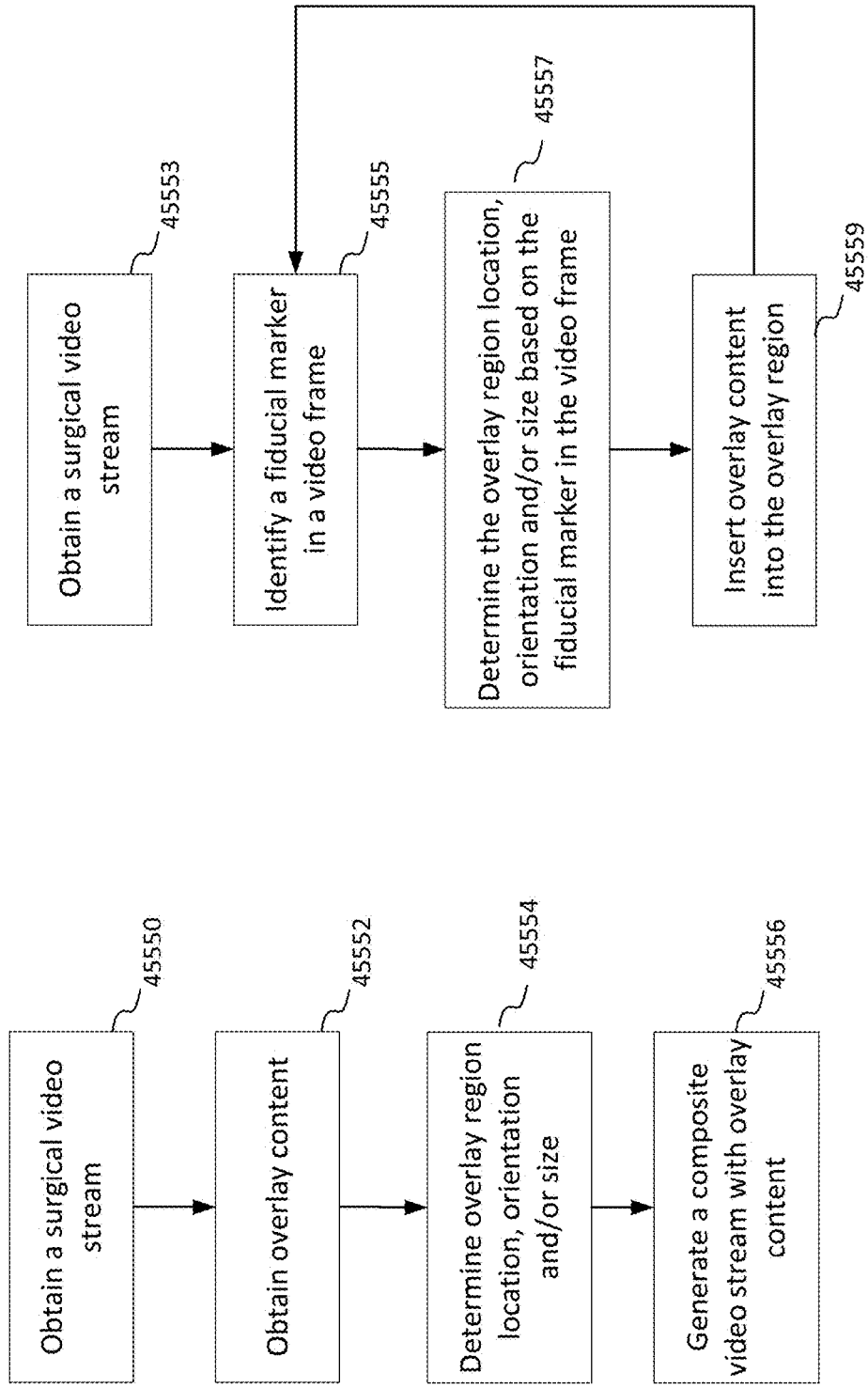

METHOD OF SURGICAL SYSTEM POWER MANAGEMENT, COMMUNICATION, PROCESSING, STORAGE AND DISPLAY

CROSS-REFERENCE TO RELATED APPLICATIONS

This application claims the benefit of Provisional U.S. Patent Application No. 63/224,813, filed Jul. 22, 2021, the disclosure of which is incorporated herein by reference in its entirety.

This application is related to the following, filed contemporaneously, the contents of each of which are incorporated by reference herein:

U.S. patent application Ser. No. 17/384,453, filed Jul. 23, 2021, titled MONITORING POWER UTILIZATION AND NEEDS WITHIN SURGICAL SYSTEMS U.S. patent application Ser. No. 17/384,455, filed Jul. 23, 2021, titled INTERCOMMUNICATION AND COOPERATIVE OPERATION OF SURGICAL DEVICES U.S. patent application Ser. No. 17/384,457, filed Jul. 23, 2021, titled DETECTION OF SURGICAL DEVICES WITHIN SURGICAL SYSTEMS U.S. patent application Ser. No. 17/384,164, filed Jul. 23, 2021, titled INTEGRATED HUB SYSTEMS CONTROL INTERFACES AND CONNECTIONS U.S. patent application Ser. No. 17/384,128, filed Jul. 23, 2021, titled LOCATION AND SURGICAL PROCEDURE SPECIFIC DATA STORAGE AND RETRIEVAL U.S. patent application Ser. No. 17/384,142, filed Jul. 23, 2021, titled SURGICAL DATA PROCESSING AND METADATA ANNOTATION U.S. patent application Ser. No. 17/384,151, filed Jul. 23, 2021, titled MULTI-LEVEL SURGICAL DATA ANALYSIS SYSTEM U.S. patent application Ser. No. 17/384,337, filed Jul. 23, 2021, titled SURGICAL DATA SYSTEM AND CONTROL U.S. patent application Ser. No. 17/384,348, filed Jul. 23, 2021, titled SURGICAL DATA SYSTEM AND CLASSIFICATION U.S. patent application Ser. No. 17/384,354, filed Jul. 23, 2021, titled SURGICAL DATA SYSTEM AND MANAGEMENT U.S. patent application Ser. No. 17/384,265, filed Jul. 23, 2021, titled REDUNANT COMMUNICATION CHANNESL AND PROCESSING OF IMAGING FEEDS U.S. patent application Ser. No. 17/384,270, filed Jul. 23, 2021, titled COOPERATIVE COMPOSITE VIDEO STREAMS LAYERED ONTO THE SURGICAL SITE AND INSTRUMENTS U.S. patent application Ser. No. 17/384,553, filed Jul. 23, 2021, titled CONFIGURATION OF THE DISPLAY SETTINGS AND DISPLAYED INFORMATION BASED ON THE RECOGNITION OF THE USER(S) AND AWARENESS OF PROCEDURE, LOCATION OR USAGE U.S. patent application Ser. No. 17/384,508, filed Jul. 23, 2021, titled HUB IDENTIFICATION AND TRACKING OF OBJECTS AND PERSONNEL WITHIN THE OR TO OVERLAY DATA THAT IS CUSTOM TO THE USER'S NEED

BACKGROUND

Surgical procedures are typically performed in surgical operating theaters or rooms in a healthcare facility such as, for example, a hospital. Various surgical devices and systems are utilized in performance of a surgical procedure. In the digital and information age, medical systems and facilities are often slower to implement systems or procedures utilizing newer and improved technologies due to patient safety and a general desire for maintaining traditional practices.

SUMMARY

Examples described herein may include a surgical power device configured to balance power needs. The surgical power device may include a first output power interface configured to supply a first surgical module having a first power expectation; a second output power interface configured to supply a second surgical module having a second power expectation; a power distribution unit configured to receive operating room power, to provide a first portion of the operating room power to the first output power interface, and to provide a second portion of the operating room power to the second output power interface; and a controller in communication with the power distribution unit. The controller may be configured to determine an available amount of operating room power, the first power expectation, and the second power expectation; determine a power budget for the first surgical module and the second surgical module based on the available amount of operating room power, the first power expectation, and the second power expectation; and control the power distribution unit, based on the power budget, to set the first portion of the operating room power and the second portion of the operating room power.

Examples described herein may include methods of balancing operating room power supplied to a power distribution unit within a surgical system. The method may determine a first power expectation associated with a first surgical module, a second power expectation associated with a second surgical module, and an available amount of operating room power within an operating room; a power budget for the first surgical module and the second surgical module based on the available amount of operating room power, the first power expectation, and the second power expectation; and control the power distribution unit, based on the power budget, to a set a first portion and a second portion of the operating room power supplied to the power distribution unit. The first portion of the operating room power may be provided to a first output power interface configured to supply the first surgical module and second portion of the operating room power may be provided to a second output power interface configured to supply the second surgical module.

Examples described herein may include a surgical system configured to balance power needs. The surgical system may include a power facility, a surgical network, a surgical power unit, and a communications interface. The surgical power unit may include a first output-power interface configured to supply a first surgical module having a first power expectation; a second output-power interface configured to supply a second surgical module having a second power expectation; a power distribution unit configured to receive operating-room power from the power facility, to provide a first portion of the operating-room power to the first output-power interface, and to provide a second portion of the operating-room power to the second output-power interface; and a controller in communication with the power distribution unit. The controller may determine an available amount of operating-room power, the first power expectation, and the second power expectation; determine a power budget for the first surgical module and the second surgical module based on the available amount of operating-room power, the first power expectation, and the second power expectation; and control the power distribution unit, based on the power budget, to set the first portion of the operating-room power and the second portion of the operating-room power. The communications interface may be in communication with the power facility and the surgical network. The communications interface may communicate the first portion and the second portion of the operating-room power to the power facility and the surgical network.

Examples described herein any include a surgical module for use within the surgical system. The surgical module may include a first port connected to a surgical hub; a second port connected to an additional surgical module; and a controller. The controller may be configured to receive surgical data; determine if the surgical data is a first type of data or a second type of data; and instruct the surgical module to send the surgical data to the first port if the surgical data is the first type of data or to the second port if the surgical data is the second type of data.

In examples, the surgical module may include a first port connected to a surgical hub; a second port connected to an additional surgical module; and a controller. The controller may be configured to receive surgical data; determine if the surgical data is a first type of data or a second type of data; instruct the surgical module to send the surgical data to the first port if the surgical data is the first type of data or to the second port if the surgical data is the second type of data; exclude control of the first type of data; and simultaneously control the second type of data.

Examples described herein may include a surgical system that provides intercommunication and cooperative operating of surgical devices. The surgical system may include a surgical hub, a surgical power system configured to power the surgical hub, and a surgical module. The surgical module may include a first port connected to the surgical hub; a second port connected to an additional surgical module; and a controller. The controller may be configured to receive surgical data from the surgical hub; determine if the surgical data is a first type of data or a second type of data; and instruct the surgical module to send the surgical data to the first port if the surgical data is the first type of data or to the second port if the surgical data is the second type of data.

Examples described herein may include a surgical computing device that directs data communications to surgical networks. The surgical computing device may include a processor that is configured to determine a present network locus, wherein the present network locus is any of a first surgical network or a second surgical network; identify a data communications session; determine a surgical data type of the data communication session, wherein the surgical data type is any of a first type of surgical data or a second type of surgical data, and direct the data communications session to the first surgical network if the surgical data type is the first type of surgical data or to the second surgical network if the surgical data type is the second type of surgical data. In examples, the surgical computing device may include a processor that is configured to determine a present network locus of the processor; wherein the present network locus is any of a first surgical network or a second surgical network; identify a data communications session, determine a surgical data type of the data communication session; and direct the data communications session to the first surgical network or the second surgical network based on the present network locus and the surgical data type of the data communication session.

Examples described herein may include a surgical system that directs data communications to surgical networks. The surgical system may include a surgical hub, a plurality of surgical modules, a first plurality of functions within a first surgical network, wherein the first surgical network is associated with a first type of surgical data; a second plurality of functions within a second surgical network, wherein the second surgical network is associated with a second type of surgical data; a processor of the surgical hub; and a processor of at least one of the surgical modules. The processor of the surgical hub may be configured to combine at least one of the first plurality of functions with at least one of the second plurality of functions to create a third surgical network, wherein the third surgical network is connected to the surgical hub and associated with a third type of surgical data. The processor of the at least one surgical module may be configured to determine a present network locus of the processor, wherein the present network locus is any of the first surgical network, the second surgical network, or the third surgical network; identify a data communications session; determine a surgical data type of the data communication session, wherein the surgical data type is any of a first type of surgical data, a second type of surgical data, or a third type of surgical data, and direct the data communications session to the third surgical network if the surgical data type is the third type of surgical data.

Systems, methods, and instrumentalities are disclosed for switching (e.g., adaptively switching) a control scheme to control a set of system modules and/or modular devices associated with a surgical hub. In an example, a surgical hub may determine a first control scheme that is configured to control a set of system modules and/or modular devices associated with the surgical hub.

The surgical hub may receive an input from one of the set of modules or a device that is located within bounds of an operating room. The surgical hub may determine that a safety status level and/or an overload status level of the surgical hub is higher than its threshold value. Based on at least the input received from one of the system modules and/or the modular device and the determination that one of the safety status level or the overload status level of the surgical hub is higher than its respective threshold, the surgical hub may determine a second control scheme to be configured and/or used to control the set of modules associated with the surgical hub. The second control scheme may be determined based on one or more of the needs of the surgical hub, priorities of the system modules and/or modular devices, and capacity of the system modules or modular devices, or capacity of the surgical hub.

The first control scheme or the second control scheme may be one of a cooperative control scheme, a notification control scheme, an antagonistic control scheme, or a hierarchical control scheme. The cooperative control scheme may include the surgical hub configuring the system modules and/or the modular devices to enable a first system module or a modular device to communicate with a second system module or the modular device such that a condition in the first system module or modular device impacts operation of the second system module or the modular device.

The notification control scheme may include the surgical hub enabling a first system module or the modular device to notify a second system module or modular device about an occurrence of an event or a parameter associated with one of the functions of the first system module or the modular device.

The antagonistic control scheme may include the surgical hub prioritizing a first task associated with a first system module or modular device over a second task associated with a second system module or modular device. The prioritization may be based on at least one of an importance of the module, a function of the first task, or a predefined configured value.

The hierarchical control scheme may include the surgical hub establishing a hierarchy of control between a first system module or modular device and a second system module or modular device.

The surgical hub may send a control program to one or more system modules and/or modular devices associated with the set of modules to establish the second control scheme. The surgical hub may determine the communication interfaces associated with the system modules and/or modular devices. The surgical hub may control the communication interfaces based on, for example, capabilities of the system modules and/or modular devices, interferences of the system modules and/or modular devices, and the data communicated by the system modules and/or modular devices. The surgical hub may identify configuration of a system module or a modular device using, for example, one of an electronic communication or a visualization using an operating room (OR) camera.

The surgical hub may adapt one of a communication limit, an interconnectivity, a master-slave control operation, a timing, or a data passing pathway based on the identified configuration of the one of the module, the equipment, or the device.

The surgical hub may identify configuration of the system module or the modular device based on a risk/harm database.

Systems, methods, and instrumentalities are disclosed for data storage and data retrieval based on processing, analysis, and/or usage needs. The data storage and data retrieval may include distributed and/or redundant data storage based on usage location of the data. Data storage and retrieval may be performed based on location and surgical procedure specific data. Data relating to, for example, a particular operating room and/or a surgical procedure may be compiled and stored together. The data may be retrieved for future use. A surgical hub may obtain location and surgical procedure specific data for a specific location and a surgical procedure. The surgical hub may generate surgical procedure information using the location and surgical procedure specific data, for example, to use for an upcoming surgical procedure. The surgical hub may communicate the surgical procedure information to modules, modular devices, and/or surgical systems, for example, to perform the surgical procedure.

The surgical hub may be configured to determine its geographic location within a medical facility. The surgical hub may be configured to determine that the geographic location is associated with a second surgical hub. The surgical hub may be configured to send a request to data storage(s) to transfer location and surgical procedure specific data, for example, that may be associated with the second surgical hub. The surgical hub may be configured to obtain the location and procedure specific data from the data storage(s). The surgical hub may be configured to generate surgical procedure information for an upcoming surgical procedure, for example, based on the obtained location and surgical procedure specific data. The surgical hub, based on the obtained location and surgical procedure specific data, may send the surgical procedure information (e.g., using one or more control programs) to modules, systems, modular devices, and/or other surgical hubs, for example, to perform the surgical procedure.

Generated surgical procedure data from a performed surgical procedure may be stored in the data storage(s). The generated surgical procedure data may be stored in the data storage(s), for example, based on the geographic location of the surgical procedure and the type of surgical procedure performed. The generated surgical procedure data may be compiled and stored for later use. For example, the generated surgical procedure data may be the location and surgical procedure specific data requested for a future surgical procedure.

Systems, methods, and instrumentalities are disclosed for data processing and creating a record of the processing for archival in metadata associated with the results of the processing. The processing may include transformations of the data. Transforming the data may generate transformed data. The processes performed may be archived, for example, in metadata associated with the transformed data. The metadata may be annotated with information associated with previous transforms performed on the transformed data. The metadata may be stored with the transformed data.

For example, a surgical hub may obtain surgical procedure data, which may be associated with a patient. The surgical hub may obtain the surgical procedure data from one or more of a module associated with the surgical hub, a surgical system located in the OR, and/or the like. The surgical hub may process the obtained surgical procedure data. For example, the surgical hub processing the surgical procedure data may include transforming the surgical procedure data. The surgical hub may generate transformed surgical procedure data using a transform. The surgical procedure may generate metadata, which may be associated with the transformed surgical procedure data. The metadata may include the information associated with the processing (e.g., transform) performed on the surgical data that generated the transformed surgical procedure data. The metadata may include information such as a time associated with the processing of the surgical procedure data, a location associated with the processing of the surgical procedure data, information indicating a portion of the surgical procedure data that was processed, a revision of the transform used to perform the transformation, and/or the like. The surgical hub may process the surgical procedure data and/or generate metadata associated with the transformed surgical procedure data, for example, using blockchain recording. The surgical hub may store the transformed surgical procedure data and the metadata comprising the processing information.

The surgical hub may include a scalable processing system, for example, that may cooperatively interact and process data from other couple hub modules and systems within the OR. The processing may include a transformation or algorithm to combine or compile multiple data elements together. The metadata attached to the transformed data may include information about the transform(s) used on the data.

For example, the surgical hub may obtain previously stored transformed data, such as previously stored transformed surgical procedure data, and metadata associated with the previously stored transformed data. The surgical hub may process the previously stored transformed data. The surgical hub may generate updated metadata associated with the transformation of the previously stored transformed data. The updated metadata may include the previously performed transformations and/or processing on the data before it was obtained and the updated metadata may include the transformation just performed on the previously stored transformed data.

Systems, methods, and instrumentalities are described herein for surgical data analysis. A computing system may obtain, from surgical hub(s) and/or other system(s), collections of unredacted data associated with different surgical procedures. The computing system, the surgical hub(s), and other system(s) may be located on a local data network. The local data network may be within a boundary protected by health insurance portability and accountability act (HIPAA) data rules.

The computing system may train machine learning model(s) based on the unredacted data. The computing system may generate information that optimizes the clinical outcome and cost effectiveness of future surgical procedure(s) based on the machine learning model(s). The computing system may send generated information to the surgical hub(s) and/or other system(s). The computing system may be in communication with a remote cloud computing system. The computing system may send the generated information to the remote cloud computing system.

Examples described herein may include a device to process and/or classify data associated with a surgical event of a surgery. The device may include a processor.

The processor may be configured to process the data associated with the surgical event based on another data. The processor may be configured to receive multiple data streams during the surgical event. The processor may be configured to select a first data stream and a second data stream from the multiple data streams. The first data stream may be selected as the primary data stream, and the second data stream may be selected as the secondary data stream. The selection of the primary data stream may be based on a surgical data interface via which the primary data stream is received. The selection of the secondary data stream may be based on a surgical data interface via which the secondary data stream is received. The processor may be configured to identify the surgical data interface that is configured to receive the primary data stream and identify the surgical data interface that is configured to receive the secondary data stream. The processor may be configured to generate situational data associated with the primary data stream based on the secondary data stream. The situational data may indicate a medical decision-making factor of the surgical event. The primary data stream and the situational data may be sent during the surgical event. The secondary data stream may include a first portion and a second portion. The processor may be configured to store the first portion of the secondary data stream and not the second portion of the secondary data stream.

The primary data stream may include a first timing element. The first timing element may indicate a first time when the first data stream is collected during the surgical event. The primary data stream and the situational data associated with the primary data stream may be sent at a second time during the surgical event, and a difference between the first time and the second time may be lower than a predetermined value. The predetermined value may be used for real-time processing. The difference that is lower than the predetermined value may indicate that the primary data stream is sent in real time, for example, as the first data stream is collected.

The primary data stream may be sent via data packets. At least one of the data packets may include a field indicative of the situational data. The situational data may be sent using at least one of an annotation for the primary data stream, a context associated with the primary data stream, or meta data that indicates the context associated with the primary data stream.

The processor may be configured to generate control instructions based on the primary data stream and the situational data associated with the primary data stream, and the processor may be configured to send the control instructions to a surgical instrument in communication with the device, for example, to change an operation of the surgical instrument.

The processor may be configured to generate a risk indicator based on the primary data stream and the situational data associated with the primary data stream. The risk indicator may include at least one of an action trigger, a notification, or a threshold. The processor may be configured to send the risk indicator, for example, to a displaying device.

The surgical event may be an ongoing surgical event. The processor may be configured to determine that the ongoing surgical event and a historical surgical event have a characteristic in common. The processor may be configured to generate the situational data further based on a data stream associated with the historical surgical event. The characteristic in common may include at least one of a same patient, a same type of surgical procedure, a same type of surgical instrument, or a same type of surgical equipment.

The processor may be configured to classify the data associated with the surgical event. The processor may be configured to receive a first surgical data stream via a first surgical data interface and receive a second surgical data stream via a second surgical data interface. The first surgical data interface may be configured to receive the first surgical data stream from a first surgical instrument. The second surgical data interface may be configured to receive the second surgical data stream from a second surgical instrument. The processor may be configured to determine a first classification parameter associated with the first surgical data stream. The processor may be configured to determine a second classification parameter associated with the second surgical data stream. The processor may be configured to identify the first surgical data interface and determine the first classification parameter based on the identified first surgical data interface. The first surgical data interface may be designated to communicate with a first type of surgical instrument. The processor may be configured to identify the second surgical data interface and determine the second classification parameter based on the identified second surgical data interface. The second surgical data interface may be designated to communicate with a second type of surgical instrument. The processor may be configured to determine the first classification parameter based on decoding the first classification parameter in the first surgical data stream. The processor may be configured to determine the second classification parameter based on decoding the second classification parameter in the second surgical data stream. In some examples, the processor may decode the first surgical data stream and infer the first classification parameter based on the decoded first surgical data stream. The processor may decode the second surgical data stream and infer the second classification parameter based on the decoded second surgical data stream. The processor may be configured to determine a mode of interaction between the first surgical data stream and the second surgical data stream. The processor may be configured to identify a surgical event associated with at least one of the first surgical data stream or the second surgical data stream and determine the mode of interaction based on the surgical event. The mode of interaction may generate situational data of the identified surgical event. The mode of interaction may include one or more of an enrichment of the first surgical data stream using the second surgical data stream, an aggregation of the first surgical data stream and the second surgical data stream, or a synthesis of the first surgical data stream and the second surgical data stream.

The processor may be configured to generate a third surgical data stream based on the mode of interaction between the first surgical data stream and the second surgical data stream. The processor may be configured to determine a third classification parameter for the third surgical data stream based on the first classification parameter associated with the first surgical data stream, the second classification parameter associated with the second surgical data stream, and the mode of interaction between the first surgical data stream and the second surgical data stream. At least one of the first classification parameter, the second classification parameter, or the third classification parameter may be multidimensional. The third classification parameter (e.g., a value of the third classification parameter) may indicate one or more of privacy of the third surgical data stream, a priority of the third surgical data stream, a content type of the third surgical data stream, a context of the third surgical data stream, a retention period associated with the third surgical data stream, or a user preference associated with the third surgical data stream.

The processor may be configured to determine a data handling scheme for the third surgical data stream based on the third classification parameter. The data handling scheme may be consistent with a healthcare data policy. The processor may be configured to perform data handling of the third surgical data stream according to the data handling scheme. The data handling scheme may include one or more of a type of storage location for the third surgical data stream or a reliability level associated with a communication path used for the third surgical data stream.

In an example, the processor may be configured to determine, based on the third classification parameter, that the third surgical data stream has the highest classification level among multiple surgical data streams that are to be transmitted. The processor may be configured to determine the communication path that has the least amount of interruption among transmission resources that are available to be used for the transmissions of the surgical data streams. The processor may be configured to send the third surgical data stream using the determined communication path. The processor may be configured to repeat the sending of the third surgical data stream based on the determination that the third surgical data stream has the highest classification level among the surgical data streams to be transmitted.

The processor may be configured to determine a data handling scheme for the second surgical data stream. The second classification parameter and the third classification parameter may be the same. The processor may be configured to determine, based on the second classification parameter, the same data handling scheme for the second surgical data stream as the data handling scheme for the third surgical data stream.

The processor may be configured to process data associated with the surgical event into a standard format. The processor may be configured to identify a surgical data interface associated with a type of surgical instrument. The surgical data interface may be configured to receive a data stream from a surgical instrument of the type associated with the surgical data interface. The processor may be configured to identify a database for receiving surgical information indicated by the data stream. The database may be in a standard format. For example, the database may be a relational database. The standard format may indicate at least one of a resolution, a sampling rate, a measurement type, a unit of measurement, or a type of data stream. The type of data stream may be a discrete data stream or a continuous data stream. The processor may be configured to select a rule set based on the identified surgical data interface associated with the type of surgical instrument and based on the identified database. The rule set may include one or more of a data cleaning rule, a data verification rule, or a data formatting rule. The processor may be configured to generate a transformed data stream in the standard format based on the selected rule set and based on the data stream received via the surgical data interface. The transformed data stream may indicate the surgical information. The processor may be configured to input the transformed data stream to the database. The processor may be configured to determine, for the first data stream, invalid data and invalid associations based on the selected rule set. The first transformed data stream may exclude the invalid data and the invalid associations. The processor may be configured to generate a second transformed data stream in the standard format based on a second data stream and generate an annotation for the first data stream based on the second data stream such that the first transformed data stream comprises the annotation.

The data stream may include visualization data, biomarker data, surgical instrument data, or surgical equipment data. In an example, the processor may be configured to receive a first data stream and generate a first transformed data stream in the standard format based on a first rule set. The processor may be configured to generate a second transformed data stream in the standard format based on a second data stream. The second data stream may include a patient data stream, a surgical instrument data stream associated with a surgical operation, or a surgical equipment data stream. The second transformed data stream and the first transformed data stream may be at a same sampling rate or a same synchronization, or linked to a same surgical event.

A computing system may use redundant communication pathways for communicating surgical imaging feed(s). The computing system may obtain multiple surgical video streams via multiple pathways. The multiple surgical video streams may include different video feeds and/or copies of the same video feed. The surgical video streams may be obtained, for example, from the same intra-body imaging feed, such as an intra-body visual light feed. For example, a first video stream may be obtained via a communication pathway, and a second video stream may be obtained via another communication pathway. The computing system may display or send a surgical video stream for display. The computing system may determine whether the video stream being displayed has encountered any issues. Upon detecting an issue with the video stream being displayed, the computing system may display another obtained surgical video stream or send another obtained surgical video stream for display. For example, a primary video stream may be displayed initially. Upon detecting an issue associated with the primary video, a secondary video stream may be displayed.

In examples, the computing system may use redundant processing paths for processing surgical imaging feed(s). The computing system may obtain a source surgical imaging stream and may process the source imaging stream using multiple processing modules. For example, at least some processing modules may process the surgical imaging stream in parallel. The computing system may determine whether any issues have been encountered at the processing modules. If no issue has been found, the processed surgical imaging streams may be merged for display. Upon detecting an issue associated with a processing module, the computing system may select a surgical imaging stream unaffected by the detected issue for display. For example, a surgical imaging stream that has not been processed by the processing module associated with the detected issue may be selected for display.

A computing system may generate a composite video stream from multiple input feeds. The computing system may obtain a surgical video stream and overlay content associated with a surgical procedure onto the surgical video stream. For example, the overlay content may be obtained from a secondary video feed or a portion of a secondary video feed. The computing system may determine the overlay region location, size and/or orientation for overlaying the overlay content by analyzing the content of surgical video stream. For example, based on the content of a frame of the surgical video stream, the computing system may determine an overlay region location in the frame for overlaying the overlay content. Based on the content of a subsequent frame of the surgical video stream, the computing system may determine another overlay region location in the subsequent frame for overlaying the overlay content. The composite video stream may be generated based on the overlay region locations determined for different frames of the surgical video stream.

The computing system may determine the overlay region location, size and/or orientation for overlaying the overlay content based on one or more fiducial marker(s) captured in the surgical video stream. For example, the computing system may identify the fiducial marker in the video frames of the surgical video stream and determine the respective location, size, and/or orientation of the fiducial marker(s) in respective video frames. For a given video frame, or a group of video frames, the computing system may determine the size, location and/or orientation of the overlay region based on the location, size and/or orientation of the fiducial marker captured therein.

Systems, methods, and/or instrumentalities for a surgical hub configuring a display may be provided. In examples, a health care provider (HCP) and/or a medical instrument may be tracked within an operating room. In examples, a first HCP and a second HCP may be tracked within an operating room. In examples, an HCP and/or a patient may be tracked within an operating room. A surgical task that uses the medical instrument during a medical procedure may be determined.

A display configuration for the display may be determined, for example, based on the surgical task and/or an interaction between the HCP and the medical instrument. In examples, a first display configuration may be determined based on a first interaction between the HCP and the medical instrument. For example, a second interaction may be determined between the HCP and the medical instrument, the HCP and the display, and/or the HCP and the patient. The display configuration may be modified based on the second interaction. The display configuration for the display may be determined based on the surgical task and an interaction between a first HCP and a second HCP. For example, the interaction between the first HCP and the second HCP may be a verbal communication. The verbal communication may be determined to be a request from the first HCP for assistance from the second HCP in performing the surgical task. The display configuration may be modified such that the display configuration may configure the display with one or more preferences that are relevant to the second HCP.

Systems, methods, and/or instrumentalities for a surgical hub providing a health care provider (HCP) with a data overlay may be provided. A state of a surgical object and/or an area of the operating room where the surgical object is located may be determined. Determining an area of the operating room where the surgical object is located may comprise using a sensor data associated with the area, a wearable device data, sensor data associated with the HCP, an image from a camera within the operating room, an ultrasonic sensor, a laser sensor, a laser doppler sensor, a radio frequency sensor, and/or a video form the camera within the operating room. A time associated with the surgical object and/or the area of the operating room may be determined. The state of the surgical object may be determined to indicate that the surgical object is ready for use in the surgical task.

A surgical task that uses the surgical object during a medical procedure may be determined. The surgical object entering the area of the operating room during the task and/or medical procedure may be determined. In examples, determining that the surgical object has entered the operating room may be based on the area of the operating where the surgical object is located. The time may indicate when the surgical object entered the operating room. In examples, it may be determined that the surgical object has left the area of the operating room. The time may indicate when the surgical object has left the area.

Systems, methods, and/or instrumentalities for a surgical hub providing a health care provider (HCP) with a data overlay may be provided. A state of a surgical object and/or an area of the operating room where the surgical object is located may be determined. Determining an area of the operating room where the surgical object is located may comprise using a sensor data associated with the area, a wearable device data, sensor data associated with the HCP, an image from a camera within the operating room, an ultrasonic sensor, a laser sensor, a laser doppler sensor, a radio frequency sensor, and/or a video from the camera within the operating room. A time associated with the surgical object and/or the area of the operating room may be determined. The state of the surgical object may be determined to indicate that the surgical object is ready for use in the surgical task.

A surgical task that uses the surgical object during a medical procedure may be determined. The surgical object entering the area of the operating room during the task and/or medical procedure may be determined. In examples, determining that the surgical object has entered the operating room may be based on the area of the operating room where the surgical object is located. The time may indicate when the surgical object entered the operating room. In examples, it may be determined that the surgical object has left the area of the operating room. The time may indicate when the surgical object has left the area.

Systems, methods, and/or instrumentalities for a surgical hub configuring a display may be provided. In examples, a health care provider (HCP) and/or a medical instrument may be tracked within an operating room. In examples, a first HCP and a second HCP may be tracked within an operating room. In examples, an HCP and/or a patient may be tracked within an operating room. A surgical task that uses the medical instrument during a medical procedure may be determined.

A display configuration for the display may be determined, for example, based on the surgical task and/or an interaction between the HCP and the medical instrument. In examples, a first display configuration may be determined based on a first interaction between the HCP and the medical instrument. For example, a second interaction may be determined between the HCP and the medical instrument, the HCP and the display, and/or the HCP and the patient. The display configuration may be modified based on the second interaction. The display configuration for the display may be determined based on the surgical task and an interaction between a first HCP and a second HCP. For example, the interaction between the first HCP and the second HCP may be a verbal communication. The verbal communication may be determined to be a request from the first HCP for assistance from the second HCP in performing the surgical task. The display configuration may be modified such that the display configuration may configure the display with one or more preferences that are relevant to the second HCP.

BRIEF DESCRIPTION OF THE DRAWINGS

FIG. 43 shows an example data stream.

FIG. 53 illustrates an example process for using redundant pipe ways for communicating surgical imaging feed(s).

FIG. 54 illustrates an example process for using redundant processing paths for communicating surgical imaging feed(s).

FIG. 55A illustrates an example process for generating a composite surgical video stream from multiple input feeds.

FIG. 55B shows an example process for generating a composite surgical video stream using a fiducial marker.

FIG. 73 depicts a method that may be performed by a surgical hub for providing adaptations and/or controls that may change based on spatial awareness of objects and personnel within the surgical OR.

DETAILED DESCRIPTION

Figure 1A:
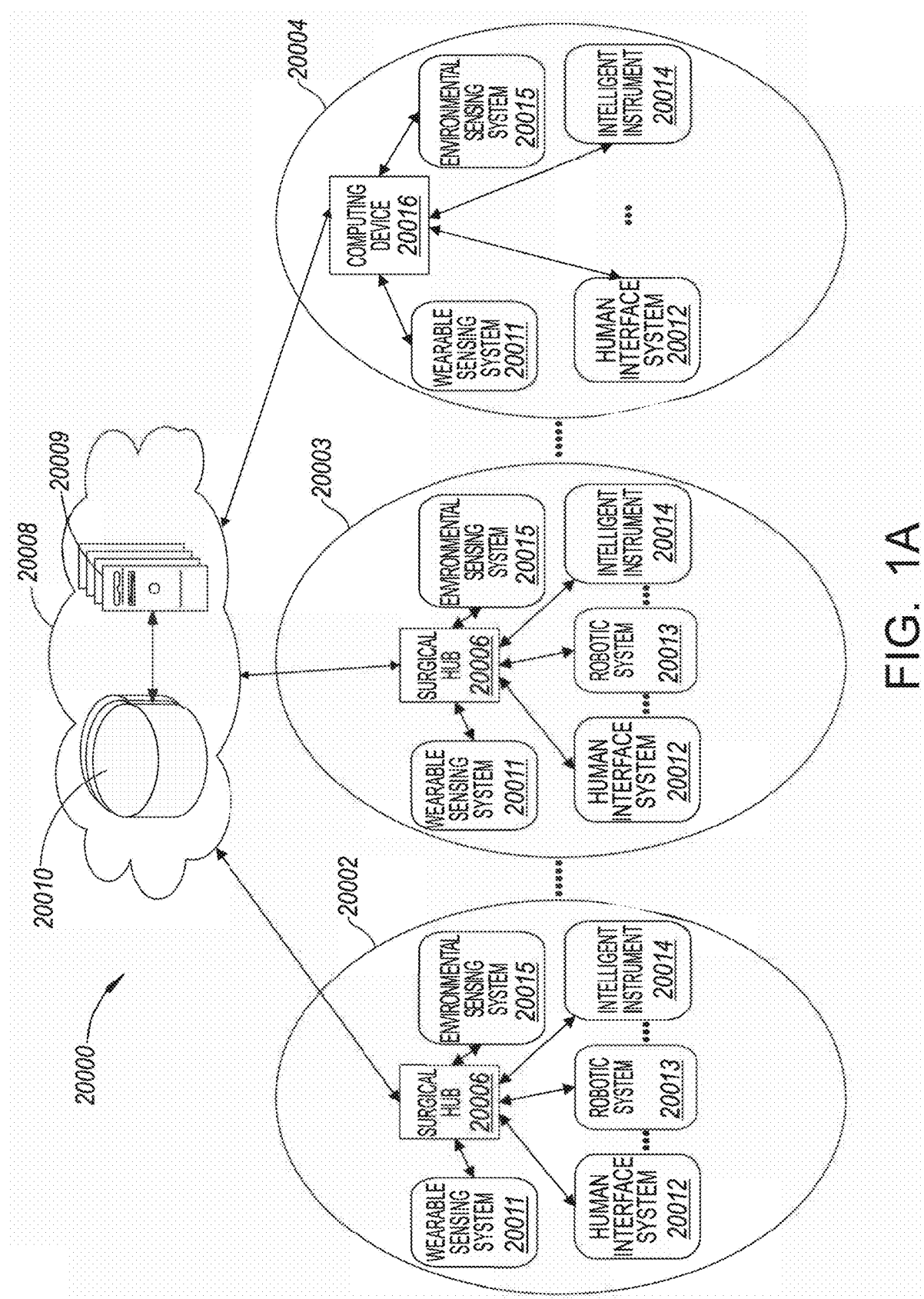
FIG. 1A is a block diagram of a computer-implemented surgical system.

FIG. 1A is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1A. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 1B:
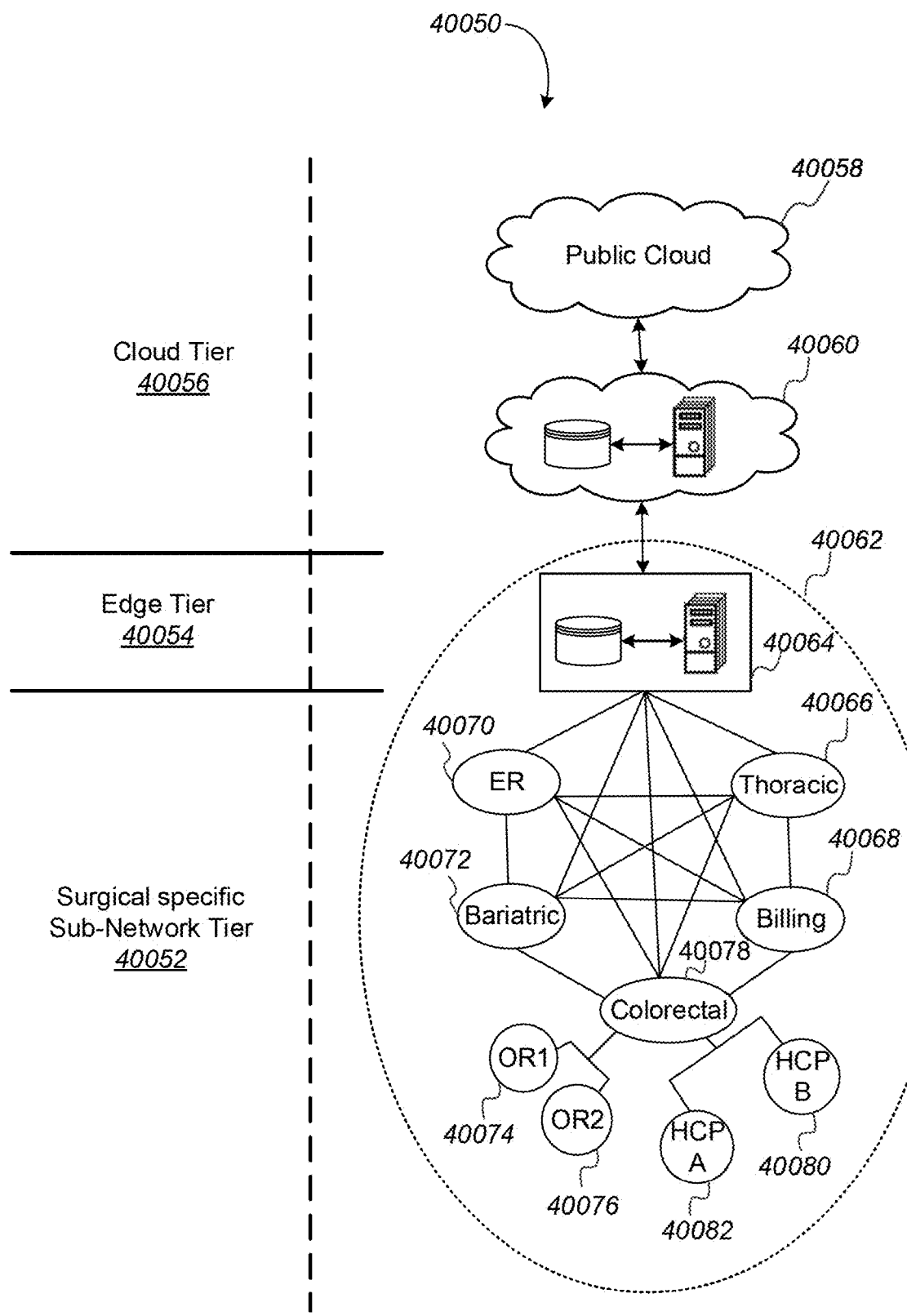
FIG. 1B is a block diagram of a computer-implemented multi-tier surgical system.

FIG. 1B is a block diagram of a computer-implemented multi-tier surgical system. As illustrated in FIG. 1B, a computer-implemented multi-tier surgical system 40050 may include multiple tiers of systems, such as a surgical specific sub-network tier system 40052, an edge tier system 40054 that is associated with the surgical specific sub-network tier system 40052, and a cloud tier system 40056.

A surgical specific sub-network tier system 40052 may include a plurality of inter-connected surgical sub-systems. For example, the surgical sub-systems may be grouped by the type of surgical procedures and/or other departments in a medical facility or a hospital. For example, a medical facility or a hospital may include a plurality of surgical procedure specific departments, such as an emergency room (ER) department 40070, colorectal department 40078, bariatric department 40072, thoracic department 40066, and billing department 40068. Each of the surgical procedure specific departments may include one or more surgical sub-systems associated with an operating room (OR) and/or a healthcare care professional (HCP). For example, the colorectal department 40078 may include a set of surgical hubs (e.g., surgical hub 20006 as described in FIG. 1A). The surgical hubs may be designated for a respective HCP, such as HCP A, 40082 and HCP B, 40080. In an example, the colorectal department may include a group of surgical hubs that may be located in respective ORs, such as OR 1, 40074 and OR 2, 40076. The medical facility or the hospital may also include a billing department subsystem 40068. The billing department subsystem 40068 may store and/or manage billing data associated with a respective department, such as the ER department 40070, colorectal department 40078, bariatric department 40072, and/or thoracic department 40066.

An edge tier system 40054 may be associated with a medical facility or a hospital and may include one or more edge computing systems 40064, for example. An edge computing system 40064 may include a storage sub-system and a server sub-system. In an example, the edge computing system comprising an edge server and/or a storage unit may provide additional processing and/or storage services to a surgical hub that is part of one of the departmental ORs (e.g., OR1 and OR2 of the colorectal department).

The surgical specific sub-network tier system 40052 and the edge tier system 40054 may be located within a Health Insurance Portability and Accountability Act (HIPAA) boundary 40062. The surgical specific sub-network system 40052 and the edge tier system 40054 may be connected to the same local data network. The local data network may be a local data network of a medical facility or a hospital. The local data network may be within the HIPAA boundary. Because the surgical specific sub-network tier system 40052 and the edge tier system 40054 are located within the HIPAA boundary 40062, patient data between an edge computing system 40064 and a device located within one of the entities of the surgical specific sub-network tier system 40052 may flow without redaction and/or encryption. For example, patient data between an edge computing system 40064 and a surgical hub located in OR1 40074 of the colorectal department 40078 may flow without redaction and/or encryption.

The cloud tier system 40056 may include an enterprise cloud system 40060 and a public cloud system 40058. For example, the enterprise cloud system 40060 may be a cloud computing system 20008 that includes a remote cloud server sub-system and/or a remote cloud storage subsystem, as described in FIG. 1A. The enterprise cloud system 40060 may be managed by an organization, such as a private company. The enterprise cloud system 40060 may be in communication with one or more entities (e.g., edge computing systems 40064, surgical hubs located in ORs (e.g., OR1 40074) of the various departments (e.g., colorectal department 40078)) that are located within the HIPAA boundary 40062.

The public cloud system 40058 may be operated by a cloud computing service provider. For example, the cloud computing service provider may provide storage services and/or computing services to a plurality of enterprise cloud systems (e.g., enterprise cloud system 40060).

Figure 1C:
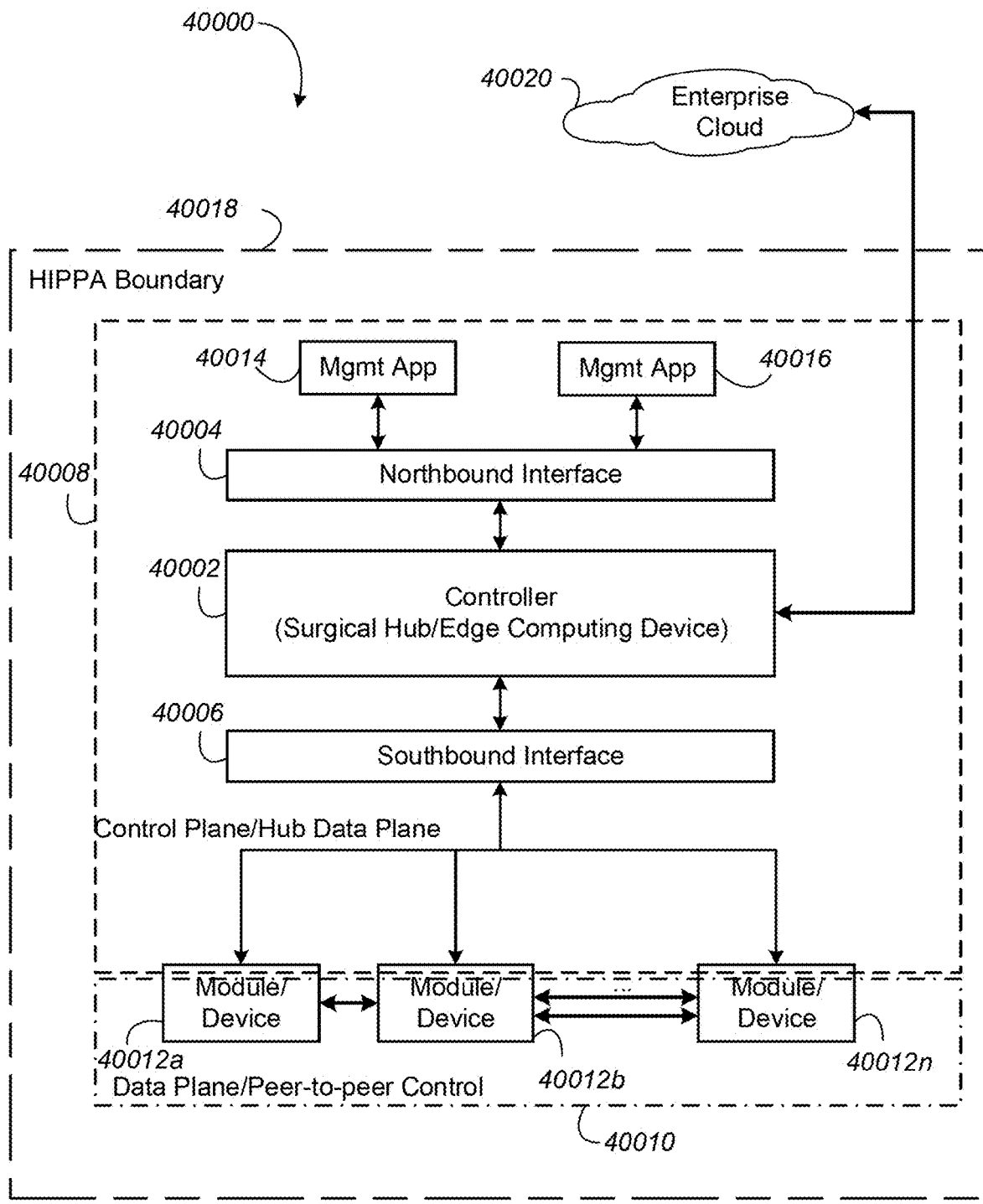
FIG. 1C is a logical diagram illustrating control plane and data plane of a surgical system.

FIG. 1C is a logical block diagram 40000 illustrating various communication planes in a surgical system. As illustrated in FIG. 1C, the communication planes between a controller 40002 and management applications 40014 and 40016 on one side and, the system modules and/or modular devices 40012a through 40012n on the other side, may use control plane 40008 and data plane 40010. In an example, in addition to the control plane 40008, a data plane may also exist between the system modules and/or modular devices 40012a through 40012n and the surgical hub. The data plane 40010 may provide data plane paths (e.g., redundant data plane paths) between the system modules and/or the modular devices 40012a through 40012n that are associated with one or more surgical hubs. A surgical hub or one of the surgical hubs (e.g., in case of a plurality of surgical hubs present in an operating room) may act as a controller 40002. In an example, the controller 40002 may be an edge computing system that may reside within a Health Insurance Portability and Accountability Act (HIPAA) boundary where the surgical system is located, for example, as illustrated in FIG. 1B. The controller 40002 may be in communication with an enterprise cloud system 40020. As illustrated in FIG. 1C, the enterprise cloud system 40020 may be located outside the HIPAA boundary 40018. Accordingly, the patient data flowing to and/or from the enterprise cloud system 40020 may be redacted and/or encrypted.

The controller 40002 may be configured to provide a northbound interface 40004 and a southbound interface 40006. The northbound interface 40004 may be used for providing a control plane 40008. The control plane 40008 may include one or more management applications 40014 and 40016 that may enable a user to configure and/or manage system modules and/or modular devices modular devices 40012a through 40012n associated with a surgical system. The management applications 40014 and 40016 may be used to obtain status of various system modules and/or the modular devices 40012a through 40012n.

The management applications 40014 and 40016 using the control plane may interact with the controller 40002, for example, using a set of application programming interface (API) calls. The management applications 40014 and 40016 may interact with the controller 40002 via a management protocol or an application layer protocol to configure and/or monitor the status of a system module and/or a modular device. The management protocols or the application layer protocols used to monitor the status and/or configure a system module or a modular device associated with a surgical system may include the simple network management protocol (SNMP), TELNET protocol, secure shell (SSH) protocol, network configuration protocol (NET-CONF), etc.

SNMP or a similar protocol may be used to collect status information and/or send configuration related data (e.g., configuration related control programs) associated with system modules and/or modular devices to the controller. SNMP or a similar protocol may collect information by selecting devices associated with a surgical system from a central network management console using messages (e.g., SNMP messages). The messages may be sent and/or received at fixed or random intervals. The messages may include Get messages and Set messages. The Get messages or messages similar to the Get messages may be used for obtaining information from a system module or a modular device associated with a surgical system. The Set message or messages similar to the Set message may be used for changing a configuration associated with a system module or a modular device associated with a surgical system.

For example, the Get messages or similar messages may include the SNMP messages GetRequest, GetNextRequest, or GetBulkRequest. The Set messages may include SNMP SetRequest message. The GetRequest, GetNextRequest, GetBulkRequest messages or similar messages may be used by a configuration manager (e.g., an SNMP manager) running on the controller 40002. The configuration manager may be in communication with a communication agent (e.g., an SNMP agent) that may be a part of a system module and/or a modular device in a surgical system. The SNMP message SetRequest message or similar may be used by the communication manager on the controller 40002 to set the value of a parameter or an object instance in the communication agent on a system module and/or a modular device of a surgical system. In an example, SNMP modules, for example, may be used to establish communication path between system modules and/or modular devices associated with a surgical system.

Based on the query or configuration related messages received from a management application, such as management applications 40014 and 40016, the controller 40002 may generate configuration queries and/or configuration data for querying or configuring the system modules and/or the modular devices associated with the surgical hub or the surgical system. A surgical hub (e.g., the surgical hub 20006 shown in FIG. 1A) or an edge computing system (e.g., the edge computing system 40064 shown in FIG. 1B) may manage and/or control various system modules and/or modular devices 40012a through 40012n associated with a surgical system. For example, the northbound interface 40004 of the controller 40002 may be used for changing control interactions between one or more modules associated and/or devices associated with a surgical system. In an example, the controller 40002 may be used for establishing one or more communication data paths between a plurality of modules and/or devices associated with a surgical system. The controller 40002 may use its southbound interface 40006 to send the control programs comprising queries and/or configuration changes to the system modules and/or the modular devices of the surgical system.

The system modules and/or the modular devices 40012a through 40012n of a surgical system, or the communication agents that may be a part of the system modules and/or the modular devices, may send notification messages or traps to the controller 40002. The controller may forward the notification messages or traps via its northbound interface 40004 to the management application 40014 and 40016 for displaying on a display. In an example, the controller 40002 may send the notification to other system modules and/or modular devices 40012a through 40012n that are part of the surgical system.

The system modules and/or the modular devices 40012a through 40012n of a surgical system or the communication agents that are part of the system modules and/or the modular devices may send responses to the queries received from the controller 40002. For example, a communication agent that may be part of a system module or a modular device may send a response message in response to a Get or a Set message or messages similar to the Get or the Set messages received from the controller 40002. In an example, in response to a Get message or a similar message received from the controller 40002, the response message from the system module or the modular device 40012*a* through 40012*n* may include the data requested. In an example, in response to a Set message or a similar message received from a system module or a modular device 40012*a* through 40012*n*, the response message from the controller 40002 may include the newly set value as confirmation that the value has been set.

A trap or a notification message or a message similar to the trap or the notification message may be used by a system module or a modular device 40012*a* through 40012*n* to provide information about events associated with the system modules or the modular devices. For example, a trap or a notification message may be sent from a system module or a modular device 40012*a* through 40012*n* to the controller 40002 indicating a status of a communication interface (e.g., whether it available or unavailable for communication). The controller 40002 may send a receipt of the trap message back to the system module or the modular device 40012*a* through 40012*n* (e.g., to the agent on the system module or a modular device).

In an example, TELNET protocol may be used to provide a bidirectional interactive text-oriented communication facility between system modules and/or modular devices 40012*a* through 40012*n* and the controller 40002. TELNET protocol may be used to collect status information and/or send configuration data (e.g., control programs) from/to the controller 40002. TELNET may be used by one of the management applications 40014 or 40016 to establish a connection with the controller 40002 using the transmission control protocol port number 23.

In an example, SSH, a cryptographic encrypted protocol, may be used to allow remote login and to collect status information and/or send configuration data about system modules and/or modular devices 40012*a* through 40012*n* from/to the controller 40002. SSH may be used by one of the management applications 40014 or 40016 to establish an encrypted connection with the controller 40002 using the transmission control protocol port number 22.

In an example, NETCONF may be used to perform management functions by invoking remote procedure calls using, for example, <rpc>, <rpc-reply>, or <edit-config> operations. The <rpc> and <rpc-reply> procedure calls or similar procedure calls may be used for exchanging information from a system module and/or a modular device associated with a surgical system. The NETCONF <edit-config> operation or a similar operation may be used for configuring the system modules and/or the modular devices associated with the surgical system.

The controller 40002 may configure the system modules and/or modular device 40012*a* through 40012*n* to establish a data plane 40010. The data plane 40010 (e.g., also referred to as a user plane or a forwarding plane) may enable a communication data path between a plurality of system modules and/or modular device 40012*a* through 40012*n*. The data plane 40010 may be utilized by the system modules and/or the modular device 40012*a* through 40012*n* for communicating data flows of data between the system modules and/or modular devices associated with a surgical system. The data flows may be established using one or more dedicated communication interfaces between the system modules and/or the modular devices associated with one or more surgical hubs of a surgical system. In an example, the data flows may be established over one or more local area networks (LANs) and one or more wide area networks (WANs), such as the Internet.

In an example, the data plane 40010 may provide support for establishing a first and a second independent, disjointed, concurrent, and redundant communication path for data flow between the system modules and/or modular devices 40012*b* and 40012*n*. As illustrated in FIG. 1C. redundant communication paths may be established between system modules/modular devices 40012*b* and 40012*n*. The redundant communication paths may carry same/redundant data flows between the system modules and/or modular devices. In an example, when or if some of the data packets are dropped on one of the redundant communication paths due to problems with one of the communication interfaces on the system modules/modular devices 40012*b* and 40012*n*, the system modules and/or the modular devices may continue to send/receive at least one copy of the dropped data packets over the second communication path.

Figure 2:
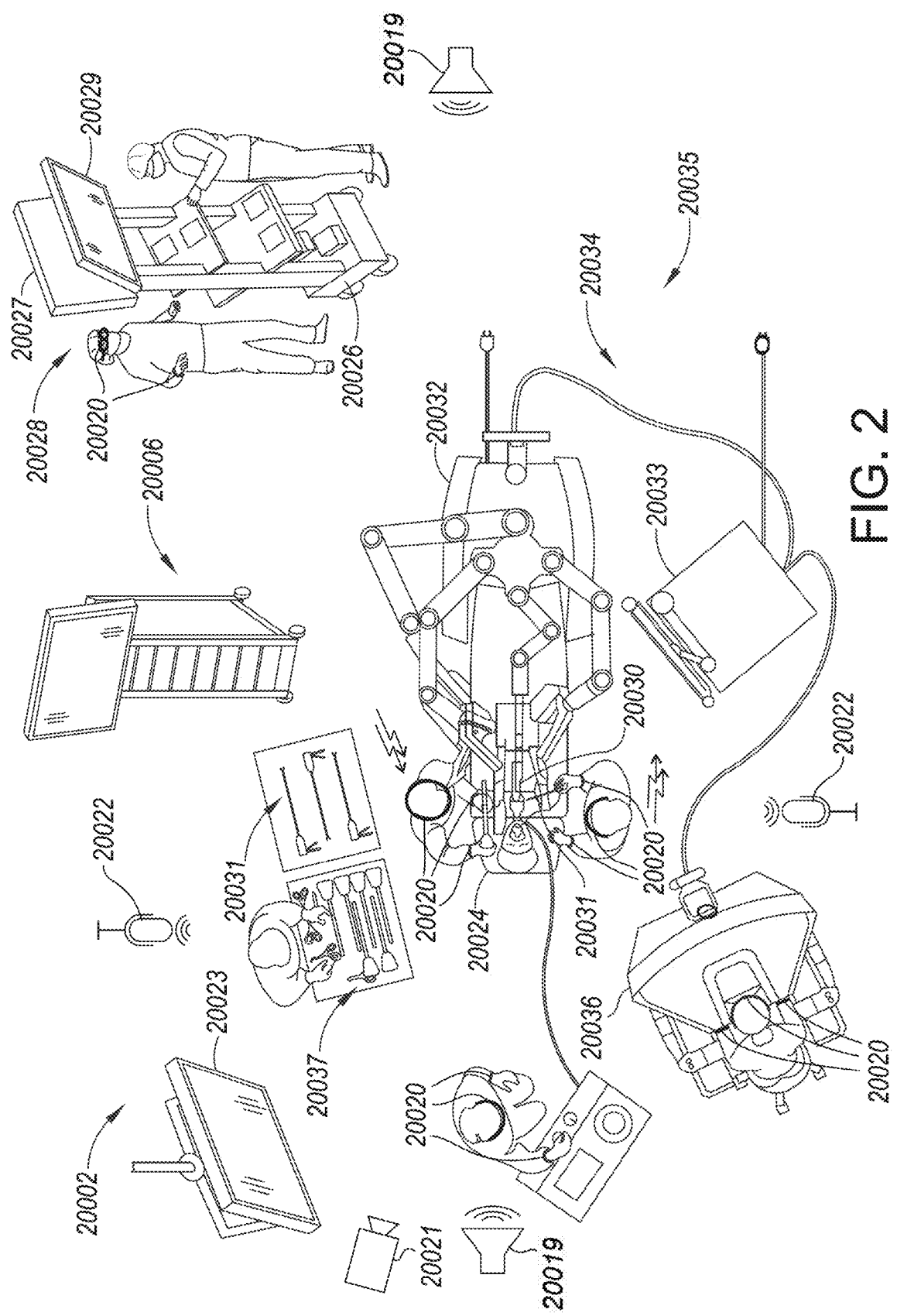
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1A. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1A may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
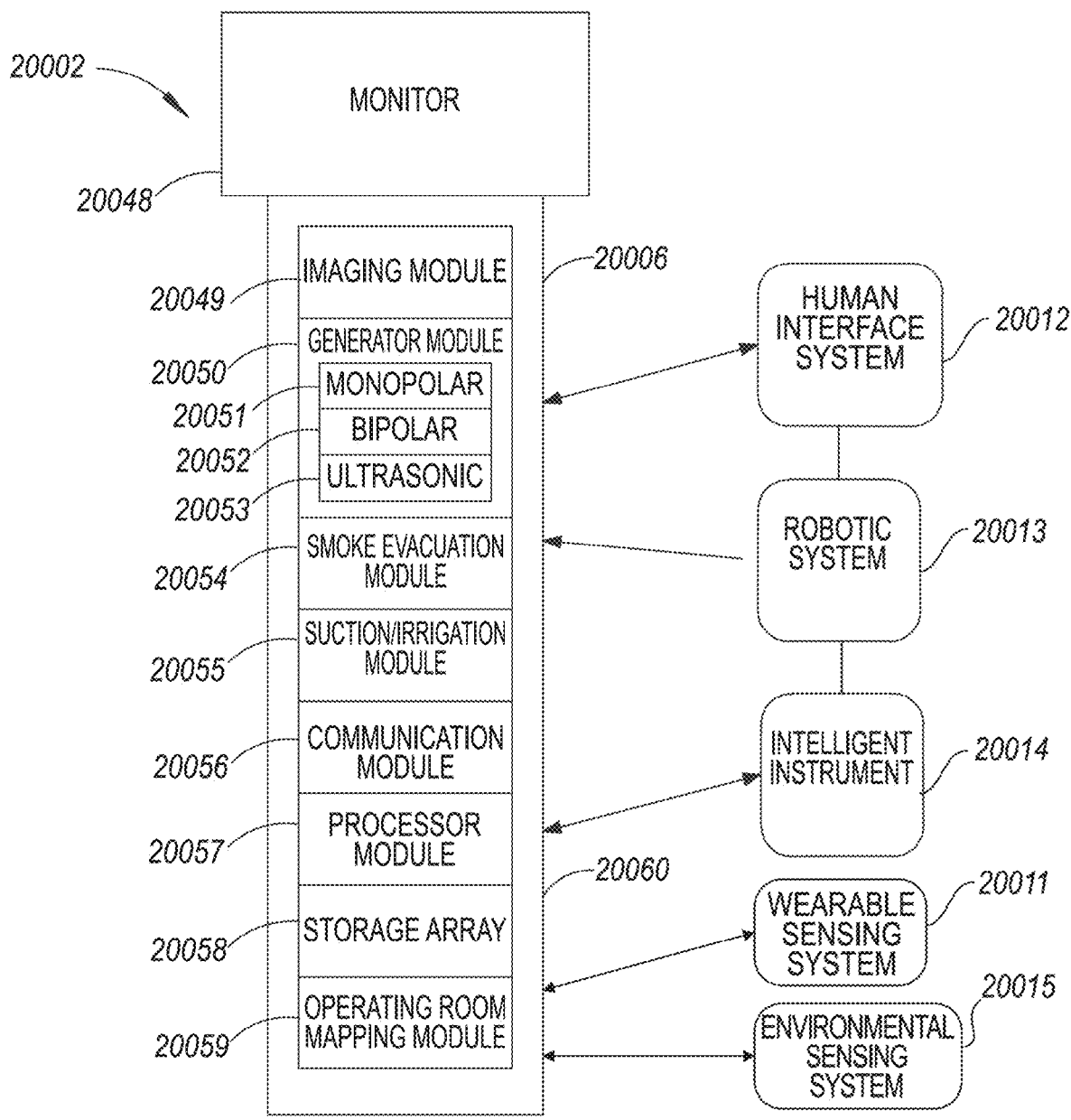
FIG. 3 illustrates an example surgical hub paired with various systems.

FIG. 3 shows an example surgical system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
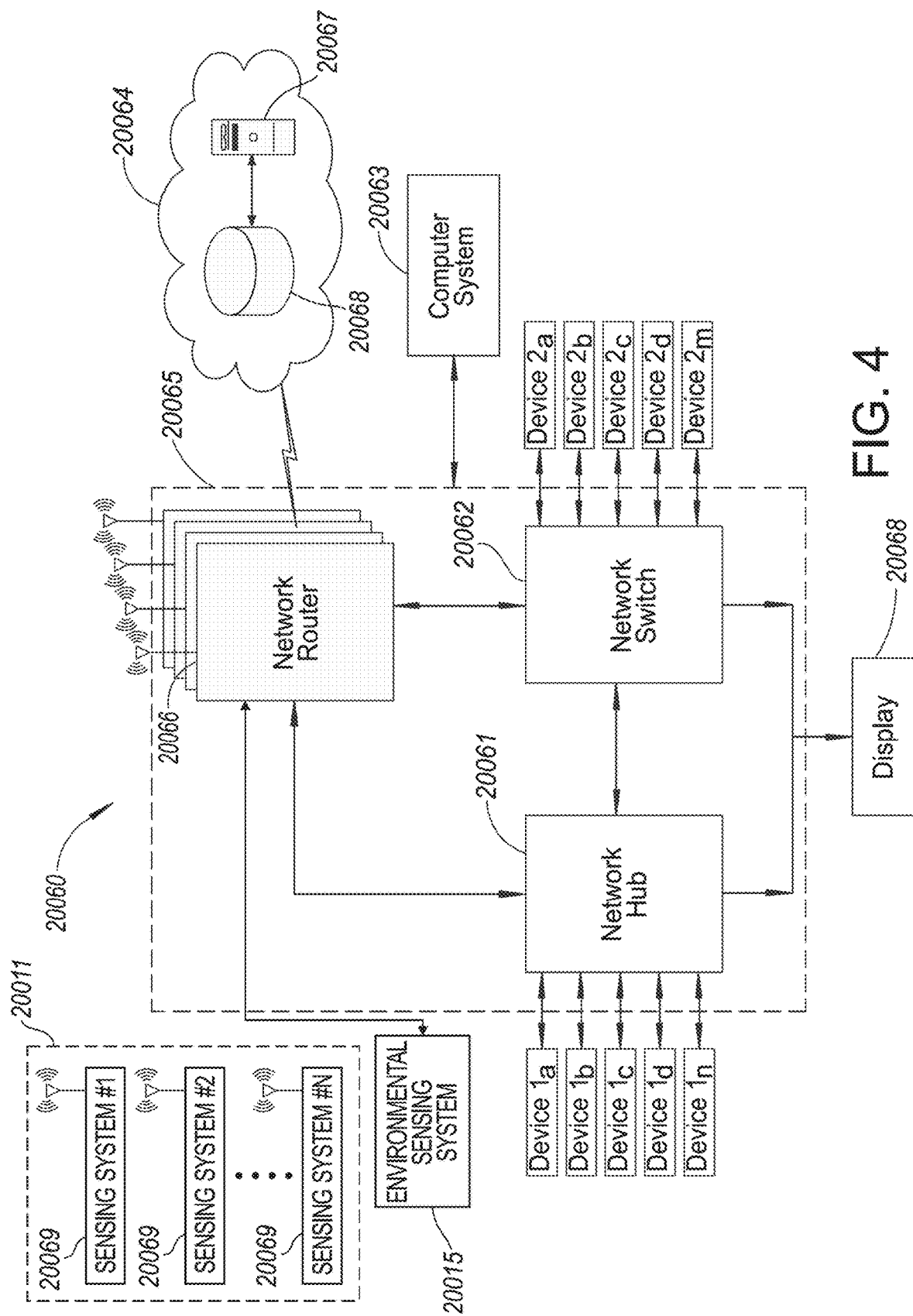
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereof, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services-such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1*a*-1*n*/2*a*-2*m*, the surgical data network can provide improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud-based computing to examine data including images of samples of body tissue for diagnostic purposes. This may include localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1*a*-1*n* may be connected to the modular communication hub 20065 over a wired channel or a wireless channel depending on the configuration of the devices 1*a*-1*n* to a network hub 20061. The network hub 20061 may be implemented, in one aspect, as a local network broadcast device that works on the physical layer of the Open System Interconnection (OSI) model. The network hub may provide connectivity to the devices 1*a*-1*n* located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1*a*-1*n* can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2*a*-2*m* may be connected to a network switch 20062 over a wired channel or a wireless channel. The network switch 20062 works in the data link layer of the OSI model. The network switch 20062 may be a multicast device for connecting the devices 2*a*-2*m* located in the same operating theater to the network. The network switch 20062 may send data in the form of frames to the network router 20066 and may work in full duplex mode. Multiple devices 2*a*-2*m* can send data at the same time through the network switch 20062. The network switch 20062 stores and uses MAC addresses of the devices 2*a*-2*m* to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1*a*-1*n*/2*a*-2*m* and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
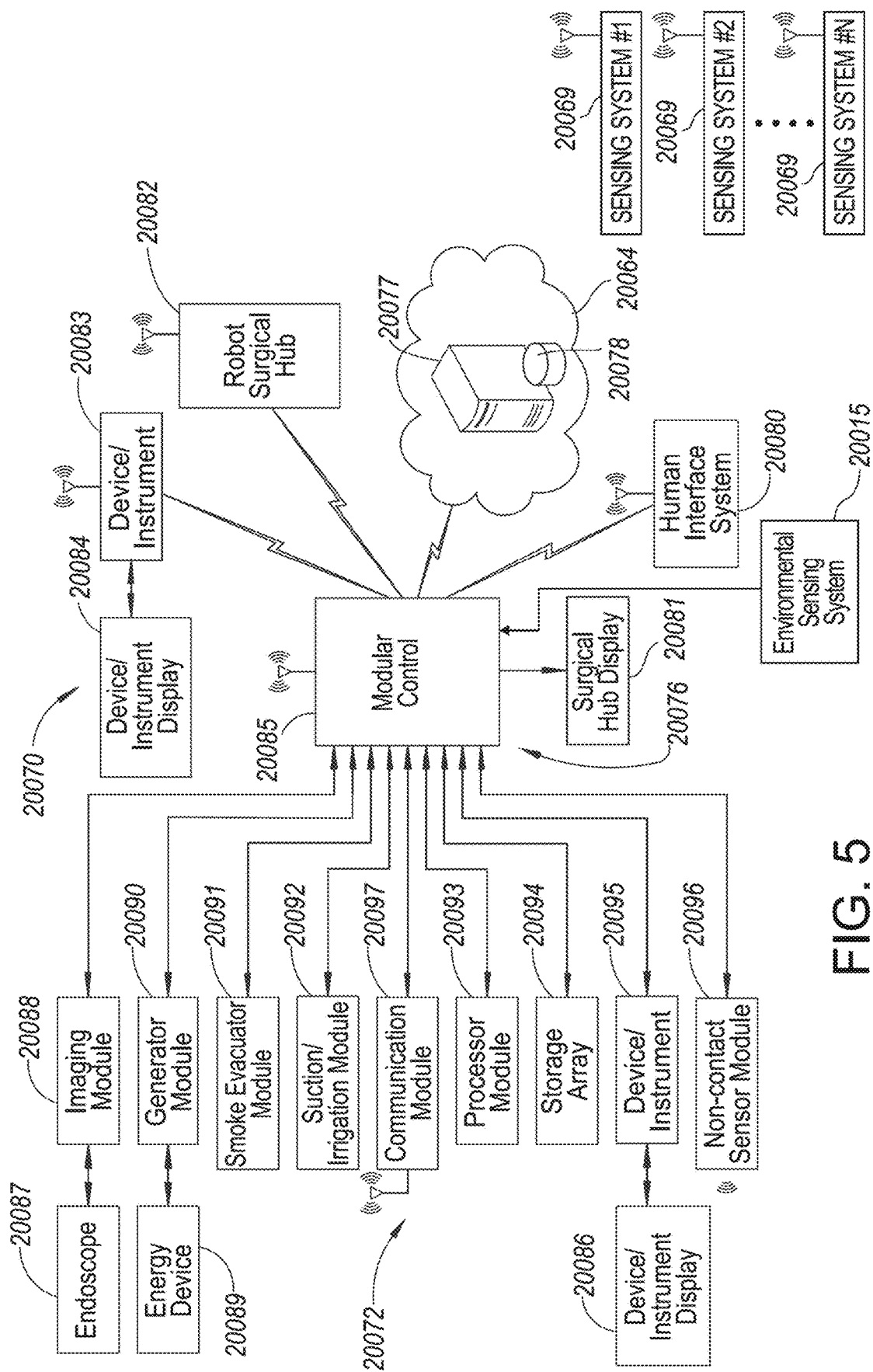
FIG. 5 illustrates an example computer-implemented interactive surgical system that may be part of a surgical system.

FIG. 5 illustrates a computer-implemented interactive surgical system 20070 that may be a part of the Surgical system 20002. The computer-implemented interactive surgical system 20070 is similar in many respects to the HCP sensing system 20002. For example, the computer-implemented interactive surgical system 20070 may include one or more surgical sub-systems 20072, which are similar in many respects to the Surgical systems 20002. Each sub-surgical system 20072 may include at least one surgical hub 20076 in communication with a cloud computing system 20064 that may include a remote server 20077 and a remote storage 20078. In one aspect, the computer-implemented interactive surgical system 20070 may include a modular control 20085 connected to multiple operating theater devices such as sensing systems 20001, intelligent surgical instruments, robots, and other computerized devices located in the operating theater.

As illustrated in the example of FIG. 5, the modular control 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The non-contact sensor module 20096 may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The modular control 20085 may also be in communication with one or more sensing systems 20069 and an environmental sensing system 20015. The sensing systems 20069 may be connected to the modular control 20085 either directly via a router or via the communication module 20097. The operating theater devices may be coupled to cloud computing resources and data storage via the modular control 20085. A robot surgical hub 20082 also may be connected to the modular control 20085 and to the cloud computing resources. The devices/instruments 20095 or 20084, human interface system 20080, among others, may be coupled to the modular control 20085 via wired or wireless communication standards or protocols, as described herein. The human interface system 20080 may include a display sub-system and a notification sub-system. The modular control 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control 20085 in conjunction with images and overlaid images.

Figure 6:
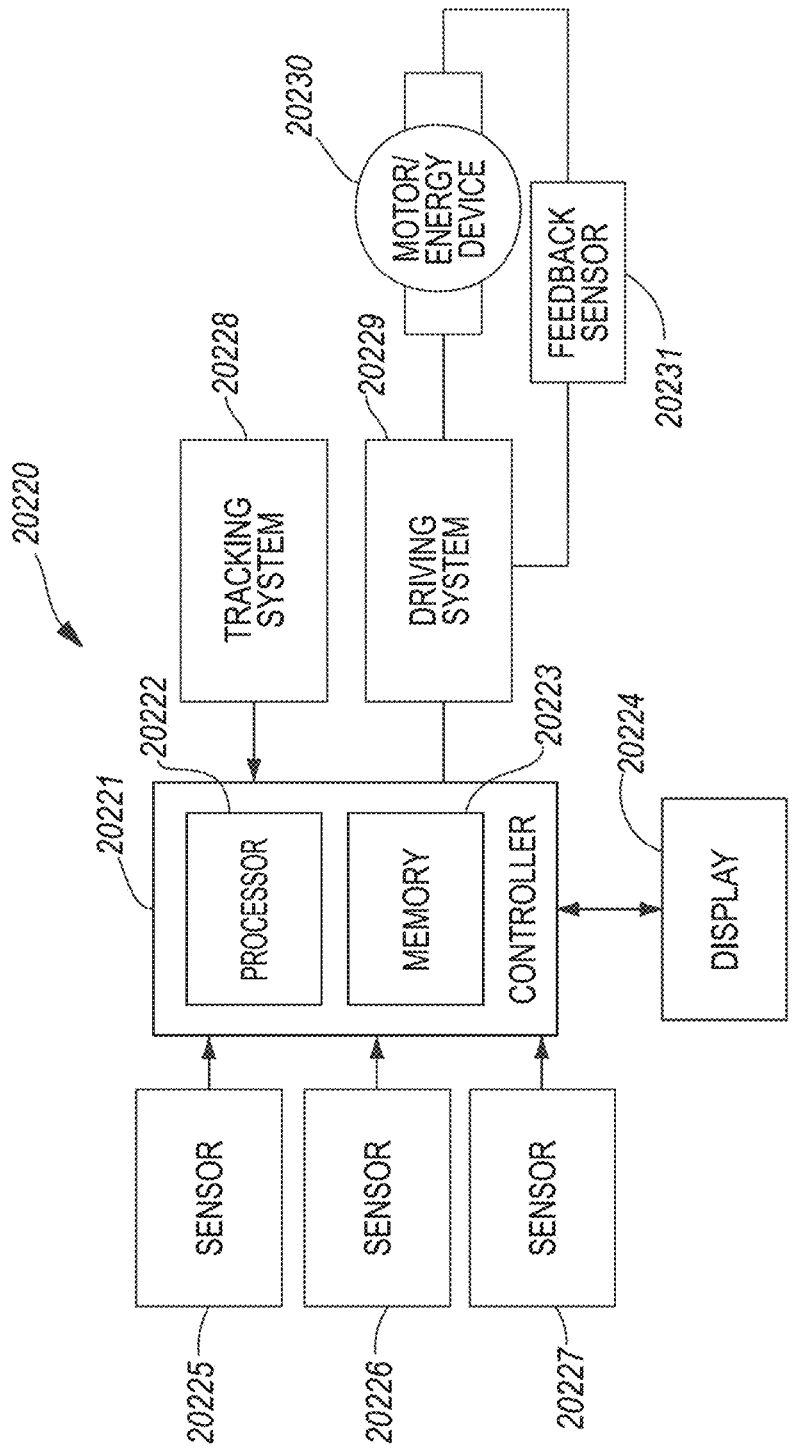
FIG. 6 illustrates a logic diagram of a control system of a surgical instrument.

FIG. 6 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like.

The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+ d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5.

Figure 7:
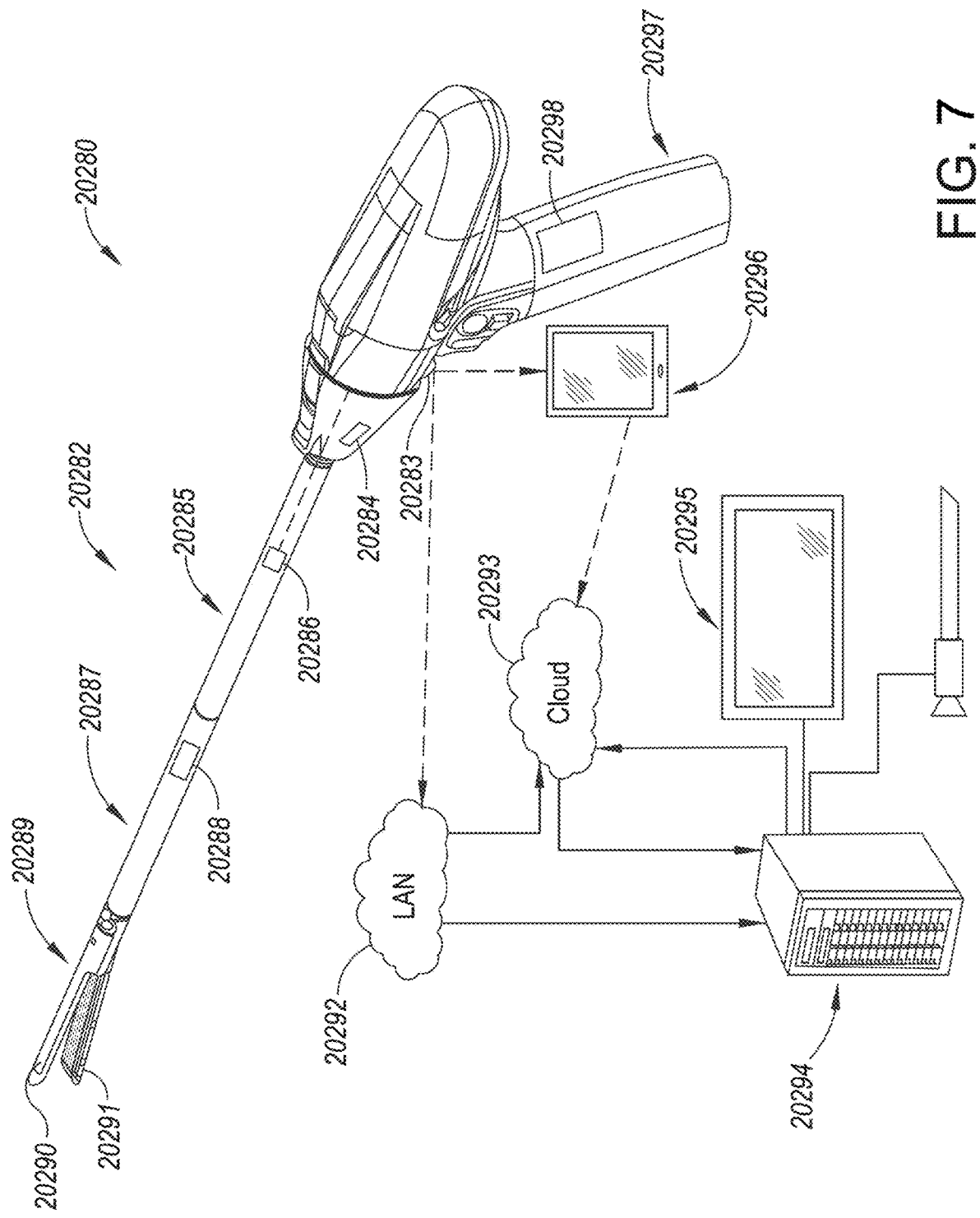
FIG. 7 shows an example surgical system that includes a handle having a controller and a motor, an adapter releasably coupled to the handle, and a loading unit releasably coupled to the adapter.

FIG. 7 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 8:
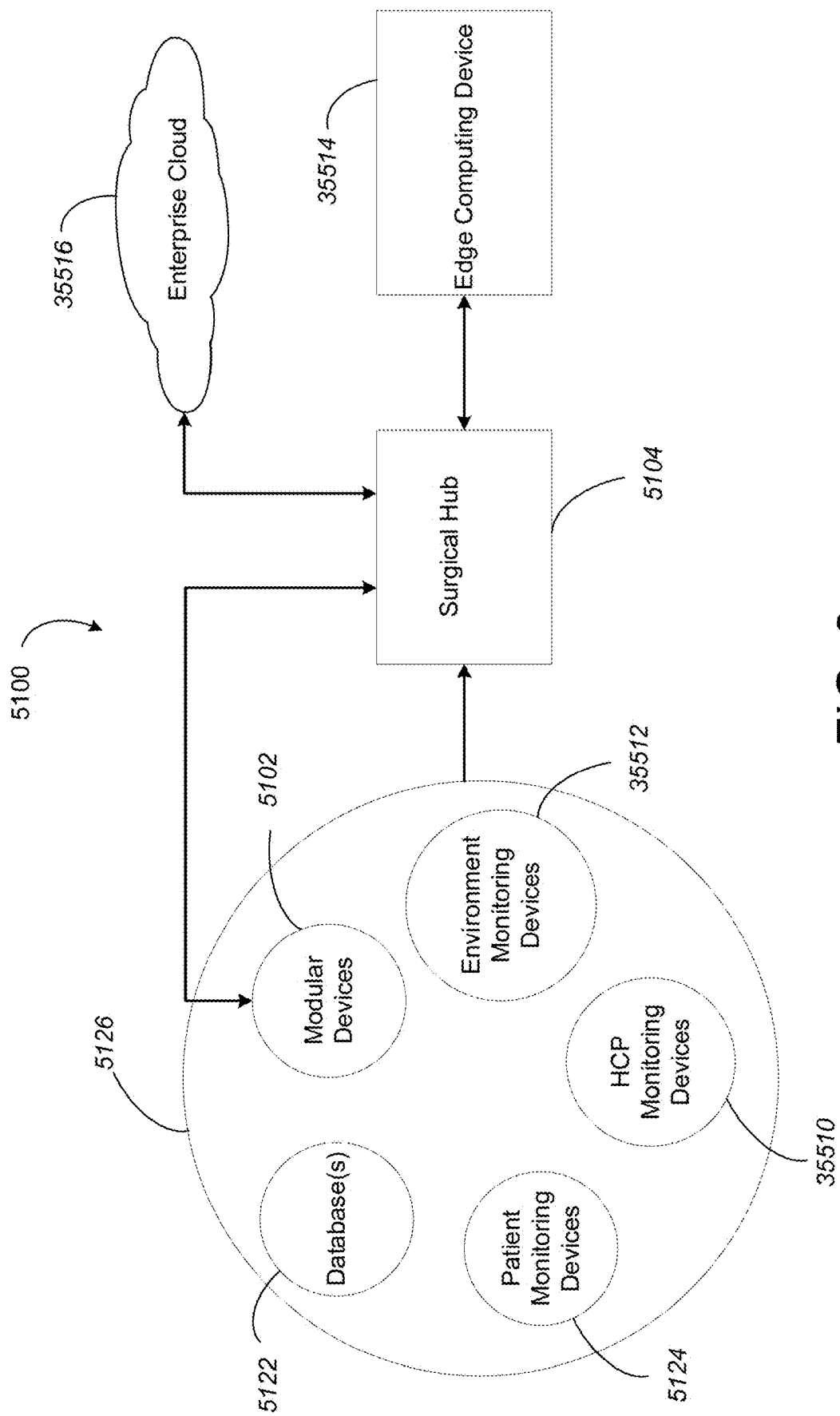
FIG. 8 shows an example situationally aware surgical system.

FIG. 8 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

A computing system may use redundant communication pathways for communicating surgical imaging feed(s). For example, surgical video feed may be sent via multiple video stream pathways to improve resilience of the feed.

Examples described herein monitor power utilization, needs, and inlet capacities to balance the distribution of power to coupled modules. A surgical power device may monitor the inlet power capacity from one or more sources. The surgical power device may balance power expectations of surgical modules with the available amount of operating room power to determine the amount of power that is distributed to each of the modules. The power expectations of the surgical modules may be based on provided forecasts of power needs, historic uses of specific surgical procedures, or prioritization of the surgical system needs. The power expectations of each of the surgical modules may cause the surgical power device to throttle the needs of each of the surgical modules. In examples, the surgical power device may restrict an amount of power to a surgical module if allowing that amount of power would be above the available amount of operating room power (e.g., the threshold operating room power). The available amount of operating room power may be a combination of inlet power as well as stored power within the operating room available to the surgical power device.

Figure 9A:
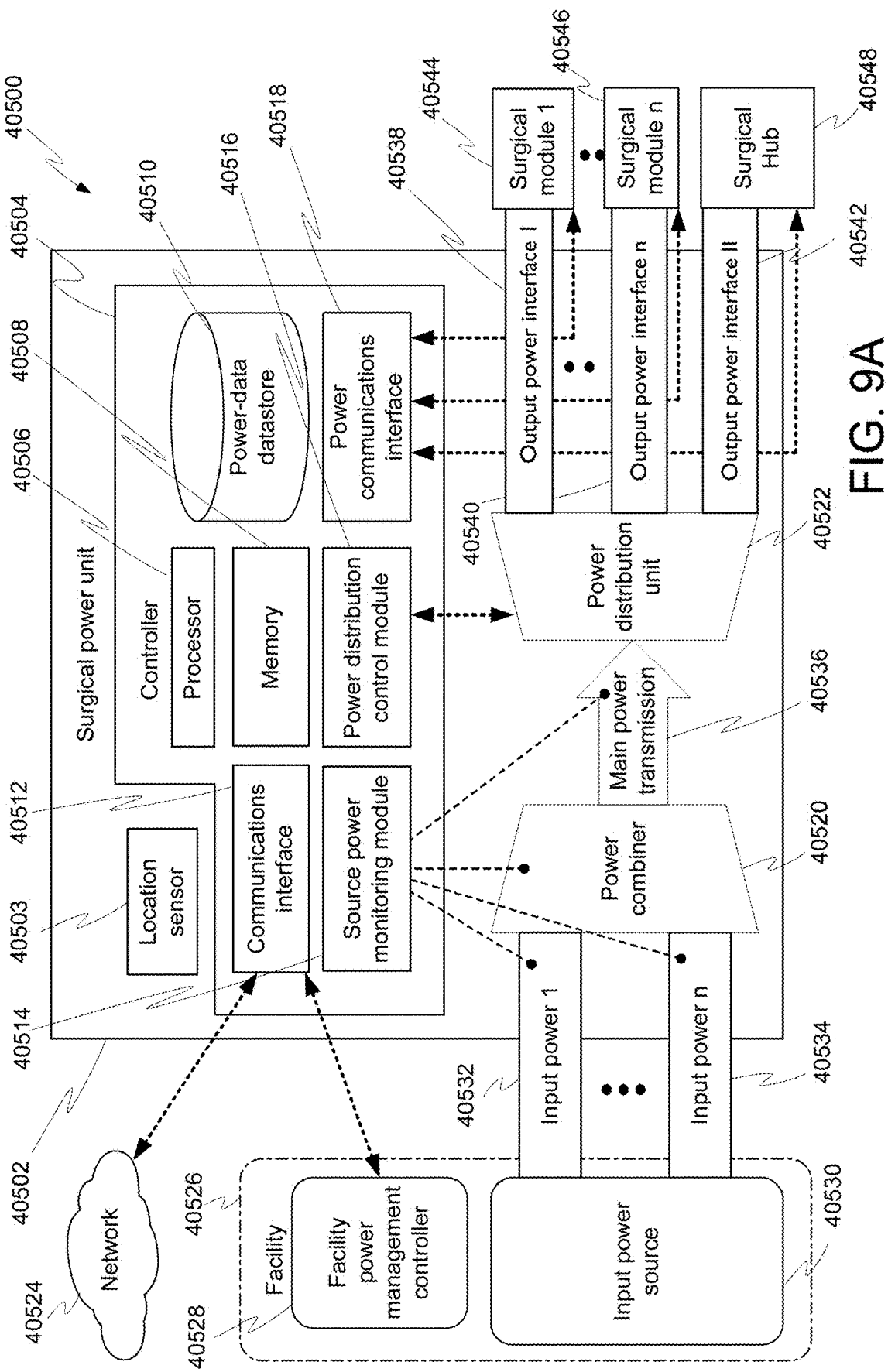
FIG. 9A shows an example of a surgical system that distributes and balances power.

FIG. 9A shows an example of a surgical system 40500 that distributes and balances power. The surgical system 40500 may include a surgical power unit 40502. The surgical power unit 40502 may include a location sensor 40503 and a controller 40504. The controller 40504 may include a processor 40506, a memory 40508, a power-data datastore 40510, a communications interface 40512, a source power monitoring module 40514, a power distribution control module 40516, and a power communications interface 40518. The surgical power unit 40502 may (e.g., may also) include a power combiner 40520 and a power distribution unit 40522.

The communications interface 40512 may communicate with a surgical network 40524 and a power facility 40526. The power facility 40526 may include a facility power management controller 40528 and an input power source 40530. The input power source 40530 may provide input power 40532, 40534 to the power combiner 40520. The power combiner 40520 may combine the input power 40532, 40534 to provide a main power transmission 40536 to the power distribution unit 40522. The source power monitoring module 40514 may monitor the input power 40352, 40534, the power combiner 40520, and the main power transmission 40536.

The power distribution unit 40522 may include output power interfaces 40538, 40540, and 40542. Output power interfaces 40538, 40540 may interface with and provide output power to surgical modules 40544, 40546 and the output power interface 40542 may interface with and provide output power surgical hub 40548. The power distribution control module 40518 may communicate with the power distribution unit 40522. The power communications interface 40518 may communicate with the surgical modules 40544, 40546 and surgical hub 40548. The surgical modules 40544, 40546 may include any number of surgical modules, although two are shown in FIG. 9, with 40546 labeled "surgical module n" to indicate there may be any number of surgical modules in the surgical system 40500. Each of the surgical modules 40544, 40546 may have power expectations. In examples, the power distribution unit 40522 may be configured to receive the input power 40532, 40534 (e.g., the operating room power). The power distribution unit 40522 may provide portions of the operating room power to each of the output power interfaces 40538, 40540.

Figure 9B:
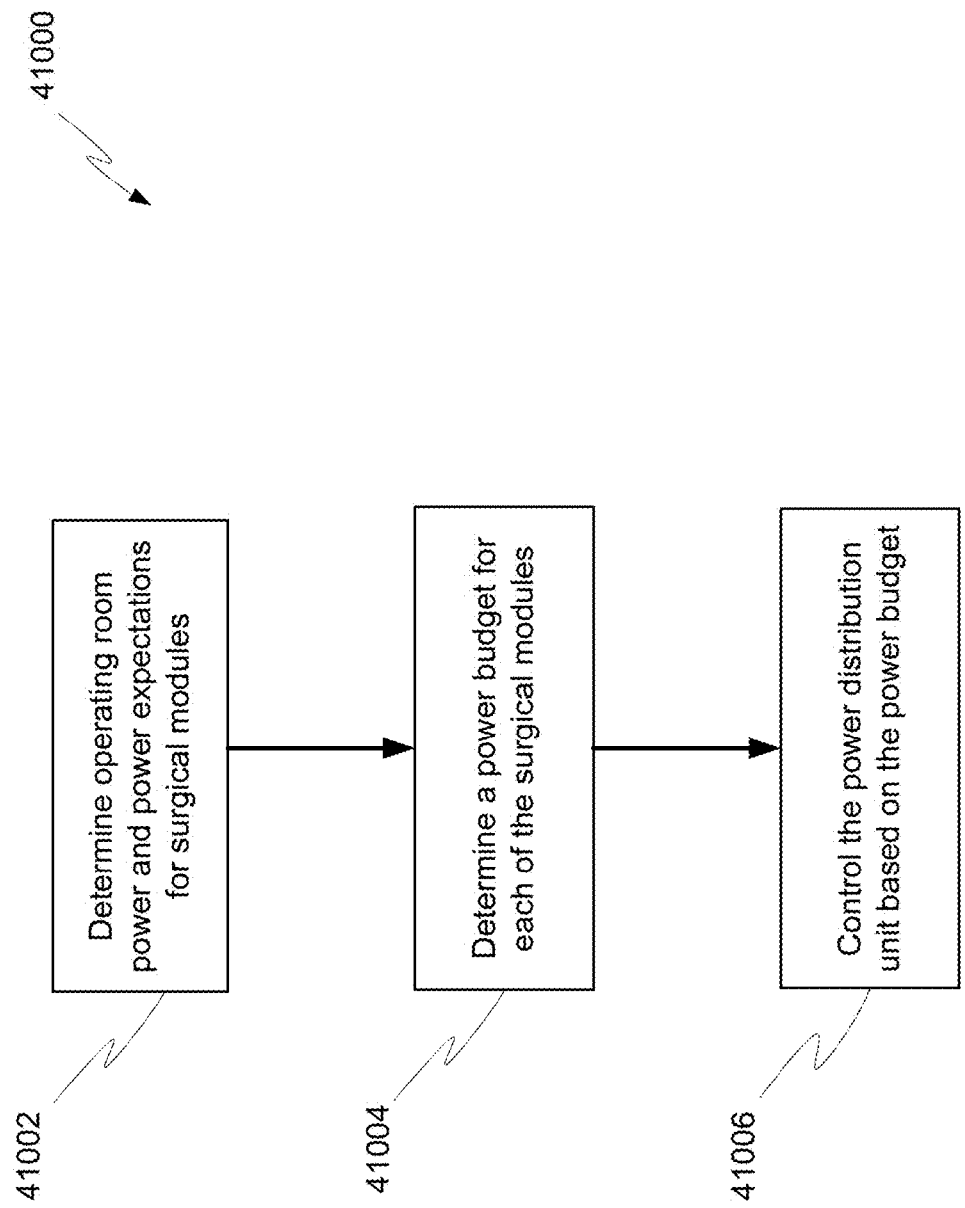
FIG. 9B shows an example flow chart for distributing and balancing power.

FIG. 9B shows an example flow chart 41000 for distributing and balancing power. At 41002, the power distribution control module 40518 of the controller 40504 may determine the amount of operating room power and each of the power expectations of each of the surgical modules 40544, 40546. At 41004, the power distribution control module 40518 of the controller 40504 may determine a power budget for each of the surgical modules 40544, 40546 based on the available amount of operating room power and each of the power expectations of each of the surgical modules 40544, 40546 determined at 41002. At 41006, the power distribution control module 40518 of the controller 40504 may control the power distribution unit 40522, based on the power budget determined at 41002, to set each of the portions of the operating room power to each of the output power interfaces 40538, 40540.

In examples, the power distribution control module 40518 of the controller 40504 may learn each of the surgical module types of each of the surgical modules 40544, 40546. The surgical module types may be a smoke evacuator, a visualization system, a generator, a header, a monitoring or imaging system, or an insufflation system. The power distribution control 40518 of the controller 40504 may set aprioritization of each of the surgical modules 40544, 40546 based on the surgical module types. Based on the prioritization of each of the surgical modules 40544, 40546, the power distribution control module 40518 of the controller 40504 may be determined for each of the surgical modules 40544, 40546. In examples, the prioritization of the surgical modules 40544, 40546 may be received directly from the surgical modules 40544, 40546. In examples, the prioritization of the surgical modules 40544, 40546 may be received from the surgical hub 40548. Each of the output power interfaces 40538, 40540, 40542 may have their own power prioritizations (e.g., a first output power interface may have a first power prioritization, etc.).

Figure 10:
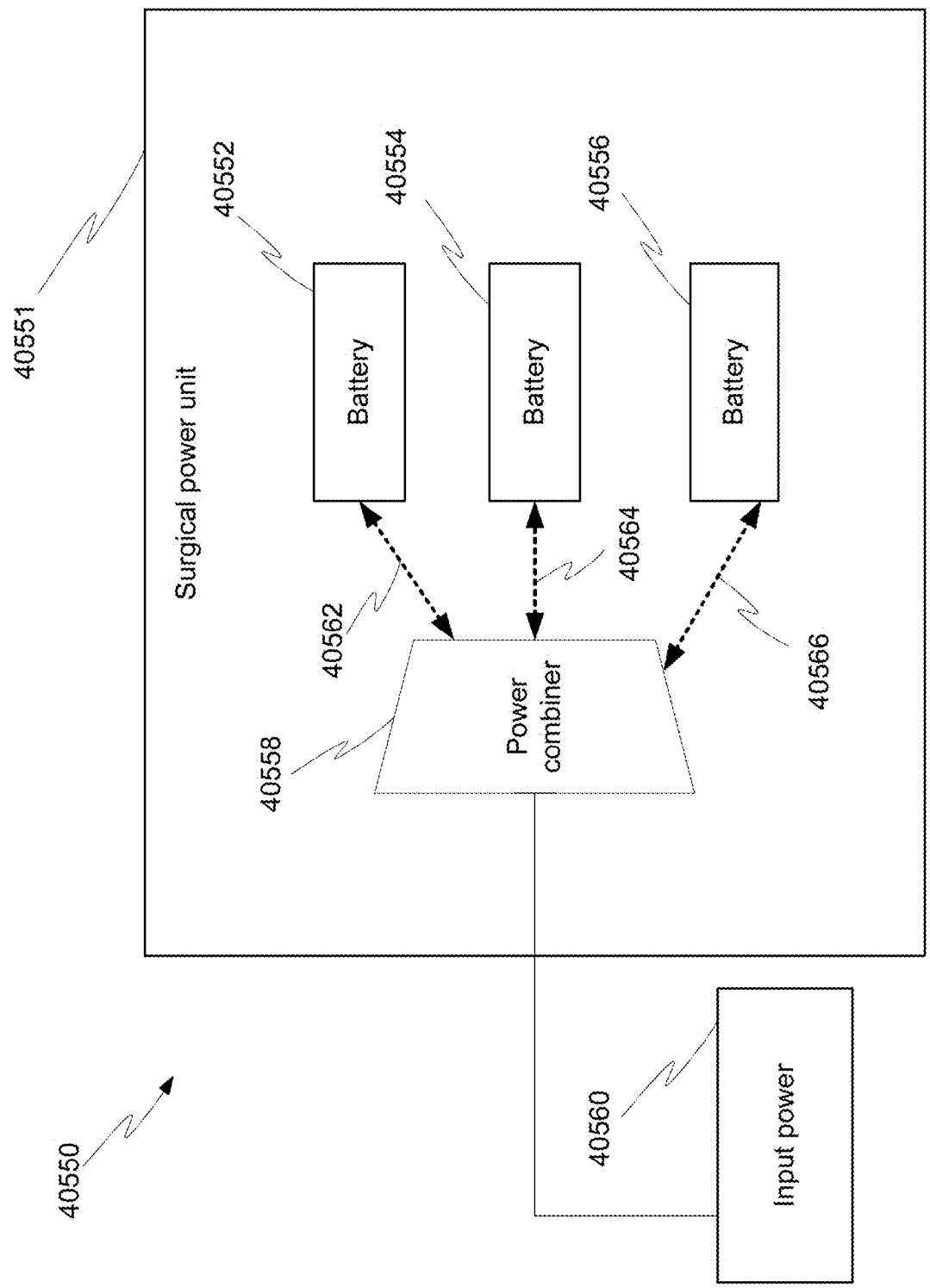
FIG. 10 shows an example of a surgical system that distributes and balances power with supplemental batteries.

FIG. 10 shows an example of a surgical system 40550 that distributes and balances power with supplemental batteries. The surgical system 40550 may include a surgical power unit 40551. The surgical power unit 40551 may include batteries 40552, 40554, 40556 that may act to balance the surgical modules 40544, 40546 (shown in FIG. 9) and surgical hub 40548 (shown in FIG. 9) power peak needs. The batteries 40552, 40554, 40556 may buffer the inlet power 40560 and may communicate with the power combiner 40558 via communication lines 40562, 40564, 40566 to increase overall power capacity and utilization. The inlet power 40560 may include alternating current (AC) power sources and/or direct current (DC) power sources. The batteries 40552, 40554, 40556 may include supplemental battery storage of energy to accommodate peak outputs. The batteries 40552, 40554, 40556 may enable the surgical system 40550 to accommodate short term peaks in the supplied power without overloading a continuous current maximum fuse or breaker. The batteries 40552, 40554, 40556 may power the surgical system 40558 for minutes or hours without direct power from the inlet power 40560. In examples, the batteries 40552, 40554, 40556 may be programmed to recharge themselves in a down procedure time or if they sense the operating room is in a dormant or low need condition.

Figure 11:
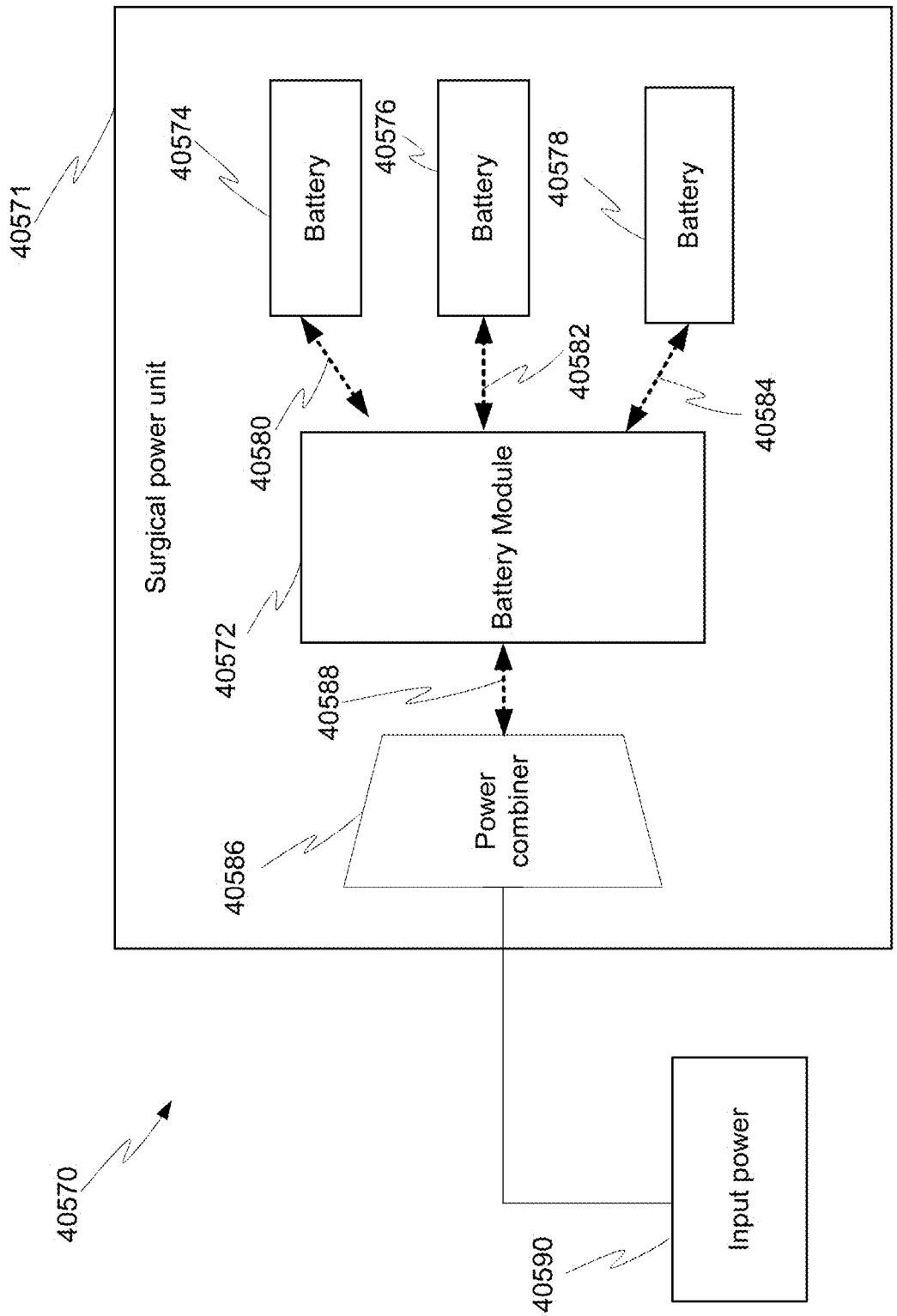
FIG. 11 shows an example of a surgical system that distributes and balances power with an integrated battery module.

FIG. 11 shows an example of a surgical system 40570 that distributes and balances power with an integrated battery module. The surgical system 40570 may include a surgical power unit 40571. The surgical power unit 40571 may include an integrated pass thru battery module 40572 that communicates with batteries 40574, 40576, 40578 via communication lines 40580, 40582, 40584 and the power combiner 40586 via communication line 40588. The integrated pass thru battery module 40572 may act as an uninterruptible power supply, a spike and through filter. The integrated pass thru battery module 40572 may accommodate power needs or peak output needs that may exceed the input power 40590 supplied to the power combiner within the operating room.

In examples, the surgical power unit 40502 (as shown in FIG. 9) may be capable of switching power coupling between the input power from the inlet power source 40530 to balance the load within power distribution unit 40522. The power distribution unit 40522 may include the output power interfaces 40538, 40540, 40542 which may be plugged to the surgical modules 40544, 40546 and the surgical hub 40548. The power distribution unit 40522 may be capable of switching and balancing the power between the surgical modules 40544, 40546 and the surgical hub 40548. The power distribution unit 40522 may use an anticipation algorithm that may estimate the needs of the surgical modules 40544, 40546 and the surgical hub 40548 for upcoming aspects of the procedures. The power distribution unit 40522 may pre-balance power to the surgical modules 40544, 40546 and the surgical hub 40548 in such a manner to anticipate peak output conditions.

The surgical power unit 40502 may provide smart metering of power into the surgical hub 40548 and may utilize the attached surgical modules 40544, 40546 to balance the needs of the surgical modules 40544, 40546. The surgical power unit 40502 may record the power usage throughout the procedures and from one procedure to the next to learn the power utilization. The surgical power unit 40502 may store the power usage information within the power data datastore 40510. The surgical power unit 40502 may attach metadata, such as metadata of procedure type, surgeon, complications, or instrument utilization to decide the power distribution profiles of the surgical module 40544, 40546 combinations during certain surgical procedures. The power distribution profiles may be sent to the power distribution unit 40522 from the power distribution control module 40516 within the surgical power unit 40502. The power distribution profiles may be reconfigured to minimize the maximum power usage in peak need situations or overall average power usage. The power distribution profiles may (e.g., may also) be used as a proxy for the heat generation of the surgical modules 40544, 40546 and may help prevent overheating. Accumulated data for power usage may be used to predict peak usages for different surgical procedures using a different combination of the surgical modules 40544, 40546. The accumulated data may be used to communicate the need to lower the power needs of the surgical modules 40544, 40546 in anticipation of an upcoming peak power usage of a different surgical module.

As the surgical system 40500 approaches the maximum current condition, the surgical power unit 40502 may utilize a prioritization matrix to inform some of the surgical modules 40544, 40546 to limit their power needs to accommodate other higher priority surgical modules 40544, 40546 or tasks. In examples, the surgical power unit 40502 may throttle the current to some of surgical modules 40544, 40546, thereby not supplying the restricted surgical modules 40544, 40546 with all the current they could use.

In examples, one of the surgical modules 40544, 40546 may be an advanced visualization system and one of the surgical modules 40544, 40546 may be a smoke evacuator. The advanced visualization system may increase resolution, processing, or multi-spectral sources above the normal envelope it uses. The surgical power unit 40502 may inform the surgical hub 40548 of its power needs and the surgical hub 40548 may require or throttle the power to the smoke evacuator compressor or blower motor to provide a buffer for the advanced visualization system, for example. The surgical hub 40502 may understand that the smoke evacuator could continue to operate with restricted power, but the advanced visualization system may not run at the needed resolution without the ability to exceed its normal power capacity.

In examples, other sensing systems within the operating room may ensure the throttled system does not prioritize its own system in relation to other critical systems. In examples, one of the surgical modules 40544, 40546 may be an insufflation system. The insufflation system may be one of the throttled systems to provide power to other critical systems. If in the throttled mode, the surgical hub 40548 monitors that the abdomen insufflation pressure drops below minimum acceptable conditions, the throttled system may be re-prioritized to eliminate the condition and then return to throttling or switch to throttling another system.

In examples, the surgical power unit 40502 may restrict power to some of the surgical modules 40544, 40546 to provide some of the other surgical modules 40544, 40546 more buffer, which may involve multiple modules and multiple restrictions or grants or differing magnitudes. In the event a power balance can not be reached, all of the surgical modules 40544, 40546 may be throttled to differing levels either automatically or by indicating to the user the issue and requesting guidance as to which systems require prioritization at which times during the procedure. The guidance may be used to make the same decisions in the future as automated reactions by learning the users needs and priorities for a given procedure.

In examples, some of the surgical modules 40544, 40546 may be supplied less power between uses, but may not be powered off, in order to minimize inrush current. Some of the surgical modules 40544, 40546 may be sequenced out of sync (e.g., slightly out of sync) of the power facility 40526. Some of the surgical modules 40544, 40546 may draw power beyond the operating room wiring capabilities. The input power 40532, 40534 may be throttled along with the current of certain modules (e.g., non-smart modules, such as the smoke evacuate module). The input power 40532, 40534 may be monitored for correlation to the output power from the output power interfaces 40538, 40540, and 40542 to adjust the thresholds of the initiation of force controls using the output power to linked systems. The inrush current and potential stepped draws may be detected. In examples, the idealization of the power utilization of equipment may be based on the startup power signature of the equipment. Startup voltage and current draw to identify a surgical system for interactive operating room usage may be utilized. Power management control may enable current draws and voltage needs beyond the standard inlet wiring capacity.

Examples described herein may relate to the intercommunication and cooperative operation between surgical modules. The intercommunication and cooperative operation may be based on the physical and communication connections between surgical modules.

Figure 12:
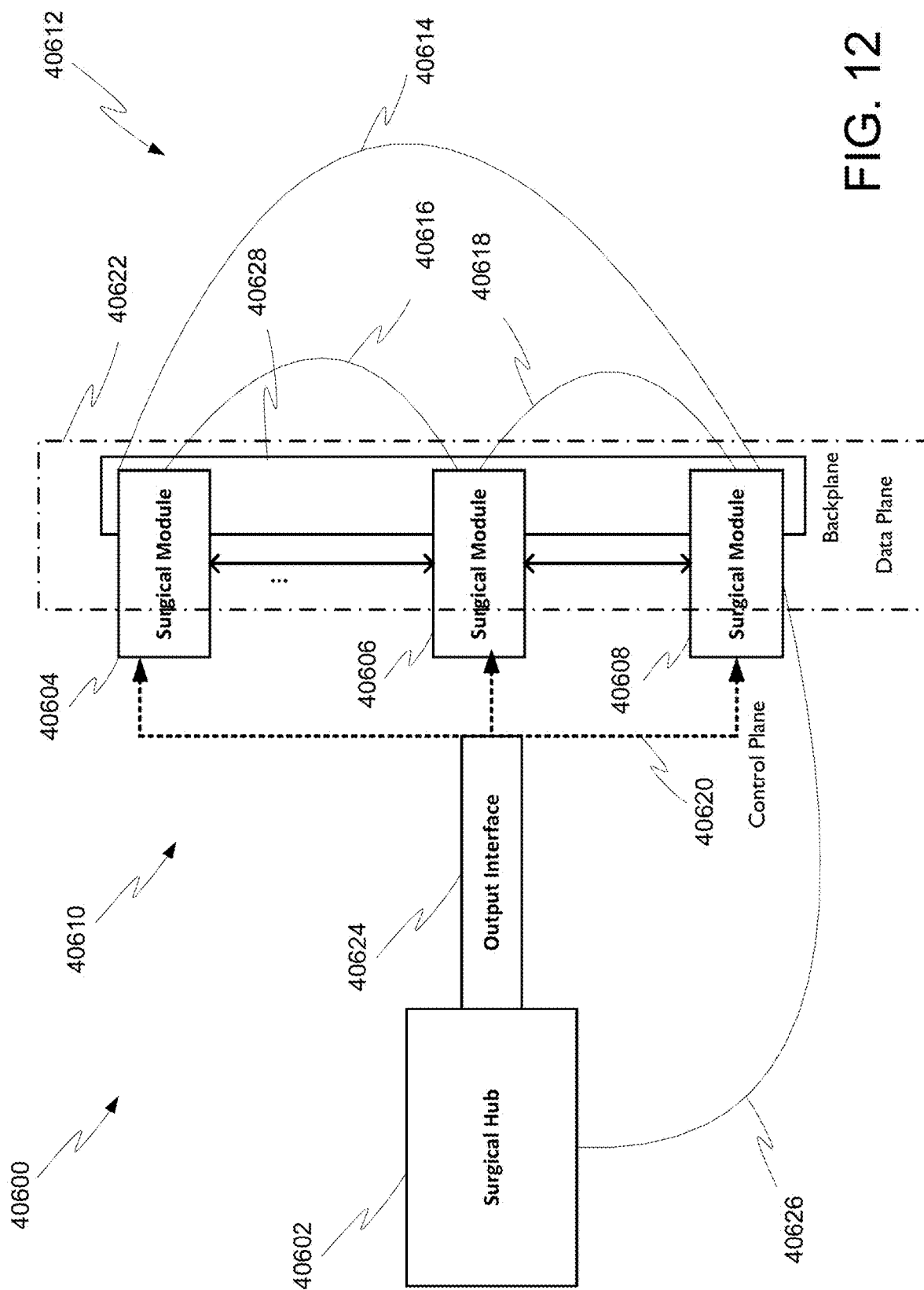
FIG. 12 shows an example of a surgical system with physical and communication connections between surgical modules and a surgical hub.

FIG. 12 shows an example of a surgical system 40600 with physical and communication connections between surgical modules and a surgical hub. The surgical system 40600 may include a surgical hub 40602 and surgical modules 40604, 40606, 40608. Although three surgical modules are shown in FIG. 12, the surgical system 40600 may include any number of surgical modules. Although one surgical hub 40602 is shown in FIG. 12, the surgical system 40600 may include multiple surgical hubs. The surgical hub 40602 may have the capacity for the surgical modules 40604, 40606, 40608 to be cumulatively coupled via a first port 40610 as well as directly coupled via a second port 40612 simultaneously. The interconnectivity of the surgical modules 40604, 40606, 40608 may enable some of the surgical modules 40604, 40606, 40608 to work cooperatively with the exclusion of some of the other surgical modules 40604, 40606, 40608 or receive data and control from multiple surgical modules 40604, 40606, 40608 simultaneously. The first port 40610 may include a control plane 40620, a data plane 40622, and a backplane 40628 that facilitate data communication between each of the surgical modules 40604, 40606, 40608 and the surgical hub 40602. The second port 40612 may be external wired connections 40614, 40616, 40618 connecting each of the surgical modules 40604, 40606, 40608 to each other separate from the first port 40610. The surgical hub 40602 may include an output interface 40624 that may interface with each of the surgical modules 40604, 40606, 40608. The connections between the surgical modules 40604, 40606, 40608 and the surgical hub 40602 may not be the same performance level. In examples, some of the connections between the surgical modules 40604, 40606, 40608 may provide redundant pathways of communication that may be used cooperatively. In examples, there may be daisy chain coupling of surgical modules 40604, 40606, 40608. There may be a coupling hierarchy based on critical functionality of certain surgical modules.

In examples, the surgical system 40600 may provide one-way monitoring communication for use in controlling aspects of another smart system. The surgical modules 40604, 40606, 40608 may be non-smart surgical modules, semi-smart surgical modules, smart surgical modules, and/or intelligent surgical modules, which is described in further detail below. The surgical system 40600 may provide integrated monitoring enabling non-smart surgical modules to be used with smart surgical modules. The integrated monitoring may include monitoring for the interference of non-smart surgical modules during the activation of smart surgical modules. This may prevent accidental simultaneous energy activation of non-smart surgical modules and smart surgical modules. In examples, the integrated monitoring may prevent a portion of the non-smart surgical modules and the smart surgical modules from activating simultaneously. For example, the ultrasonic advanced energy portion of a smart surgical module may be used in combination with a monopolar radio frequency application from another surgical module while preventing the smart surgical module's radio frequency portion to be used simultaneously with the monopolar radio frequency application. For example, the surgical module 40604 may be a non-smart surgical module and surgical module 40606 may be a smart surgical module. Each of the surgical modules 40604 and 40606 may work independently from one another or together during certain times of certain procedures. The smart module may incrementally control the non-smart module. In examples, the surgical modules 40604, 40606 may be a generator and smoke evacuator. The generator may a step electrical potential output to indicate the increase airflow, the activation of the energy device to increment the smoke evacuator, or the increase/decrease of speed without other cooperative communication.

Figure 13:
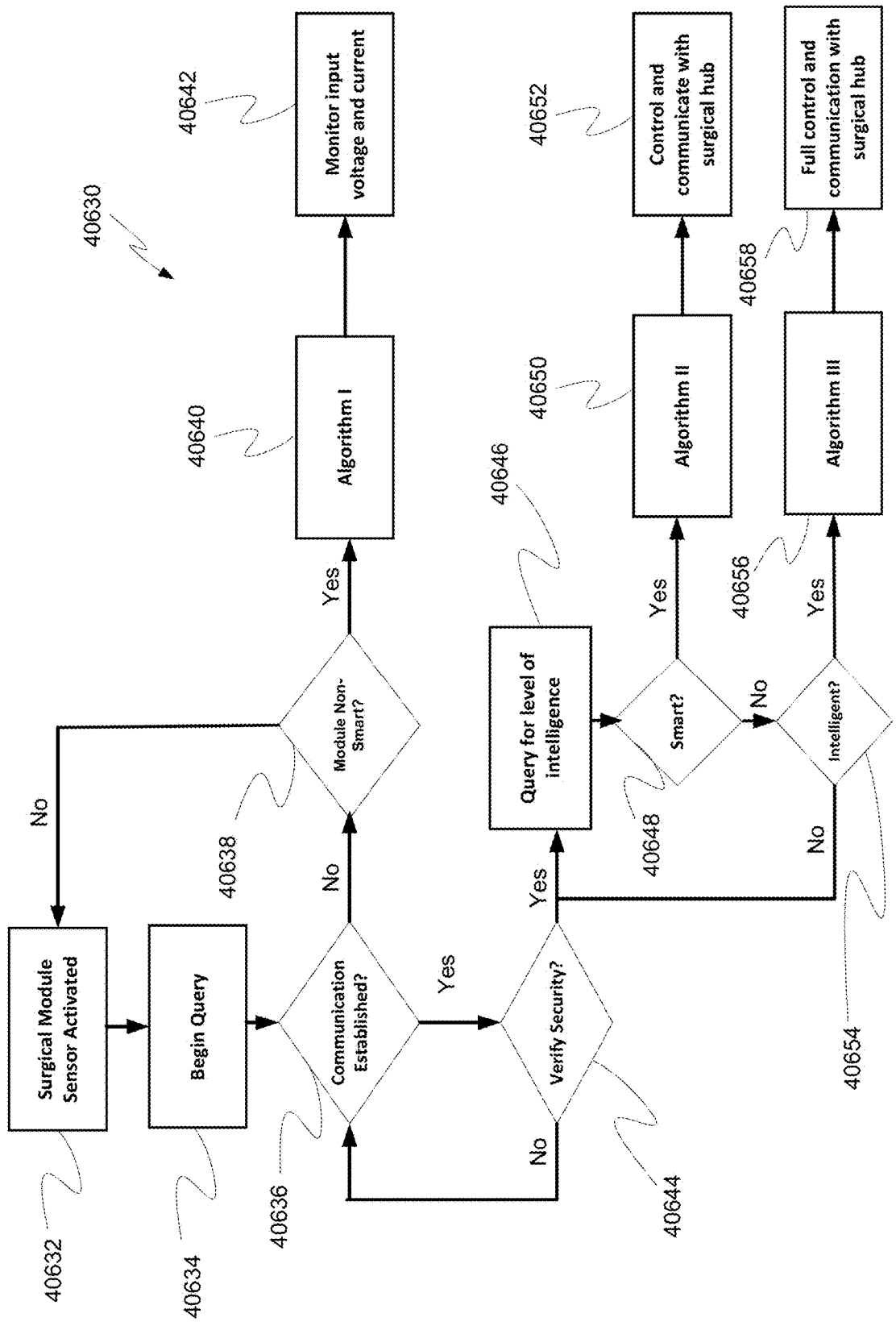
FIG. 13 shows an example of a flow chart of attaching a surgical module to an existing group of surgical modules.

FIG. 13 shows an example of a flow chart 40630 of attaching a surgical module to an existing group of surgical modules. The surgical module may in the form of a monopolar generator. At 40632, the surgical module sensor may be activated. At 40634, the surgical system may begin a query of the newly attached surgical module to establish communication with the existing surgical modules. The surgical system may be surgical system 40600 described in FIG. 12, but may be other surgical systems as well. At 40636, the surgical system may determine if communications are established. If no, then at 40638, the surgical system may determine if the surgical module is non-smart. If no, then the surgical module sensor may be activated again at 40632. If yes, then at 40640, a first algorithm may be performed by the surgical module. At 40642, the surgical module may monitor input voltage and current as performed by the first algorithm.

If communications are established at 40636, then at 40644, the surgical system may verify security. If security is not verified, then the surgical system may determine if communications are established again at 40636. If security is verified, then the surgical system may query for the level of intelligence the surgical module at 40646. At 40648, the surgical system may determine if the surgical module is smart. If yes at 40648, then at 40650, a second algorithm may be performed by the surgical module. At 40652, the surgical module may control and communication the surgical hub as performed by the second algorithm. If no at 40648, then at 40654, the surgical system may determine if the surgical module is intelligent. If no at 40654, then the surgical system may query for the level of the surgical module again at 40646. If yes at 40654, then at 40656, a third algorithm may be performed by the surgical module. At 40658, the surgical module may have full control and communication with the surgical hub as performed by the third algorithm.

Figure 14:
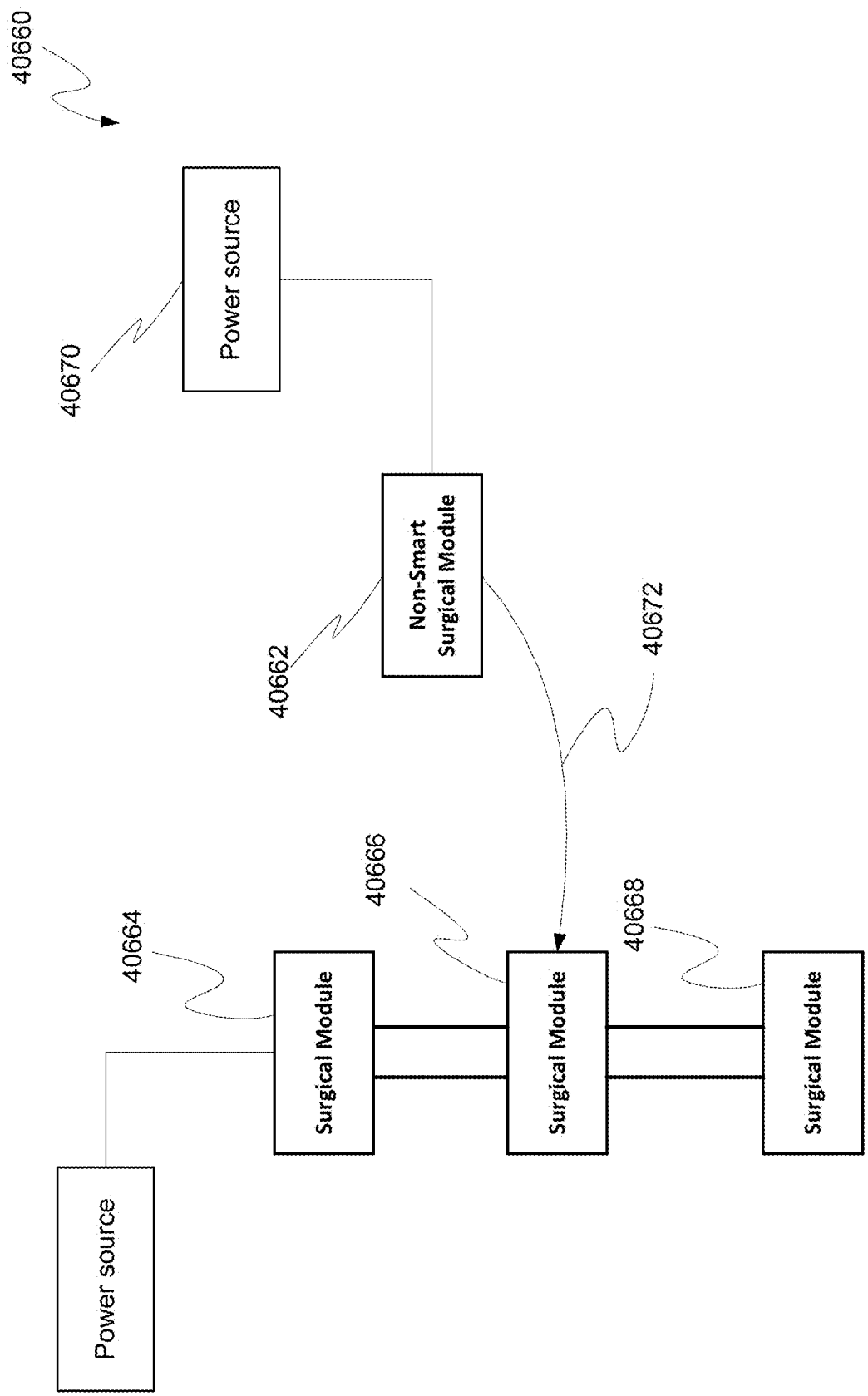
FIG. 14 shows an example of a surgical system with a non-smart surgical module.

FIG. 14 shows an example of a surgical system 40660 with a non-smart surgical module. The surgical system 40660 may include a non-smart surgical module 40662 attached to the surgical modules 40664, 40666, 40668. The non-smart surgical module 40662 may be power independent from the surgical modules 40664, 40666, 40668, having its own power source 40670. The non-smart module 40662 may have one way data flow 40672 with minimal communications with the surgical modules 40664, 40666, 40668.

Figure 15:
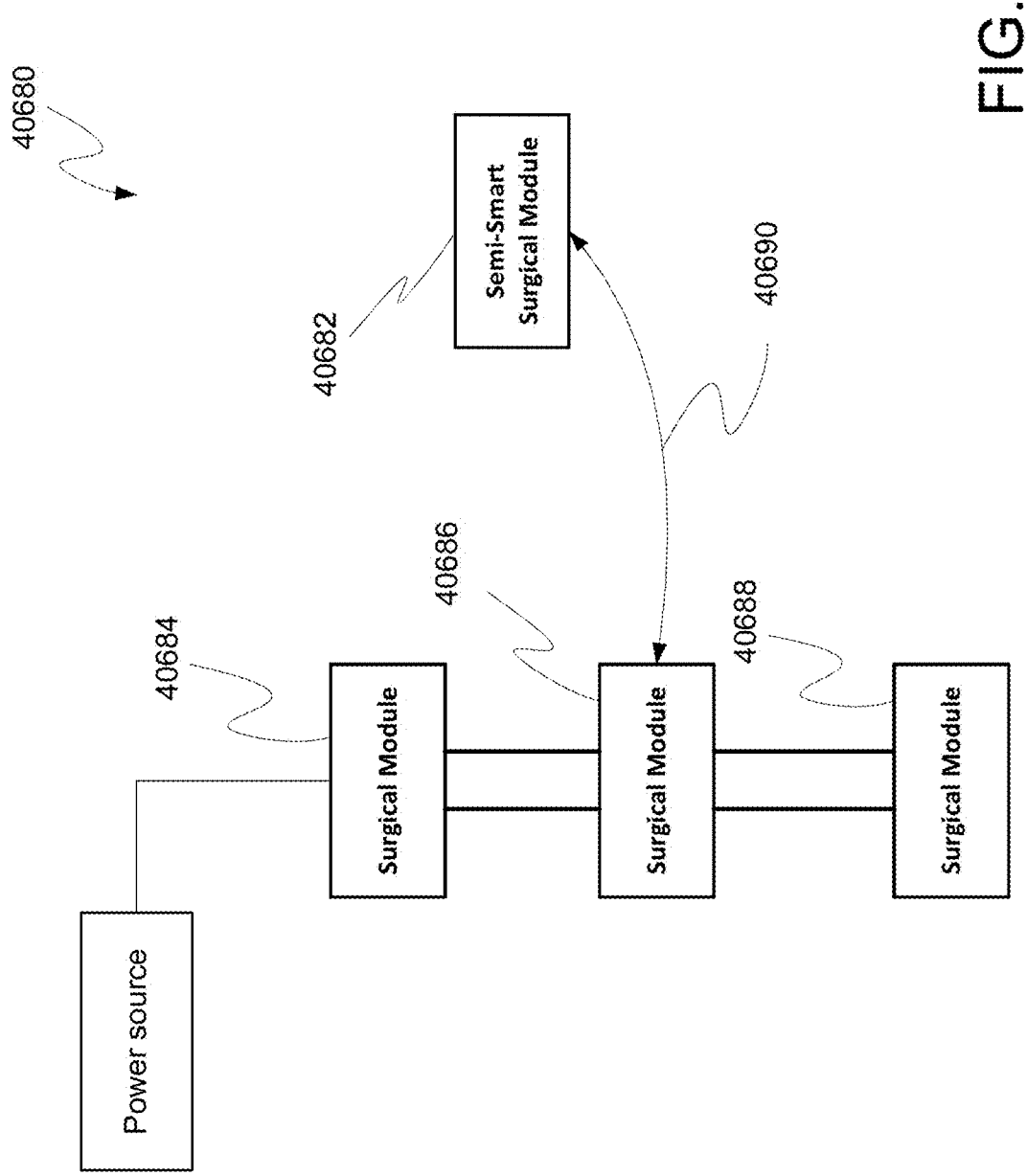
FIG. 15 shows an example of a surgical system with a semi-smart surgical module.

FIG. 15 shows an example of a surgical system 40680 with a semi-smart surgical module. The surgical system 40680 may include a semi-smart surgical module 40682 attached to the surgical modules 40684, 40686, 40688. The semi-smart surgical module 40682 may include two way communication 40690 with the surgical modules 40684, 40686, 40688. The semi-smart surgical module 40682 may monitor the input power. The semi-smart surgical module 40682 may have minimal command and control of its functions.

Figure 16:
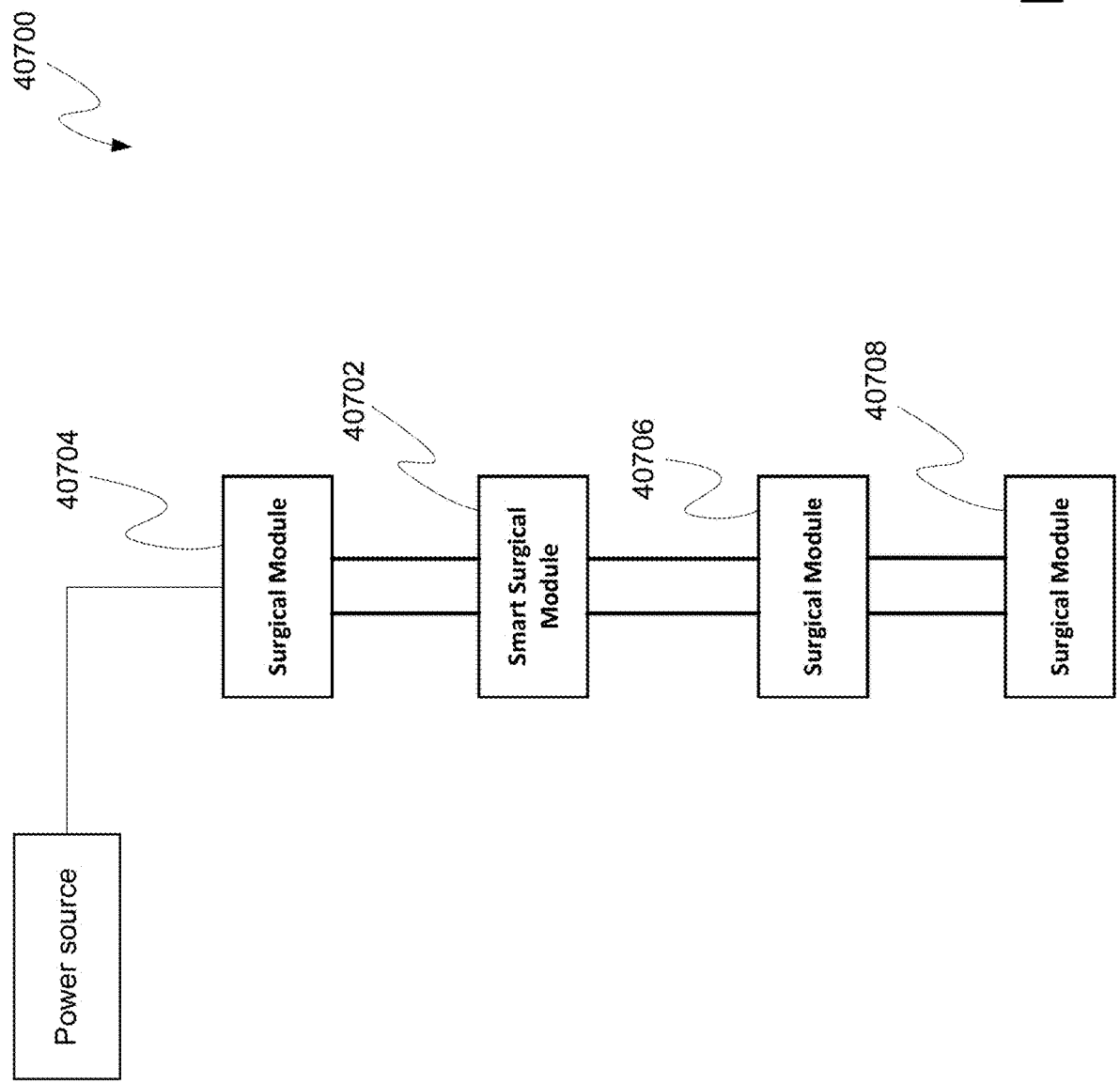
FIG. 16 shows an example of a surgical system with a smart surgical module.

FIG. 16 shows an example of a surgical system 40700 with a smart surgical module. The surgical system 40700 may include a smart surgical module 40702 attached to the surgical modules 40704, 40706, 40708. The smart surgical module 40702 may include two way communication with the surgical modules 40704, 40706, 40708, which may include a bipolar generator. The smart surgical module 40702 may have enhanced command and control of its functions. The smart surgical module 40702 may monitor its inputs and outputs.

In examples, the surgical systems described herein may include an intelligent surgical module. The intelligent surgical module may include multiple communication paths. The intelligent surgical module may have full command and control of its functions.

The surgical system 40600 (shown in FIG. 12) may include a configuration to a surgical hub port available when the surgical modules 40604, 40606, 40608 in communication with the surgical hub 40602 by sharing a bus. Each surgical module 40604, 40606, 40608 may have a specific identification. The surgical modules 40604, 40606, 40608 may be in close proximity to each other to align well with a serial protocol. In examples, the surgical system 40600 may be set up in a primary source/secondary source configuration. The surgical hub 40602 may be the primary source and the surgical modules 40604, 40606, 40608 may be the secondary sources. The surgical hub 40602 may be connected to the surgical modules 40604, 40606, 40608 via a first port 40610. The surgical modules 40604, 40606, 40608 may directly connect to each other via a second port 40612. Extra cables 40614, 40616, 40618 may allow data pass from the surgical modules 40604, 40606, 40608 and an optional cable 40626 may allow data to optionally pass from surgical modules 40604, 40606, 40608 to surgical hub 40602. In examples, data may pass to the surgical hub 40602 via the second port 40612. In examples, the data may not pass to the surgical hub 40602 via the second port 40612. Certain functions and data transfers may be isolated from the surgical hub 40602 via the second port 40612. Certain functions and data transfers may be communicated to the surgical hub 40602 via the first port 40610. In examples, the second port 40612 between each of the surgical modules 40604, 40606, 40608 may be an additional slow communication portal. In examples, the second port 40612 may include an auxiliary data path from a surgical module 40604, 40606, 40608 to the surgical hub 40602.

Figure 17:
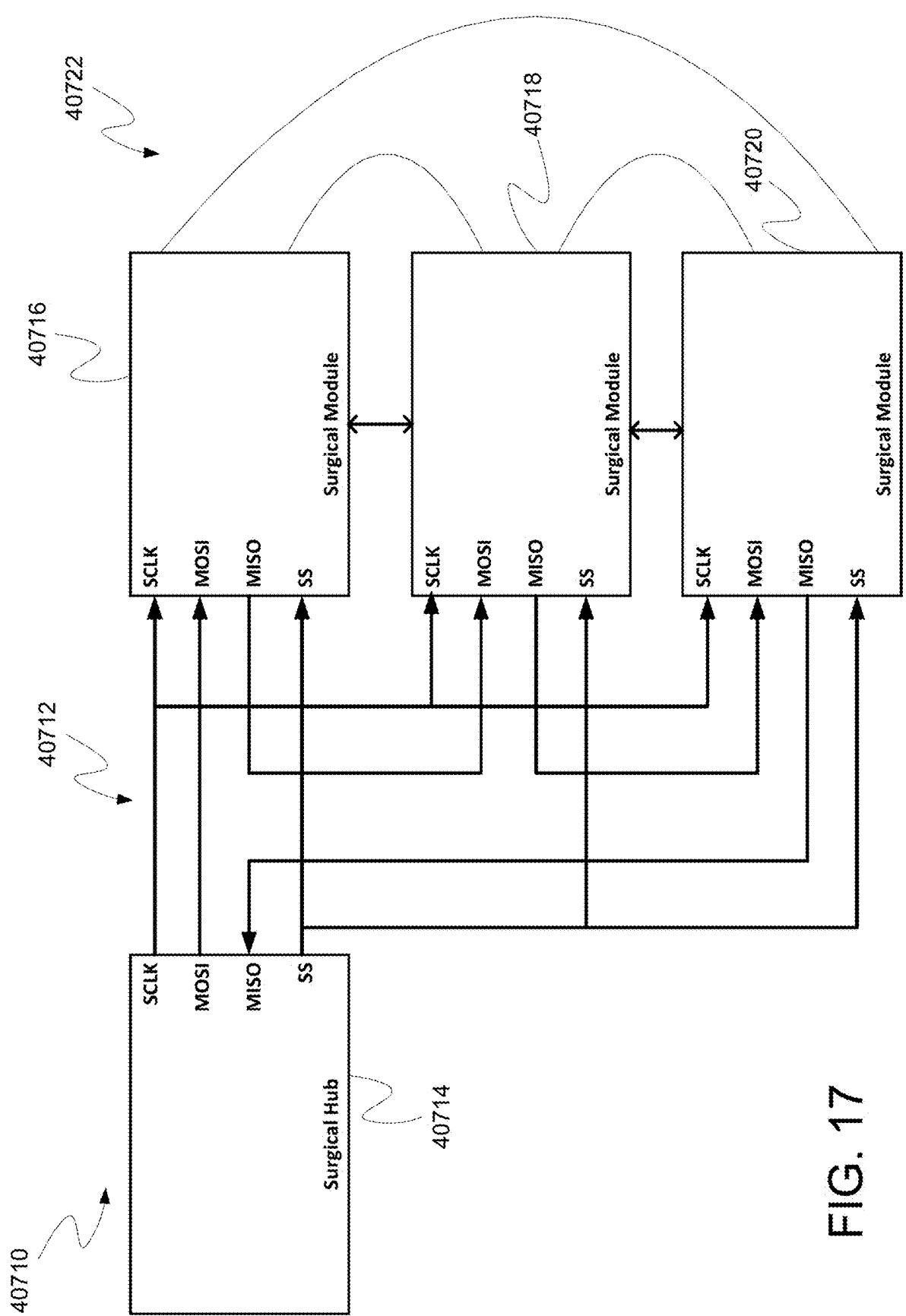
FIG. 17 shows an example of a surgical system with a SPI communication layout.

FIG. 17 shows an example of a surgical system 40710 with a SPI communication layout. In examples, the surgical system 40710 may be two independent communication paths. One communication pathway (e.g., the primary communication pathway) may be a SPI communication bus 40712 between the surgical hub 40714 and the surgical modules 40716, 40718, 40720. A secondary communication pathway 40722 (e.g., the secondary communication pathway) may be a surgical module to surgical module bus.

In examples, at least one of the surgical modules 40716, 40718, 40720 may be set up in a monopolar configuration and at least one of the surgical modules 40716, 40718, 40720 may be configured in a bi-polar mode. If a surgeon picks up the monopolar device, the surgical hub 40710 may acknowledge this activity and ensure full input power is available for the at least one surgical module 40716, 40718, 40720 set up in a monopolar configuration. The surgical hub 40710 may alert the remaining surgical modules 40716, 40718, 40720 that the at least one surgical module 40716, 40718, 40720 set up in a monopolar configuration may be energized. For example, the at least one surgical module 40716, 40718, 40720 set up in a monopolar configuration may be a smoke evacuator and may acknowledge the information and begin to power up into idle mode. The at least one surgical module 40716, 40718, 40720 set up in a bipolar configuration may acknowledge this information and lock out any activation activity. The at least one surgical module 40716, 40718, 40720 set up in a monopolar configuration may receive a signal from the at least one surgical module 40716, 40718, 40720 set up in a bipolar configuration that the energizing switch has been depressed. In response, the at least one surgical module 40716, 40718, 40720 set up in a bipolar configuration may send a high speed status update to surgical module bus the secondary communication pathway 40722 while simultaneously alerting the surgical hub 40714 of the device change of state. The surgical modules 40716, 40718, 40720 may receive this high speed message and change their states. In examples, if the at least one surgical module 40716, 40718, 40720 set up in a monopolar configuration is a smoke evacuator module, it may spin up and begin pulling more smoke from the site. If the at least one surgical module 40716, 40718, 40720 set up in a bipolar configuration is an advanced visualization module, it may increase the intensity of the main light to compensate for the additional smoke in the field. The surgical hub 40714 may increase the input voltage to the remaining modules 40716, 40718, 40720 to compensate for the loss due to the at least one surgical module 40716, 40718, 40720 set up in a monopolar configuration. In examples, other communication pathways between a surgical hub and surgical modules may be a USB data connect, an Rs-232 dedicated interface, and/or a I2C interface.

As shown in FIG. 12, the surgical system 40600 may control the interrelationship between surgical modules 40604, 40606, 40608. In examples, the surgical modules 40604, 40606, 40608 may connect as a peer-to-peer network allowing some surgical modules 40604, 40606, 40608 to run completely autonomous to one another even when connected. In examples, there may be server-bus connection where if a surgical module 40604, 40606, 40608 is connected, the surgical module 40604, 40606, 40608 may surrender some or all of its control to the server module. The surgical modules 40604, 40606, 40608 may run separately from the surgical hub 40602 as an independent stand alone system and if connected to the surgical hub 40602, recognize the connect and adjust its autonomy to that of the surgical hub 40602.

In examples, each of the surgical modules 40604, 40606, 40608 within the surgical system 40600 may be connected via the first port 40610 to the surgical hub 40602. Each of the surgical modules 40604, 40606, 40608 may be connected via the second port 40612 to each other (e.g., each surgical module may be connected to at least one additional surgical module). Each of the surgical modules 40604, 40606, 40608 may have a controller (not shown) configured to receive surgical data. The controller of each of the surgical modules 40604, 40606, 40608 may determine if the surgical data is a first type of data or a second type of data. Based on the determination, the controller of each of the surgical modules 40604, 40606, 40608 may instruct each of the surgical modules 40604, 40606, 40608 to send the surgical data to the first port 40610 if the surgical data is the first type and to the second port 40612 if the surgical data is the second type. In examples, the second port 40612 may excluded from the surgical hub 40602. In examples, the second port 40612 may be included with the surgical hub 40602. Each of the surgical modules 40604, 40606, 40608 may be a non-smart surgical module, a semi-smart surgical module, or a smart surgical module. Each of the surgical modules 40604, 40606, 40608 may be a smoke evacuator, a visualization system, a generator, a header, a monitoring or imaging system, or an insufflation system.

Figure 18:
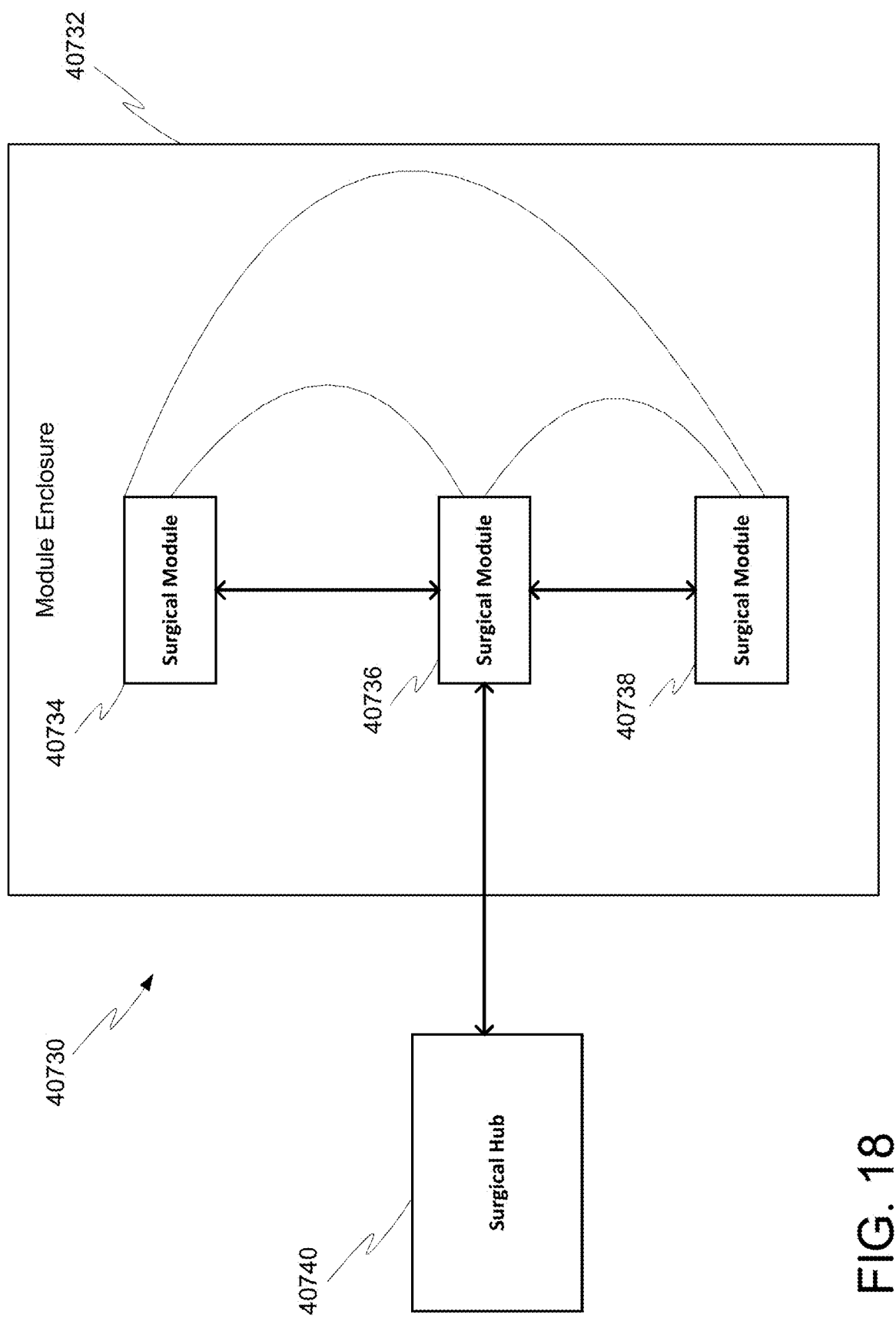
FIG. 18 shows an example of a surgical system with a module enclosure.

FIG. 18 shows an example of a surgical system 40730 with a module enclosure. The surgical system 40730 may include a modular enclosure 40732 that physically couples the surgical modules 40734, 40736, 40738. The modular enclosure 40732 may include a stacking and electrical connection. Each module enclosure 40732 may include both a physical connection mechanism and an electrical connection mechanism which may be stacked. In examples, the electrical connection may establish power and communication to each of the surgical modules 40734, 40736, 40738 within the module enclosure 40732. In examples, the electrical connection may establish communication without establishing power to each of the surgical modules 40734, 40736, 40738 within the module enclosure 40732. Each surgical module 40734, 40736, 40738 may have separate individual power plugs and a connection bus to create bus architecture for communication (not shown). The modular enclosure 40732 may include a communication or header module which includes the processing power to manage communication between the surgical modules 40734, 40736, 40738 in a surgical network or bus format. Information may be communicated to an outside edge server and/or cloud. In examples, one of the surgical modules 40734, 40736, 40738 may be a header module. The header module may include a processor which may perform additional processing and algorithm work. The header module may include a memory and/or other storage modules. The stacking of the module enclosure 40732 may be vertical or horizontal connection. The module enclosure 40732 may have a predefined enclosure with a set number of connection points for surgical modules 40734, 40736, 40738. Different module enclosures may connect with each other either wired or wirelessly to make virtual larger surgical hubs within different operating rooms. The module enclosure 40732 may include locking features that alert viable additions to the set of surgical modules 40734, 40736, 40738.

The surgical system 40730 may provide heat management based on the surgical module 40734, 40736, 40738 or surgical hub 40740 utilization. The heat buildup of the module enclosure 40732 may be used as a monitored aspect that is in turn used to change the heat generation or heat exhaust of the surgical system 40730. The surgical system 40730 may include a supplemental heat exchange or fan systems that may cool the surgical hub 40740 and the surgical modules 40734, 40736, 40738. The fans may be controlled based on the monitored heat generation of the combined surgical modules 40734, 40736, 40738 and/or surgical hub 40740. The surgical hub 40740 may instruct the individual surgical module heat exhaust systems to increase or decrease utilization as the surgical system 40730 monitors heat within a main enclosure of the module enclosure 40732. A controller may direct control of heat generation aspects of the surgical modules 40734, 40736, 40738. The controller may throttle or control aspects that are generating heat. The surgical system 40730 may switch power loads to surgical modules 40734, 40736, 40738 to control heating aspects.

Monitoring parameters from at least one of the surgical modules 40734, 40736, 40738 may be used to control or adjust at least one of the other surgical modules 40734, 40736, 40738. In examples, one of the surgical modules 40734, 40736, 40738 may be a video of a monitoring or imaging system and one of the surgical modules 40734, 40736, 40738 may be a smoke evacuator. The video of a monitoring or imaging system may be used to determine visibility issues between one time and the next, which may be used to control the increase or decrease of the smoke evacuator motor speed. Electrosurgery may create a by-product known as surgical smoke (e.g., also referred to as cautery smoke, surgical plume, diathermy plume, smoke plume, or plume). The smoke may emanate from the surgical cut site creating a potent odor, as well as reducing visibility for the surgeon. Removing surgical smoke from the air has become important (e.g., increasingly important) as electrosurgical procedures have become more common. Smoke evacuators may have fluid and solid filtering means to include particles and motors that may be operated to provide just enough evacuation to remove the smoke plume without causing other issues. Smoke evacuators may be activated via a link to the energizing of the energy device, which may cause a lag in response not proportionate to the size of the smoke plume. Influencers may contribute both an amount of smoke and type of smoke created to include tissue type, patient bio-markers, and type of device (e.g., monopolar electrosurgery, RF electrosurgery, ultrasonic cutting, a sagittal saw) selected to complete the intended task.

In examples, the surgical hub 40740 may utilize the video monitoring and/or image system to detect the type of tissue and the patient biomarkers to control the speed of the smoke evacuation and duration at which the smoke evacuation is on or off, which may minimize the smoke buildup. The operating room video system (not shown) and/or surgical hub 40740 may identify which energy device is attached or which energy device the surgeon was intending to use to control the smoke evacuation and the duration at which the smoke evacuation is on or off. The surgical hub 40740 may monitor or learn the visibility that is being displayed to the surgeon throughout the surgery and adjust the parameters on the smoke evacuation system to minimize obstruction to the surgeon based on each use of a particular instrument, tissue type, and/or knowing the next performed action of that procedure type. In examples, one of the surgical modules 40734, 40736, 40738 may be a visualization system. The visualization system may be used as a trigger and/or proportionate control of the smoke evacuator response. The denseness the smoke plume, the size of the smoke plume, and duration of the smoke plume may all relate to the amount of power needed for the smoke evacuator. The denseness the smoke plum, the size of the smoke plume, and duration of the smoke plume may be detected by the visualization system, which may communicate the information to the smoke evacuator. The smoke evacuator may use the appropriate amount of power to clear and control the smoke plume based on the information provided by the visualization system. The visualization system may (e.g., may also) detect the direction of the motion of the smoke plume as a means to adjust the control of the smoke evacuator.

In examples, the surgical hub 40740 may utilize the camera to detect micro smoke plumes and arcing of electrosurgical devices to verify an energy activation location. In examples, if using a monopolar device, using the lowest possible generator setting to achieve the desired tissue therapeutic treatment may be desired. Higher than necessary voltages may be sign that arcing is occurring. If the surgeon continues to ask for a higher voltage, this may be a signal that the integrity of the skin/dispersive pad interface is compromised. Using the visualization system to monitor aching may be used to control and/or adjust the amount of energy that is delivered. Monitoring the arching over time may be used to identify if continued energy increases are needed over a period of time. Monitoring the arching over time may be used to determine if the pad/return path is compromised. If the pad/return path is compromised, the user may be instructed to check the pad before additional power is applied. In examples, the visualization system may monitor the tip of the monopolar device (e.g., as an additional check) prior to the surgical hub 40740 adjusting the energy level of the surgical device. For example, during surgery, eschar (e.g., dead tissue from burning) may build up on the tip, in which electrical impedance increases may cause arcing, sparking, or ignition and flaming of the eschar. The visualization system may monitor the tip of the monopolar device to detect whether it has eschar buildup on the tip. If it does not have build up on the tip, the visualization system may increase the energy level. If it does have build up on the tip, the visualization system may require the user clean the monopolar device prior to allowing energy activation. In examples, the visualization system may detect the arc color. The arc color may determine the amount of power to apply to the smoke evacuator. In examples, a visual camera of the visualization system may monitor the cauterization site for released plume of steam, smoke, or aerosol.

In examples, the smoke evacuator motor may be activated based on energy handpiece activation. The tissue source and cutting method along with the type of energy device selected (e.g., ultrasonic, RF, and monopolar) may influence the smoke generated during use. The energy devices that may be used during surgery include monopolar electrosurgery, RF electrosurgery, and ultrasonic, each having different power outlets and maximum temperature limits. A higher level the power may cause a higher level of thermal spread and charring, which may generate different levels of smoke plume. Based on this information, the surgical hub 40740 may know which energy device was being used and adjust the power level of the smoke evacuator accordingly. The smoke evacuator motor speed may be adjusted based on the determined power level.

Figure 19A:
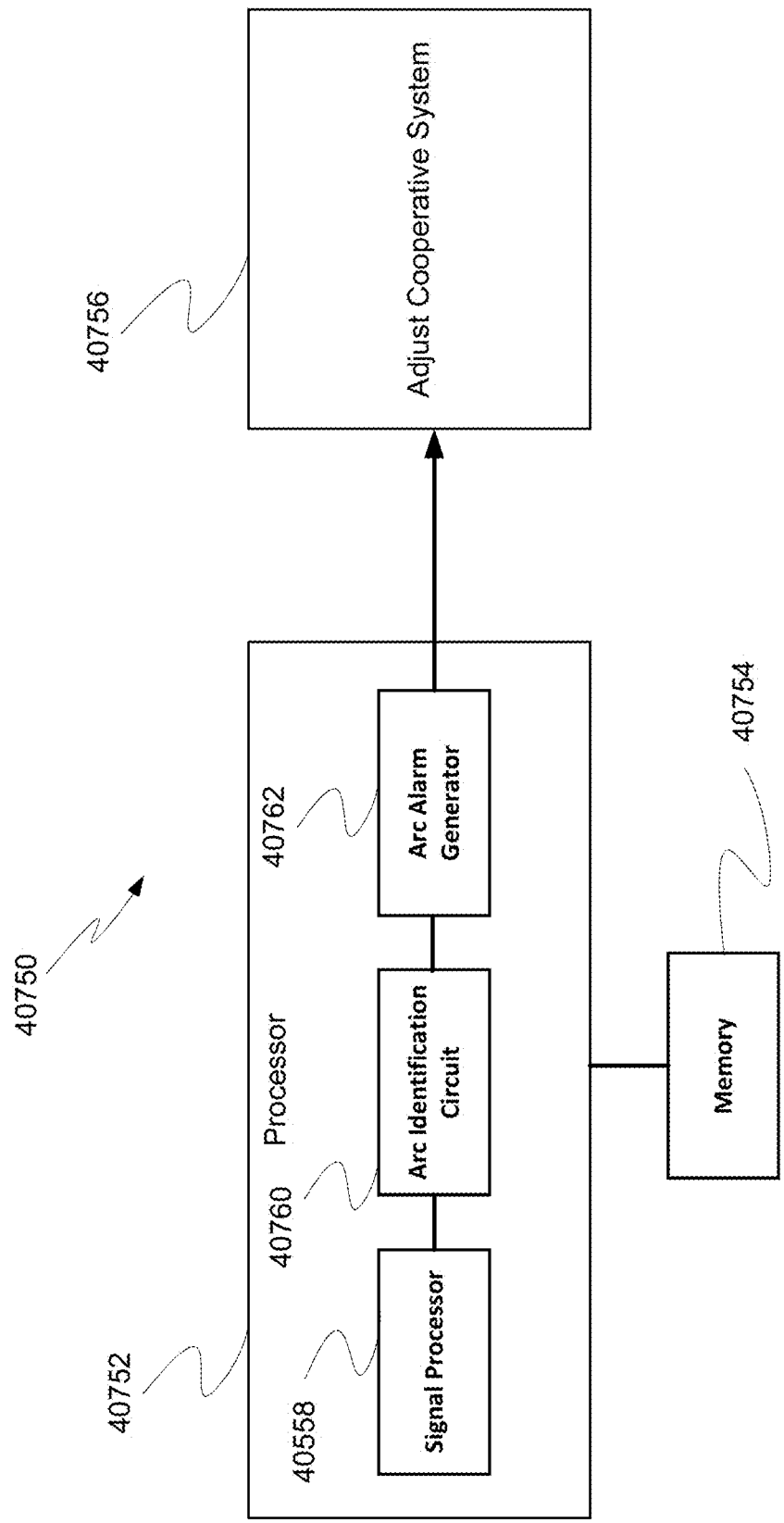
FIGS. 19A-19B show an example and a flow chart of a surgical system that detects arcing.
Figure 19B:
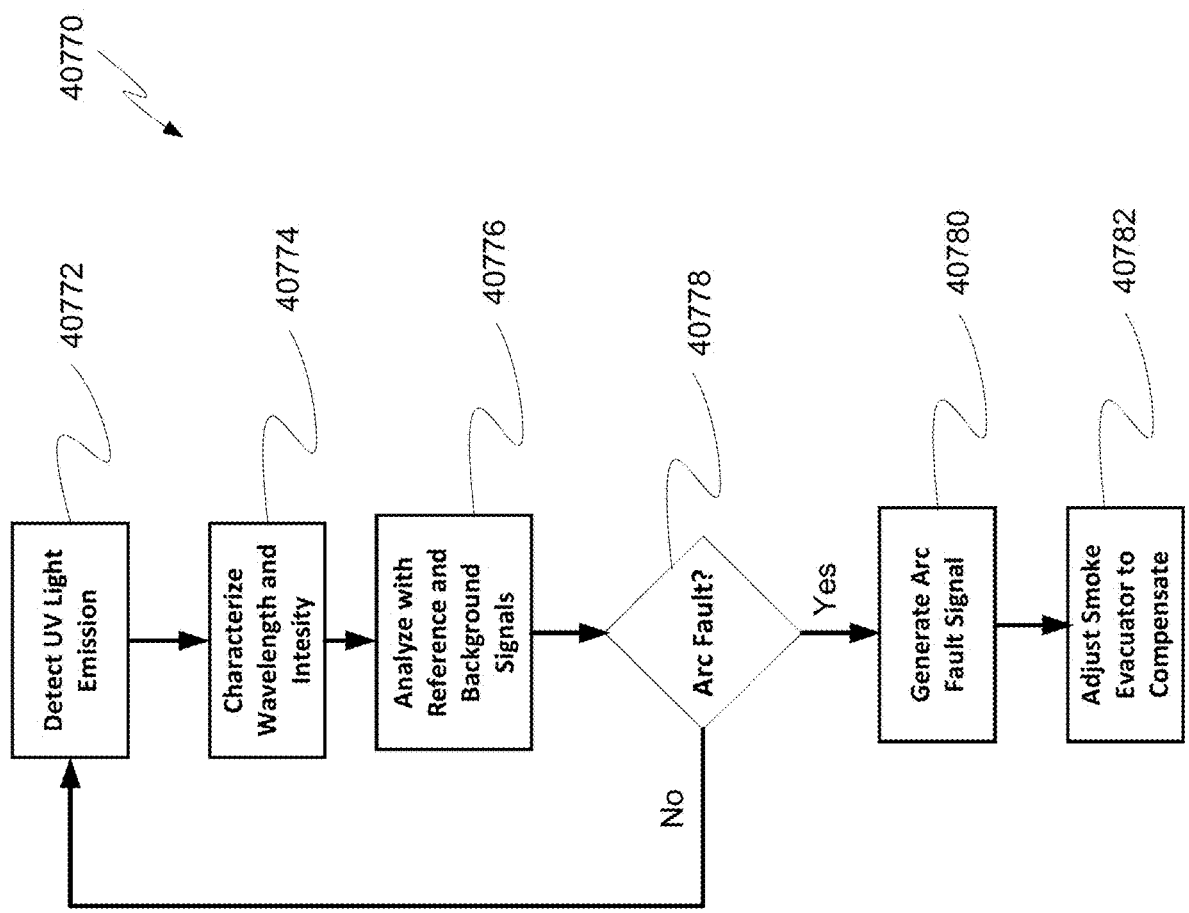

FIGS. 19A-19B show an example and flow chart of a surgical system 40750 that detects arcing. The surgical system 40750 may include a processor 40752 and a memory 40754. In examples, the processor 40752 may be a surgical hub processor. The processor 40752 may include a signal processor 40558, an arc identification circuit 40760, and an arc alarm generator 40762. If the processor 40752 detects an arcing event, it may adjust a cooperative system 40756. A flow chart 40770 may show how the processor 40752 of the surgical system 40750 detects an arcing event and adjusts the cooperative system 40756. In examples, the cooperative system 40756 may be a smoke evacuator. At 40772, the processor 40752 may detect the UV light emission. At 40774, the processor 40752 may adjust the characterize the wavelength and intensity. At 40776, the processor 40752 may analyze the arcing with reference and background signals. At 40778, the processor 40752 may determine whether or not there is an arc fault. If no at 40778, then the processor 40752 may return to detecting the UV light emission at 40772. If yes at 40778, then at 40780, the processor 40752 may generate an arc fault signal. At 40782, the processor 40752 may adjust a smoke evacuator to compensate for the arcing.

Examples described herein include a surgical hub that may detect its location within current past surgical networks. The surgical hub may reestablish necessary connections and bandwidths to support the expected protocol needs of the surgical hub. The surgical hub may detect its physical location, the network topology, and connectivity. The surgical hub may compare changes from previous uses with certain procedures and surgeons and then use it to adjust its connectivity to surgical networks to maximize its access and connection to the data stored and the surgical component it needs to support the procedure being used. The connectivity adjustments may involve connection to additional networks and parsing the data transfer needs between them to establish the overall throughput it needs to provide the data to the user from the remote locations. The connectivity adjustments may involve establishing virtual private connections to ensure the data exchanged between the remote location and the surgical hub remains at the security level necessary for the data being transferred. The connectivity adjustments may involve connection to surgical networks that may take the data of the facility and then back to the facility.

Figure 20:
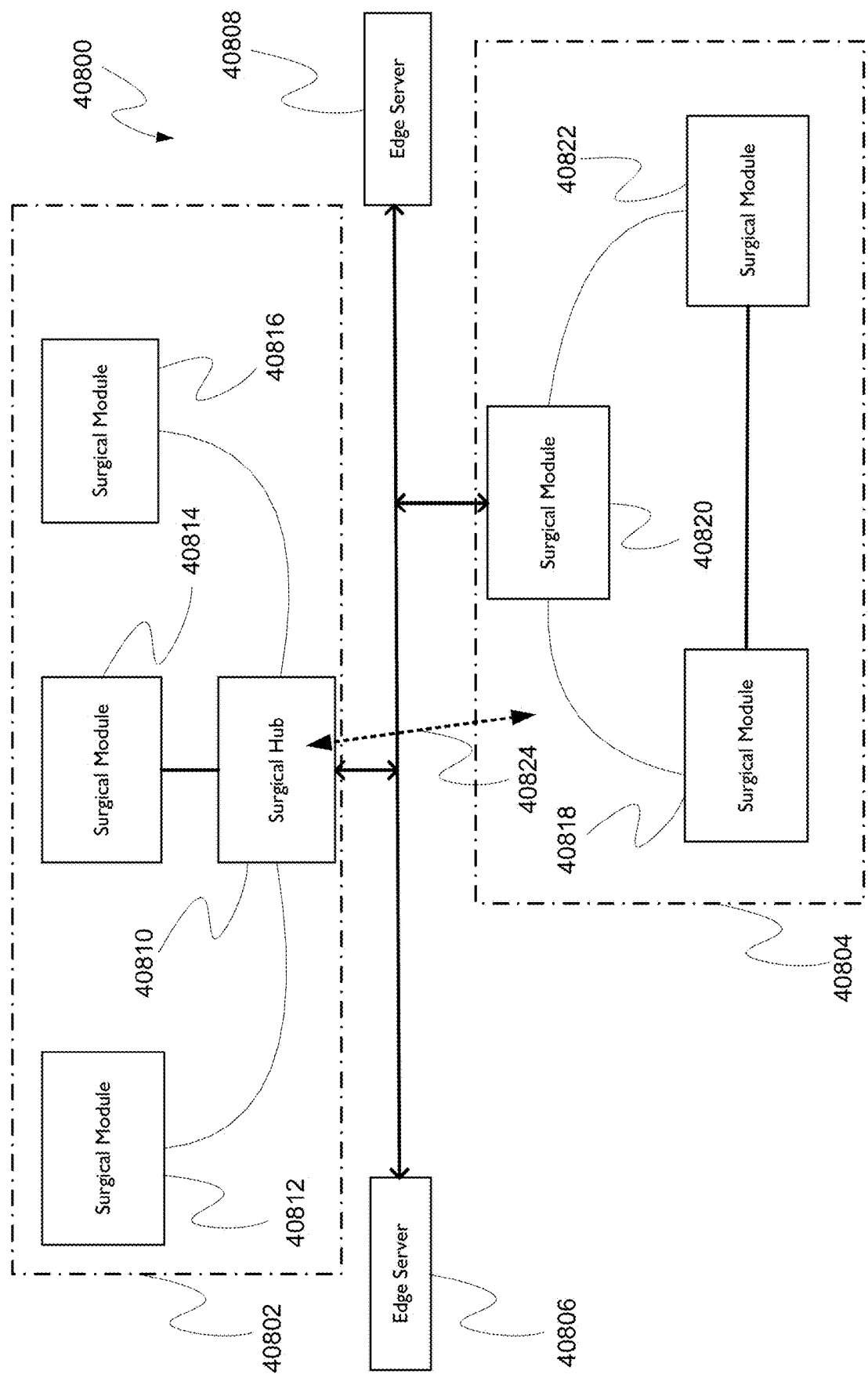
FIG. 20 shows an example of a surgical system with multiple surgical networks.

FIG. 20 shows an example of a surgical system 40800 with multiple surgical networks. The surgical system 40800 may include a first surgical network 40802 and a second surgical network 40804. Although two surgical networks are shown in FIG. 20, the surgical system 40800 may include any number of surgical networks. In examples, the first surgical network 40802 may be the primary surgical network and the second surgical network 40804 may the secondary surgical network. The first surgical network 40802 and second surgical network 40804 may each be connected to edges servers 40806, 40808. The first surgical network 40802 may include a surgical hub 40810 and surgical modules 40812, 40814, 40816. The second surgical network 40804 may include surgical modules 40818, 40820, 40822.

The connectivity adjustments within the surgical system 40800 may be based on may be latency, data transfer parameters, bandwidth, message handling, service available, and service reliability. Latency parameters may include propagation delay, packet length and data rate, header processing size and integrity, queuing delay, and the number of interconnected systems that respond when asked for polling of addresses. The propagation delay may relate to the distance and the physical connection of the interconnected systems. The queuing delay may relate to the time a packet is waiting in the queue to be processed. The data transfer parameters may include prioritization, filtering, encryption, routing/load balancing, and data compression. The filtering may be achieved by virus scanning, intrusion detection, and/or firewalls.

The data for one surgical specialty may be different than that of other specialties. For example, the digital assets of the thoracic surgery department may include lung tumors, thoracic anatomy models, chest cavity imaging, and algorithms for interpreting, identifying, and locating thoracic tumors, transbronchial imaging systems, procedure data related to their procedures, etc. Access to this data may be needed by all the thoracic operating rooms but not any of the other operating rooms or department in the facility. However, much of this data is large and having instant access to the primary network may require significant network resources. As such, specialties and departments may have secondary networks that interconnect through the primary network rarely. Moving the secondary network assets from one network location to another network may have impacts on both the network they are moving to and the network they are moving from.

The bandwidth may relate to the maximum message payload size that can be handled by the message broker may be considered. The larger payloads may be split into multiple smaller payloads, which may create more latency and computing overhead. The service availability may relate to geographical proximity, time of day, and usage patterns. The service reliability may relate to synchronization in case of failure, swapping in case of failure, and ensuring message idempotency.

The surgical system 40800 may monitor and provide oversight to the first surgical network 40802 and the second surgical network 40804 and the edge behavior and identification of the adjustments needed. The surgical system 40800 monitoring may include monitoring the first surgical network 40802 and second surgical network 40804 for faults and issues, network congestion, direct name servers monitoring, traceroute monitoring, border gate protocol monitoring, and endpoint monitoring. The monitoring of the first surgical network 40802 and the second surgical network 40804 may include timing of restarts or reboots to establish clean protocols and the detection and elimination of faulty connections or hardware. The network congestion may include scheduling of interconnections for lower priority timing and traffic shaping control. The traffic shaping control may include smart linked systems and non-interactive traffic generators. The smart linked systems may include the sharing of traffic patterns and how much the smart system can interconnect with the surgical hub, other devices, and the cloud. The non-interactive traffic generators may include throttling or adjusting the bandwidth of devices.

The surgical system 40800 may utilize the edge servers 40806, 40808 to interact with the surgical hub 40810 and to adjust the first surgical network 40802 and the second surgical network 40804 based on the utilization and needs of the operating rooms. The utilization of the edge servers 40806, 40808 may include load sharing and smart network application. The load sharing may include a number of servers and their utilization. The load sharing may balance the traffic on a wireless or wired connection. The load sharing may introduce low throughput systems that may slow the system waiting on data to move through the lower speed of the port system. The load sharing may include a facility that may have three or more layers of distributed cooperative computing. The first surgical network 40802 may be made up the surgical hub 40810 within an operating room (not shown) which may allow the surgical hub 40810 to supervise or oversee a user's interaction with connected systems. Depending on how the other surgical networks are laid out, surgical hubs in adjacent operating rooms may share processing, stored data, or a plan. In examples the surgical system 40810 is a star network layout, the department, operating room ward, or floor may have a local central server or system that oversees the interaction of communications between the different surgical networks. In examples, the local area network (LAN) may be hooked into the main facility network which may (e.g., may also) have a primary server or edge computing server. Each level of this hierarchy may help distribute processing, share communication bandwidth, or do processing for the other levels to help prevent processing from having to be done by only the limited systems. As shown in FIG. 20, the smart network application may include an overview of the network topologies of the surgical hub 40810 to the edge servers 40806, 40808 and each topology to each of the first surgical network 40802 and the second surgical network 40804. The smart energy over internet gateway configuration may enable interconnected devices to be powered from the gateway itself.

The surgical system 40800 may detect network topology and integrate or automatically adjust the topology based on the surgical procedure, department, or staff affiliations. The network topologies may include a bus topology, a ring or dual ring topology, a mesh topology, a star topology, and a hybrid tree topology. The bus topology may include a primary backbone to the network with the surgical hub nodes (e.g., all the surgical hub nodes connected off the backbone). The ring or dual ring topology may include surgical hubs interconnected in a pass through configuration where each system may be connected in an adjacent system. The mesh topology may have nodes (e.g., every node) in the mesh connected to all of the nodes in the mesh. The star topology may have nodes (e.g., every node) connected off of a central server or node. Hybrid tree topology may have any number of networks that are interconnected via a primary topology. In examples, the hybrid tree topology may be a bus topology with other ring, bush, and mesh topologies off of the primary bus.

The interconnection of network and flow may be monitored. The location and proximity of the networks within the operating room may be physically detected. In examples, the communication parameters may be adjusted based on the connection type, distance from the surgical hub, obstacles, etc. WiFi may have frequencies between 2.5 GHz and 5 GHz. Vertical and horizontal polarized antenna array choices may provide directionality of the antennas to the communication units. The registration and location indication of a surgical network's detection or probe location be monitored in relation to other surgical networks. The surgical system 40800 may automatically detect and monitor an overall view of the network topology. In examples, the surgical system 40800 may create a view of data moving through the operating room and in between the first surgical network 40802 and the second surgical network 40804 in order to automatically adjust connected network configurations to balance the need for interconnection with the speed of communications. The surgical system 40800 may monitor and track the network flow over the procedure and between procedure.

In examples, surgical hub 40810 may be connected by surgical discipline, which may enable the surgical hub 40810 to stay within its own network to retrieve and store procedural video and interactions with staff. The surgical hub 40810 may be detected outside of the first surgical network 40802 and the establishment of a virtual private network (VPN) may connect the surgical hub 40802 back to the first surgical network 40802, even if the physical network is not directly connected to the preferred network. If the operating room area is broken into departments and each uses a mesh network, then the surgical hub 40810 may convert the department into a ring or star network configuration and behave autonomous to the first surgical network 40802 with the surgical hub 40810 being the interface. In examples, the physical wiring may be supplemented by wireless connection between the surgical hub 40810 and the surgical modules 40812, 40814, 40816, 40818, 40820, 40822 to form the hybrid network interconnection. The adjustment of the local network to a department concentric system may help minimize confusion and improve access to relevant people and files. The network utilization may be defined by the security, throughput, and type of data. Critical data or private data may be secured (e.g., encrypted) and/or sent along a more secured network.

In examples, the thoracic surgeon may normally conduct surgery in a first operating room which is in a star network off the facility's bus network, which is indicated as the first surgical network 40802 in FIG. 20. The edge servers 40806, 40806 may be interconnected to several hospitals' primary surgical networks (e.g., via a cloud). The surgeon may have a patient that requires surgery but needs CT scanning intra-surgery, so the surgery may be scheduled in a second operating room where a CT scanner is permanently installed. The second operating room may be on a different floor from the thoracic network and the imaging operating rooms may be a part of the second surgical network 40804 that may (e.g., may also) be connected to the first surgical network 40802. The surgeon may need not only the advanced energy devices commonly need, but the generator may be one of the surgical modules 40812, 40814, 40816 within the first surgical network 40802 of the first operating room. In examples, the surgeon may need a mobile robot for imaging and treatment. The mobile robot may act as a secondary hub in the thoracic operating room.

The surgical hub 40810 may be moved from the first surgical network 40802 to the second surgical network 40804, as shown by 40824. In examples, the surgical hub 40810 may be moved from the first surgical network 40802 within a thoracic surgery floor in a first operating room to the second surgical network 40804 of advanced imaging operating rooms on a different physical floor (not shown). When turned on, the surgical hub 40810 may seek to determine where it is located and to what network it is attached. If the surgical hub 40810 determines it is part of a connected but separate network from where it normally is, it may seek to establish a connection back to the first surgical network 40802. The surgical hub 40810 may do this because procedure plans, simulations, videos, and other digital aids may be stored in the first surgical network 40802 distributed between the other surgical hubs (not shown) and the thoracic surgery start server that links them all. The surgical hub 40810 may determine that the network traffic through the facility bus network is too congested for real time streaming and is (e.g., only) useful for limits bandwidth communications. To compensate for this, the surgical hub 40810 may both connect to one or more wireless LANs and connect to the first surgical network 40802 via VPNs. The VPN data may be divided between the first surgical network 40802 and the second surgical network 40804 and the surgical hub 40810 may be connected to and may send and receive data through both network connections simultaneously. The data may be encrypted and kept separated from the rest of the network traffic to ensure a stable connected and that the data is not leaked to other systems. In examples, if the certain surgical modules are detected, the network traffic may be rerouted to improve throughput, latency, and minimize packet loss and errors. This adjusted hybrid design may allow surgical hubs to share data faster and allow the machine learning to have a predefined arena to operate when reducing data.

In examples, a surgical computing device may each have a processor (not shown) configured to determine a present network locus, wherein the primary network locus is the first surgical network 40802 or a second surgical network 40804. The surgical computing device may be any of the surgical modules 40812, 40814, 40816, 40818, 40820, 40822 or the surgical hub 40810. Each of the processors may identify a data communications session and determine the surgical data type of the data communication session. The surgical data may be any of a first type of surgical data or a second type of surgical data. Based on the determination, each of processors may direct the data communications session to the first surgical network 40802 if the surgical data is the first type of surgical data or to the second surgical network 40804 if the surgical data is the second type of surgical data.

Determining whether the surgical is the first type of surgical data or the second type of surgical data may be based on the connectivity adjustments of the first surgical network 40802 and the second surgical network 40804. In examples, the connectivity adjustments may be based on latency, data transfer parameters, bandwidth, message handling, service available, or service reliability. In examples, the first surgical network 40802 may be the primary surgical network and the second surgical network 40804 may be the secondary surgical network. Each of the first surgical network 40802 and the second surgical network 40804 may be connected to the edge servers 40806, 40808. The edge servers 40806, 40808 may be connected to a surgical cloud (not shown). In examples, the first surgical network 40802 and the second network 40804 may be configured in a bus topology, a ring or dual ring topology, a mesh topology, a star topology, or a hybrid tree topology.

In examples, each of the processors of the surgical computing device may be moved from a first operating room to a second operating room. Each of the processors may be configured to determine the present network locus is different than a previous network locus. The first surgical network 40802 may be present at the first operating room and the second surgical network 40804 may be present at the second operating room.

In examples, the surgical hub 40810 may have a processor (not shown) configured to combine at least one of a first plurality of functions with at least one of a second plurality of functions to create a third surgical network (not shown). The third surgical network may be connected to the surgical hub 40810. Each of the processors of the surgical computing device may determine a present network locus of the processor. The present network locus may be any of the first surgical network 40802, the second surgical network 40804, or the third surgical network (not shown). The surgical computing device may be any of the surgical modules 40812, 40814, 40816, 40818, 40820, 40822 or the surgical hub 40810. Each of the processors may identify a data communications session and determine the surgical data type of the data communication session. The surgical data may be any of a first type of surgical data, a second type of surgical data, or a third type of surgical data. Based on the determination, each of processors may direct the data communications session to the third surgical network if the surgical data is the third type of surgical data. The determination of whether the surgical data is the third type of surgical data may be based on the connectivity adjustments of the third surgical network. The connectivity adjustments may be based on latency, data transfer parameters, bandwidth, message handling, service available, or service reliability. The first plurality and second plurality of functions may (e.g., may also) be based on latency, data transfer parameters, bandwidth, message handling, service available, or service reliability to create the third surgical network.

Figure 21:
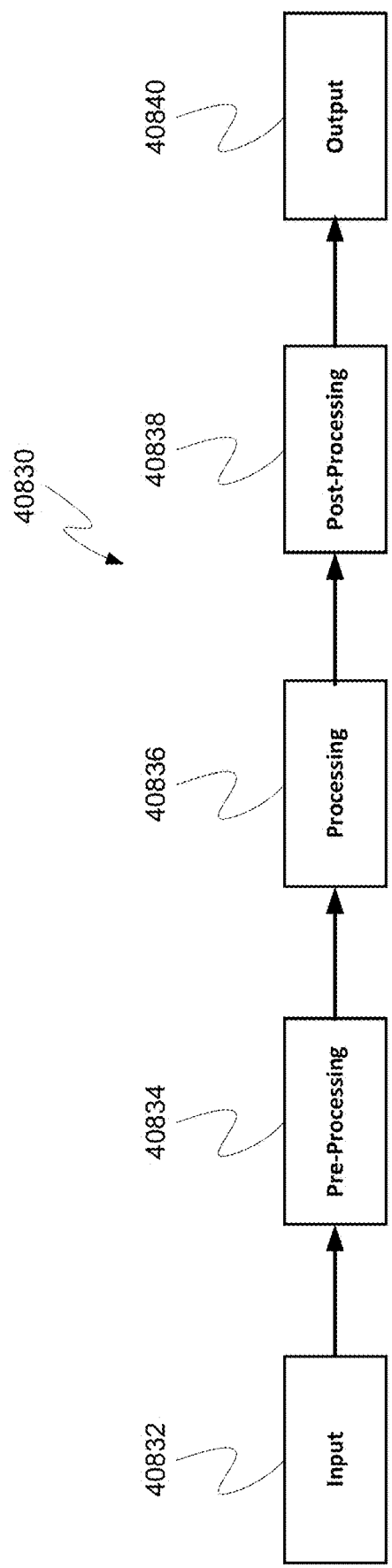
FIG. 21 shows an example surgical system that requests communication access based on subscriptions.

FIG. 21 shows an example surgical system 40830 that requests communication access based on subscriptions. Subscription based requesting access of communication access may include the prioritization of access, the scalable access to individual systems or actuators, the scalable access to individual systems or actuators, an asynchronous method, or a process control description. The input module 40832 may publish the messages on a pre-processing topic 40834. The processing module 40836 may not subscribe to the pre-processing topic 40834 to receive all messages published by the input module 40832. The processing module 40836 may act as the publisher of processing messages on the post-processing topic 40838. The output module 40840 may subscribe to this topic. The input module 40832 may publish messages on a private chat or a public chat. The private chat may be an open temporary topic. The public chat may be standard subscriber or a publisher framework.

Scalable access of individual systems or actuators may include static scaling and dynamic scaling. Static scaling may have an input line for each subscriber. Dynamic scaling may allocate lines based on current subscriber traffic. The asynchronous method may provide an advantage of the subscription based approach in that events may not have to happen at specific times and/or things are not running off the same clock or time frame. The publisher may publish at its discretion to the broker. The subscriber may then permit to view or see subject matter at a time most appropriate to the subscriber. This could be at a computational low period or during idle cycles, which may allow for greater flexibility when the system does not have to follow the same clocking sequence. The process control description may include a publisher, subscriber, and broker. The publisher may be the supplier of information or messages. The subscriber may be the consumer of information. The broker may decouple communication between devices that publish information and other devices that subscribe to the information.

Figure 22:
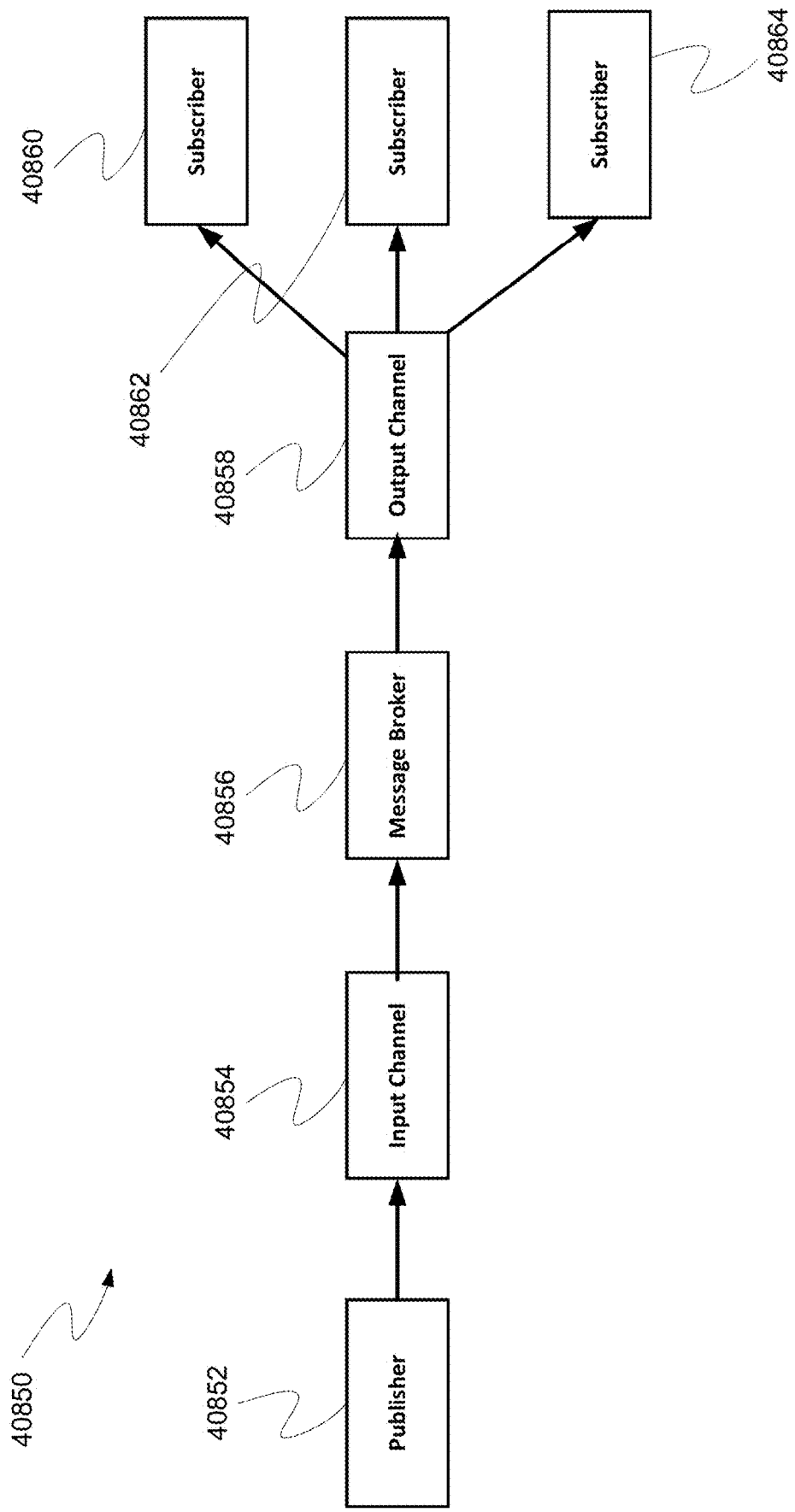
FIG. 22 shows an example of a surgical system that publishes information to a broker.

FIG. 22 shows an example of a surgical system 40850 that publishes information to a broker. The surgical system 40850 may include a publisher 40852. The publisher 40852 may input information via an input channel 40854 to a broker 40856. The broker 40856 may output the information via an output channel 40856 to subscribers 40860, 40862, 40864. In examples, in podcasts, the publisher 40852 (e.g., the content creator) may upload (e.g., publish) the latest version of a podcast to "google podcasts" (e.g., broker 40856). Users that follow or subscribe (e.g., the subscribers 40860, 40862, 40864) to the podcast to the podcast may be alerted that new content is available. The subscribers 40860, 40862, 40864 may then go to "google podcasts" and watch or listen to the content. In examples, surgical hubs may publish the updated list or devices within the operating room boundaries to the broker area. The broker 40856 may ping the connected devices in the operating rooms (e.g., all the operating rooms) that have subscribed to a subject or channel. The devices may pull the information during an idle period and each device may know the others in the operating room.

Systems and/or instrumentalities may be provided for a surgical hub of a surgical system to pair and/or control one or more modules and/or devices located within an operating room. As described in FIG. 3 or FIG. 5, a surgical system may include a surgical hub that is communicatively connected to a plurality of modules, for example, a generator module, a smoke evacuation module, etc. The surgical hub may include a control circuit that may enable the surgical hub for form and/or remove pairings with and/or among devices of the surgical system. The surgical hub may enable the communication module to selectively pair one or more surgical devices that may be used in a surgical procedure.

In an example that involves the situational awareness, the surgical hub may selectively connect or disconnect devices of the surgical system within an operating room based on the type of surgical procedure being performed or based on a determination of an upcoming step of the surgical procedure that requires the devices to be connected or disconnected. The hub situational awareness is described in greater detail below in connection with FIG. 8.

Referring to FIG. 8, the surgical hub may track the progression of surgical steps in a surgical procedure and may coordinate pairing and unpairing of the devices of the surgical system based upon such progression. For example, the surgical hub may determine that a first surgical step requires use of a first surgical instrument, while a second surgical step, occurring after completion of the first surgical step, requires use of a second surgical instrument. Accordingly, the surgical hub may assign a surgical instrument controller to the first surgical instrument for the duration of the first surgical step. After detecting completion of the first surgical step, the surgical hub may cause the communication link between the first surgical instrument and the surgical instrument controller to be severed. The surgical hub may then assign the surgical instrument controller to the second surgical instrument by pairing or authorizing the establishment of a communication link between the surgical instrument controller and the second surgical instrument.

A surgical system may include one or more interconnected surgical hubs that may be connected to one or more edge computing devices and an enterprise cloud system, as described herein in FIG. 1C. The surgical hubs and the computing edge devices may be located within a HIPPA boundary. Each of the surgical hubs may be associated with one or more system modules and/or modular devices (as described in connection with FIG. 3, for example). The system modules may be receivable within a surgical hub and the modular devices or surgical devices or instruments may be connected to the various system modules to connect or pair with the corresponding surgical hub. The connection or paring may be through wired or wireless medium. The modular devices may include intelligent surgical instruments, medical imaging devices, suction/irrigation modules, smoke evacuator module, energy generators, ventilators, insufflators, and surgical hub displays. The modular devices described herein may be controlled by control algorithms or control programs. The control algorithms or control programs may be executed on one or more modular devices, or on one or more surgical hubs to which the modular devices are paired, or on both the modular devices and the surgical hubs, for example, using a distributed computing architecture, as described herein. In an example, control programs associated with the modular devices may control the modular devices based on data sensed by the modular device itself (e.g., by sensors in, on, or connected to the modular device). This data may be related to the patient being operated on (e.g., insufflation pressure) or the modular device itself (e.g., the rate at which a smoke evacuation module is removing gas and particles from the abdomen of a patient).

A plurality of operating rooms located in multiple locations may each be equipped with a surgical hub. The surgical hubs may be connected to one or more edge computing devices. The edge computing devices may be used as an extension of processing and/or storage capabilities of each of the surgical hubs. One of the surgical hubs or the edge computing device may act as a controller that may control interactions between the surgical hubs, the system modules and/or the modular devices associated with each of the surgical hubs. The control interactions between the system modules and/or the modular devices associated with one or more surgical hubs may be based on one of the control schemes including, for example, a cooperative control scheme, a notification control scheme, an antagonistic control scheme, or a hierarchical control scheme. A surgical hub may switch (e.g., adaptively switch) control scheme(s) associated with one or more system modules or one or more modular devices from a first control scheme to a second control scheme.

One or more surgical hubs as well as system modules and/or modular devices associated with the surgical hubs may use cooperative control scheme. In case of a cooperative control scheme, a system module or a modular device may have a functional operation that is part of a linked surgical system. Each of the system modules and/or modular devices that are part of a surgical system may be in communication with the other system modules and/or modular devices. The system modules and/or modular devices may exchange information with the other system modules and/or modular devices thereby having the ability to impact operations of the system modules and/or modular devices associated with the surgical system.

In an example, each of an insufflator system module providing insufflation services and a smoke evacuator system module, as described herein, may have separate and/or independent metering of gas functions. For example, the smoke evacuation system module may be used for removing gas and particles from a patient's abdomen based on the activation and visibility concerns from an energy device. The insufflation system module may be used for pumping $CO_2$ to keep the patient's abdomen inflated, for example, at a predefined pressure. The smoke evacuation system module may be in communication with the insufflation system module. The smoke evacuation system module and the insufflation system module may communicate via a surgical hub or directly over one of the communication interfaces using a peer-to-peer control link (e.g., as described in FIG. 1C and FIG. 24). The smoke evacuation system module and the insufflation system module may set their capacity ranges such that operation of one system does not overwhelm that of the other. In an example, one of the smoke evacuation system modules or one of the insufflation system modules may determine that it may exceed other system module's capacity. For example, the insufflation system module may determine that the highest rate at which it may be able to pump $CO_2$ into the patient's abdomen is less than the rate at which the smoke evacuation system module may remove the $CO_2$ gas and other particles. In such a case, the insufflation system may indicate (e.g., indicate first) to the smoke evacuation system module to reduce its evacuation response in order to better balance the two system modules. The insufflation system may send control messages or control programs (e.g., via the surgical hub or directly) to the smoke evacuation system module indicating to the smoke evacuation system module to reduce its evacuation rate.

One or more surgical hubs as well as system modules or modular devices associated with the surgical hubs may use notification control scheme, for example, to notify (e.g., via a notification message or a control program) a first system module or a modular device about its function to a second system module or a modular device. The first system module or the modular device may send notification messages or control programs to the second system module or modular device without the second system module or modular device being able to change the first system module's or modular device's operation. In an example, the first system module or the modular device may send notification messages or control programs to the second system module or modular device via one of the surgical hubs that may be a part of a surgical system. In an example, the first system module or the modular device may send notification messages or control programs to the second system module or modular device directly, for example, using peer-to-peer control messages.

In an example, a surgical system among other system modules and/or modular devices may include a monopolar generator. A user may request activation of the monopolar generator. A surgical hub that is part of the surgical system may use sensing mechanisms and/or visual mechanisms to initiate activation and pairing of the monopolar generator. The surgical hub may perform the sensing and/or pairing operations based on situational awareness information indicating the use of the monopolar generator in an upcoming step of a surgical procedure. The monopolar generator may send one or more notification messages to other advanced energy modular devices and/or system modules. The notification messages may indicate to the other advanced energy modular devices and/or system modules about the activation and/or the power level of the monopolar generator, for example, to warn the other advanced energy modular devices and/or system modules of the anticipated disruption in their sensing systems while active. The notification messages may also indicate a time interval during which the monopolar generator may be active. The notification messages may act as a warning to the other advanced energy modular devices and/or system modules and enable them to ignore a predefined noise interference that may be caused by the operation of the monopolar generator. The notification messages may also enable the other advanced energy modular devices and/or system modules to not interpret the noise caused by the operation of the monopolar generator as unintended noise and/or unexpected changes, for example, in a system module's monitoring functionality. While the notification messages from the monopolar generator to the other advanced energy modular devices and/or system modules may inform them about the monopolar generator's activation/operation, none of the other advanced energy modular devices and/or system modules in case of notification control scheme may be able to indicate to the monopolar generator to deactivate or activate.

One or more surgical hubs as well as system modules or modular devices associated with the surgical hubs may use an antagonistic control scheme. An antagonistic control scheme may allow a plurality of system modules and/or modular devices contesting for the same system resources to offset each other, thereby changing the balance of the system resources from one system module or modular device to another system module or modular device. In an example, under antagonistic control scheme, the balance of the system resources may be changed based on the priority associated with the task or the priority of the system involved.

In an example, one or more system modules and/or modular devices associated with a surgical system may need additional power, communication, or processing resources while the resources being used by the system modules and/or the modular devices of the surgical system are also being shared with another system module or modular device. For example, a storage module may attempt to upload data to an edge computing device or download data from a cloud service, and an advanced visualization system may also need resources (e.g., computing resources) or the power being used by the storage module to process and/or display the visualization information. In such a case, based on, for example, priority of system module, the system module or the modular device with higher priority may pull the resources that it may share with another system module or the modular device with lower priority. For example, the advanced visualization system over the storage module, the advanced visualization system may pull the resources that it may share with the storage module. Once no longer being utilized by the advanced visualization system, it may return the resources back to the other processes, modules, or devices. The pulling and pushing of resources may imply that there may be a tradeoff between these systems since there is not infinite resources to be shared.

The prioritization of one process, system module, or modular device over other process, system module, or modular device may be based on the importance of the module or function to the task at hand. For example, one or more modules may have inherent higher priority, while performing tasks including, for example, critical (e.g., life critical) tasks, insufflation, etc. In an example, a process, system module, or modular device may have higher priority over another process, system module, or modular device based on external monitored aspects, including for example, surgeon selection, network bandwidth, network down time, or priority value associated with the data, etc.

One or more surgical hubs as well as system modules or modular devices associated with the surgical hubs may use hierarchical control scheme. A hierarchical control scheme may include a hierarchy of control. In an example, a surgical hub may be the main control and decision making element of a surgical system. In another example, the hierarchical control scheme may define a hierarchy (e.g., predefined hierarchy) of system modules, and/or modular devices. In such a case, a system module, or modular device may be configured as the main control and/or decision making element for a set of system modules, or modular devices.

The hierarchical control scheme may be based on a tree with the surgical hub or one of the system modules, or a modular device being a master, and one or more system modules and/or modular device being the subordinate modules and/or modular devices. Control information or control program generated at the surgical hub or the system module acting as a master may be sent to the subordinate system modules and/or modular devices.

In an example, the control interactions between the surgical hub and system modules/modular devices or among the system modules or modular devices on may be based on the type of the system modules/modular devices involved and/or priorities of the processes within the surgical hub that are associated with the system modules and/or modular devices.

Systems and/or instrumentalities may be provided for a surgical hub of a surgical system to pair and/or control one or more modules and/or devices located within an operating room. As described in FIG. 3 or FIG. 5, a surgical system may include a surgical hub that is communicatively connected to a plurality of modules, for example, a generator module, a smoke evacuation module, etc. The surgical hub may include a control circuit that may enable the surgical hub for form and/or remove pairings with and/or among devices of the surgical system. The surgical hub may enable the communication module to selectively pair one or more surgical devices that may be used in a surgical procedure.

In an example that involves the situational awareness, the surgical hub may selectively connect or disconnect devices of the surgical system within an operating room based on the type of surgical procedure being performed or based on a determination of an upcoming step of the surgical procedure that requires the devices to be connected or disconnected. The hub situational awareness is described in greater detail below in connection with FIG. 8.

Referring to FIG. 8, the surgical hub may track the progression of surgical steps in a surgical procedure and may coordinate pairing and unpairing of the devices of the surgical system based upon such progression. For example, the surgical hub may determine that a first surgical step requires use of a first surgical instrument, while a second surgical step, occurring after completion of the first surgical step, requires use of a second surgical instrument. Accordingly, the surgical hub may assign a surgical instrument controller to the first surgical instrument for the duration of the first surgical step. After detecting completion of the first surgical step, the surgical hub may cause the communication link between the first surgical instrument and the surgical instrument controller to be severed. The surgical hub may then assign the surgical instrument controller to the second surgical instrument by pairing or authorizing the establishment of a communication link between the surgical instrument controller and the second surgical instrument.

A surgical system may include one or more interconnected surgical hubs that may be connected to one or more edge computing devices and an enterprise cloud system, as described herein in FIG. 1C. The surgical hubs and the computing edge devices may be located within a HIPPA boundary. Each of the surgical hubs may be associated with one or more system modules and/or modular devices (as described in connection with FIG. 3, for example). The system modules may be receivable within a surgical hub and the modular devices or surgical devices or instruments may be connected to the various system modules to connect or pair with the corresponding surgical hub. The connection or paring may be through wired or wireless medium. The modular devices may include intelligent surgical instruments, medical imaging devices, suction/irrigation modules, smoke evacuator module, energy generators, ventilators, insufflators, and surgical hub displays. The modular devices described herein may be controlled by control algorithms or control programs. The control algorithms or control programs may be executed on one or more modular devices, or on one or more surgical hubs to which the modular devices are paired, or on both the modular devices and the surgical hubs, for example, using a distributed computing architecture, as described herein. In an example, control programs associated with the modular devices may control the modular devices based on data sensed by the modular device itself (e.g., by sensors in, on, or connected to the modular device). This data may be related to the patient being operated on (e.g., insufflation pressure) or the modular device itself (e.g., the rate at which a smoke evacuation module is removing gas and particles from the abdomen of a patient).

A plurality of operating rooms located in multiple locations may each be equipped with a surgical hub. The surgical hubs may be connected to one or more edge computing devices. The edge computing devices may be used as an extension of processing and/or storage capabilities of each of the surgical hubs. One of the surgical hubs or the edge computing device may act as a controller that may control interactions between the surgical hubs, the system modules and/or the modular devices associated with each of the surgical hubs. The control interactions between the system modules and/or the modular devices associated with one or more surgical hubs may be based on one of the control schemes including, for example, a cooperative control scheme, a notification control scheme, an antagonistic control scheme, or a hierarchical control scheme. A surgical hub may switch (e.g., adaptively switch) control scheme(s) associated with one or more system modules or one or more modular devices from a first control scheme to a second control scheme.

One or more surgical hubs as well as system modules and/or modular devices associated with the surgical hubs may use cooperative control scheme. In case of a cooperative control scheme, a system module or a modular device may have a functional operation that is part of a linked surgical system. Each of the system modules and/or modular devices that are part of a surgical system may be in communication with the other system modules and/or modular devices. The system modules and/or modular devices may exchange information with the other system modules and/or modular devices thereby having the ability to impact operations of the system modules and/or modular devices associated with the surgical system.

In an example, each of an insufflator system module providing insufflation services and a smoke evacuator system module, as described herein, may have separate and/or independent metering of gas functions. For example, the smoke evacuation system module may be used for removing gas and particles from a patient's abdomen based on the activation and visibility concerns from an energy device. The insufflation system module may be used for pumping CO2 to keep the patient's abdomen inflated, for example, at a predefined pressure. The smoke evacuation system module may be in communication with the insufflation system module. The smoke evacuation system module and the insufflation system module may communicate via a surgical hub or directly over one of the communication interfaces using a peer-to-peer control link (e.g., as described in FIG. 1C and FIG. 24). The smoke evacuation system module and the insufflation system module may set their capacity ranges such that operation of one system does not overwhelm that of the other. In an example, one of the smoke evacuation system modules or one of the insufflation system modules may determine that it may exceed other system module's capacity. For example, the insufflation system module may determine that the highest rate at which it may be able to pump CO2 into the patient's abdomen is less than the rate at which the smoke evacuation system module may remove the CO2 gas and other particles. In such a case, the insufflation system may indicate (e.g., indicate first) to the smoke evacuation system module to reduce its evacuation response in order to better balance the two system modules. The insufflation system may send control messages or control programs (e.g., via the surgical hub or directly) to the smoke evacuation system module indicating to the smoke evacuation system module to reduce its evacuation rate.

One or more surgical hubs as well as system modules or modular devices associated with the surgical hubs may use notification control scheme, for example, to notify (e.g., via a notification message or a control program) a first system module or a modular device about its function to a second system module or a modular device. The first system module or the modular device may send notification messages or control programs to the second system module or modular device without the second system module or modular device being able to change the first system module's or modular device's operation. In an example, the first system module or the modular device may send notification messages or control programs to the second system module or modular device via one of the surgical hubs that may be a part of a surgical system. In an example, the first system module or the modular device may send notification messages or control programs to the second system module or modular device directly, for example, using peer-to-peer control messages.

In an example, a surgical system among other system modules and/or modular devices may include a monopolar generator. A user may request activation of the monopolar generator. A surgical hub that is part of the surgical system may use sensing mechanisms and/or visual mechanisms to initiate activation and pairing of the monopolar generator. The surgical hub may perform the sensing and/or pairing operations based on situational awareness information indicating the use of the monopolar generator in an upcoming step of a surgical procedure. The monopolar generator may send one or more notification messages to other advanced energy modular devices and/or system modules. The notification messages may indicate to the other advanced energy modular devices and/or system modules about the activation and/or the power level of the monopolar generator, for example, to warn the other advanced energy modular devices and/or system modules of the anticipated disruption in their sensing systems while active. The notification messages may also indicate a time interval during which the monopolar generator may be active. The notification messages may act as a warning to the other advanced energy modular devices and/or system modules and enable them to ignore a predefined noise interference that may be caused by the operation of the monopolar generator. The notification messages may also enable the other advanced energy modular devices and/or system modules to not interpret the noise caused by the operation of the monopolar generator as unintended noise and/or unexpected changes, for example, in a system module's monitoring functionality. While the notification messages from the monopolar generator to the other advanced energy modular devices and/or system modules may inform them about the monopolar generator's activation/operation, none of the other advanced energy modular devices and/or system modules in case of notification control scheme may be able to indicate to the monopolar generator to deactivate or activate.

One or more surgical hubs as well as system modules or modular devices associated with the surgical hubs may use an antagonistic control scheme. An antagonistic control scheme may allow a plurality of system modules and/or modular devices contesting for the same system resources to offset each other, thereby changing the balance of the system resources from one system module or modular device to another system module or modular device. In an example, under antagonistic control scheme, the balance of the system resources may be changed based on the priority associated with the task or the priority of the system involved.

In an example, one or more system modules and/or modular devices associated with a surgical system may need additional power, communication, or processing resources while the resources being used by the system modules and/or the modular devices of the surgical system are also being shared with another system module or modular device. For example, a storage module may attempt to upload data to an edge computing device or download data from a cloud service, and an advanced visualization system may also need resources (e.g., computing resources) or the power being used by the storage module to process and/or display the visualization information. In such a case, based on, for example, priority of system module, the system module or the modular device with higher priority may pull the resources that it may share with another system module or the modular device with lower priority. For example, the advanced visualization system over the storage module, the advanced visualization system may pull the resources that it may share with the storage module. Once no longer being utilized by the advanced visualization system, it may return the resources back to the other processes, modules, or devices. The pulling and pushing of resources may imply that there may be a tradeoff between these systems since there is not infinite resources to be shared.

The prioritization of one process, system module, or modular device over other process, system module, or modular device may be based on the importance of the module or function to the task at hand. For example, one or more modules may have inherent higher priority, while performing tasks including, for example, critical (e.g., life critical) tasks, insufflation, etc. In an example, a process, system module, or modular device may have higher priority over another process, system module, or modular device based on external monitored aspects, including for example, surgeon selection, network bandwidth, network down time, or priority value associated with the data, etc.

One or more surgical hubs as well as system modules or modular devices associated with the surgical hubs may use hierarchical control scheme. A hierarchical control scheme may include a hierarchy of control. In an example, a surgical hub may be the main control and decision making element of a surgical system. In another example, the hierarchical control scheme may define a hierarchy (e.g., predefined hierarchy) of system modules, and/or modular devices. In such a case, a system module, or modular device may be configured as the main control and/or decision making element for a set of system modules, or modular devices.

The hierarchical control scheme may be based on a tree with the surgical hub or one of the system modules, or a modular device being a master, and one or more system modules and/or modular device being the subordinate modules and/or modular devices. Control information or control program generated at the surgical hub or the system module acting as a master may be sent to the subordinate system modules and/or modular devices.

In an example, the control interactions between the surgical hub and system modules/modular devices or among the system modules or modular devices on may be based on the type of the system modules/modular devices involved and/or priorities of the processes within the surgical hub that are associated with the system modules and/or modular devices.

Figure 23:
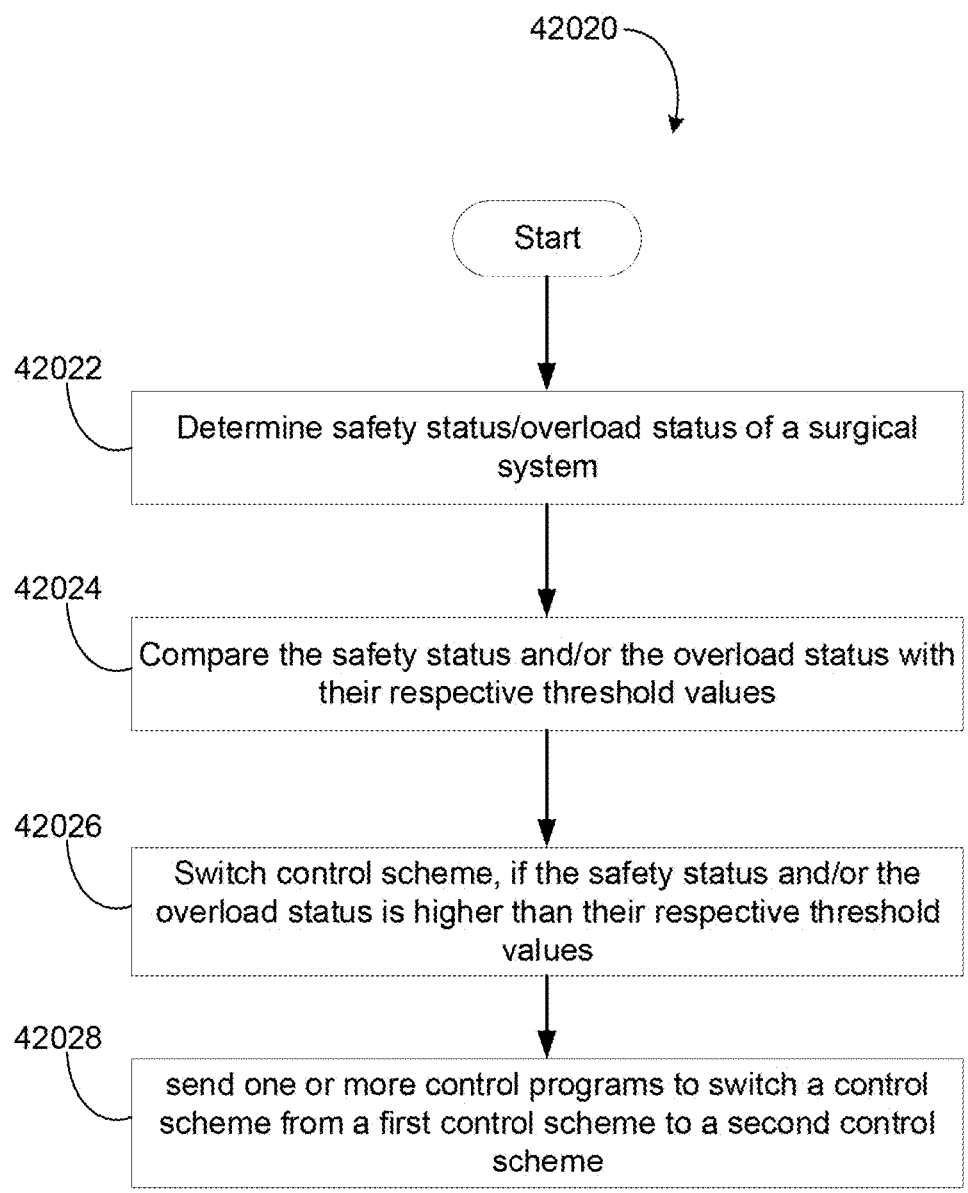
FIG. 23 is a flow diagram illustrating switching of control scheme.

FIG. 23 illustrates an example 42020 of a surgical hub switching a control scheme from a first control scheme to a second control scheme. At 42022, a surgical hub or a master system module or a master modular device may determine safety status and/or overload status of a surgical system. At 42024, the surgical hub or the master system module or the master modular device may compare the safety status and/or the overload status with their respective threshold values (e.g., a predetermined threshold values). At 42026, the surgical hub or the master system module or the master modular device may make a determination of switching the control scheme associated with the surgical hub and/or the modular devices, for example, if the safety status and/or the overload status of the surgical system risk is higher than the respective threshold values. At 42028, the surgical hub or the master system module or the master modular device may send one or more control programs to switch a control scheme from a first control scheme (e.g., a notification control scheme) to a second control scheme (e.g., a hierarchical or an antagonistic control scheme). The switching of the control schemes may be performed, for example, to prevent the system from exceeding maximum limits of the system (e.g., maximum limits of the surgical hub).

Examples described herein may relate to the interconnection of system modules and/or modular devices. The interconnection may include one or more of the following connection types: individual, redundant, smart, or dumb.

Figure 24:
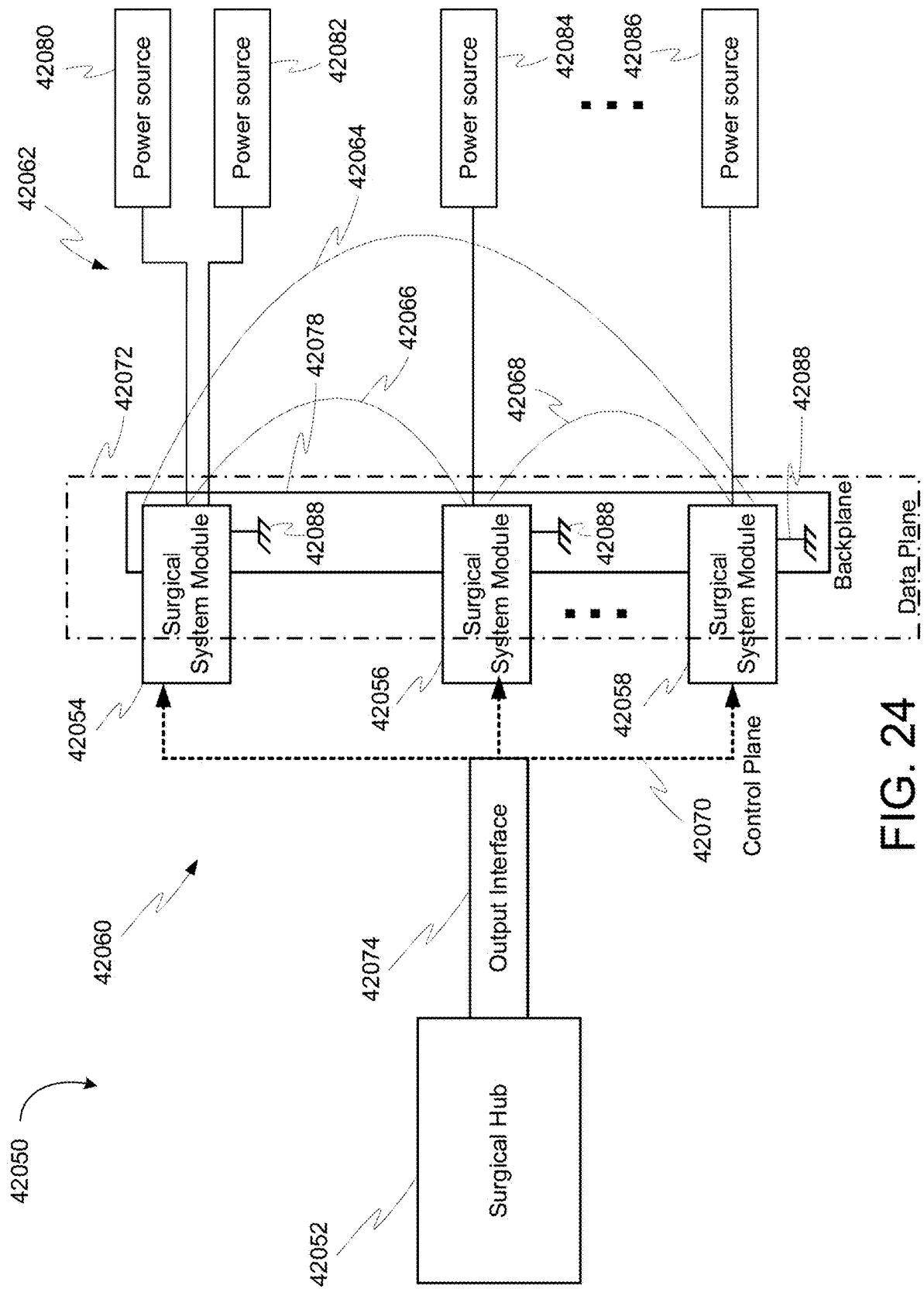
FIG. 24 illustrates an example of a surgical system with physical and communication connections among the surgical system modules, and between the surgical system modules and a surgical hub.

FIG. 24 shows an example of a surgical system 42050 with physical and communication connections between surgical system modules and a surgical hub. The surgical system 42050 may include one or more surgical hubs (e.g., a surgical hub 42052) and one or more surgical system modules (e.g., surgical system modules 42054, 42056, 42058). The surgical hub 42052 may have the capacity for the surgical system modules 42054, 42056, 42058 to be cumulatively coupled via a first port 42060 as well as directly coupled via a second port 42062 simultaneously. The interconnectivity of the surgical system modules 42054, 42056, 42058 may enable some of the surgical system modules 42054, 42056, 42058 to work cooperatively with the exclusion of some of the other surgical system modules 42054, 42056, 42058 or receive data and control from multiple surgical system modules 42054, 42056, 42058 simultaneously. The first port 42060 may include a control plane 42070, a data plane 42072, and a backplane 42078 that facilitate data communication between each of the surgical system modules 42054, 42056, 42058 and the surgical hub 42052. The second port 42062 may be external wired connections 42064, 42066, 42068 connecting each of the surgical system modules 42054, 42056, 42058 to each other separate from the first port 42060. The surgical hub 42052 may include an output interface 42074 that may interface with each of the surgical system modules 42054, 42056, 42058. The connections between the surgical system modules 42054, 42056, 42058 and the surgical hub 42052 may not be the same performance level. In examples, some of the connections between the surgical system modules 42054, 42056, 42058 may provide redundant pathways of communication that may be used cooperatively. In examples, there may be daisy chain coupling of surgical system modules 42054, 42056, 42058. There may be a coupling hierarchy based on critical functionality of certain surgical system modules.

In examples, the surgical system 42050 may provide one-way monitoring communication for use in controlling aspects of another smart system. In an example, one or more of the surgical system modules 42054, 42056, 42058 may be non-smart surgical system modules, semi-smart surgical system modules, smart surgical system modules, and/or intelligent surgical system modules.

In an example, the surgical system 42050 may include a dumb (or non-smart) surgical system module that may be connected to other surgical system modules. The dumb surgical system module may be power independent and connected to its own power source. For example, surgical system module 42056 may have its own power source 42084 that is separate from the other power sources 42080 and 42082, or 42086 that powers other surgical system modules 42054 or 42058 respectively.

In an example, the surgical system 42050 may include a non-smart surgical system module that may be connected to other surgical system modules. The non-smart surgical system module may be power independent from the surgical system modules connected to the surgical hub 42052. The non-smart module may have one way data flow with minimal communications with the surgical system modules.

In an example, the surgical system 42050 may include of a semi-smart surgical system module that may be connected to other surgical system modules. The semi-smart surgical system module may include two way communication with the surgical system modules. The semi-smart surgical system module may monitor the input power. The semi-smart surgical system module may have minimal command and control of its functions.

In an example, the surgical system 42050 may include a smart surgical system module that is connected to the other surgical system modules. The smart surgical system module may include two way communication with the surgical system modules which may include a bipolar generator. The smart surgical system module may have enhanced command and control of its functions. The smart surgical system module may monitor its inputs and outputs.

In other examples, the surgical systems described herein may include an intelligent surgical system module. The intelligent surgical system module may include multiple communication paths. The intelligent surgical system module may have full command and control of its functions.

The surgical system 42050 may provide integrated monitoring enabling non-smart surgical system modules to be used with smart surgical system modules. The integrated monitoring may include monitoring for the interference of non-smart surgical system modules during the activation of smart surgical system modules. This may prevent accidental simultaneous energy activation of non-smart surgical system modules and smart surgical system modules. In examples, the integrated monitoring may prevent a portion of the non-smart surgical system modules and the smart surgical system modules from activating simultaneously. For example, the ultrasonic advanced energy portion of a smart surgical system module may be used in combination with a monopolar radio frequency application from another surgical system module while preventing the smart surgical system module's radio frequency portion to be used simultaneously with the monopolar radio frequency application. For example, the surgical system module 42054 may be a non-smart surgical system module and surgical system module 42056 may be a smart surgical system module. The surgical system modules 42054 and 42056 may work independently from one another or together during certain times of certain surgical procedures. The smart module may incrementally control the non-smart module. In examples, the surgical system modules 42054, 42056 may be a generator and smoke evacuator respectively. The generator may generate a step electrical potential output to indicate the increase airflow, the activation of the energy device to increment the smoke evacuator, or the increase/decrease of speed without other cooperative communication.

In an example, one of the surgical system modules, for example, surgical system module 42054 may have an ability to be connected to more than one (e.g., two) power sources 42080 and 42082. The surgical system module 42054 may be receivable in a backplane with two outlets where the power sources 42080 and 42082 may be available for connection. The power sources 42080 and 42082 may be connected to the two outlets of the backplane. Each of the power sources 42080 and 42082 may be a part of an independent power circuit. The independent power circuits may be in communication or isolated from each other. Each of the power sources 42080 and 42082 may be an AC power source or a DC power source. In an example, the surgical hub 42052 or the surgical system module 42054 may determine that the surgical system module 42054 to be powered on may require power from both the available power sources 42080 and 42082. In such an example, based on at least that the surgical system module 42054 may require power from both the available power sources 42080 and 42082, the surgical system module 42054 may be powered using both the power sources 42080 and 42082.

The surgical system 42050 (as illustrated in FIG. 24) may include a configuration to a surgical hub port available when the surgical modules 42054, 42056, 42058 in communication with the surgical hub 42052 by sharing a bus. Each surgical module 42054, 42056, 42058 may have a specific identification. The surgical modules 42054, 42056, 42058 may be in close proximity to each other to align well with a serial protocol. In examples, the surgical system 42050 may be set up in a primary source/secondary source configuration. The surgical hub 42052 may be the primary source and the surgical modules 42054, 42056, 42058 may be the secondary sources. The surgical hub 42052 may be connected to the surgical modules 42054, 42056, 42058 via a first port 42060. The surgical modules 42054, 42056, 42058 may directly connect to each other via a second port 42062. Extra cables 42064, 42066, 42068 may allow data pass from the surgical modules 42054, 42056, 42058. Although the extra cables 42064, 42066, 42068 are shown in the figure to be connected via the backplane 42078, in some cases, the extra cables 42064, 42066, 42068 may be connected between the surgical modules 42054, 42056, 42058 on the front side of the surgical modules 42054, 42056, 42058.

In an example, the extra cables 42064, 42066, 42068 may be enabled to establish an analog connection between the surgical system modules 42054, 42056, 42058, for example, by sensing analog aspects of the connection. In an example, the extra cables 42064, 42066, 42068 may be configured to establish a digital connection between the surgical system modules 42054, 42056, 42058.

In an example, the communication interface between the surgical system modules 42054, 42056, 42058 may be configured to establish a serial connection via a serial bus using a serial protocol. In an example, the communication interface between the surgical system modules 42054, 42056, 42058 may be configured to establish a communication path using for example a serial peripheral interface (SPI). In an example, multiple communication paths may be established, for example, one communication pathway (e.g., the primary communication pathway) may be a SPI communication bus between the surgical hub 42052 and the surgical system modules 42054, 42056, 42058. A secondary communication pathway may be established using a surgical module to surgical module serial bus.

In an example, data may pass to the surgical hub 42052 via the second port 42062. In examples, the data may not pass to the surgical hub 42052 via the second port 42062. Certain functions and data transfers may be isolated from the surgical hub 42052 via the second port 42062. Certain functions and data transfers may be communicated to the surgical hub 40602 via the first port 42060. In examples, the second port 42062 between each of the surgical modules 42054, 42056, 42058 may be an additional slow communication portal. In examples, the second port 42062 may include an auxiliary data path from a surgical module 42054, 42056, 42058 to the surgical hub 42052.

In an example, each of the surgical system modules 42054, 42056, 42058 and the backplane 42078 may be connected to a common ground 42088. In an example, the surgical hub may detect that the one of the surgical system modules 42054 may not be connected to the common ground 42088 and/or the connection to common ground is interrupted. The surgical system module 42054 may send a notification message via the control plane 42070 to the surgical hub 42052. The surgical hub may then present (e.g., display) the control plane message to a user or an HCP.

In an example (e.g., when a new surgical procedure is initiated), after detecting that the surgical system module 42054 is not connected to the common ground 42088, the surgical system module 42054 may be disabled. The surgical system module 42054 may be disabled based on a control program received by the surgical system module 42054 from the surgical hub 42052.

In an example (e.g., when a surgical procedure is being performed), after detecting that the surgical system module 42054 is not connected to the common ground 42088, the surgical system module 42054 may not be disabled. The surgical system module 42054 may be disabled once the surgical procedure being performed ends or based on situational awareness and/or surgical plan, the surgical hub 42052 determines that the module will no longer be needed during the ongoing surgical procedure.

Systems and methods may be provided for handling loss of communication between the surgical hub and the system modules/modular devices or between the system modules/modular devices. In an example, either the surgical hub or one or more of the system modules and/or the modular devices associated with a surgical system may detect a loss of communication. The loss of communication may be detected based on interrupted and/or irregular communications on one or more communication modules associated with a system module or modular device. A loss of communication, for example, detected by a system module or a modular device may be indicated using a visual, audio, or an audiovisual indication. The indication of an alarm may be based on the severity of the communication loss. For example, a total loss of communication on a critical surgical system module may be indicated by all means possible including, for example, providing the information to one or more HCPs via the main display or other displays present in an OR.

Figure 25:
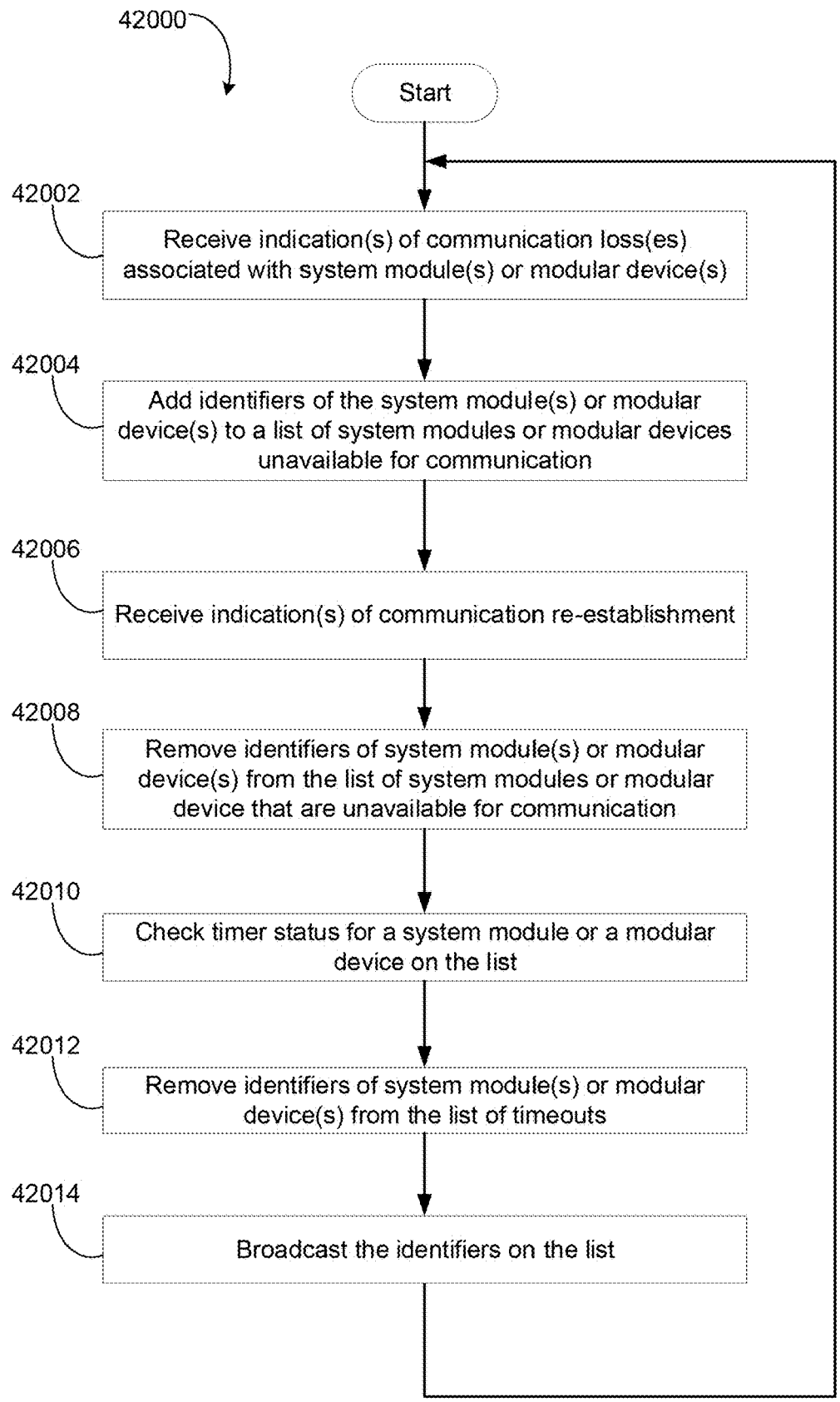
FIG. 25 is a flow diagram illustrating an exemplary process of a loss of communication between system modules and/or modular devices.

FIG. 25 illustrates processing of a loss of communication between system modules and/or modular devices, 42000. At 42002, a surgical hub may receive, from one or more system modules or modular devices, one or more indication(s) of communication loss(es) associated with a system module or a modular device. At 42004, the surgical hub may add identifiers associated with the system modules or modular devices to a list of system modules or modular devices that are unavailable for communication. The surgical hub may send (e.g., as a broadcast or a unicast message) the updated list of system modules or modular devices that are unavailable for communication to other system modules or modular devices and/or a display unit for displaying the loss of communication of a system module or a modular device.

At 42006, the surgical hub may receive, from one or more system modules or modular devices, one or more indication(s) of communication re-establishment of a communication loss associated with a system module or a modular device. At 42008, the surgical hub may remove identifiers associated with the system modules or modular devices from the list of system modules or modular devices that are unavailable for communication. The surgical hub may then send (e.g., as a broadcast or a unicast message) the updated list of system modules or modular devices that are unavailable for communication to other system modules or modular devices and/or a display unit for displaying the loss of communication of a system module or a modular device. In an example, the surgical hub, based on situational awareness and/or locational awareness, may determine that the system module or the modular device with loss of communication is to be used in a critical step of a surgical procedure. The surgical hub may escalate the severity associated with a loss of communication state of the system module or the modular device. The surgical hub may send the escalated loss of communication status message associated with the system module or the modular device to the main display for immediate attention.

The surgical hub (e.g., using an identifier) may start a timer associated with a system module or a modular device. For example, the surgical hub may start a timer a communication loss or communication re-establishment associated with a system module or a modular device. At 42010, the surgical hub may check the timer status associated with the system module or the modular device. At 42012, the surgical hub may remove an identifier associated with the system module or the modular device, for example, if the timer associated with the system module or the modular device crosses a threshold (e.g., a predefined threshold). At 42014, the surgical hub may send (e.g., broadcast) the identifiers on the list on of system modules or modular device that are unavailable for communication to other surgical hubs, system modules, modular device, and/or display devices.

In an example of a system module or a modular device with redundant communication connections that reports a communication loss regarding one of its redundant communication connections, the surgical hub may send a control program to the system module or the modular device to activate and/or use the second available communication connection. In an example, a system module or a modular device may autonomously activate the second available communication connection, for example, after detecting a loss of communication one of the communication connections.

In an example, after detecting a loss of communication on one of the communication interfaces, a system module or a modular device may continue to operate in the last connected state.

Surgical procedures may be performed by different HCPs at different locations. For a given surgical procedure, one or more system modules, modular devices and/or one or more parameters associated with the system modules or modular devices that are part of a surgical system may be selected, for example, as an attempt to realize a desired outcome. In an example, for a given surgical procedure which utilizes energy supplied by a generator, an HCP may rely on experience for determining a modular device or a mode of a modular device to utilize, the output power level to utilize, the application duration of the energy, etc., in order to attempt to realize the desired outcome. To increase the likelihood of realizing desired outcomes for a plurality of different surgical procedures, each HCP may be provided with best practice recommendations, system module and/or modular device selection, and/or settings for the system modules and/or the modular devices. Such a selection of best practice recommendations, system modules and/or modular device selection, and/or settings for the system modules and/or modular devices may be based on relationships (e.g., important relationships) identified within large, accurate data sets of information associated with multiple surgical procedures performed in multiple locations over time.

In an example, a surgical hub may identify an optimized or a preferable combination of system modules and/or modular devices and/or configuration associated with the system modules and/or modular devices for a surgical procedure. The system modules and/or modular devices may be plugged into the surgical system. The system modules and/or modular devices may be wirelessly connected to the surgical hub or may be present within the surgical hub's surroundings (e.g., within an OR) ready to be connected to the surgical hub. The surgical hub may identify the optimized or the preferable combination of system modules and/or modular devices and their configuration based on one or more of the following: the interfacing system modules and/or modular devices, the awareness of the surgical procedure plan, the surgical procedure type (e.g., thoracic vs colorectal), and a surgeon's previous preferences. In an example, the surgical hub may identify the optimized or the preferable combination of system modules and/or modular devices and their configuration based on a risk/harm database.

Figure 26:
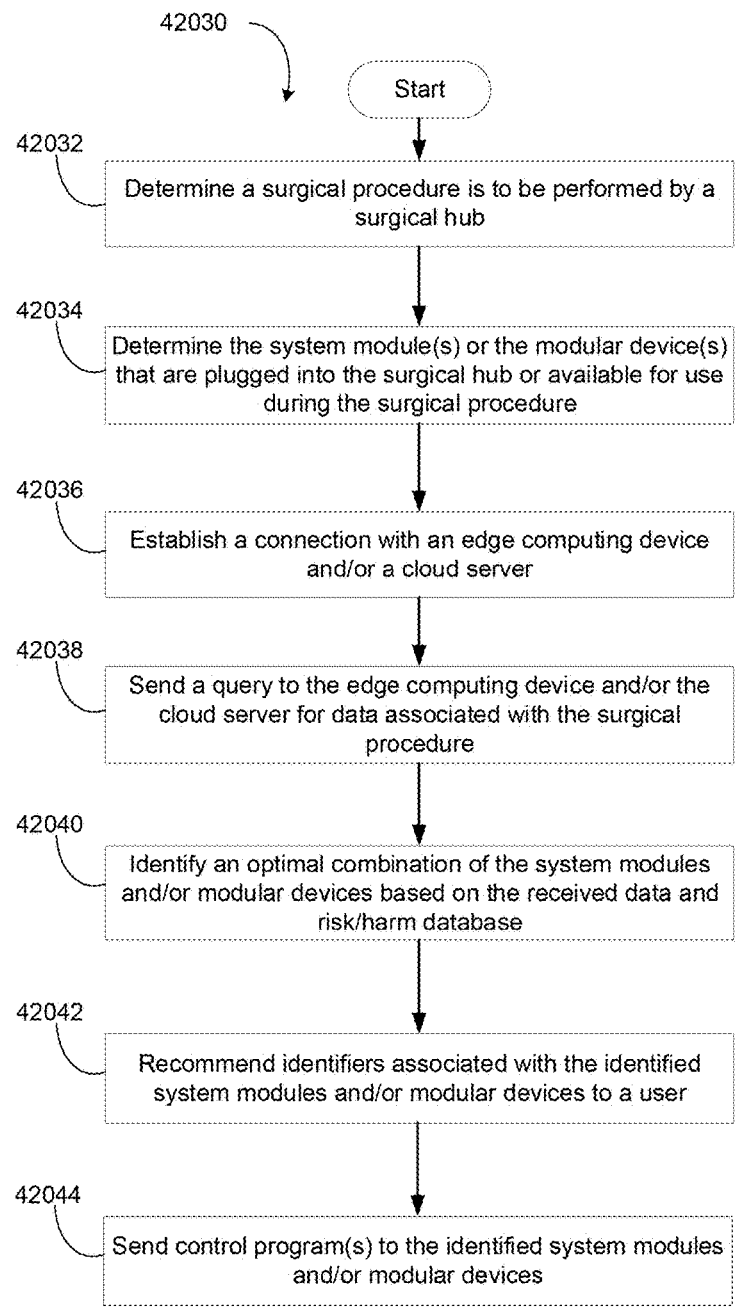
FIG. 26 is a flow diagram illustrating an example of a surgical hub identifying an optimal combination of system modules and/or modular devices.

FIG. 26 illustrates an example of a surgical hub identifying an optimal combination of system modules and/or modular devices. At 42032, a surgical hub may determine that a surgical procedure is to be performed by the surgical hub in an OR.

At 42034, the surgical hub may determine the system modules and/or modular devices that may be plugged into a surgical system including the surgical hub or available for use during the surgical procedure. At 42036, the surgical hub may establish a connection with an edge computing device and/or a cloud server.

At 42038, the surgical hub may send a query to the edge computing device or the cloud server requesting for surgical procedure data associated with the surgical procedure. At 42040, the surgical hub may identify an optimal combination of the system modules and/or the modular devices to be used for performing the surgical procedure. The surgical hub may identify the optimal combination of the system modules and/or the modular devices to be used for performing the surgical procedure at least based on the surgical procedure to be performed, the location of the surgical hub and/or where the surgical procedure is being performed, and/or the surgical procedure data received from the server. The optimal combination identified may further be based on a database identifying the risks/harms associated with the combination. For example, a surgical hub may identify three energy devices plugged or available for use during a surgical procedure—an ultrasonic energy generator, a bipolar RF energy generator, and a monopolar RF energy generator.

At 42042, the surgical hub may provide a recommendation including identifiers associated with the optical combination of the system modules and/or modular devices to the user (e.g., an HCP).

The surgical hub may determine whether it is configured with the identified optimal combination of the system modules and/or the modular devices. At 42044, the surgical hub may send control programs to the identified system modules and/or modular devices, for example, if the surgical hub determines that it is not configured with the identified optimal combination of the system modules and/or the modular devices.

Medical facilities may contain multiple operating rooms where the operating rooms may be designated for specific medical specialties such as thoracic surgery. Healthcare professionals (HCPs) may use predefined locations within the facility and a predefined set of operating rooms based on the surgery type. Surgical specialties may have a typical instrument mix combined with a set of advanced devices and capital based on the anatomy that is the focus of the surgery. For example, surgical equipment used and/or prepared for a thoracic surgery may be different from the surgical equipment used and/or prepared for a colorectal surgery.

Operating rooms may use procedure-specific surgical hub systems based on the type of surgery. For example, a local hub system for a thoracic operating room may be different from a local hub system for a colorectal operating room. The procedure-specific surgical hub system may include data related to the specific procedure (e.g., thoracic-specific data) such as data of simulations, procedure plans, best-practices, example videos (e.g., for surgical steps), and/or the like.

Hybrid operating rooms may be a specialty operating room that may include a combination of specialized imaging equipment in addition to normal operating room equipment. Robotic theaters may be a specialty operating room with dedicated specialized equipment. Specialty operating rooms may be used based on scheduling. The specialty operating rooms may not contain surgery specific surgical hubs for a given procedure. For example, a thoracic surgery may be scheduled for the specialty operating room, but the specialty operating room may not contain a thoracic hub. A procedure-specific surgical hub may be transported to the specialty operating room. The movement of surgical hubs may interrupt the normal networks, storage, and access of localized data from a group.

Figure 27:
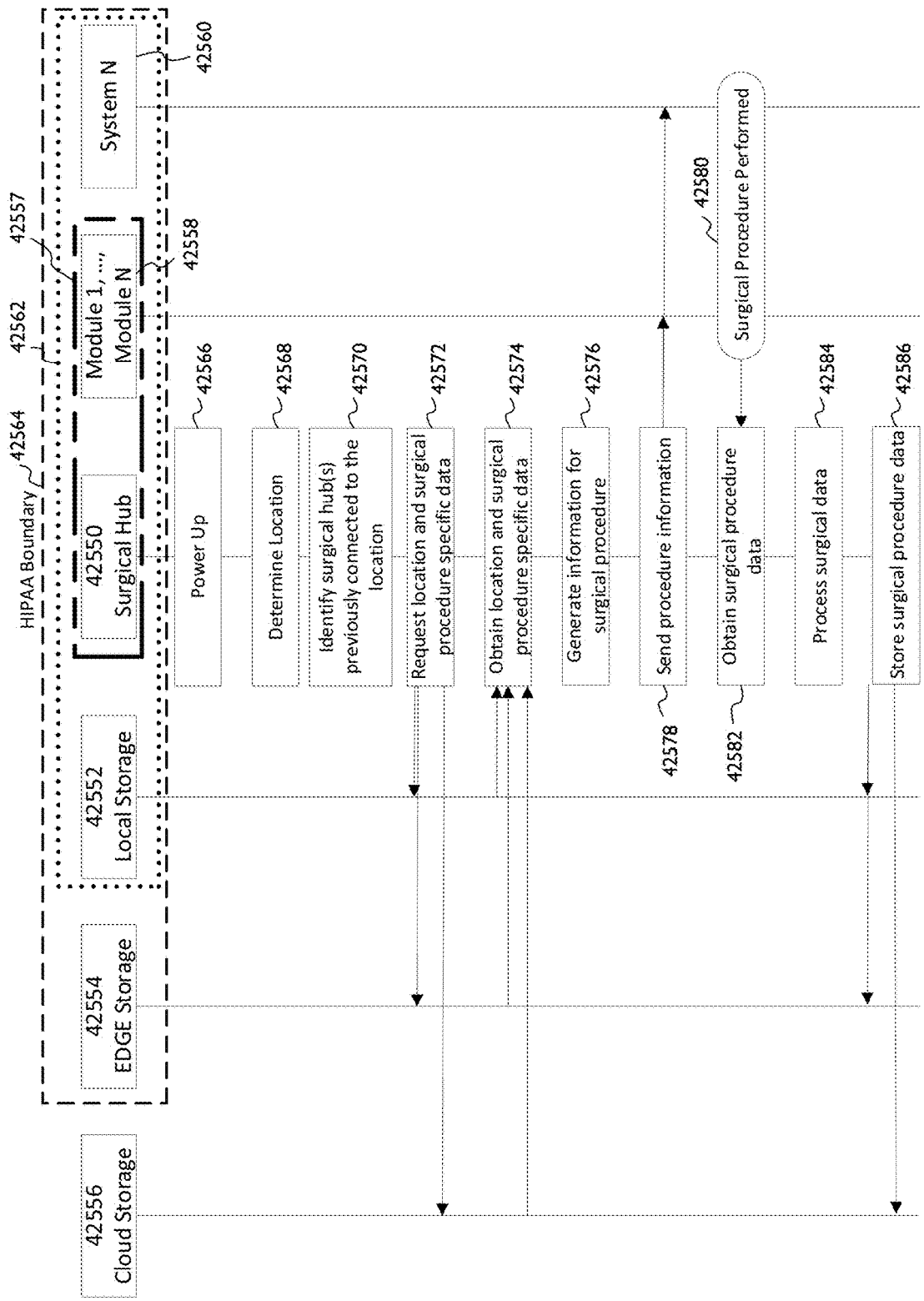
FIG. 27 is an example sequence diagram of a computing system receiving and storing location and surgical procedure specific data.

FIG. 27 is an example sequence diagram of a computing system receiving and storing location and surgical procedure specific data. A surgical computing system may be a surgical hub 42550. The surgical hub 42550 may communicate with one or more data storages to obtain and/or store data. The one or more data storages may include a local storage 42552, an edge network storage 42554, and/or a cloud network storage 42556. The surgical hub 42550 that is part of a first surgical system 42557 may communicate with other surgical systems 42560 (e.g., surgical hubs and/or modules associated with other surgical systems) or modules 42558 associated with the surgical systems. The surgical hub 42550 may be located within an operating room 42562. The operating room 42562 may include the surgical hub 42550, local storage 42552, modules 42558, and/or surgical system 42560. The operating room 42562 and the edge network storage 42554 may be located within a HIPAA boundary 42564. A Health Insurance Portability and Accountability Act (HIPAA) boundary 42564 may prevent private data from being communicated outside of a medical facility, for example, without proper redaction of the private information. The cloud storage 42556 associated with the surgical system may be located outside of the HIPAA boundary 42564, as illustrated in FIG. 27.

The computing system (e.g., a surgical computing system) and/or surgical hub 42550 may include a surgical hub 20002 as described herein with respect to FIG. 2. For example, the surgical computing system may include at least one of the following: a surgical hub 20006 in communication with a cloud computing system 20008, for example, as described in FIG. 2. The surgical computing system may include at least one of the following: a surgical hub 20006 or a computing device 20016 in communication with a cloud computing system 20008. The computing system may be or may include an HCP monitoring system such as the HCP monitoring system 20000, 20002, 20003, or 20004 as described herein with respect to FIGS. 1-3. The computing system may be a computing system operatively connected to the HCP monitoring system(s) 20000, 20002, 20003, and/or 20004. The computing system may be or may include the computing system 20271 described herein with respect to FIG. 27. The computing system may be or may include the computer system 20063 described herein, for example, with respect to FIG. 4.

The data storage(s) may be a local data storage 42552, an edge network storage 42554, a cloud network storage 42556, a surgical hub storage, a medical department storage, and/or the like. The data storage(s) may be located within the HIPAA boundary 42564. For example, the data storages located within the medical facility, such as the local storage 42552, edge network storage 42554, surgical hub storage, medical department storage, may be located within the HIPAA boundary 42564. The cloud network storage 42556 may be located outside the HIPPA boundary 42564. The cloud network storage 42556 may include or may be the remote cloud storage unit 20010 as described herein with respect to FIG. 2.

The HIPAA boundary 42564 may refer to an area where electronic health care transactions, such as data transfer, may be subject to the Health Insurance Portability and Accountability Act (HIPAA). HIPAA may establish baseline safeguards for ensuring confidentiality, integrity, and availability of protected health information (PHI). PHI may include personally identifiable information, such as mental health history, healthcare services, payments for healthcare, and/or other identifiable information (e.g., patient's name, address, or Social Security number). Protected health information (PHI) may undergo redaction and/or removal of identifying information. Data with PHI transferred outside of the HIPAA boundary must remove and/or redact the PHI associated with the data. Processing of private data may be performed within the HIPAA boundary, for example. For example, surgical hubs within the medical facility and HIPAA boundary may transfer data between themselves without removing and/or redacting PHI because it is within the HIPPA boundary. For example, a surgical hub transferring data to a cloud network outside the HIPPA boundary may perform a check that the PHI associated with the data is removed and/or redacted before the transfer.

The surgical hub 42550 may be connected to multiple modules 42558. The surgical hub 42550 and modules 42558 may be included within the first surgical system 42557. The modules may be or may be included within a hub modular enclosure, which may be the hub modular enclosure 20060 as described herein with respect to FIG. 3. The modules 42558 may be one or more of an imaging module, generator module, smoke evacuation module, suction/irrigation module, communication module, processor module, storage array module, operating room mapping module, and/or the like, as described herein with respect to FIG. 3. The hub modular enclosure may facilitate communication between the modules within the hub modular enclosure. The surgical hub may communicate the various connected modules, for example, to perform a surgical procedure.

The surgical hub 42550 and/or first surgical system 42557 may be connected to multiple external surgical systems 42560. The external surgical systems may include surgical equipment, surgical instruments, other surgical hubs, sensing systems, monitoring systems, and/or the like. For example, the external surgical systems 42560 may be or may include any of the surgical systems as described herein with respect to FIG. 2. For example, the external surgical systems may include sensing systems such as patient sensing systems, surgeon sensing systems, environmental sensing systems, and/or the like. The external surgical systems may include other surgical hubs, for example, that may be located in a different operating room.

As shown at 42566 in FIG. 27, a surgical hub may be powered up. At 42568, the surgical hub may determine its geographic location, which may be an operating room (OR), for example. At 42570, the surgical hub may identify surgical hubs previously connected to the geographic location. For example, a previously connected surgical hub may have been used for a surgical procedure in the OR previously. The previously connected surgical hub may be currently connected at a different geographic location, such as a different OR or a specialized OR. At 42572, the surgical hub may send a request for location and/or surgical procedure specific data, for example, from one or more data storages. At 42574, the surgical hub may obtain the requested location and/or surgical procedure specific data. At 42576, the surgical hub may generate information for performing a surgical procedure, for example, using the obtained location and surgical procedure specific data. At 42578, the surgical hub may send the procedure information (e.g., in the form of a control program to modules or external systems). At 42580, a surgical procedure may be performed. At 42582, the surgical hub may obtain surgical procedure data associated with the surgical procedure being performed. At 42584, the surgical hub may process the surgical procedure data. At 42586, the surgical hub may send the surgical procedure data for storage, for example, to one or more data storages.

The surgical hub may determine its geographic location. The geographic location may be located within the medical facility. For example, the geographic location may be located on a specific floor in the medical facility. The geographic location may be associated with a medical department or medical specialty, such as the thoracic, colorectal, or bariatric department, for example. The geographic location may be an operating room. The operating room may be associated with a designated surgical procedure. For example, the surgical hub may determine its geographic location to be in an operating room designated for hysterectomies.

The surgical hub may determine its geographic location, for example, based on nearby surgical systems. For example, the surgical hub may identify surgical equipment and/or surgical instruments that are located nearby or connected to the surgical hub. The surgical hub may identify a medical practice area associated with the surgical instrument mix and/or surgical equipment. For example, the surgical hub may determine that its geographic location is a hybrid-OR based on the presence of specialized imagine equipment and normal OR equipment. For example, the surgical hub may determine that its geographic location is a robotic theater.

The surgical hub may determine and/or identify a second surgical hub. For example, the surgical hub may determine and/or identify a second surgical hub that was previously located in the geographic location that the surgical hub is located. The second surgical hub may have been previously located in an OR but moved to a hybrid-OR, and the surgical hub replaced the second surgical hub in the OR. The surgical hub may determine and/or identify the second surgical hub based on the determined geographic location. The surgical hub may determine and/or identify previously connected surgical hubs and/or devices that were connected or located in the determined geographic location.

For example, a main surgical hub may be associated with an OR, such as a thoracic surgery OR. The main surgical hub may be moved to a hybrid-OR, for example, to enable imaging to be used in combination with the main hub for surgery. A rotating surgical hub may be moved into the thoracic surgery OR to replace the main surgical hub while the main surgical hub is in the hybrid-OR. The rotating hub may power up in the thoracic surgery OR, and the rotating hub may determine and/or identify its geographic location. The rotating hub may determine/identify surgical hubs previously located in that thoracic surgery OR using the geographic location. For example, the rotating hub may determine/identify the main surgical hub as being previously located within the same thoracic surgery OR.

The surgical hub may send a request for location and surgical procedure specific data. Location and surgical procedure specific data may be data associated with a geographic location, for example, where the data may have been generated. For example, the location and surgical procedure specific data may be associated with a particular OR, such as a thoracic surgery OR. The location and surgical procedure specific data may be data associated with a specific surgical procedure, such as a hysterectomy, for example. The location and surgical procedure specific data may be data generated from a surgical procedure (e.g., previously performed surgical procedure) in a geographic location. The location and surgical procedure specific data may include data pertaining to a medical practice area, such as colorectal surgeries.

For example, the location and surgical procedure specific data may be data generated from a surgical instrument during a colorectal surgery in a specific operating room. For example, a surgical procedure, such as a colorectal surgery, may be performed in an OR. Surgical procedure data may be generated based on the surgical procedure. The surgical procedure data may be tagged with data indicating the procedure performed and the geographic location that the procedure was performed. The surgical procedure data may be associated with metadata indicating the procedure performed and the geographic location that the procedure was performed. The surgical procedure data may be linked back to the surgical procedure performed and the geographic location.

The location and surgical procedure specific data may include data associated with sensing systems, such as patient sensing systems, surgeon sensing systems, environmental sensing systems, and/or the like. The data associated with the patient sensing systems and/or surgeon sensing systems may include biomarker data, movement data, positioning data, and/or the like. For example, the location and surgical procedure specific data may include heart rate biomarker data generated during a surgical procedure in a particular OR. The heart rate biomarker data may be tagged with the geographic location and surgical procedure, for example, for future reference and/or analysis.

The location and surgical procedure specific data may be associated with a surgeon. For example, the location and surgical procedure specific data may be associated with the surgical procedures performed by a particular surgeon. The location and surgical procedure specific data may include the surgeon's preferences, surgical instrument settings used for a surgical procedure, procedure simulations and plans viewed by the surgeon, videos, annotations, and/or transcriptions associated with the surgeon, and/or the like. For example, the surgeon may use a particular set of surgical instrument settings for a surgical procedure. The location and surgical procedure specific data may include the particular set of surgical instrument settings. For example, the location and surgical procedure specific data may include surgeon preferences for the procedure, OR setup layout and plans, instrument instructions for use, local area network topography and equipment for cooperative access, procedure simulations and plans, specific patient data for upcoming or previous surgeries, example videos, annotations, transcriptions for the surgery, algorithms, transformations, analyses, and applications relative to specialized equipment in the OR, OR utilization data, OR identifying and tracking data, and/or the like.

The surgical hub may request the location and surgical procedure specific data from one or more data storages, such as a local storage, an edge network storage, a cloud storage unit, and/or the like, for example. The surgical hub may send separate requests to each of the data storages, for example, based on the data storage. For example, the local storage 42552 and/or edge network storage 42554 may be located within the HIPPA boundary, and the cloud network storage 42556 may be located outside the HIPAA boundary. The cloud network storage 42556 may include data that is stripped of private information, for example, to comply with HIPAA guidelines. Based on the privacy associated with the cloud network storage, the surgical hub may send a separate request to the cloud network storage from the request to the local storage and/or edge network storage (e.g., as shown in FIG. 27).

The surgical hub may obtain the location and surgical procedure specific data, for example, based on the request. The surgical hub may obtain the location and surgical procedure specific data from the data storage(s). The surgical hub may process the location and surgical procedure specific data. The surgical hub may generate information and/or control programs for a surgical procedure using the location and surgical procedure specific data. The surgical hub may generate information for the surgical procedure, for example, to provide instructions for modules and/or surgical systems. For example, the surgical hub may generate instructions for using a surgical instrument in a surgical procedure based on the location and surgical procedure specific data. The instructions may be associated with surgical instrument settings data in the location and surgical procedure specific data, for example, that were used in a previous surgery. For example, the surgical hub may generate information for displaying during a surgical procedure, such as surgical procedure models, simulations, procedure steps, instructions, and/or the like.

The surgical hub may send generated control programs, for example, to the modules. The control programs, for example, may aid the modules and/or surgical systems in a surgical procedure. The modules may be connected to the surgical hub and may perform services and/or surgical processes. For example, the surgical hub may be connected to a smoke evacuation module in an operating room. The surgical hub may send control programs, based on the location and procedure specific data, for the smoke evacuation module during the surgical procedure. For example, the control programs may configure the smoke evacuation module to operate, such as removing air particles in the OR, during the surgical procedure. Air particles may be generated, for example, if an energy device is in operation during a surgical procedure. The control programs may configure the smoke evacuation module to operate based on detection of air particles above a threshold.

The surgical hub may send the generated information and/or control programs, for example, to surgical systems. The generated information and/or control programs may be used, for example, to perform a surgical procedure. The surgical systems may be located within the OR. The surgical systems may include surgical equipment, surgical instruments, surgical imaging systems, surgical robots, and/or the like. The surgical systems may include surgical hubs located in a different OR, which may or may not be within the same department or medical specialty. For example, the surgical hub may generate information and/or control programs for a surgical procedure and send it to a different surgical hub in a different OR. The different surgical hub in the different OR may perform surgical procedures using the sent information and/or control programs.

A surgical procedure may be performed, for example, using a surgical hub, modules associated with the surgical hub, surgical systems, and/or the like. Data associated with the surgical procedure may be generated, for example, by the modules and/or surgical systems associated with the surgical procedure. The surgical procedure data may include surgical instrument data, surgical equipment data, biomarker data (e.g., patient biomarker data and HCP biomarker data), OR layout data, surgical plan data, patient data, and/or the like. The surgical hub may receive the surgical hub data, for example, during the surgical procedure and/or as it is generated.

The surgical hub may process the surgical procedure data. For example, the surgical hub may filter and segment the surgical procedure data. The surgical hub may filter and segment types of data as it is obtained. The surgical hub may filter and segment types of data based on the usage location of the data. The usage location of the data may include the geographic location where the generated information and/or control programs are used to perform the surgical procedure. The usage location of the data may include the location where the data was generated, for example, where the surgical procedure was performed.

The surgical hub may filter and segment types of data based on the associated sensing system, module, surgical system, surgical instrument, surgical equipment, and/or the like, that generated and/or collected the data. The surgical hub may filter and segment types of data, for example, based on the HCP performing the surgical procedure. For example, the surgical hub may filter and segment data associated with a particular surgical instrument within an OR. The surgical hub may filter and segment data, such as duration of use and/or number of uses, associated with a surgical instrument.

The surgical hub may process the surgical procedure data, for example, based on the surgeon performing the surgical procedure and/or the OR staff associated with the surgical procedure. For example, the surgical hub may tag the obtained surgical procedure data with the lead surgeon. The tag may indicate that the data is associated with the surgeon who performed the surgical procedure. Analysis of the data may indicate trends of the surgeon during a particular surgical procedure. For example, a surgeon with relatively more experience may perform many successful surgical procedures which other surgeons aim to model. Surgeons, such as surgeons with relatively less experience, may access data associated with the surgeon with relatively more experience to model their surgical plans and procedures for optimization.

The surgical hub may process the surgical procedure data, for example, by determining a classification associated with the data. The data classification may be associated with security. For example, the classifications may include restricted data, public data, confidential data (e.g., private data protected by HIPAA), and/or the like. Restricted data may be sensitive data that may cause great risk if compromised. Public data may be non-sensitive data that may cause little or no risk to an entity, if accessed. Confidential or private data may be moderately sensitive data that may cause a moderate risk to the entity, if compromised. Data classification may group data according to the level of sensitivity associated with the data. Security controls and access methods may be used based on the data classification. For example, fewer security measures may be used for public data compared to the security measures used for restricted data. Restricted data may be associated with security measures limiting access to a need-to-know basis. Public data may be associated with loose security measures and/or no security measures. Confidential or private data may be associated with security measures limiting access to internal use, such as access limited to a company or department owning the data.

The classification may be associated with HIPAA data classification. HIPAA may establish baseline safeguards for ensuring confidentiality, integrity, and availability of protected health information (PHI). PHI may include personally identifiable information, such as mental health history, healthcare services, payments for healthcare, and/or other identifiable information (e.g., patient's name, address, or Social Security number). For example, the surgical hub may process data based on the associated HIPAA data classification. The surgical hub may determine that obtained surgical procedure data is associated with PHI and classify the data as confidential. Processing private data (e.g., aggregated procedure reduction with private data) may be performed within the facility. Processing of private data may be performed within the HIPAA boundary, for example. Protected health information (PHI) may undergo redaction and/or removal of identifying information. The surgical hub may process data such that PHI is redacted and/or has identifying information removed.

The surgical hub may process the surgical procedure data, for example, by performing encryption. Encryption may include transforming data into a form that may be unreadable, for example, without a decryption and/or decryption key. Encryption may ensure privacy by keeping information inaccessible without proper clearances. Authorized access may be permitted by using a decryption. Encryption may use symmetric encryption or asymmetric encryption. Symmetric encryption may use an encryption key and a decryption key where the encryption key and the decryption key are the same. Asymmetric encryption may use unique keys to both encrypt and decipher information. Encryption may include hashing.

Authorized users may access data based on security classifications. Different authentication and/or access levels may be used to access different security classifications. For example, the highest access level may access all data, but a low access level may access public data (e.g., only public data). Access and/or authentication may be performed using a subscription and/or tier package that may grant access to a user for a given data storage. For example, the hospital network may be granted access to all storage locations. For example, a device manufacturer may be granted access to device-use data and/or device errors data (e.g., only device-use data and/or device errors data). For example, a reordering entity may have access to data associated with reordering/resupplying equipment and/or devices. The surgical hub may perform hashing. The surgical hub may perform hashing, for example, to create unique signatures which may be used to identify parties accessing information and tracking any changes made.

The surgical hub may store the processed surgical procedure data, for example, in data storage(s). For example, the surgical hub may store the processed surgical procedure data in the local storage associated with the OR, the edge network storage, the cloud network storage, the internal surgical hub storage, and/or the like. The surgical hub may write data or store data in separate data storage locations, for example, based on the type of data, classification data, associated security assigned to the data, and/or the like. The processed surgical procedure data may be redundant or distributed in data storages. The stored surgical procedure data may be stored for future use, for example, for future surgical procedures. The stored surgical procedure data may be used, for example, by a surgical hub requesting the data based on usage location and sending it to modules and systems for a surgical task.

For example, the surgical hub may store surgical procedure data based on usage location. The surgical hub may obtain surgical procedure data. The surgical procedure data may be associated with modules, surgical systems, surgical equipment, and/or surgical instruments in an operating room. The surgical hub may process the surgical procedure data, such as tagging the surgical procedure data with usage location data. The usage location data may include the OR the surgical procedure data was generated, the type of OR the surgical procedure was generated, the surgeon who performed the surgical procedure, and/or the like. The surgical hub may store surgical procedure data based on the determined usage location for future use. The stored surgical procedure data may be retrieved at a later point, such as for a future surgical procedure. For example, a surgical hub may request location and surgical procedure specific data associated with a particular OR and a particular surgical procedure. The surgical hub may request the location and surgical procedure specific data to use for an upcoming surgical procedure.

For example, the surgical hub may store surgical procedure data based on classification. The surgical hub may obtain surgical procedure data. The surgical hub may determine a classification for the data, such as restricted, public, or confidential, for example. The surgical hub may determine which data storages to store the data based on the classification. The surgical hub may store data within the HIPAA boundary without removing PHI or confidential information. For example, the surgical hub may store patient PHI in internal surgical hub storage, local storage associated with an OR, a medical department storage within the medical facility, the edge network storage, and/or any other storage within the HIPAA boundary. The surgical hub may redact confidential information and/or PHI associated with surgical procedure data. The redacted data may be stored in data storages outside the HIPAA boundary, such as the cloud network storage, for example.

Confidential information and/or PHI associated with data may be protected by encryption. For example, the data may be encrypted to prevent unauthorized access to the data. Writing or transferring encrypted data may be slower than writing on unencrypted data, for example, because a writing operating may go through an encryption algorithm. The surgical hub may determine a storage located based on the classification. For example, the surgical hub may determine that confidential information be stored within the HIPAA boundary, such as in the edge data storage. The surgical hub may determine not to store the confidential information in the cloud network storage, for example, because the process of encrypting the data to comply with HIPAA rules would be inefficient or use resources that may be better suited for other tasks. The surgical hub may be configured with different data storages, such as local or cloud based, for example, based on classification of the data. The data storage may be configured with different segments within a hard drive that may be partitioned based on security levels. For example, the surgical hub may obtain data, process the data (e.g., based on the type and classification of the data), and redirect the data to an appropriate storage reservoir.

The surgical hub may write data in data storages associated with edit permissions. For example, a data storage may be associated with edit permissions, such as read-only or write-once. Read-only permissions may indicate that data may not be edited or modified. Write-once permissions may indicate that data may be edited once and/or edited in a certain manner. For example, write-once permissions may allow data to be updated in a certain manner, such as updating a usage time and/or number. Data storages may include read-only access portions with once-write sections, such as for permanent indexing of the number of uses or duration of use, for example. A surgical hub may have once-write or permanent write sections of a memory, for example, enabled to monitor usage time, number of uses, and/or other parameters that may determine life span, service updates, and/or operational issues.

For example, a data storage may have a section associated with write-once permissions. Once-write permissions may allow information to be written, but not modified. The section associated with write-once permissions may be associated with surgical instrument data, such as number of uses, for example. The once-write permissions may allow a surgical hub to store information relating to a number of times the surgical instrument was used. The number may be used for maintenance purposes of the surgical instrument. For example, the surgical hub may store information relating to the number of uses a surgical instrument has performed since last maintenance. The number may indicate that the surgical instrument is due for maintenance.

The surgical hub may send surgical procedure data, for example, to the edge network. The surgical hub may send surgical procedure data to the edge network for processing. The edge network may process the data more efficiently than the surgical hub. The edge network may be located within the HIPAA boundary. The edge network, based on the location within the HIPAA boundary, may process confidential and/or private data, for example.

In examples, a surgical hub may obtain location and surgical procedure specific data to use in a surgical procedure and may store data from the surgical procedure based on usage location for use in future surgical procedures. The surgical hub may be moved to a thoracic OR, for example. The surgical hub may generate surgical procedure information and/or control programs based on the location and surgical procedure specific data, for example, for use in a surgical procedure. The surgical hub may send the generated surgical procedure information and/or control programs to one or more modules and/or systems associated with a surgical procedure. The system(s) may include surgical hubs in other ORs. For example, the surgical hub may send the generated surgical procedure information and/or control programs to a different surgical hub located in a different OR (e.g., within the same surgical hub network), and the data may be used for a surgical procedure being performed in the different OR. The generated surgical procedure information and/or control programs may include surgeon preferences, OR setup layout(s) and plans, instrument instructions for use, procedure simulations and plans, and/or the like, which may be used in the surgical procedure. The surgical hub may obtain surgical procedure data associated with the surgical procedure, which may be performed in the thoracic OR or the different OR. The surgical hub may process the obtained surgical procedure data, for example, by classifying the data. The surgical hub may store the processed surgical procedure data, for example, in one or more data storages, for example, based on usage location and/or classification. For example, the surgical hub may store the processed surgical procedure data based on the surgical procedure data being generated in the thoracic OR and/or the different OR. The stored surgical procedure data may be used in future surgical procedures. For example, the stored surgical procedure data may be sent when a surgical hub requests the location and surgical procedure specific data for the OR that the stored surgical procedure data was generated in.

In examples, the surgical hub may be configured with automatic transfer protocols. The automatic transfer protocols may enable the surgical hub to transfer data across systems when the surgical hub moves to different locations. For example, the surgical hub may move room to room and request location and surgical procedure specific data (e.g., automatically request location and surgical procedure specific data) associated with the room it is moved to. For example, the surgical hub may move from a first OR to a second OR. The surgical hub, when connected to the second OR, may automatically request location and surgical procedure specific data associated with the second OR. The surgical hub may store the location and surgical procedure specific data associated with the second OR in internal surgical hub storage and/or may send the location and surgical procedure specific data to modules and/or surgical systems in the second OR and/or a different OR (e.g., such as one in the same surgical hub network).

In examples, a main surgical hub routinely used in a thoracic surgery OR may be moved to a hybrid-OR, for example, such that imaging may be used in combination with the main surgical hub for surgery. A rotating surgical hub may be moved into the thoracic OR (e.g., theater) where the main surgical hub was previously located, for example, to act as a replacement for that OR while the main surgical hub is in the hybrid-OR. The rotating surgical hub may power up (e.g., connect) in the thoracic OR. On power up, the rotating surgical hub may request and download all the location and surgical procedure specific data (e.g., local storage data) that the main surgical hub had in the thoracic OR. For example, the location and surgical procedure specific data may include data associated with the thoracic OR, such as surgeon preferences, OR setup layout(s) and plan(s), instrument instructions for use, local area topography and equipment for cooperative access, procedure simulation(s) and plan(s), specific patient data for upcoming and/or previous surgeries, example videos, example annotations, example transcriptions, algorithms, transformations, analyses, and/or applications relative to specialized equipment in the OR, OR utilization data, OR identifying and tracking data, and/or the like. The rotating surgical hub receiving the location and surgical procedure specific data may enable other surgical hubs (e.g., other surgical hubs within the hub network, such as other thoracic surgical hubs) that may have regularly communicated with the main surgical hub to have access to the resources, for example, that they may have used for surgical procedures. For example, other surgical hubs may obtain location and surgical procedure specific data that the main surgical hub used in surgical procedures, such as previously viewed simulations and/or procedures, surgical procedure setup, and/or user preferences.

In examples, a surgical hub to be used by a surgeon with relatively less experience may obtain the user preferences associated with a surgical hub that was used by a surgeon with relatively more experience. A surgeon with relatively more experience may use a particular OR, and the surgeon with relatively more experience may use a different OR. The surgical hub in the OR of the surgeon with relatively less experience may request location and surgical specific data associated with the OR and surgical hub of the surgeon with relatively more experience and surgical hub. The surgical hub of the surgeon with relatively less experience may obtain the data from one or more data storages, which may include the surgical hub of the surgeon with relatively more experience. The location and surgical procedure specific data may include data that the surgeon with relatively more experience uses for surgical procedures, such as preferred surgical models, surgical instrument settings, OR layout, and/or the like. The surgical hub of the surgeon with relatively less experience may obtain the location and surgical procedure specific data of the surgeon with relatively more experience and may use the data in an upcoming surgical procedure.

The surgical hub may communicate with modules, external surgical systems, and/or other surgical hubs, for example, in a surgical hub network. The surgical hub network may include multiple surgical hubs located within the medical facility, such as, for example, different operating rooms. The surgical hub may provide services to other surgical hubs and/or transfer data with the other surgical hubs within the surgical hub network. The surgical hub may provide data processing services, for example, to modules, external surgical systems, and/or other surgical hubs that are in a high utilization phase of operation (e.g., a surgical hub during an important and/or critical surgical procedure step) or have limited processing capabilities (e.g., a biomarker sensing system). The surgical hub may prove data transfer services, for example, such as receiving data from modules, external surgical systems, and/or other surgical hubs and sending the received data to the edge network or cloud network. Transferring data between surgical hubs in a hub network may use less processing power than transferring data from a surgical hub to the edge network or cloud network. For example, to conserve processing capacity, a surgical hub may receive surgical procedure data to be processed at the edge network tier from a different surgical hub in a high utilization phase of operation (e.g., during an important and/or critical procedure step) and transfer the surgical procedure data to the edge network tier.

Figure 28:
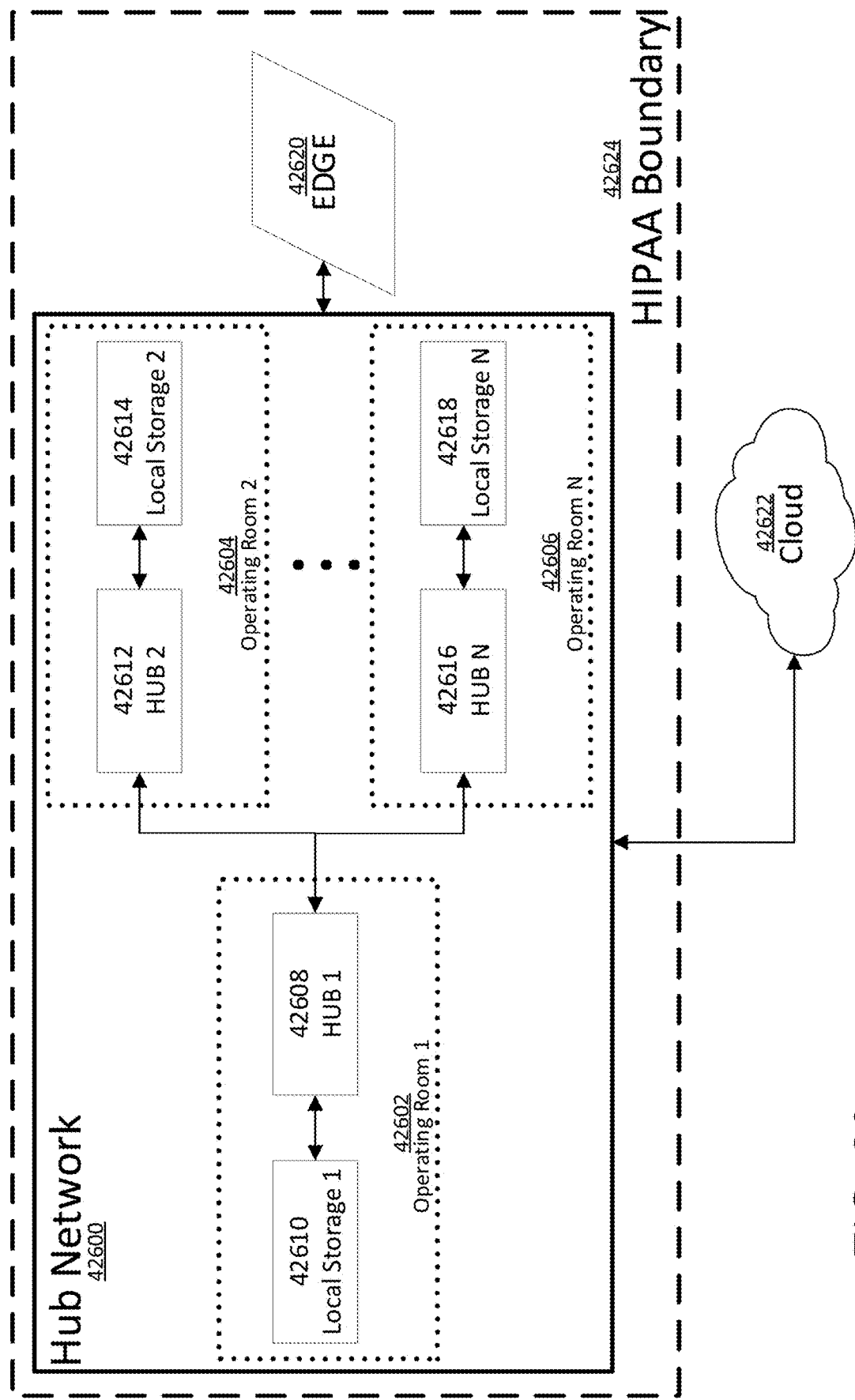
FIG. 28 illustrates an example surgical hub network.

FIG. 28 illustrates an example surgical hub network. A hub network 42600 may include a plurality of surgical hubs within a medical facility. The medical facility may include multiple operating rooms, such as a first operating room 42602, a second operating room 42604, and up to an Nth operating room 42606. Each operating room may include a hub and a local data storage. For example, the first OR 42602 may have a first hub 42608 and first local data storage 42610, the second OR 42604 may have a second hub 42612 and second local data storage 42614, and the Nth OR 42606 may have an Nth surgical hub 42616 and Nth local data storage 42618. The hub network 42600 may communicate with other tiers, such as the edge tier 42620 and/or the cloud tier 42622. As shown in FIG. 28, a HIPAA boundary 42624 may be a boundary that prevents private data from being communicated outside of a medical facility, for example, without proper removal of the private information. The HIPAA boundary 42624 may include the hub network 42600 and/or the edge tier 42620.

The surgical hub network may enable communication between surgical hubs within the network. For example, the first surgical hub 42608 in the first operating room 42602 may provide services to the second surgical hub 42612 in the second operating room 42604. The services provided may include data processing, data storage, data transfer, and/or the like. For example, the second surgical hub 42612 may be performing a surgical procedure and generating surgical procedure data. The second surgical hub 42612 may be performing a critical step in the surgical procedure, for example, such that the second surgical hub 42612 devotes its processing capacity to the procedural step. For example, the second surgical hub 42612 may pause surgical procedure data transfer to the edge tier and/or cloud tier during the critical surgical procedure step. The second surgical hub 42612 may transfer the surgical procedure data to the first surgical hub 42608. Transferring data between devices within the hub network may be faster than transferring data from a surgical hub to the edge tier and/or cloud tier. For example, transferring the data to the first surgical hub 42608 in the hub network may be performed faster than transferring the data to the edge tier or cloud tier. This way, the second surgical hub 42612 spends less time transferring data during the critical surgical procedure step and may focus on the critical surgical procedure step.

Surgical hubs within the hub network may act as and/or provide redundant local storage. The surgical hubs within the hub network may act as and/or provide redundant local storage, for example, based on storage means and distributed storage locations. For example, the surgical hub may act as and/or provide redundant local storage of short-term data and/or long-term data. The short-term data may include data awaiting upload to the edge tier and/or cloud tier. The long-term data may include user preferences, operational algorithms, recently connected systems, and/or the like. A surgical hub within the hub network may include multiple storage locations, for example, arrayed in a raid array and/or using a similar redundant backup method.

The hub network may enable distributed storage between surgical hubs within the hub network. For example, if a local surgical hub has more capacity than other surgical hubs within the same hub network, the local surgical hub may configure itself to act as a distributed storage means within the local hub network. For example, if the local surgical hub has less utilization than other surgical hubs within hub network, the local surgical hub may configure itself to act as a distributed storage means within the hub network.

The local surgical hub may provide momentary storage, for example, acting as a momentary storage node, for the hub network and/or for other surgical hubs. The momentary storage may be provided, for example, until the hub network or local surgical hub transfer the data to the edge tier and/or cloud tier. The local surgical hub may provide momentary storage, for example, until the hub network and/or other surgical hubs enter a lower utilization phase of operation. For example, the hub network may pause transferring data to the edge tier and/or cloud tier. The pause may occur based on the hub network or surgical hubs within the networking entering a high utilization phase of operation. The local surgical hub may receive data and act as a momentary storage node until the hub network resumes transferring data to the edge tier and/or cloud tier.

Figure 29:
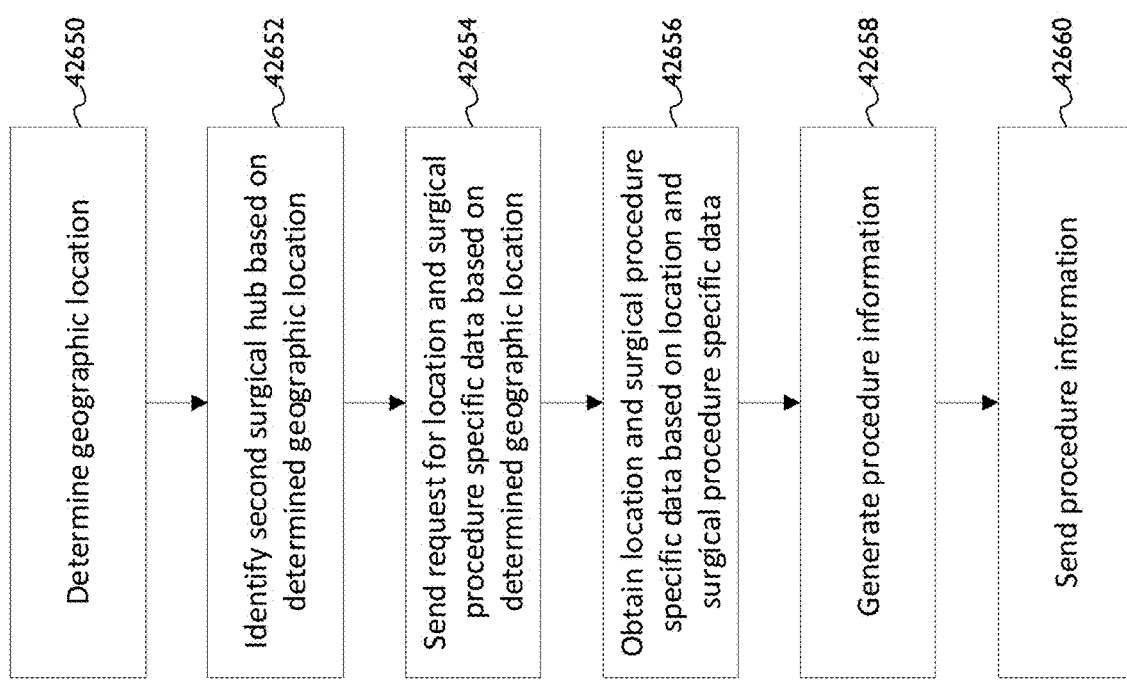
FIG. 29 is a flow diagram of example processing associated with receiving location and surgical procedure specific data and generating procedure information for a surgical procedure.

FIG. 29 is a flow diagram of example processing associated with receiving location and surgical procedure specific data and generating procedure information for a surgical procedure. The processing may be performed by a surgical hub, a computing system, and/or the like. As shown at 42650 in FIG. 29, a geographic location may be determined. The geographic location may be associated with a first surgical hub. The geographic location may be located within a medical facility.

At 42652 in FIG. 29, a second surgical hub may be identified and/or determined, for example, based on the second surgical hub being previously connected at the determined geographic location. For example, the second surgical hub may have been previously connected in the OR associated with the geographic location to perform surgical procedures. The second surgical hub may have been moved from the geographic location to a different geographic location and may be connected at a different OR. In examples, the second surgical hub may have been moved from an OR to be connected at a specialty OR.

At 42654 in FIG. 29, a request for location and surgical procedure specific data may be sent. The location and surgical procedure specific data may include any data associated with the determined geographic location. The location and surgical procedure specific data may include data associated with a particular type of surgical procedure performed in the geographic location. The request for data may be sent to one or more data storages, such as, for example, a local storage, edge network storage, cloud storage unit, surgical hub storage, and/or the like. The cloud storage may be located outside the HIPAA boundary.

At 42656 in FIG. 29, data, such as the location and surgical procedure specific data, may be obtained, for example, from the one or more data storages. At 42658 in FIG. 29, procedure information may be generated, for example, based on the obtained location and surgical procedure specific data. The procedure information may include information for performing a surgical procedure. For example, the procedure information may include surgeon preferences, OR setup layout and plans, surgical instrument instructions, surgical instrument settings, procedure simulations and plans, specific patient data for upcoming or previous surgeries, example videos, annotations, and/or transcriptions, algorithms, transformations, and/or analyses relative to specialized equipment in the OR, OR utilization data, OR identifying and tracking data, and/or the like. For example, based on the obtained location and procedure specific data, surgical procedure information may be generated, such as device settings for a surgical stapler.

At 42660 in FIG. 29, the generated procedure information may be sent, for example to module(s) and/or surgical system(s). The generated procedure information may be sent to a module connected to a surgical hub, which may be associated with performing a surgical procedure. The procedure information may be sent to an external surgical system associated with performing the surgical procedure. The procedure information may be sent to a surgical hub, such as one in a different geographic location (e.g., different OR), associated with performing the surgical procedure.

Figure 30:
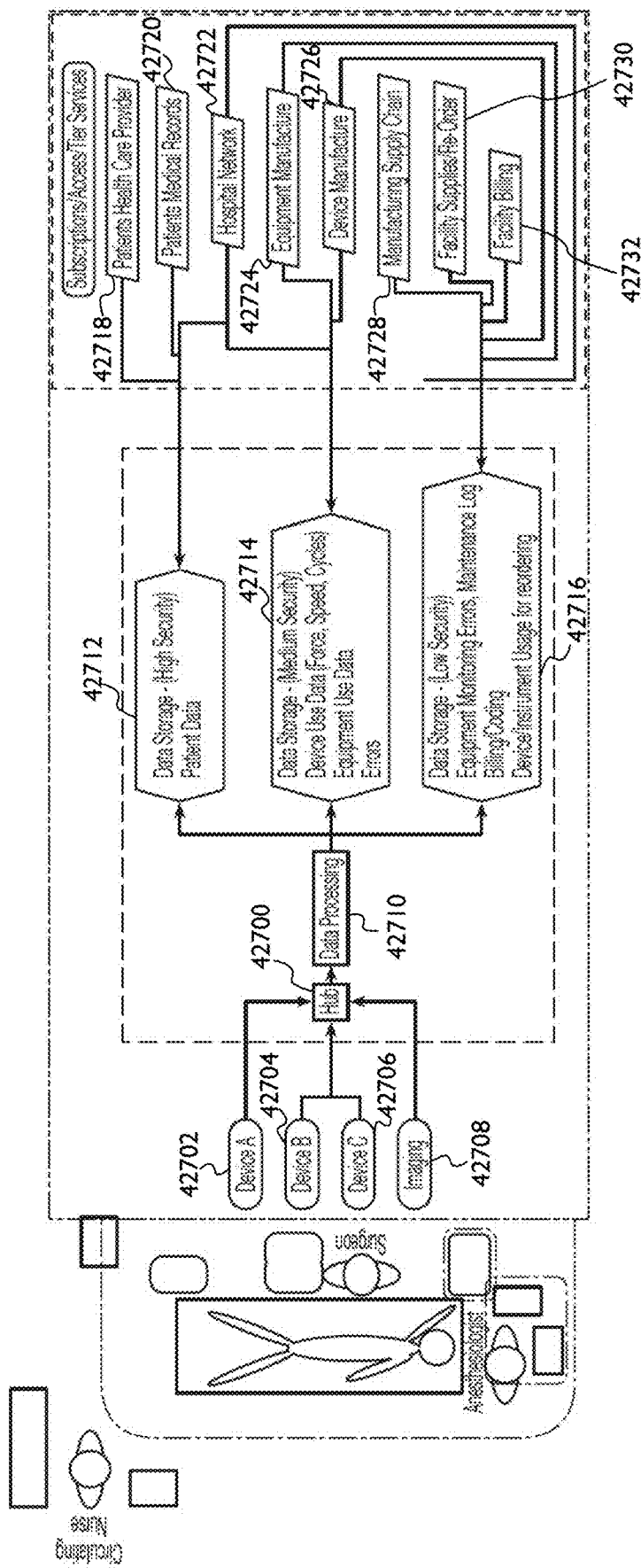
FIG. 30 illustrates an example tiered access model for retrieving data generated by a surgical procedure.

FIG. 30 illustrates an exemplary tiered access model for retrieving data generated by a surgical procedure. As shown on the left of FIG. 30, a surgical procedure may be performed in an operating room. The surgical procedure may be performed using a surgical hub 42700. The surgical procedure may be performed using surgical instruments and/or surgical equipment, such as Device A 42702, Device B 42704, Device C 42706, and an imaging device 42708. The surgical instruments and/or surgical equipment may generate data throughout the surgical procedure and may send the surgical procedure data to the surgical hub 42700. As shown at 42710, the surgical hub may process the surgical procedure data. The surgical hub 42700 may send the processed surgical procedure data to one or more data storages, such as a high security data storage 42712, a medium security data storage 42714, and/or a low security data storage 42716. The one or more data storages may be accessed, for example, by medical entities (e.g., hospital network), device manufacturer entities, and/or the like. The one or more data storages may be a local storage, surgical hub storage, operating room storage, medical department storage, edge tier storage, cloud tier storage, and/or the like. The one or more data storages may be located within the HIPAA boundary.

The surgical hub may process the surgical procedure data, for example, by assigning classifications to the data based on the type of data. The assigned classifications may include security classifications, such as high security, medium security, and/or low security. Types of data associated with high security may include patient data, protected health information, and/or the like. Types of data associated with medium security may include device use data, such as force, speed, and/or cycles associated with the device use, equipment use data, device errors, and/or the like. Types of data associated with low security may include equipment monitoring errors, maintenance logs, billing and/or coding, device/instrument usage for reordering, and/or the like. The surgical hub may classify the surgical procedure data based on the sensitivity of the data.

For example, the surgical hub may assign sensitivity classifications, such as restricted, public, confidential or private, and/or the like. Restricted information may include sensitive data that may cause great risk if the data is compromised. The restricted information may be accessed based on a need-to-know basis. Public information may include non-sensitive data that may cause little or no risk if the data is compromised. The public information may be associated with loose or uncontrolled data access. Confidential or private information may include moderately sensitive data that may cause a moderate risk if the data is compromised. The confidential or private information may be accessed by the company internally and/or by the department that owns the data.

The data storage(s) may be accessed, for example, by entities, such as, for example, medical entities, device manufacturer entities, and/or the like. For example, as shown in on the right portion of FIG. 30, the entities may include the patient health care provider 42718, the patient medical records department 42720, the hospital network 42722, the equipment manufacturer 42724, the device manufacturer 42726, the manufacturing supply chain 42728, the facility supplies/re-ordering department 42730, the facility billing department 42732, and/or the like. The entities may have an access level corresponding with the data storages. For example, an entity may be granted access to the low security data storage(s) (e.g., only the low security data storage(s)). The entity may be granted access to the high security data storage(s), which may include access to the medium security and low security data storage(s).

For example, surgical procedure data may be generated based on a performed surgical procedure. The surgical procedure data may be processed, for example, by the surgical hub. The processed surgical procedure may be sent (e.g., diverted) to a defined storage reservoir (e.g., data storage), for example, based on a classification of the data. The data stored in the storage reservoirs may be accessed, for example, by entities that are granted access to the data storage.

The one or more data storages may be accessed, for example, based on a subscription/tier package. Entities may be granted and/or assigned an access level and/or permission. The access level and/or permission may allow the entities to access certain data storages. For example, an entity with highest access permissions may access all data storage locations, such as the high security, medium security, and/or security data storages. An entity may be limited to accessing low security data storage(s) based on the access level. For example, the hospital network may be granted access to all storage locations. For example, a device manufacturer may be granted access to data storage(s) associated with device use data and/or device errors reported data. For example, a reordering department may be granted access to data storage(s) associated with device/instrument usage for reordering data.

The data storage(s) may include multiple levels and/or sections of data storage. For example, the data storage(s) may include multiple levels and/or sections of data storage based on data security needs. The multiple levels and/or sections may be associated with data security levels and/or access permissions. The data storage(s) may use a multi-level secure vault control of data, for example, based on the data source, data confidentiality, usage needs, risk of misuse, authentication of user level, and/or the like. The data storage(s) may be monitored, for example, for unauthorized intrusions. The data storage(s) may use multi-level access keys, for example, to provide varying access levels to restricted data. Secured internal system data associated with the data storage system and the data storage system's operation may be included.

Figure 31:
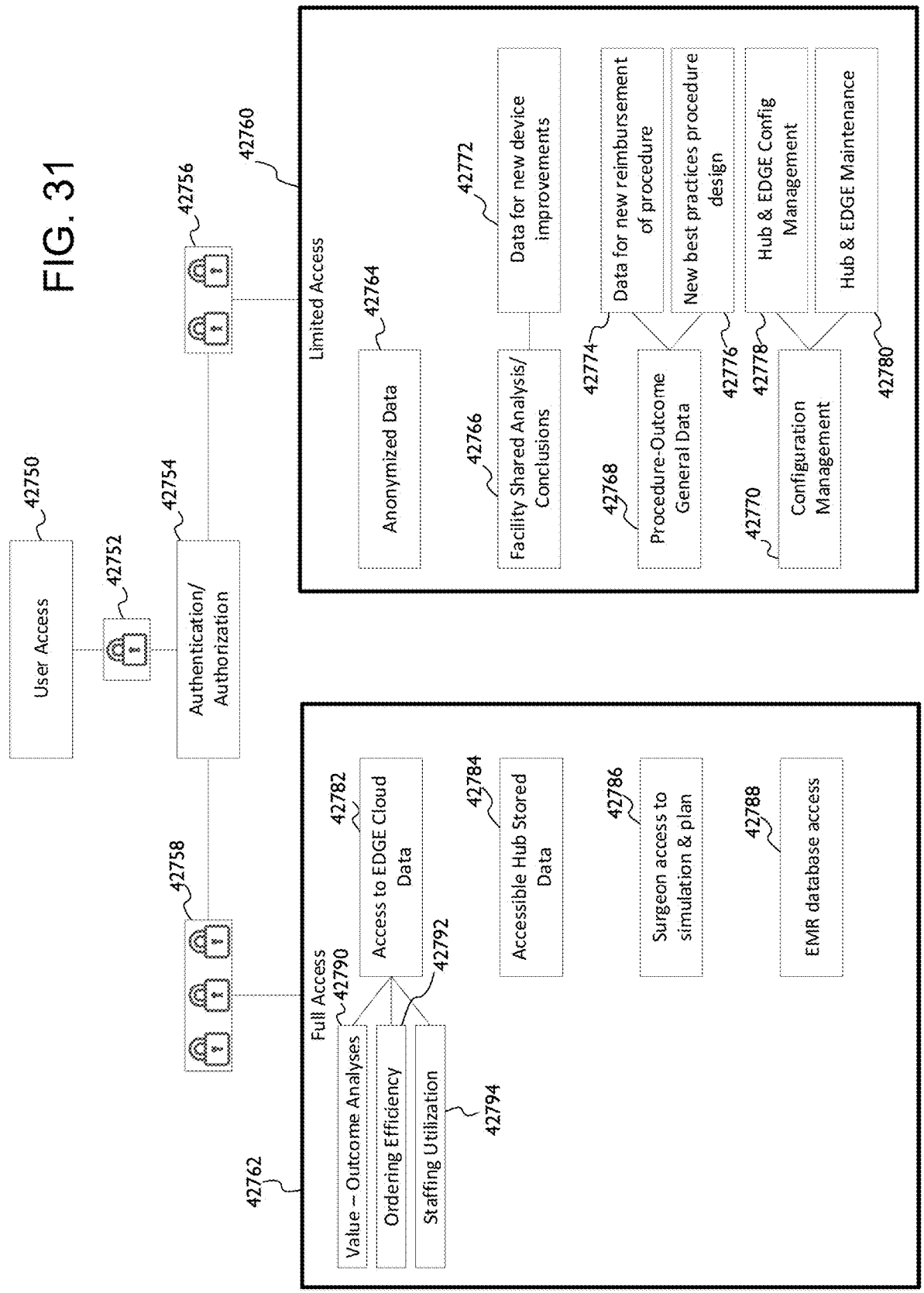
FIG. 31 illustrates an example multi-level security system for a data storage.

FIG. 31 illustrates an example multi-level security system for a data storage. At 42750, a user may access the data storage. The user may access the data storage with a first level of access permission 42752. Authentication/authorization may be performed for a user accessing the data storage. Based on the access permissions of the user, such as a second level of access permission 42756 or a third level of access permission 42758, the user may access different levels of the data storage. The second level of access permission 42756 may grant limited access to the data storage. The third level of access permission 42758 may grant full access to the data storage. A user with the second level of access permission 42756 may access the limited access portion of the data storage 42760. A user with the third level of access permission 42758 may access the full access portion of the data storage 42762 and the limited access portion of the data storage 42760.

As shown in FIG. 31, the limited access portion of the data storage 42760 may include anonymized data 42764, facility shared analysis/conclusions data 42766, procedure-outcome general data 42768, configuration management data 42770, and/or the like. The facility shared analysis/conclusions data 42766 may include data for new device improvements 42772. The procedure-outcome general data 42768 may include data for new reimbursement of procedure 42774 and/or best practices procedure design 42776. The configuration management data 42770 may include data for surgical hub and edge configuration management 42778 and/or hub and edge maintenance 42780. The full access portion of the data storage 42762 may include access to edge and/or cloud data 42782, accessible hub stored data 42784, surgeon access to simulation and plan data 42786, and/or electronic medical records (EMR) database access 42788. The access to the edge and/or cloud data 42782 may include data associated with value and outcome analyses 42790, ordering efficiency 42792, and/or staffing utilization 42794.

Secured data extraction may be provided. Secured data extraction may be provided, for example, based on authentication, needs, and/or usage. The data storages may use secured data access controls, for example, for moving data into and out of the system. Secured access control may be a security technique which may regulates who and/or what can view data.

Secured access control methods may include physical and/or logical secured access control. Physical access control may limit access to the facility, buildings, rooms, physical IT assets, and/or the like. Logical access control may limit connections to computer networks, system files, data, and/or the like. Access control systems may perform identification authentication and authorization of users, for example, by evaluating login credentials. The login credentials may include passwords, personal identification numbers, biometric scans, security tokens, and/or similar authentication factors. Secured access control may minimize security risk, such as unauthorized access to physical and/or logical systems. Secured access control models may include mandatory access control (MAC), discretionary access control (DAC), role-based access control (RBAC), rule-based access control, and/or the like.

Mandatory access control may be a security model where access rights may be regulated, for example, by a central authority based on multiple levels of security. The surgical hub may use MAC, for example, as access controls for data going in and/or out of the surgical hub. The surgical hub may use MAC, for example, to control which entity is allowed to have data permissions, such as read-only permissions or read and write permissions. In an example, a video may be recorded during a surgical procedure and stored in the data storage. Certain credentials and/or access permissions may allow access to the recorded video. For example, the surgeon may have access permissions to review the video and/or edit the video prior or after the video is archived. Other entities may have access permissions to review the video but not edit the video. In an example, a circulating nurse and/or a surgeon may be granted access to pull a correct procedure planned for a surgery. In an example, a scrub nurse may be granted access to check off on tracking and/or using equipment after the surgical procedure is completed before the data is transferred to the central database.

Discretionary access control may be an access control method, for example, which may allow owners and/or administrators of the protected system, data, and/or resource, set policies defining who or what is authorized to access the resource.

Role-based access control may be an access control method that may restrict access, for example, to computer resources. RBAC may restrict access to computer resources, for example, based on individuals or groups with defined business functions rather than identities of individual users. RBAC may use a structure of role assignments, role authorizations, and/or role permissions which may be developed using role engineering, for example, to regulate employee access to systems.

The surgical hub may use RBAC, for example, to control incoming and/or outgoing data between the surgical hub and the cloud and/or other internal networks. RBAC may control restricted and/or confidential data, such as patient data, that may not be accessible unless the user with access was within a defined distance from the surgical hub. RBAC may allow access to be controlled using a radio frequency identification (RFID) chip with a surgeon's ID badge. For example, OR video surveillance may be used as a verification, for example, based on facial recognition. The facial recognition may confirm and/or allow access and/or the exchange of data between the surgical hub and other systems and/or visibility and use of the data.

The surgical hub may use RBAC, for example, to communicate with interfacing equipment and/or devices that are attached and/or identified within the room. For example, RBAC may allow steps-for-use, equipment, and/or devices to be altered and/or modified within the set range controlled by the manufacturer. RBAC may be used to control which steps-for-us and/or device information are permitted to be pulled from the cloud, which may minimize the amount of data needed to be downloaded to the surgical hub.

Rule-based access control may be an access control model, for example, that may allow the system administrator to define the rules that govern access to resource objects.

Systems, methods, and instrumentalities are disclosed for surgical procedure data processing and creating a record of the processing for archival in metadata associated with the results of the processing. The processing may include transforming the data. For example, processing surgical procedure data may include using a transformation or algorithm. The transformation or algorithm may combine or compile multiple data elements together. Transforming the surgical procedure data may generate transformed surgical procedure data. Information associated with the transforms used for processing the surgical procedure data may be archived, for example, in metadata associated with the transformed surgical procedure data. The metadata may be annotated with information associated with transforms performed on the transformed surgical procedure data. The metadata may be stored with the transformed surgical data.

For example, a surgical hub may obtain surgical procedure data associated with a patient. The surgical hub and/or hub may be the surgical hub 20002 as described herein with respect to FIG. 2. The surgical hub may obtain the surgical procedure data from one or more of a module associated with the surgical hub, a surgical system located in the OR, and/or the like. The surgical hub may process the obtained surgical procedure data. For example, the surgical hub processing the surgical procedure data may include transforming the surgical procedure data. The surgical hub may generate transformed surgical procedure data using a transform. The surgical procedure may generate metadata associated with the transformed surgical procedure data. The metadata may include information associated with the processing (e.g., transform) performed on the surgical procedure data that was used in generating the transformed surgical procedure data. The metadata may include information such as a time associated with the processing of the surgical procedure data, a location associated with the processing of the surgical procedure data, information indicating a portion of the surgical procedure data that was processed, a revision of the transform used to perform the transformation, and/or the like. The surgical hub may process the surgical procedure data and/or generate metadata associated with the transformed surgical procedure data, for example, using blockchain recording. The surgical hub may store the transformed surgical procedure data and the metadata comprising the processing information.

The surgical hub may annotate metadata, for example, for transforms of surgical procedure data tied to transformed surgical procedure data. The annotated metadata may be used for tracking and interpreting the transformed data. For example, metadata associated with transformed surgical procedure data may allow for interpretation of the transformed surgical procedure data. HCPs may use the metadata to interpret the result of a transformation, for example. The surgeon may use the metadata to determine the raw surgical procedure data before processing.

Figure 32:
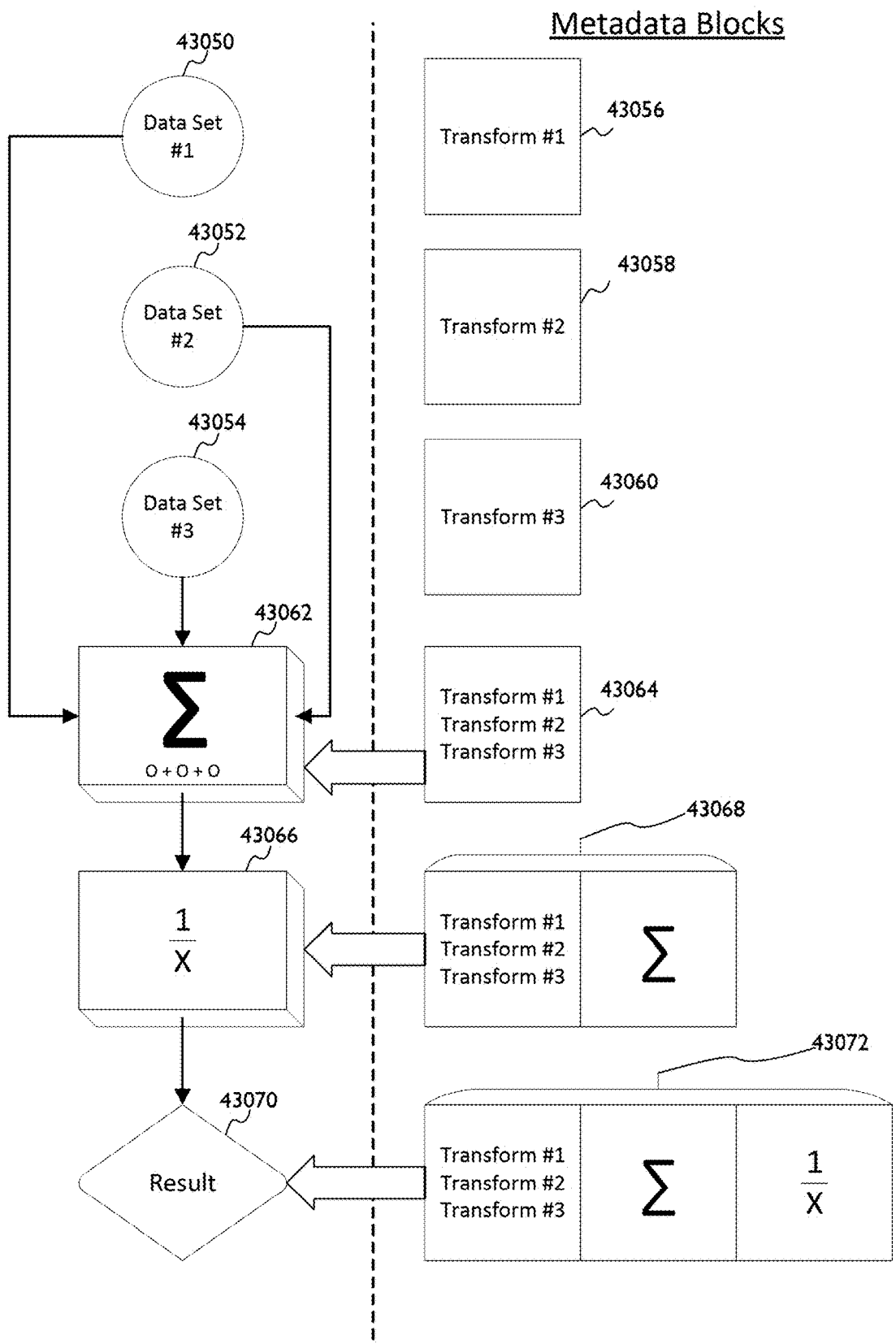
FIG. 32 illustrates an example processing of surgical procedure data and annotation of metadata associated with the processed surgical procedure data.

FIG. 32 illustrates an example processing of surgical procedure data and annotation of metadata associated with the processed surgical procedure data. A surgical hub may obtain surgical procedure data. A surgical hub may process obtained surgical procedure data. The surgical procedure data may be associated with respective metadata. The respective metadata may include information associated with transforms performed on the surgical procedure data set(s). The metadata may comprise metadata blocks. The metadata blocks may be subsets of the metadata. For example, a metadata block may be associated with a first transformation and a second metadata block may be associated with a second transformation. The surgical hub may process the surgical procedure data set(s). Using the transformation, the surgical hub may generate a result. The surgical hub may annotate metadata associated with the generated result, for example, based on the performed processing on the surgical procedure data set(s).

For example, as shown in FIG. 32, surgical procedure data sets, such as data set #1 43050, data set #2 43052, and data set #3 43054, may be processed. Each surgical procedure data set may be associated with respective metadata. The metadata may comprise metadata block(s). The metadata block(s) may include information associated with transforms used on the surgical procedure data set(s) For example, data set #1 43050 may be associated with a first metadata block 43056, data set #2 43052 may be associated with a second metadata block 43058, and data set #3 may be associated with a third metadata block 43060. For example, the first metadata block 43056 associated with data set #1 43050 may include information associated with the previous transforms performed on data set #1 43050, such as transform #1. For example, the second metadata block 43058 associated with data set #2 43052 may include information associated with the previous transforms performed on data set #2 43052, such as transform #2. For example, the third metadata block 43060 associated with data set #3 43054 may include information associated with the previous transforms performed on data set #3 43054, such as transform #3.

Surgical procedure data sets may be processed, for example, by a surgical hub. The processing may include combining the surgical procedure data sets, for example. The processing may include compiling data elements together. The processing may include using a transform and/or algorithm on the surgical procedure data set(s). The transformation may include synchronizing the surgical procedure data sets. For example, as shown at 43062 in FIG. 32, the surgical procedure data sets may be transformed using a Σ transformation, which may include combining the surgical procedure data sets. A fourth metadata block 43064 may be associated with the raw surgical procedure data used for the Σ transformation (e.g., the surgical procedure data sets before undergoing the Σ transformation). The fourth metadata block 43064 may include the information associated with the processing and/or transformations performed on the raw surgical procedure data used for the Σ transformation, such as any transformations that were performed on the surgical procedure data sets. For example, the fourth metadata block 43064 may include information associated with transform #1, transform #2, and transform #3, which may have been performed on the surgical procedure data sets.

The Σ transformation may generate transformed surgical procedure data, for example, using the Σ transformation. The transformed surgical procedure data may be the combination of the surgical procedure data sets and/or the compiled data elements of the surgical procedure data sets. For example, the transformed surgical procedure data from the Σ transformation may be the summation of the surgical procedure data sets. Metadata associated with the transformed surgical procedure data, may be generated, for example, by a surgical hub. The metadata may include information associated with the performed Σ transformation. The metadata associated with the performed Σ transformation may be included in a metadata block. The metadata block associated with the performed Σ transformation may be a different metadata block than the fourth metadata block 43064 associated with the transforms performed on the raw surgical procedure data. The information associated with the performed Σ transformation may be added to the metadata associated with the raw surgical procedure data (e.g., the fourth metadata block 43064). For example, the raw surgical procedure data for the Σ transformation was associated with metadata that included information about the transforms performed on the raw surgical procedure data (e.g., transform #1, transform #2, and transform #3). The metadata may be modified and/or annotated to include the Σ transformation. For example, as shown at 43068, the metadata associated with the transformed surgical procedure data from the Σ transformation may include information associated with transform #1, transform #2, transform #3, and the Σ transformation. The metadata may include separate metadata blocks associated with the individual transforms used. For example, as shown at 43068, the metadata may include two separate metadata blocks. The two separate metadata blocks in combination may enable interpretation of the history of transforms used on the data sets. The transformed surgical procedure data from the Σ transformation and the associated metadata may be stored, for example. The transformed surgical procedure data from the Σ transformation may undergo further processing, for example.

As shown at 43066 in FIG. 32, the transformed surgical procedure data from the Σ transformation may be transformed further, for example, using a second transform, such as an inverse transform (e.g., 1/X transform). The transformed surgical procedure data from the Σ transformation used for the inverse transform (e.g., the input to the inverse transform) may be associated with metadata, which may include information associated with the transforms performed on the transformed surgical procedure data from the Σ transformation, such as shown at 43068. The inverse transform process may generate a result 43070. The inverse transform process may generate metadata associated with the result 43070, for example, as shown at 43072. The metadata may include information about the performed process, for example, such as the inverse transform. The metadata may comprise separate metadata blocks associated with the individual transforms performed. The metadata may include information associated with the transforms performed on the result 43070. For example, as shown in FIG. 32 at 43072, the metadata may include information associated with transform #1, transform #2, transform #3, the Σ transform, and the inverse transform. The metadata may indicate the processing history of the result.

For example, the surgical hub may obtain previously stored transformed surgical procedure data. The surgical hub may obtain previously stored transformed surgical procedure data and metadata associated with the previously stored transformed surgical procedure data. The surgical hub may transform the previously stored transformed surgical procedure data. The surgical hub may generate updated metadata associated with the transformation of the previously stored transformed surgical procedure data. The surgical hub may generate updated metadata based on the transformed used on the previously stored transformed surgical procedure data and/or metadata associated with the previously stored transformed surgical procedure data. For example, the updated metadata may include the transform(s) used on the previously stored transformed surgical procedure data prior to storage and the updated metadata may include the transform(s) used on the previously stored transformed surgical procedure data.

The metadata associated with transformed surgical procedure data may be editable. For example, the metadata may be updated based on subsequent transforms performed on a surgical procedure data set. The surgical hub may process surgical procedure data multiple times. The surgical hub may update the metadata associated with the surgical procedure data based on each process performed. For example, the surgical hub may update the metadata to include information associated with each transform used on the surgical procedure data.

Metadata may include information associated with a revision associated with the transform performed on surgical procedure data. For example, a transform may be associated with a revision. The revision may be a revision number. The revision may indicate the version of the transform used on the surgical procedure data. A transform that has been updated may be associated with a different revision and/or revision number. For example, a transform may be updated from a first version to a second version. The first version may be associated with a first revision number and the second version may be associated with a second revision number. The revision number may be used to determine the version of the transform that was used. The metadata associated with transformed surgical procedure data may include information associated with the revision and/or revision number of the transform. For example, the metadata may be used to determine the version of the transform based on the revision information. The revision may be used to interpret the transformed data, for example, because the revision number may indicate whether the transform used for the processing was an older version or an updated version.

The surgical hub may transform the surgical procedure data associated with a revision number. The metadata may include information associated with the transform performed on the surgical procedure data. The information associated with the transform may include the revision number associated with the transform. The metadata may be used to determine the transform performed on the surgical procedure data and/or the revision number of the transform performed on the surgical procedure data.

Metadata may include information associated with where the surgical procedure data was processed and/or transformed. For example, the metadata may include information associated with a location where the processing and/or transformation of the surgical procedure data occurred. The metadata may include information associated with a processing tier that transformed the surgical procedure data. For example, the metadata may include information indicating that the transformation was performed at the surgical hub, the edge tier, the cloud tier, and/or the like. The metadata may include information associated with a module and/or surgical system that processed the surgical procedure data.

For example, a surgical hub may perform a first transform on surgical procedure data and generate metadata associated with the first transform on the surgical procedure data. The metadata may include information indicating that the first transform was performed in the surgical hub. The transformed surgical procedure data and associated metadata may be sent to the edge tier for further processing. The previously transformed surgical procedure data may undergo a second transform in the edge tier and generate twice-transformed surgical procedure data. Updated metadata associated with the twice-transformed surgical procedure data may be generated based on the second transform and the existing metadata. The updated metadata may include information indicating that the second transform was performed at the edge tier. The updated metadata may include information associated with both the first and second transform, such as, for example, that the first transform was performed at the surgical hub and the second transform was performed at the edge tier. The metadata may be used to determine in which tier each transformation occurred.

Metadata may include information associated with a time when the surgical procedure data was processed and/or transformed. Metadata may include information associated with data used to transform the surgical procedure data. For example, a process and/or transform may use data to process and/or transform surgical procedure data.

For example, the surgical hub may transform the surgical procedure data partially. For example, the transform may be performed on a portion of the surgical procedure data such that a subset of the surgical procedure data is transformed. Metadata may be generated based on the partial transformation. The metadata may include information associated with the partial transformation. For example, the metadata may include information indicating the portion (e.g., subset) of the surgical procedure data that was transformed. The metadata may be used to interpret which portion of the surgical procedure data was transformed.

Blockchain recording may be used. Blockchain recording may use a distributed database. For example, blockchain recording may be used for record keeping. Blockchain may refer to a chain of blocks that contain information. Each block in the chain of blocks may contain information about digital information. The blocks in the chain may include previous information about the digital information. A block may be attached to the blockchain to add information to the digital information. Blockchain may be used for the secure transfer of digital information, such as medical data, for example.

For example, a surgical hub may transform surgical procedure data, for example, using blockchain recording. The surgical hub may generate, annotate, and/or modify metadata associated with the transformed surgical procedure data using blockchain recording. The metadata associated with the transformed surgical procedure data may include blockchain, for example, blocks of information associated with the transformations performed on the surgical procedure data. Information associated with the transform used to process the surgical procedure data may be added to the blockchain, in a block, for example.

Surgical procedure data associated with a surgical system may be processed and/or transformed, for example, in preparation to be sent to a different surgical system and/or data tier. For example, the surgical system and/or data tier may be included in the surgical specific sub-network tier system 40052, as described herein with respect to FIG. 1B. For example, the surgical sub-systems may be grouped by the type of surgical procedures and/or other departments in a medical facility or hospital (e.g., surgical procedure specific departments, ER departments, colorectal departments, bariatric departments, thoracic departments, and/or billing departments). Metadata associated with the transformed surgical procedure data may be sent with the transformed surgical procedure data. Transformed surgical procedure data may be sent to a different data tier, for example, to be further processed and/or stored. The data tier may be the edge tier, a manufacturer cloud tier, a surgical hub tier, an HCP tier, and/or the like. Transformed surgical procedure data may be sent to HCPs (e.g., surgeons) for interpretation and/or analysis. The surgical hub may determine a data tier to be used for storing and/or further processing the transformed surgical procedure data and the metadata associated with the transforms used on the surgical procedure data. The surgical hub may select a data storage, for example, based on the data tier. The surgical hub may select multiple data storages, for example. The surgical hub may store the transformed surgical procedure data and the metadata associated with the transformation (e.g., including information associated with the transform used on the surgical procedure data), using the selected data storage.

For example, the surgical hub may determine the data tier to be used to store and/or process the transformed surgical procedure data and the metadata associated with the transformed surgical procedure data. The data tier to be used may be based on the type of data, how the data will be used, security classification of the surgical procedure data, and/or the like. For example, if the surgical procedure data requires additional processing, the surgical hub may determine to send the surgical procedure data and metadata to the edge tier. The edge tier may provide more efficient processing. The surgical hub may determine to use the edge tier, for example, based on the HIPAA boundary. For example, the edge tier may be determined to be used for private health information. The surgical hub may determine to use the surgical hub tier, for example, for surgical procedure data relating to procedure simulations and/or user settings for surgical procedures. Surgical instrument settings and OR layout information may be stored in the surgical hub tier, for example, such that future surgical procedures may easily access the information. The surgical hub may determine to use the HCP tier, for example, to enable HCPs to interpret and/or analyze the transformed surgical procedure data. The surgical hub may determine to use the manufacturer's cloud tier, for example, for long-term data storage. The surgical hub may determine to use the manufacturer's cloud tier, for example, for non-HIPAA data.

The surgical hub may encrypt the transformed surgical procedure data, for example, based on the determined data tier. For example, surgical procedure data may be encrypted before transferring to a different data tier. Data tiers, such as the cloud tier, may be outside the HIPAA boundary. Surgical procedure data sent to a device outside the HIPPA boundary may be encrypted to provided extra security precautions, for example.

For example, the surgical hub may determine to use the manufacturer's cloud tier data tier for the transformed surgical procedure data and the metadata. Based on the determination, the surgical hub may encrypt the transformed surgical procedure data and the metadata, for example, because the manufacturer cloud tier is outside the HIPAA boundary. For example, the surgical hub may determine to use the surgical hub storage for the transformed surgical procedure data and the metadata. Based on the determination, the surgical hub may send the transformed surgical procedure data and the metadata without encryption, for example, because the surgical hub storage is within the HIPAA boundary.

Figure 33:
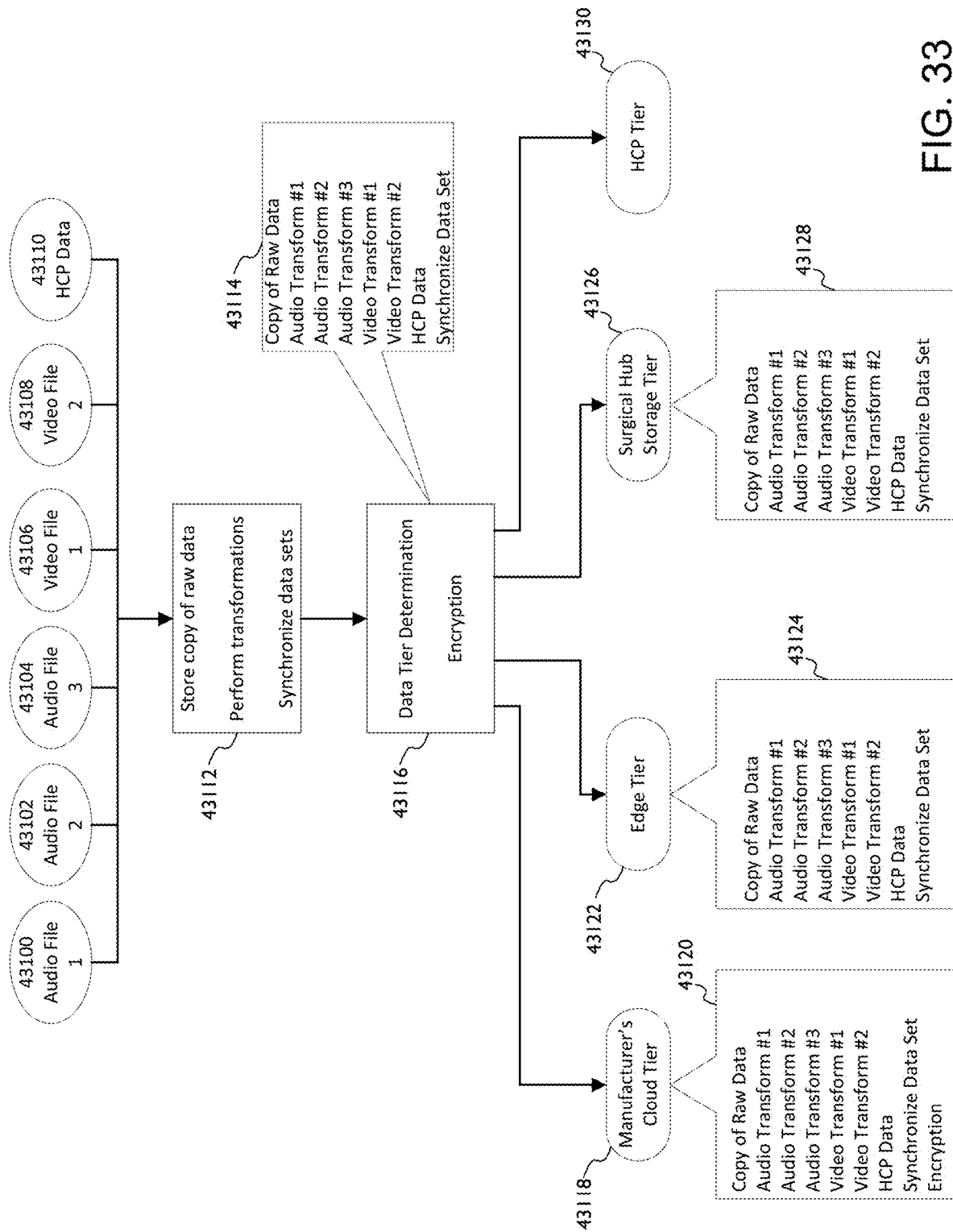
FIG. 33 illustrates an example data tier determination for transformed surgical procedure data and the metadata associated with the transformed surgical procedure data.

FIG. 33 illustrates an example data tier determination for transformed surgical procedure data and the metadata associated with the transformed surgical procedure data. For example, as shown in FIG. 33, surgical procedure data may include a first audio file 43100, second audio file 43102, third audio file 43104, first video file 43106, second video file 43108, and HCP data 43110. The surgical procedure data may be transformed, for example, by a surgical hub. A data tier may be determined for the transformed surgical procedure data. The transformed surgical procedure data may be sent to the determined data tier.

As shown at 43112, the surgical procedure data may be processed and/or transformed. The processing and/or transformation may include storing a copy of the raw surgical procedure data. The processing and/or transformation may include synchronizing the surgical procedure data sets. Synchronizing the surgical procedure data sets may enable interpretation of the surgical procedure data sets. The processing and/or transformations may include compiling data elements, combining the surgical procedure data sets, and/or similar processing and transforms, for example, as described herein. Metadata may be generated based of the processing and/or transformations performed on the surgical procedure data. As shown at 43114, the metadata may include the processes and/or transformations performed on the transformed surgical procedure data.

As shown at 43116, a data tier may be determined, for example, to send the transformed surgical procedure data. Multiple data tiers may be determined. The data tiers may include, for example, the manufacturer's cloud tier 43118, the edge tier 43122, the surgical hub storage tier 43126, the surgeon tier 43130, and/or the like. The data tier may be determined, for example, based on the surgical procedure data and the metadata associated with the surgical procedure data (e.g., as shown at 43114). The edge tier may be determined, for example, to enable additional processing on the surgical procedure data. The surgical hub storage tier may be determined for example, if the surgical procedure data includes user preferences for surgical procedures, OR setup layout and/or plans, surgical instrument instructions and/or settings, and/or the like.

Based on the determined data tier, encryption for the surgical procedure data sets may performed. For example, encryption may be performed on surgical procedure data sets that may be sent to data tiers outside the HIPAA boundary, such as the cloud tier (e.g., manufacturer's cloud tier). If the surgical procedure data is sent within the HIPAA boundary, encryption may be skipped.

If encryption is performed, the metadata associated with the transformed surgical procedure data may be updated, for example, to include information about the performed encryption. For example, the surgical hub may determine to send the transformed surgical procedure data and metadata associated with the transformed surgical procedure data to the manufacturer's cloud tier. Based on the manufacturer's cloud tier determination, the transformed surgical procedure data and the metadata associated with the transformed surgical procedure data may be encrypted. The metadata associated with the transformed surgical procedure data may be updated to include the encryption. The encrypted transformed surgical procedure data and the updated metadata may be stored in the manufacturer cloud tier. As shown at 43120, the updated metadata may include the previous transformations associated with the stored surgical procedure data, including the encryption.

For example, the edge tier and/or surgical hub storage tier may be determined as the data tier to store the surgical procedure data. The surgical hub may skip encryption, for example, because the edge tier and the surgical hub storage are within the HIPAA boundary. The surgical hub may store the transformed surgical procedure data in the edge tier and/or the hub storage. The metadata (e.g., as shown in 43124 and 43128) associated with the transformed surgical procedure data may be stored with the transformed surgical procedure data. The metadata may not include information indicating encryption, for example, because encryption was not performed on the transformed surgical procedure data.

In an example, the surgical hub may obtain a procedure plan. The procedure plan may have been created in the edge processing network. The procedure plan may be created in the edge processing network based on collected surgical procedure data from previous surgical procedures. For example, the edge processing network may collect surgical procedure data from previous surgical procedures and develop a simulation to emulate a predicted surgical procedure. The model surgical procedure may be used to compare to surgical procedures performed in the future. The model surgical procedure may be used as guidance for future surgical procedures.

The surgical hub may send surgical procedure data to the edge processing network, for example, for the edge processing network to create procedure plans. The surgical hub may organize the surgical procedure data for the edge processing network's use, for example, in creating the procedure plans. The surgical procedure data sent to the edge processing network may expand the edge processing network's data set and accessible information. Expanded data sets and accessible information may allow the edge processing network to create a more accurate and/or better procedure plan for the surgical procedure.

The surgical hub may simulate the procedure plan, for example, during a surgical procedure. The simulated procedure plan may allow the surgical hub to follow patterns in the procedure plans. The simulated procedure plan may allow the surgical hub to look for deviations within the performed surgical procedure. For example, the surgical procedure may encounter an event that deviates from the procedure plan. The procedure plan may provide added information for the surgical procedure to the surgical hub.

Figure 34:
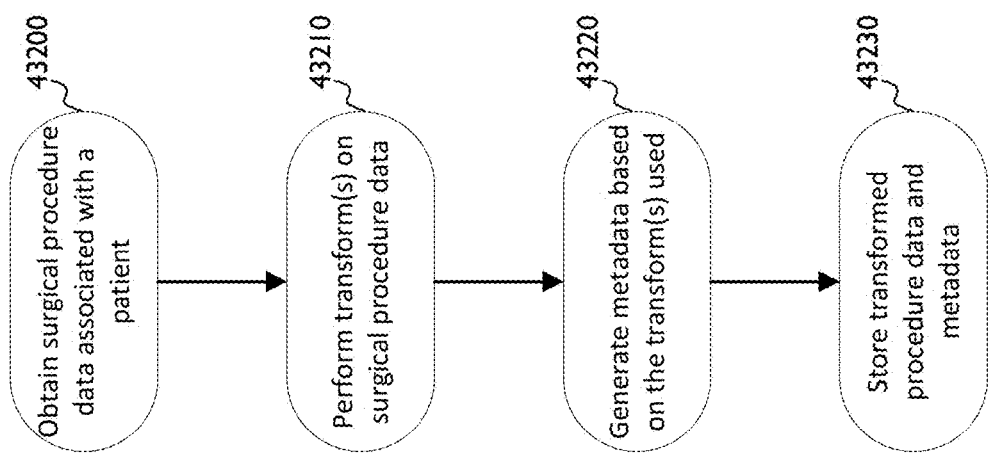
FIG. 34 illustrates an example process for transforming surgical procedure data and generating metadata associated with the transformed data for storage.

FIG. 34 illustrates an example process for transforming surgical procedure data and generating metadata associated with the transformed surgical procedure data for storage. As shown at 43200, surgical procedure data may be obtained. The surgical procedure data be associated with a patient. The surgical procedure data may be obtained from a module associated with the surgical hub and/or a surgical system within the OR. The surgical procedure data may be obtained from a data storage.

As shown at 43210, the surgical procedure data may be processed, for example, using transformations and/or algorithms. The transformations and/or algorithms may combine and/or compile multiple data elements together. The surgical procedure data may be processed, for example, to generate transformed surgical procedure data.

As shown at 43220, metadata may be generated, for example, based on the transform used on the surgical procedure data. The metadata may include information associated with the transformation that was performed on the surgical procedure data. The metadata may include information associated with previous transformations.

As shown at 43230, the transformed surgical procedure data and metadata may be stored, for example, in a data storage and/or data tier. The data storage may be a local OR data storage, the surgical data storage, an edge tier data storage, a cloud tier data storage, a department specific data storage, a facility specific data storage, and/or the like. The transformed surgical procedure data and metadata may be stored for future use. For example, the surgical procedure data may be further processed, and the metadata may be updated based on the further processing.

Tasks performed during a surgical procedure may be prioritized. Tasks performed during the surgical procedure may include data processing, communication, a surgical hub response, surgical procedure tasks, and/or the like. For example, the surgical hub may perform data processing, data communication, and controlling surgical instruments (e.g., simultaneously) during a surgical procedure. The surgical hub may prioritize the controlling of the surgical instruments over the data processing and data communication. For example, the surgical hub may determine to pause data processing and/or data communication based on the surgical procedure reaching a critical procedure step.

Tasks performed during a surgical procedure may be prioritized, for example, based on the classification of the surgical procedure task. For example, the classification of surgical procedure task(s) may be associated with the risk and/or harm level of the surgical procedure task performed. The priority of the surgical hub response and interaction with surgical equipment and/or surgical devices attached to the surgical hub may be determined based on the risk and/or harm level that is imparted on the patient or user. The classifications of the surgical procedure tasks may be cosmetic, moderate, serious, or critical (e.g., life threatening). The surgical hub may prioritize interactions with surgical devices and/or equipment that involve critical surgical procedure tasks.

The surgical hub may use situational awareness, for example, based on obtained surgical procedure data, to determine classification types for surgical procedure tasks. The surgical hub may be included in the situationally aware surgical system 5100 as described herein with respect to FIG. 8. Situational awareness may enable the surgical hub to derive and/or infer information related to the surgical procedure, for example, based on received data. The surgical hub may determine the current surgical procedure step and/or current risk level of the surgical procedure. Based on the determined classification types, the surgical hub may determine priorities associated with the surgical procedure tasks. The surgical hub may modify its interactions with coupled modules, surgical equipment, and/or surgical devices, based on the priorities associated with the surgical procedure tasks.

For example, the surgical hub may be performing a first task and a second task. The surgical hub may use situational awareness to determine a first classification type associated with the first task and a second classification type associated with the second task. The surgical hub may determine a first priority based on the first classification type and a second priority based on the second classification type. The surgical hub may determine that the first priority is higher than the second priority. The surgical hub may pause the second task based on the determination that the first priority is higher than the second priority.

For example, a surgical hub may pause data processing and/or data communication to perform a different surgical procedure task. An energy device may be used for manipulation of tissue and to apply therapeutic treatment. If the energy device is used for grasping and manipulating tissue that may be classified as cosmetic or moderate harm, the hub may perform other tasks, such as data processing and/or data communication, simultaneously. The surgical hub may complete the data processing and/or data communication in real time (e.g., at the time surgical procedure data is generated) and/or place the data processing and/or data communication in a holding spot until the other surgical procedure task was completed. If the energy device and/or other interfacing device is applying therapeutic treatment, which may be classified as critical or serious harm, the hub may pause data processing or communication, for example, until the critical and/or serious task was completed. The pausing may ensure no interruptions and/or delays with power and/or communication would disrupt the critical and/or serious task.

For example, situational awareness may affect prioritization of tasks performed during surgical procedures. The surgical procedure data monitored from a module and/or system (e.g., or data obtained from the data sources 5126 as described herein with respect to FIG. 8) may change the prioritization to be higher, for example based on the utilization of that surgical procedure data by another high priority system. The surgical procedure data monitored from a module and/or system may change the prioritization of a task, for example, if the surgical procedure data is used in combination with another device and/or system to complete a task. The surgical hub may identify surgical equipment and/or devices attached to the system that may work in combination. The surgical hub may reassign priority of a system, for example, based on the risk and/or impact the system may have on the next procedural steps in the surgical procedure. For example, the surgical hub may obtain smoke evacuation control data. The smoke evacuation control data may affect the prioritization of the advanced visualization system, for example, to project surgeon critical structure data adjacent to and/or onto an occluded instrument shaft.

For example, the surgical hub may identify that the surgeon's visualization display, energy device, and smoke evacuation system is paired. Prioritization of the smoke evacuation system may normally be lower than the priority of the surgeon's visualization display and the priority of the energy device. The surgical hub may reassign the prioritization to alter the priority status based on a system risk and/or harm, which may improve the outcome of the next surgical procedure step.

In an example, the surgical hub may reassign priority between the visualization display, energy device, and smoke evacuation system. The surgical hub may identify the next user step (e.g., procedure step) to include applying energy to seal a vessel. The smoke evacuation control data stream may be used for the advanced visualization system, for example, to project surgeon critical structure data adjacent and/or onto an occluded instrument shaft. The surgical hub may identify, based on the smoke evacuation system working in conjunction with the visualization system and the energy device activation, that the user's field of view is obstructed with smoke plumb. Based on the obstruction, the surgical hub may reassign priority such that the smoke evacuation may take priority over the energy activation (e.g., where normally the energy activation is a higher priority than the smoke evacuation), for example, to clear the view of the user prior to activating energy on the device. Reprioritizing the smoke evacuation may minimize the risk and/or harm of the user applying energy to unintended areas, such as vessels or critical structures.

In an example, the surgical hub may reassign priority between the visualization system, energy device, and smoke evacuation system. The surgical hub may identify that the next procedure step is to apply energy to dissect. The surgical hub may determine that no vessels and/or critical structures are within the surrounding area (e.g., surgical site). For example, the surgical hub may determine the surrounding area includes tissue or fat. The surgical hub may allow the energy to be applied and refrain from changing the smoke evacuation to a higher priority.

Automated transcriptions may be provided for recorded audio. The surgical hub may transcribe verbal information created by the surgeon and/or HCPs in the operating room. The transcription may be linked to stored video of the surgical procedure. The automated transcription may be used to document issues or document key data points, for example, in the surgical procedure.

The surgical hub may receive surgical procedure data, such as audio files and/or video files. The audio files may be obtained from audio recorders and/or microphones, which may be placed in the OR and/or worn by the surgeons and/or HCPs. Smart wearable devices may be work by surgeons and/or HCPS to record OR conversations. The video files may be obtained from cameras in the OR.

The surgical hub may perform processes on the surgical procedure data to generate transcriptions. For example, the surgical hub may synchronize the surgical procedure data sets, such as the audio data and the video data. The audio may be synchronized with modules, surgical systems, surgical devices, and/or other OR systems. For example, the audio may be synchronized with generator data. For example, the audio may be synchronized with a surgical data recording, management, and learning system, such as the C-SATS system.

Automated transcriptions may be created, for example, off the video in real time. Automated transcriptions off the video in real time may be transcribed, for example, into a different language. The automated transcriptions may allow a user watching the video to both view the surgical procedure and view what is being said in the OR. The transcriptions may allow better interpretation of the surgical procedure. For example, an observer may speak a different language than is being spoken in the OR during the surgical procedure. The automated transcriptions may translate the audio to the observer's native language to allow better understanding of occurrences in the OR.

Automated transcriptions may be created, for example, and transposed and stored for access in the future. The transcriptions may be translated. The translation may be transposed over the associated video file, for example, similar to closed caption. The transposed translation may allow users to watch and understand the recorded surgical procedure.

The automated transcriptions may be edited. The surgery environment is unrehearsed, which may lead to incorrect statements being spoken, for example. Many things may be spoken incorrectly or not said at all due to focus on the event or action. An automated transcription may enable users to review the audio and video. Based on the reviewed audio and video, the transcription may be edited, corrected, and/or added to, before storing the files. For example, the files may be used for training and/or instructional purposes. Correcting the audio files used for training before storing the files would prevent incorrect audio files being used.

Figure 35:
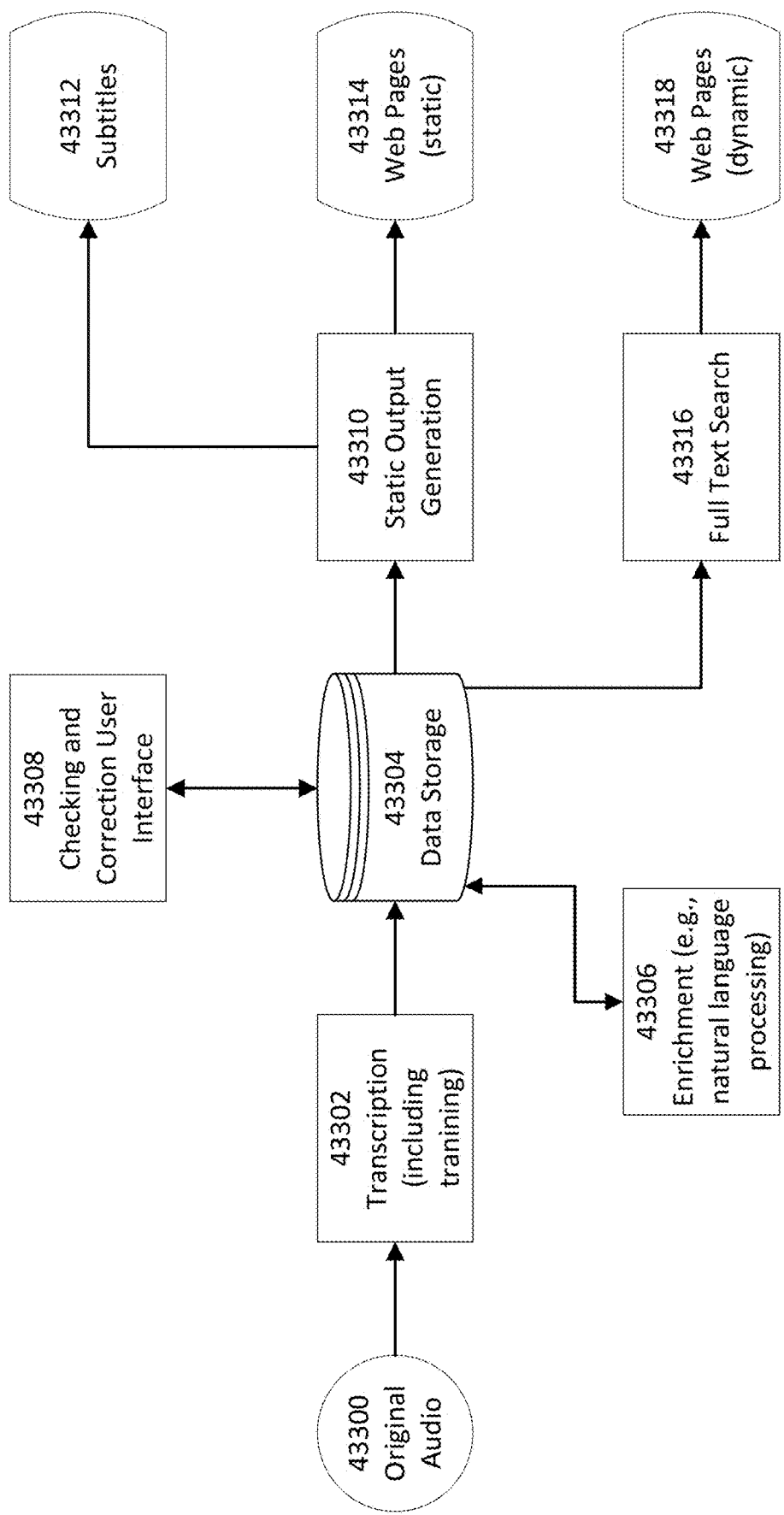
FIG. 35 illustrates an example transcription of audio from an OR during a surgical procedure.

FIG. 35 illustrates an example transcription of audio from an OR during a surgical procedure. Original audio 43300 may be generated during the surgical procedure. The original audio 43300 may be transcribed at 43302. The transcription may include training the audio data. The transcribed audio may be sent to a data storage 43304. The audio transcription may be enriched, for example, as shown at 43306. The audio transcription may be sent to a checking and correction user interface 43308, for example, to be checked for errors and corrected. Static output generation may be performed at 43310, for example, based on the transcribed audio. The static output generation may create subtitles 43312 and/or a static webpage 43314. As shown at 43316, a full text search may be performed on the transcribed audio. The full text search information may be sent to a dynamic webpage 43318.

For example, the enrichment of the transcribed audio may include natural language processing. Natural language processing may include using artificial intelligence to understand the text and spoken words in the transcribed audio. Natural language processing may use computational linguistics with statistical, machine learning, and/or deep learning models. The transcribed audio may be processed to determine the meaning and/or intent of the speaker(s) in the transcribed audio. Natural language processing may include speech recognition, speech/grammar tagging, word sense disambiguation, named entity recognition, co-reference resolution, sentiment analysis, natural language generation, and/or the like. For example, the enrichment may be performed to determine summaries of the transcribed audio.

For example, the checking and correction user interface 43308 may process the transcribed audio. The user interface may check for errors within the transcribed audio. If the user interface detects error(s), the user interface may correct the transcribed audio and store the corrected transcription in the data storage.

Scalable processing may be performed. For example, scalable processing may be performed using scalable processing modules. Scalable processing modules may be used for individual and/or cooperative use within a surgical hub. Cooperative couple of scalable processing modules may enable the modules to share processing needs. For example, if multiple modules are connected within the same surgical hub, the modules may be capable of pairing together to cooperatively operate. The modules may share their combined processing capacity to augment the surgical hub modules. The modules may share their combined processing capacity to augment the surgical hub modules, for example, in a prioritized fashion.

Scalable processing may be performed, for example, using a processor module. The processor module may supplement other surgical hub modules, for example, by providing surge processing. Scalable distributed processing may be provided, for example, for processing tasks by other surgical hub attached modules and/or systems. Scalable distributed supplemental processing modules may distribute processing needs of a surgical hub system and/or attached surgical hub module. Scalable distributed supplemental processing modules may share processing capabilities of the surgical hub, for example, to increase or supplement processing capabilities within the module or surgical hub. Scalable distributed processing may be used, for example, to signal process data from biometric sensors, which may not have intelligence, processing capabilities, and/or storage capabilities.

Machine learning may be supervised (e.g., supervised learning). A supervised learning algorithm may create a mathematical model from training a dataset (e.g., training data). The training data may consist of a set of training examples. A training example may include one or more inputs and one or more labeled outputs. The labeled output(s) may serve as supervisory feedback. In a mathematical model, a training example may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function may determine the output for one or more inputs that may not have been a part of the training data. Example algorithms may include linear regression, logistic regression, and neutral network. Example problems solvable by supervised learning algorithms may include classification, regression problems, and the like.

Machine learning may be unsupervised (e.g., unsupervised learning). An unsupervised learning algorithm may train on a dataset that may contain inputs and may find a structure in the data. The structure in the data may be similar to a grouping or clustering of data points. As such, the algorithm may learn from training data that may not have been labeled. Instead of responding to supervisory feedback, an unsupervised learning algorithm may identify commonalities in training data and may react based on the presence or absence of such commonalities in each train example. Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model the training process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum may be reached, the optimized hypothesis function with its layers of adjusted biases and weights may be deemed trained and constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronic medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g. logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. In an example, a patient's integrated data record of pre-surgical EMR record data and biomarker measurement data, surgical data, and post-surgical data may be in a rational database. Such data record may be converted to a flat file format for model training. In an example, the patient's pre-surgical EMR data may include medical data in text format, such as the patient's diagnoses of emphysema, pre-operative treatment (e.g., chemotherapy, radiation, blood thinner). Such data may be mapped to numeric values for model training. For example, the patient's integrated data record may include personal identifier information or other information that may identifier a patient such as an age, an employer, a body mass index (BMI), demographic information, and the like. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0 and 1 for model training. For example, the preprocessed data may include data values that carry more meaning when aggregated. In an example, there may be multiple prior colorectal procedures a patient has had. The total count of prior colorectal procedures may be more meaningful for training a model to predict surgical complications due to adhesions. In such case, the records of prior colorectal procedures may be aggregated into a total count for model training purposes.

Model training may be another aspect of the machine learning lifecycle. The model training process as described herein may be dependent on the machine learning algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning lifecycle. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning cycle. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art will appreciate that post-deployment model updates may not be a one-time occurrence and may occur as frequently as suitable for improving the deployed model's accuracy.

Figure 36:
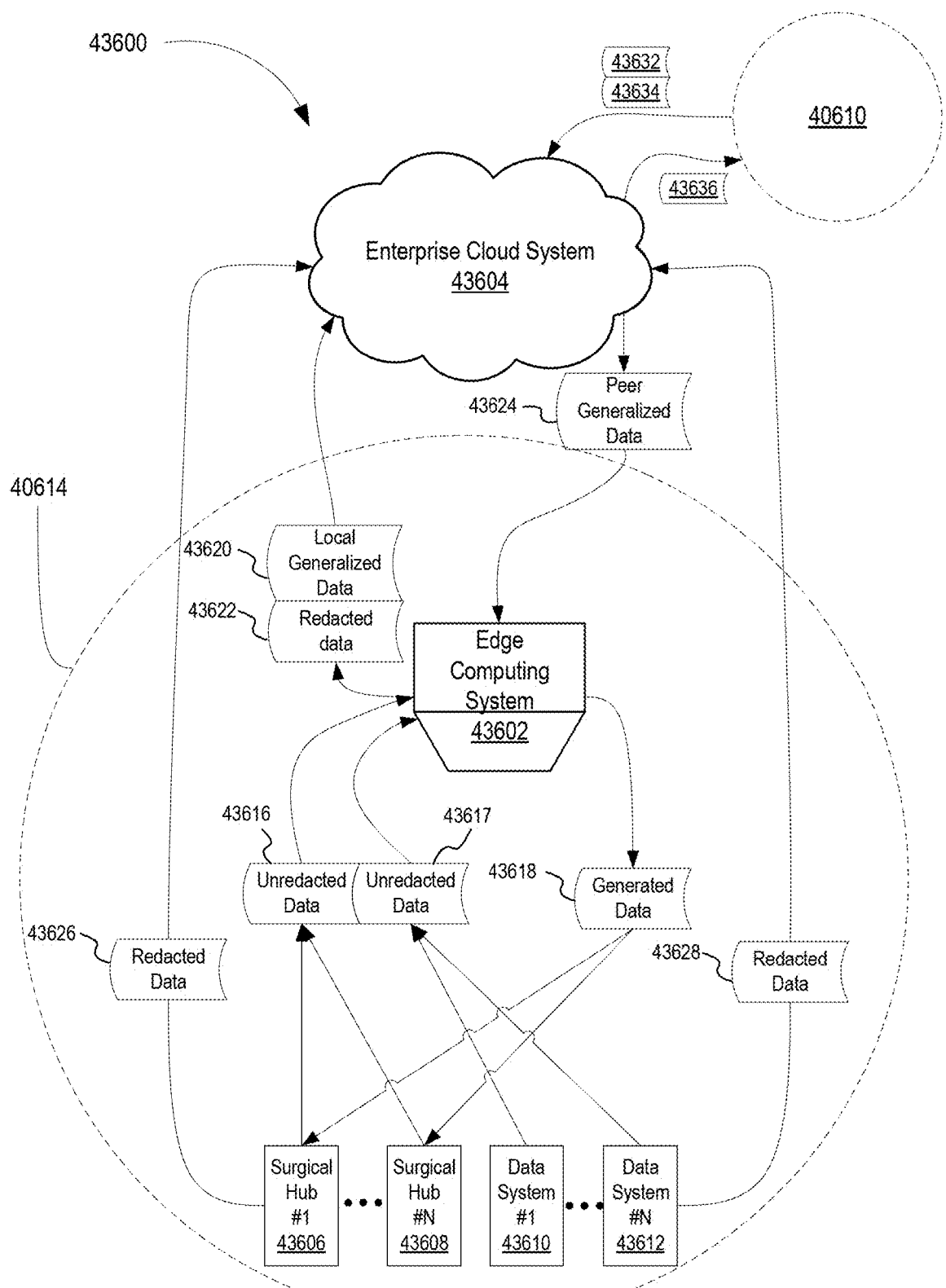
FIG. 36 shows an example multi-level surgical data analysis system.

FIG. 36 shows an example multi-level surgical data analysis system 43600. The system 43600 may include multiple levels of systems, such as a lower-level system, a mid-level system, and a higher-level system. A lower-level system may include sub-systems. For example, the sub-systems may include surgical hub #1 (43606) through surgical hub #N (43608), such as surgical hub 2006 as described in FIG. 1A. For example, the sub-systems may include data system #1 (43610) through data system #N (43612). A mid-level system may include an edge computing system 43602. For example, the edge computing system 43602 may be a local cloud computing system that includes a local cloud server and a local cloud storage unit. The higher-level system may include an enterprise cloud system 43604. For example, the enterprise cloud system 43604 may be a cloud computing system 20008 that includes a remote cloud server 20009 and a remote cloud storage unit 20010, as described in FIG. 1A.

The lower-level system and the mid-level system may be co-located on a local data network. For example, surgical hubs 43606 through 43608 and data systems 43610 through 43608 may be co-located with the edge computing system 43602 on a local data network. The local data network may be a local data network of a hospital, such as hospital B (e.g., the medical facility or hospital associated with the edge tier system 40054 in FIG. 1B). The local data network may be within a data boundary. For example, a data boundary 43614 may be defined by rules that patient data privacy are preserved within the boundary. The rules may be health insurance portability and accountability act (HIPAA) related data rules. In an example, a patient's private data may be redacted before being sent outside the boundary. The patient's private data flows without redaction between the edge computing system 43602, and surgical hubs 43606 through 43608 and data systems 43610 through 43608.

The higher-level system may be outside the local data network. For example, the enterprise cloud system 43604 may be outside the data boundary 43614. The enterprise cloud system 43604 may be remote to the edge computing system 43602, and surgical hubs 43606 through 43608 and data systems 43610 through 43608.

The higher-level system may be in communication with more than one local data network. For example, the enterprise cloud system 43604 (e.g., enterprise cloud system 40060 shown in FIG. 1B) may be in communication with the local data network of hospital B that is within the data boundary 43614 (e.g., 40062 shown in FIG. 1B). The enterprise cloud system 43604 may be in communication with the local data network of hospital A (e.g., the medical facility or hospital associated with the edge tier system 40054 in FIG. 1B) that is within a data boundary 40610. For example, the data boundary 40610 may include an edge computing system, surgical hubs, and data systems on the local data network of hospital A.

The lower-level system may provide patient data and clinical data to the mid-level system. For example, surgical hubs 43606 through 43608 in the lower-level system may be in operating room(s) of one or more hospital B's departments, such as the colorectal department, the bariatric department, the thoracic department, or the emergency room (ER) department. One or more of the surgical hubs may provide unredacted data 43616, such as patient personal data and patient clinical data, to the edge computing system 43602.

For example, patient personal data may include a patient's demographics information, such as age, gender, place of residence, occupation, employer, and family status. Patient personal data may include a patient identifier. Patient personal data may be from a patient electronic Medical Record (EMR) database. The interaction between surgical hubs and the EMR database is described in greater detail under the heading of "Data Management and Collection" in U.S. Patent Application Publication No. US 20190206562 A1 (U.S. patent application Ser. No. 16/209,385), tided Method of hub communication, processing, storage and display, filed Dec. 4, 2018, the disclosure of which is herein incorporated by reference in its entirety.

Patient clinical data may include a patient's pre-surgery data (e.g., preoperative data), in-surgery data (e.g., intraoperative data), and post-surgery data (e.g., postoperative data). Preoperative data, intraoperative data, and postoperative data are described in greater detail in FIG. 194's detailed description in U.S. Patent Application Publication No. US 20190206562 A1 (U.S. patent application Ser. No. 16/209,416), tided Method of hub communication, processing, display, and cloud analytics, filed Dec. 4, 2018, the disclosure of which is herein incorporated by reference in its entirety.

Pre-surgery data may include pre-surgery monitoring data. Pre-surgery monitoring data is described in greater detail in U.S. patent application Ser. No. 17/156,318, tided PREDICTION OF ADHESIONS BASED ON BIOMARKER MONITORING, filed Jan. 22, 2021; U.S. patent application Ser. No. 17/156,309, titled PREDICTION OF BLOOD PERFUSION DIFFICULTIES BASED ON BIOMARKER MONITORING, filed Jan. 22, 2021; U.S. patent application Ser. No. 17/156,306, titled PREDICTION OF TISSUE IRREGULARITIES BASED ON BIOMARKER MONITORING, filed Jan. 22, 2021; and U.S. patent application Ser. No. 17/156,321, titled PREDICTION OF HEMOSTASIS ISSUES BASED ON BIOMARKER MONITORING, filed Jan. 22, 2021, the disclosure of which are herein incorporated by reference in its entirety.

In-surgery data may include in-surgery monitoring data. In-surgery monitoring data is described in greater detail in U.S. patent application Ser. No. 17/156,269, titled PRE-SURGICAL AND SURGICAL PROCESSING FOR SURGICAL DATA CONTEXT, filed Jan. 26, 2021, the disclosure of which is herein incorporated by reference in its entirety.

Post-surgery data may include post-surgery monitoring data. Post-surgery monitoring data is described in greater detail in U.S. patent application Ser. No. 17/156,281, titled COLORECTAL SURGERY POST-SURGICAL MONITORING, filed Jan. 22, 2021; U.S. patent application Ser. No. 17/156,272, titled THORACIC POST-SURGICAL MONITORING AND COMPLICATION PREDICTION, filed Jan. 22, 2021; U.S. patent application Ser. No. 17/156,279, titled HYSTERECTOMYSURGERY POST-SURGICAL MONITORING, filed Jan. 22, 2021; U.S. patent application Ser. No. 17/156,284, titled BARIATRIC SURGERY POST-SURGICAL MONITORING, filed Jan. 22, 2021, the disclosure of which are herein incorporated by reference in its entirety.

The lower-level system may provide other patient data to the mid-level system. For example, one of more of the data systems 43610 through 43612 may provide unredacted data 43617 to the edge computing system 43602. One or more data systems may be billing data systems. The unredacted data 43617 may include billing data, payment data, and/or reimbursement data associated with one or more surgical procedures.

For example, the edge computing system 43602 may receive from the lower-level system patient personal data, patient clinical data, and other patient data associated with surgical procedures. Patient clinical data may include pre-surgery data, in-surgery data, and post-surgery data. Other patient data may include billing data, payment data, and reimbursement data. The edge computing system 43602 may perform pre-processing of the received data. For example, the edge computing system 43602 may link patient personal data, patient clinical data, and other patient data using patient identifiers. A data record may be created for a surgical procedure associated with a patient. For example, a data record may include the patient's personal data. For example, a data record may include the surgical procedure's pre-surgery data, in-surgery data, and/or post-surgery data. For example, a data record may include the surgical procedure's billing data, payment data, and/or reimbursement data.

A data record (e.g., a linked data record) may be associated with a surgical procedure type. For example, a linked data record may be created for a colorectal surgical procedure (e.g., a laparoscopic sigmoid colectomy procedure). For example, a linked data records may be created for a bariatric surgical procedure (e.g., a laparoscopic sleeve gastrectomy). For example, a linked data record may be created for a thoracic surgical procedure (e.g., a lung segmentectomy procedure).

A surgical procedure may include surgical steps. For example, a laparoscopic sigmoid colectomy procedure may include the following surgical steps: initiate, access, mobilize colon, resect sigmoid, perform anastomosis, and conclude.

A surgical step may include surgical tasks. For example, the surgical step "initiate" for a laparoscopic sigmoid colectomy procedure may include the following surgical tasks: make incisions, place trocars, and assess adhesions. For example, the surgical step "access" may include the following surgical tasks: dissect adhesions, dissect mesentery, and identify ureter.

A surgical task may include a surgical instrument selection and surgical choices. For example, in surgical step "initiate" of the laparoscopic sigmoid colectomy procedure, the surgical task "make incisions" (e.g., for trocar placement) may include a surgical instrument selection 33016 of scalpel. The surgical task may include a surgical choice of incision length of 10 mm for a laparoscope port. The surgical task may include a surgical choice of incision location of umbilicus for a laparoscope port. The surgical task may include a surgical choice of incision length of 5 mm for a grasper port. The surgical task may include a surgical choice of incision location of upper right quadrant of abdomen for a grasper port. The surgical task may include a surgical choice of incision length of 5 mm for a harmonic energy device port. The surgical task may include a surgical choice of incision location of lower right quadrant of abdomen for a harmonic energy device port.

For example, the surgical task "dissect mesentery" in the surgical step "access" of the laparoscopic sigmoid colectomy procedure may include a surgical instrument selection of grasper. The surgical task may include a surgical instrument selection of a harmonic energy device. The surgical task may include a surgical choice of performing dissection in the direction of medial-to-lateral. The surgical task may include a surgical choice of performing dissection in the direction of lateral-to-medial.

The surgical steps, surgical tasks, surgical choices, surgical instrument selection, and post-surgery care choices described herein may be a part of a surgical procedure plan.

A surgical procedure plan may include post-surgery care choices. In examples, a post-surgery care choice may be length of stay before discharge, duration of ventilator use, intensive care unit (ICU) monitoring, or performing a spirometry test.

The edge computing system 43602 may create the linked data records in its memory for further processing. The edge computing system 43602 may store the linked data records in a datastore for further processing.

The linked data records may be further processed. For example, the linked data records may be split into subsets and one subset of the linked data records may be further processed. In an example, a subset A of the linked data records may be the records associated with a laparoscopic sigmoid colectomy procedure and where the respective post-surgery data portion of each of the records indicates there were no post-surgery complication(s) or readmission(s).

Subset A of the linked data records may be further processed in preparation for training a machine learning model A. For example, a new data field may be created and appended to each data record of subset A. The new data field may be derived from billing data and reimbursement data of each data record. For example, a new data field may indicate whether a surgical procedure has a reimbursement rate of at least 80% or not. A reimbursement rate of at least 80% of billed amount for medical services provided may be a typical reimbursement rate in the health care industry.

The new data field may serve as each subset A data record's label for training model A using a supervised machine learning algorithm (e.g., a neutral network or a decision tree algorithm). Those of skill in the art will appreciate any suitable machine learning algorithm may be used for training model A. Machine learning algorithms are described in greater detail in U.S. patent application Ser. No. 17/156,293, titled MACHINE LEARNING TO IMPROVE ARTIFICIAL INTELLIGENCE ALGORITHM ITERATIONS, filed Jan. 22, 2021.

In an example, when model A is deemed suitably trained, one or more patterns may be detected in the model (e.g., decision points detected using a decision tree algorithm). An example pattern ("pattern #1") may be that the laparoscopic sigmoid colectomy procedures with no post-surgery complication(s) or readmission(s) and with the following additional characteristics have a reimbursement rate of at least 80%: (1) they were performed on patients that are 20-45 in age, male, with no pre-conditions, and no prior surgeries in the past; (2) there were no in-surgery complication(s); and (3) the post-surgery length of stay before discharge is two days or more. The characteristics may be decision points in the decision tree from model A. An implication of pattern #1 is that for a laparoscopic sigmoid colectomy procedure with no post-surgery complication(s) or readmission(s) and with characteristics (1) and (2), reducing a post-surgery length of stay from more than two days to two days, there may be no decline in quality of clinical outcome or in reimbursement rate for the medical facility in question (e.g., hospital B).

An example pattern ("pattern #2") may be that the laparoscopic sigmoid colectomy procedures with no post-surgery complication(s) or readmission(s) and with the following additional characteristics have a reimbursement rate of at least 80%: (1) they were performed on patients that are 20-45 in age, male, with at least one pre-condition, and with at least one prior colorectal surgery in the past; (2) there were no in-surgery complication(s); and (3) the post-surgery length of stay before discharge is four days or more. An implication of pattern #2 is that for a laparoscopic sigmoid colectomy procedure with no post-surgery complication(s) or readmission(s) and with characteristics (1) and (2), reducing a post-surgery length of stay from more than four days to four days, there may be no decline in quality of clinical outcome or in reimbursement rate for the medical facility in question (e.g., hospital B).

For example, a subset B of the linked data records may be split from the linked data records and further processed. Subset B of the linked data records may be the records associated with a laparoscopic sigmoid colectomy procedure and where either the respective in-surgery data portion or the respective post-surgery data portion of the each of the records indicates at least one in-surgery complication or at least one post-surgery complication, respectively.

Subset B of the linked data records may be further processed in preparation for training a machine learning model B. For example, a new data field may be created and appended to each data record of subset B. The new data field may be derived from billing data and reimbursement data of each data record. For example, a new data field may indicate whether a surgical procedure has a denied claim or not.

The new data field may serve as each subset B data record's label for training model B using a supervised machine learning algorithm (e.g., a neutral network or a decision tree algorithm). Those of skill in the art will appreciate any suitable machine learning algorithm may be used for training model B.

In an example, when model B is deemed suitably trained, one or more patterns may be detected in the model (e.g., decision points detected using a decision tree algorithm). An example pattern ("pattern #3") may be that the laparoscopic sigmoid colectomy procedures with at least one in-surgery complication or at least one post-surgery complication and with the following additional characteristics have a denied claim for a medical procedure performed: (1) they were performed on patients that are 20-45 in age, male, with no pre-conditions, and no prior surgeries in the past; (2) an in-surgery complication of at least one damaged ureter; and (3) a sharp dissection tool is used in the access step's dissect mesentery surgical task. The characteristics may be decision points in the decision tree from model B. An implication of pattern #3 is that for a laparoscopic sigmoid colectomy procedure with characteristics (1), if a dull dissection tool is used instead of the sharp dissection tool, the in-surgery complication of damaged ureter(s) may be prevented, and the denied claim may be prevented. Accordingly, there may be both an improvement in the quality of clinical outcome and an improvement in reimbursement amount (e.g., for the medical facility in question (e.g., hospital B).

An example pattern ("pattern #4") may be that the laparoscopic sigmoid colectomy procedures with at least one in-surgery complication or at least one post-surgery complication and with the following additional characteristics have a denied claim for a medical procedure performed: (1) they were performed on patients that are 20-45 in age, male, with no pre-conditions, and no prior surgeries in the past; (2) an in-surgery complication of at least one damaged ureter; and (3) a surgical choice made to not identify ureter before dissecting mesentery in the access step's dissect mesentery surgical task. The characteristics may be decision points in the decision tree from model B. An implication of pattern #4 is that for a laparoscopic sigmoid colectomy procedure with characteristics (1), if a surgical choice is made to identify ureter before dissecting mesentery, the in-surgery complication of damaged ureter(s) may be prevented, and the denied claim may be prevented. Accordingly, there may be both an improvement in the quality of clinical outcome and an improvement in reimbursement amount (e.g., for the medical facility in question (e.g., hospital B).

An example pattern ("pattern #5") may be that the laparoscopic sigmoid colectomy procedures with at least one in-surgery complication or at least one post-surgery complication and with the following additional characteristics have a denied claim for a medical procedure performed: (1) they were performed on patients that are 20-45 in age, male, with no pre-conditions, and no prior surgeries in the past; (2) an in-surgery complication of at least one damaged ureter; and (3) the ultrasonic device's (dissection tool) maximum period for energy application is above a threshold T. The characteristics may be decision points in the decision tree from model B. An implication of pattern #5 is that for a laparoscopic sigmoid colectomy procedure with characteristics (1), if the ultrasonic device's maximum period for energy application is below threshold T, potential lateral thermo damage may be reduced. Accordingly, the in-surgery complication of damaged ureter(s) may be prevented and the denied claim may be prevented. Accordingly, there may be both an improvement in the quality of clinical outcome and an improvement in reimbursement amount (e.g., for the medical facility in question (e.g., hospital B).

The edge computing system 43602 may create generated data 43618. The generated data 43618 may include a suggestion for surgical choice in a surgical procedure plan, a suggestion for post-surgery care choice in a surgical procedure plan, a suggestion for a surgical instrument selection, or an operating parameter adjustment for a selected surgical instrument.

For example, the edge computing system 43602 may create generated data 43618 based on the patterns detected in machine learning models as described. In an example, generated data 43618 may be a suggestion for a post-surgery care choice in a surgical procedure plan based on pattern #1. The suggestion may be that for any future laparoscopic sigmoid colectomy procedure if the procedure's patient personal data, patient clinical data, and other patient data match pattern #1, a post-surgery care choice may include two days (and not more than two days) of post-surgery stay before discharge.

In an example, generated data 43618 may be a suggestion for a post-surgery care choice in a surgical procedure plan based on pattern #2. The suggestion may be that for any future laparoscopic sigmoid colectomy procedure if the procedure's patient personal data, patient clinical data, and other patient data match pattern #2, the associated surgical procedure plan includes a post-surgery care choice of four days (and not more than four days) of post-surgery stay before discharge.

In an example, generated data 43618 may be a suggestion for a surgical instrument selection in a surgical procedure plan based on pattern #3. The suggestion may be that for any future laparoscopic sigmoid colectomy procedure if the procedure's patient personal data, patient clinical data, and other patient data match pattern #3, a dull dissection tool may be a selected surgical instrument for the access step's dissect mesentery surgical task in the associated surgical procedure plan.

In an example, generated data 43618 may be a suggestion for a surgical choice in a surgical procedure plan based on pattern #4. The suggestion may be that for any future laparoscopic sigmoid colectomy procedure if the procedure's patient personal data, patient clinical data, and other patient data match pattern #4, a surgical choice of identifying ureter before dissecting mesentery may be included as part of the access step's dissect mesentery surgical task in the associated surgical procedure plan.

In an example, generated data 43618 may be an operational parameter adjustment of a surgical instrument selected in a surgical instrument plan based on pattern #5. The adjustment may be that for any future laparoscopic sigmoid colectomy procedure if the procedure's patient personal data, patient clinical data, and other patient data match pattern #5, a control program update is generated to reduce a selected ultrasonic device's maximum period for energy application to below threshold T.

The edge computing system 43602 may create generated data 43618 automatically. For example, after machine learning models (e.g., models A and B) are trained, the edge computing system 43602 may create generated data 43618 without a request for it. The automatically created generated data 43618 and associated trained model may be sent to one or more of surgical hubs #1 (43606) through surgical hub #N (43608) to optimize a surgical procedure's clinical outcome and/or cost effectiveness.

For example, the suggestions based on pattern #1 through pattern #4 may be implemented as computer-executable instructions (e.g., scripts, executables, and the like) and sent with the respective trained model to one or more of surgical hubs #1 through #N. The suggestions and the respective models may be stored on the surgical hubs. In an example, when a surgeon is planning a laparoscopic sigmoid colectomy procedure (e.g., on a surgical procedure planning interface coupled with a surgical hub), the trained models may be executed using a laparoscopic sigmoid colectomy procedure's associated data, including patient personal data, patient clinical data, and other patient data as input. If the input data matches the detected pattern associated with a stored suggestion and the trained model predicts an output that corresponds with the pattern, the stored suggestion may be retrieved and presented. For example, if the input data matches pattern #1 and model A predicts a reimbursement rate of at least 80% using data associated with the laparoscopic sigmoid colectomy procedure under planning, the suggestion for a post-surgery care choice of two days may be presented.

For example, the operational parameter adjustment based on pattern #5 may be implemented as computer-executable instructions (e.g., script(s), executable(s), and the like) and sent with the respective trained model to one or more of surgical hubs #1 through #N. The adjustment and the respective model may be stored on the surgical hubs. In an example, when a surgeon is planning a laparoscopic sigmoid colectomy procedure (e.g., on a surgical procedure planning interface coupled with a surgical hub), the trained models may be executed using a laparoscopic sigmoid colectomy procedure's associated data, including patient personal data, patient clinical data, and other patient data as input. If the input data matches the detected pattern associated with a stored adjustment and the trained model predicts the output that corresponds with the pattern, the adjustment is retrieved and sent to the target surgical instrument when the instrument becomes linked to the surgical hub. For example, if the input data matches pattern #5 and model B predicts a denied claim using data associated with the laparoscopic sigmoid colectomy procedure under planning, a control program update associated with reducing a selected ultrasonic device's maximum period for energy application to below threshold T may be retrieved and sent to the target surgical instrument linked to the surgical hub.

The edge computing system 43602 may create generated data 43618 upon request. For example, after machine learning models (e.g., models A and B) are trained, the edge computing system 43602 may create generated data 43618 upon a request. In an example, the suggestions based on pattern #1 through pattern #4 may be implemented as application programming interface (APIs) on the edge computing system 43602. When a surgeon is planning a laparoscopic sigmoid colectomy procedure (e.g., on a surgical procedure planning interface coupled with a surgical hub), the surgical hub may invoke an API on the edge computing system 43602 with a data record that includes the laparoscopic sigmoid colectomy procedure's associated data as input, including patient personal data, patient clinical data, and other patient data. When the API is invoked, the trained models may be executed using the input. If the input data matches the detected pattern associated with a stored suggestion and the associated trained model predicts the output that corresponds with the pattern, the stored suggestion is sent back as an API response to the surgical hub. For example, if the input data matches pattern #1 and model A predicts a reimbursement rate of at least 80% using the input data, the suggestion for a post-surgery care choice of two days may be send back as an API response to the surgical hub.

The edge computing system 43602 may send local generalized data 43620 to enterprise cloud system 43604. For example, the local generalized data 43620 may include trained machine learning model(s), such as model A or model B described herein. For example, the local generalized data 43620 may include generated data 43618 described herein that are associated with the trained machine learning models.

The edge computing system 43602 may receive peer generalized data 43624 from the enterprise cloud system 43604. For example, peer generalized data may be the local generalized data 43620 as described herein that have been further processed. For example, models trained by the edge computing system 43602 (e.g., model A and/or model B) may be sent as generalized data 43636 to a second edge computing system at a second medical facility or hospital (e.g., hospital A in data boundary 40610). The models may be further trained by the second edge computing system using data associated with laparoscopic sigmoid colectomy procedures in data boundary 40610. The further trained models may be used at the second medical facility or hospital. The further trained models may be sent as generalized data 43632 back to enterprise cloud system 43604. The further trained models may be sent as a part of the peer generalized data 43624 to other medical facilities or hospitals, such as the edge computing system 43602 in data boundary 43614.

In response to receiving the peer generalized data 43624, the edge computing system 43602 may further process the peer generalized data 43624. For example, the further trained models included in the peer generalized data 43624 may be further trained using data associated with laparoscopic sigmoid colectomy procedures in data boundary 40614, such as the training of model A or model B by the edge computing system 43602 described herein. Accordingly, the generated data 43618 may be recreated based on the further trained models and sent to one or more of surgical hubs 43606 through 43608. The local generalized data 43620 may be recreated based on the further trained models and the updated generated data 43618, and sent to the enterprise cloud system 43604.

Systems at a medical facility or hospital may send redacted data to enterprise cloud system 43604. For example, the edge computing system 43602 may send redacted data 43622 to enterprise cloud system 43604. In an example, the redacted data 43622 may be output data from further processing the unredacted 43616 (e.g., patient personal data and patient clinical data). The further processing may be to strip patient private information from the unredacted 43616. The patient private information may be age, employer, body mass index (BMI), or any data that can be used to ascertain the identity of a patient. The redaction process is described in greater detail under the heading of "Data Management and Collection" in U.S. Patent Application Publication No. US 20190206562 A1 (U.S. patent application Ser. No. 16/209,385), titled Method of hub communication, processing, storage and display, filed Dec. 4, 2018, the disclosure of which is herein incorporated by reference in its entirety.

For example, surgical hubs #1 through N may send redacted data 43626 to the enterprise cloud system 43604. Data systems #1 through N may send redacted data 43626 to the enterprise cloud system 43604.

For example, the edge computing system in data boundary 40610 may send redacted data 43634 (e.g., similar to redacted data 43622) to the enterprise cloud system 43604.

An edge computing network may be an edge cloud system (e.g., the edge computing system 43602 in FIG. 36). The edge cloud system may communicate with a cloud system (e.g., remote server(s), such as the enterprise cloud system 43604 in FIG. 36) and the intra-OR hub network (e.g., the interactive hub-to-hub intra-network 43660 in FIG. 37.

Local facility and/or network aggregation of in-network full patient data records (e.g., unredacted data 43616 and unredacted 43617 in FIG. 36) may be performed. Local facility and/or network outcome aggregation may be performed. The edge computing system's processing and data storage may be within a data network of a treatment facility (e.g., hospital B described in FIG. 36). The edge computing system may use expanded patient data. The expanded patient data may be linked to other intra-network systems (e.g., data systems 43610 through 43612 in FIG. 36), such as a billing system, an ordering and supply system, a clinical system, and/or a laboratory system. A billing system may include reimbursement data, patient payment data, and other data. An order and supply system may include cost of product data, utilization rate of product vs. waste data, on-hand stack and delivery frequency data. A clinical system may include outcomes data, readmittance rate data, time in the hospital data, infection rate data, and ER room visits data. A laboratory system may include frequency of testing data, efficacy of the test on outcomes of the patient data, speed or processing and lab backlog data, and/or lab costs data.

Balancing treatments and costs for a specific facility may be performed. Treatment improvements may be determined. For example, improved treatments may be used as a default procedure(s) and treatment regime(s) for a surgeon and/or doctor to start a surgical procedure plan from (e.g., generated data 43618 in FIG. 9). Value analysis of outcomes may be performed (e.g., for surgical procedure planning). For example, machine learning may be used to determine optimized combinations of treatments and procedure for value-based outcomes of the patient (e.g., as described in FIG. 9). For example, cost and/or outcome changes may be highlighted based on the proposed deviations from the machine learning and/or artificial intelligence (AI)-derived optimized combinations of treatments and procedure for value-based outcomes of the patient.

Staff and OR utilizations may be optimized. For example, a mix of surgeons may be determined to drive the profit of departments to hospital usage. For example, scheduling and staffing surge may be tracked to determine optimized staff utilizations.

Advance imaging or other supplementation of surgical procedure may be determined for value and/or outcome improvements. For example, the number of robots to purchase may be determined to balance OR usage to patient throughput.

The local small cloud system (e.g., the edge cloud system/edge computing system) may enable the facility limited machine learning using full patient records (e.g., unredacted data 43616 and unredacted 43617 in FIG. 36).

Some cloud system (e.g., the enterprise cloud system 43604 in FIG. 36) may perform analysis using redacted and anonymized systems, such as longitudinal databases. The cloud system may perform global analyses. The global analyses may use larger subject populations (e.g., millions) and may lack the resolution of specific costs and/or specific treatments. The global analyses be useful for changes in best-practices, new reimbursement codes, etc. Longitudinal databases used in the global analyses may track specific patients through time to analyze complications, medication, and/or patient response to treatments. The data in the longitudinal databases may be anonymized (e.g., redacted). The anonymized data may not provide needed information to provide a hospital or facility specific recommendations for balancing their facility aspects and costs. The longitudinal databases may be a bariatric outcomes longitudinal database (BOLD). The longitudinal databases may be MarketScan. The types of data that may be analyzed using the longitudinal databases are recoveries and complications, biometrics before and after, and/or medication usage.

Analysis by the edge cloud system may compare specific billing to one of more of patient outcomes, most successful reimbursement and reimbursement code usage, and/or best starting point procedures to be most successful for reimbursement with lowest cost, staffing skill needs, staffing utilization and OR usage, etc.

The edge cloud may supply anonymized datasets (e.g., the redacted data 43622 in FIG. 36), generalized conclusions (e.g., local generalized data 43620 in FIG. 9), and product specific data to systems outside of the HIPAA protected networks (e.g., data boundary 40614 in FIG. 9). The data-sharing may allow the facility to use machine learning to improve their operational parameters and outcomes (e.g., as generated data 43618 is generated using machine learning, as described in FIG. 9). The edge cloud may share the anonymized data to a remote cloud system (e.g., a remote cloud server, such as the enterprise cloud system 43604 in FIG. 36). The remote cloud system may build more global, instrumentation, and/or treatment conclusions.

Figure 37:
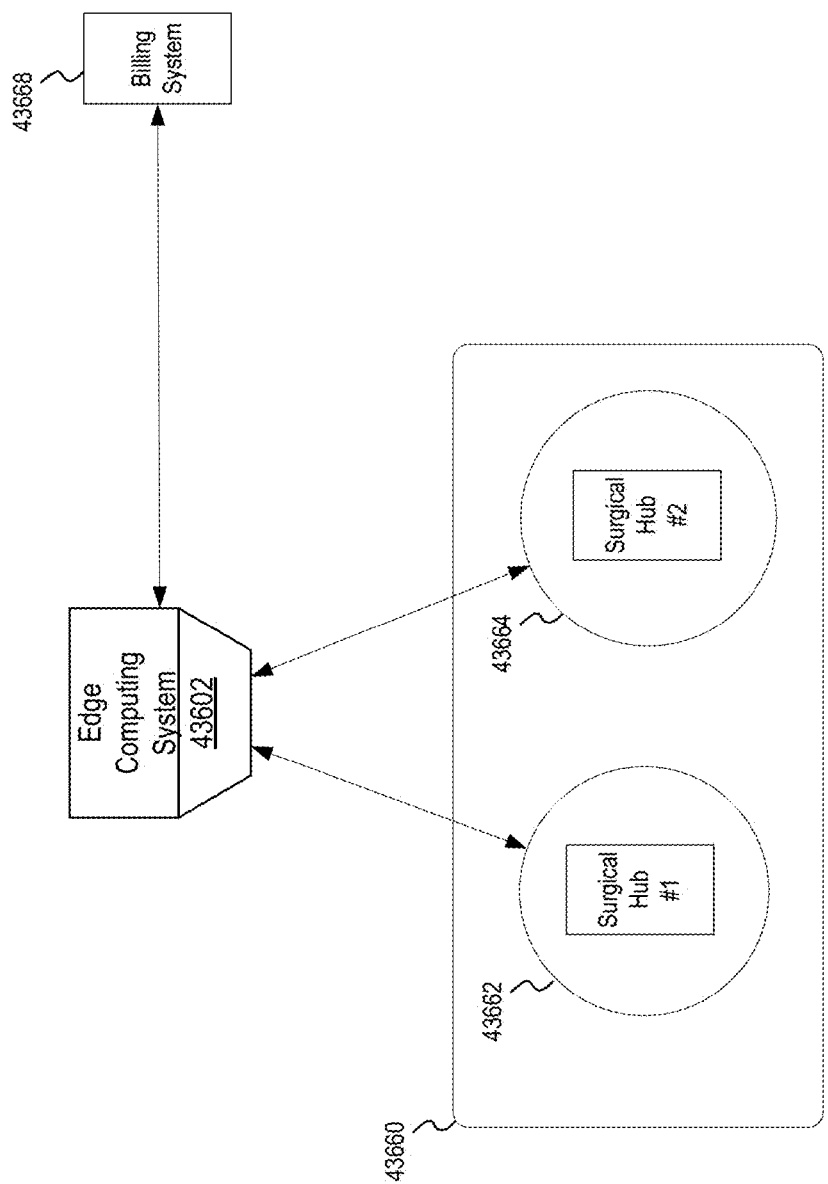
FIG. 37 is a block diagram of an example edge computing system operating with an intra-surgical hub network.

FIG. 37 is a block diagram of an example edge computing system operating with an intra-surgical hub network. Surgical hub(s) may be in different ORs. The OR surgical hub(s) may form an intra-network. The OR surgical hub(s) may be coupled to an edge computing network and/or system (e.g., edge computing system 43602 shown in FIG. 36) to create an interactive hub-to-hub intra-network. In examples, surgical hub #1 and surgical hub #2 (e.g., surgical hubs 43606 through 43608 in FIG. 36) may be in OR 43662 and OR 43664, respectively. Surgical hub #1 and surgical hub #2 may be coupled with the edge computing system 43602 to create an interactive hub-to-hub intra-network 43660.

The edge computing system 43602 may create leverageable competitive data systems over their competitor networks (e.g., competitor treatment networks). The edge computing system may be within a medical facility's (e.g., hospital B described in FIG. 36) confidential network (e.g., the data boundary 40614 in FIG. 9). The HIPAA data from patient(s) may be used in combination with clinical outcomes data to determine treatments (e.g., new or value-added treatments).

For example, a procedure's reimbursement rate may be used with the outcomes data to instruct surgical procedure plan(s) and/or recovery plan(s). In an example, reimbursement data from billing system 43668 (e.g., a system from data systems 43610 through 43612 in FIG. 36) and outcomes data from surgical hub #1 and surgical hub #2 in OR 43662 and OR 43664, respectively, may be balanced to identify value-added treatments as a starting point for surgical procedure plan(s) and/or recovery plan(s). In an example, a treatment or a recovery plan may deviate from the starting point (e.g., a value-added plan or treatment), the impacts on outcomes, probabilities of complication, and/or cost may be determined for the deviation. In an example, when value-added treatments result from a combination of secondary costs (e.g., duration of hospital stay, hospital acquired infection treatment, readmission rates, and/or emergency services secondary rates), the data may be used to support changes in the value-added treatment reimbursement categorization, or indications for use expansion.

For example, when a surgeon is within the intra-network 43660 (e.g., when operating on surgical hub #1), the surgeon may build or rely on the value-added treatment(s) of another surgeon (e.g., from surgical hub #2) within the intra-network 43660 to increase efficiency, outcomes or low complication rates.

The edge computing system 43602 may suggest changes to other systems (e.g., (e.g., a system from data systems 43610 through 43612 or surgical hubs 43606 through 43608 in FIG. 36) such as, a billing system, an ordering system, a sterilization system, etc. The change(s) may increase the value for the facility for good outcomes. For example, the change(s) to the payment system may be leveraged and may allow patients to pay for outcomes and share in the cost and savings of treatment adjustments. The treatment adjustments may help a facility (e.g., a medical facility) adjust staffing, utilization rate, order timing, etc. For example, surgical procedures may be scheduled with patient treatment outcomes and low burden on the health care facility to balance surge capacity needs.

Figure 38:
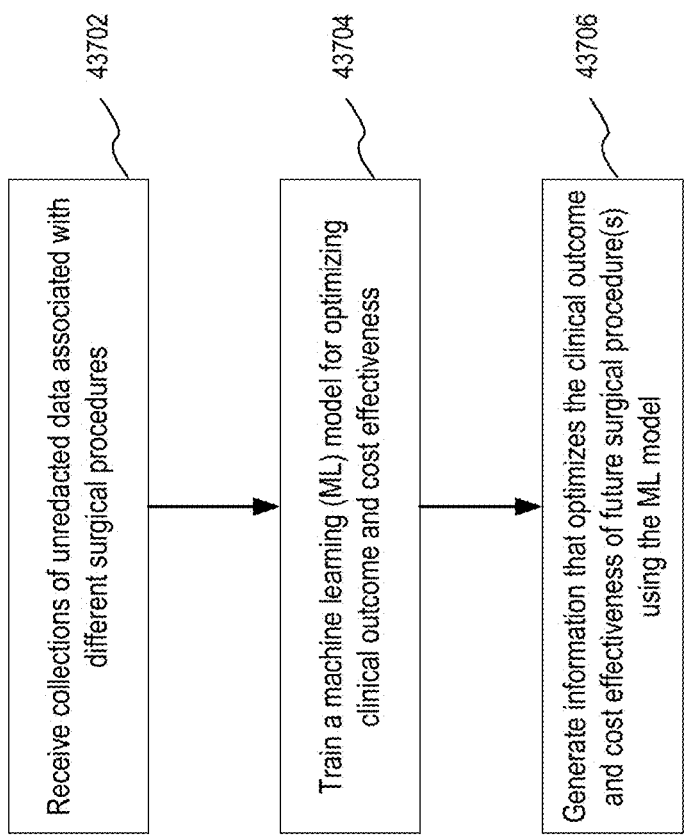
FIG. 38 is the flow chart of an example operation of an edge computing system.

FIG. 38 is the flow chart of an example operation of an edge computing system. The edge computing system may be the edge computing system 43604 described in FIG. 36.

At 43702, collections of unredacted data associated with different surgical procedures may be received. For example, a first collection of unredacted data associated with a first surgical procedure may be received. For example, a second collection of respective unredacted data associated with a second surgical procedure may be received. The first surgical procedure and the second surgical procedure may be past surgical procedures. The first collection of unredacted data and the second collection of unredacted data may be received from at least one of a surgical hub or a data system on a local data network. The first collection of unredacted data or the second collection of unredacted data may include patient personal data, patient clinical data, and other patient data. The local data network may be within a boundary protected by health insurance portability and accountability act (HIPAA) data rules.

For example, the patient personal data may include a patient identifier. The patient clinical data may include a patient identifier. The other patient data may include a patient identifier.

For example, the patient personal data may include one or more of demographics information, such as age, gender, place of residence, occupation, or family status. For example, the patient clinical data includes one or more of pre-surgery data, in-surgery data, or post-surgery data. For example, the other data may include one or more of billing data, payment data, or reimbursement data.

At 43704, a machine learning (ML) model may be trained for optimizing clinical outcome and cost effectiveness of future surgical procedure(s) using the collections of unredacted data associated with different surgical procedures For example, the future surgical procedure(s) may include a third surgical procedure. The third surgical procedure may be a same type of surgical procedure as the first surgical procedure and the second surgical procedure.

At 43706, information that optimizes the clinical outcome and cost effectiveness of future surgical procedure(s) using the ML model may be generated. For example, the information that optimizes the clinical outcome and cost effectiveness of the third surgical procedure may include one or more of aspects of a surgical procedure plan associated with the third surgical procedure, such as a surgical choice, a surgical instrument selection, or a post-surgery care choice. For example, the information that optimizes the clinical outcome and cost effectiveness of the third surgical procedure may include an operational parameter for a surgical instrument associated with the surgical instrument selection.

The information that optimizes the clinical outcome and cost effectiveness of future surgical procedure(s) may be sent to a surgical hub from the at least one of a surgical hub or a data system. The information that optimizes the clinical outcome and cost effectiveness of future surgical procedure(s) may be sent to a surgical procedure planning user interface.

For example, a request for the information that optimizes the clinical outcome and cost effectiveness of future surgical procedure(s) may be received. For example, the request may be from the surgical hub from the at least one of a surgical hub or a data system. For example, in response, the information may be sent to the surgical hub.

For example, the information that optimizes the clinical outcome and cost effectiveness of future surgical procedure(s) may be sent to a cloud computing system.

For example, the first collection of unredacted data may be redacted. The second collection of unredacted data may be redacted. The redacted first collection of unredacted data and the redacted second collection of unredacted data may be sent to the cloud computing system.

Predictive maintenance of an individual hub system or node may be directed by an edge cloud system. An edge cloud system may be defined as an edge computing system concentric to a facility's gateway to a cloud system and acts as a sub-cloud system, e.g., with only the in-network interactions to react to and/or draw from. The edge cloud is within the HIPAA controlled private data network. The edge cloud may act on data and interactions of hubs that for privacy reasons. The data and interactions may not be shared with systems outside of their network.

The edge cloud system may monitor each of the hub systems for security, data storage capacity, and errors. As a hub system reaches a predefined timing, a predefined utilization of resources, or a number of detected errors (e.g., numbers of reboots, communication errors, out of date software, etc.), it may schedule and may initiate a maintenance activity. If the maintenance is beyond an automated check, a notification to service personal and administration may be flagged. If the hub system is flagged for manual maintenance, the hub system may be automatically swapped with another hub system that may automatically be configured and downloaded with all the information from the out-for-service hub system, e.g., to make interaction in the operating room (OR). If the errors detected are during a procedure the hub system may notify users in the OR of the issue and go into a limp mode. The limp mode may be where the system shuts off all non-room critical functions to avoid error propagation and allows for the completion of the procedure before being backed up and taken out of service.

Each hub system may have a standard interaction cadence of reporting function, local analysis of the attached systems, usage, and/or life remaining of consumables. This may be accomplished as part of the daily and/or weekly update of the data from the procedures run. A hub system may download any errors which occurred as part of the system and its instruments since the last data download.

The edge cloud may confirm and/or interrogate networked equipment and/or devices (e.g., on a predefined interval), e.g., to each of the local hub systems prior to use against the manufacturing acceptance test to monitor wear, degradation and/or life limited components. The check may be completed as part of a start-up or shutdown procedure of a local hub system. In the procedure, the data may be stored or sent to facility server or the edge cloud system and/or a manufacture to indicate when maintenance or service should be conducted. The check may be triggered based on a network congestion level (e.g., during times of no use or low use), local hub system down times, or scheduling related time (e.g., holidays, weekends, etc.)

Manufactures may do a type of acceptance check on the equipment and or device prior to packaging to confirm it meets acceptable performance. Using a system hub to check itself and/or other equipment and/or devices against the same metrics and/or acceptance testing prior to use could reassure and/or minimize issues when performing the procedure. The results may be evaluated against the initial acceptance check during manufacturing to confirm the shift in performance from storage condition and/or storage time and use. This may provide insight on when maintenance or service may be needed and/or indicate which components may be impacted based on performance indicators.

Figure 39:
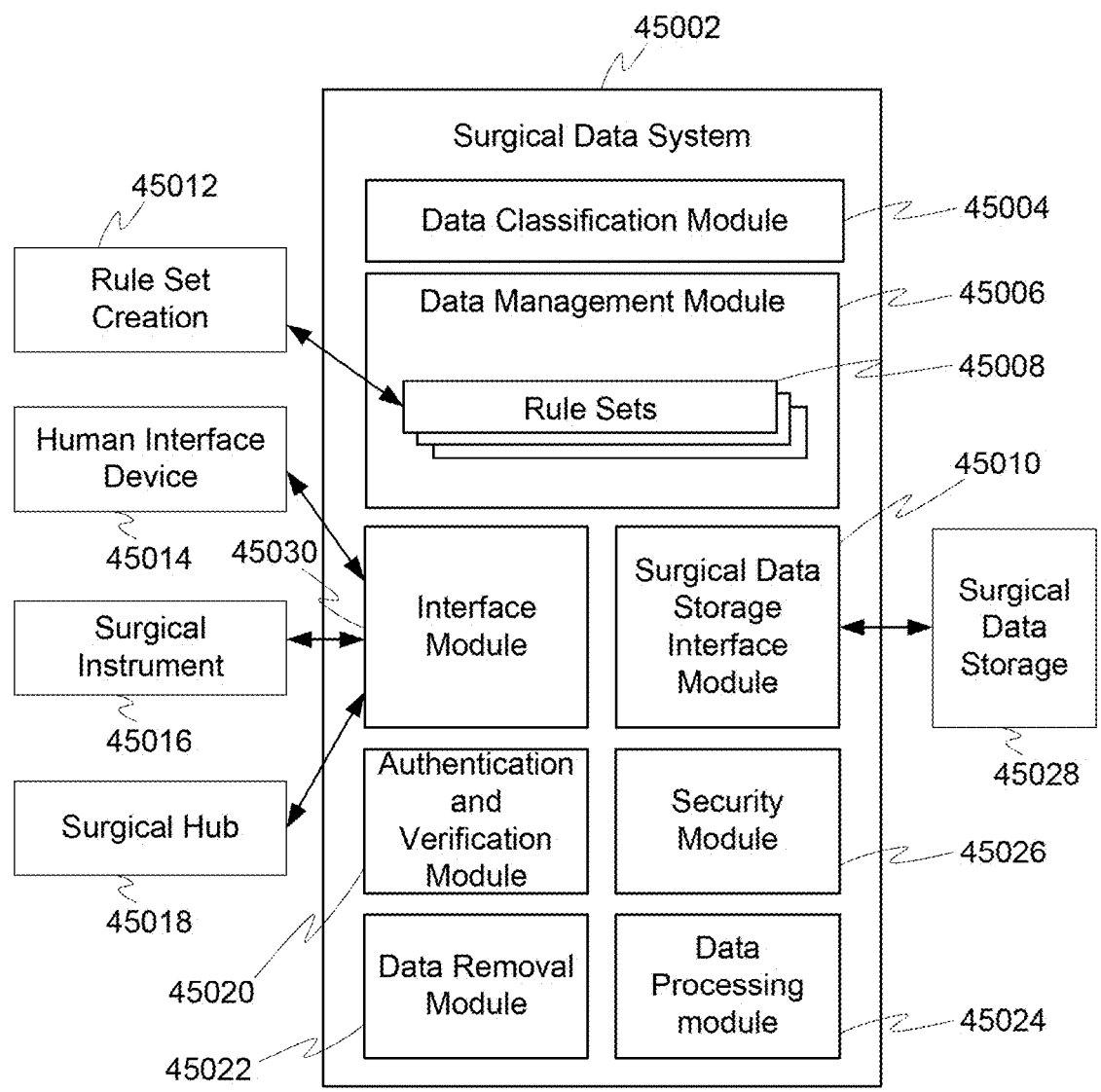
FIG. 39 shows an example surgical data system.

FIG. 39 shows an example surgical data system. The surgical data system 45002 may support functionalities of a surgical hub, for example, the surgical hub 20006 in FIG. 3. The surgical data system 45002 may support functionalities of various modules of a surgical hub, for example, the various modules in the surgical hub 20006 of FIG. 3. The surgical data system 45002 may be part of a surgical hub, for example, the surgical hub 20006 in FIG. 3. The surgical data system 45002 may be part of a processor module of a surgical hub, for example, the processor module 20057 of the surgical hub 20006. The surgical data system 45002 may be a stand-alone system.

The surgical data system 45002 may include any hardware and/or software suitable for providing functionalities of managing and processing surgical information. The surgical data system 45002 may provide functionalities to support the structure and/or functions described in connection with FIGS. 1-8 and 39-48 herein. For example, the surgical data system 45002 may support one or more elements of a computer-implemented interactive surgical system 20070 in FIG. 5. Examples of data processing that are suitable for use with the surgical data system 45002 are described in U.S. Patent Application Publication No. US 2019-0201033 A1 (U.S. patent application Ser. No. 15/940,663), titled SURGICAL SYSTEM DISTRIBUTED PROCESSING, filed Mar. 29, 2018, the disclosure of which is herein incorporated by reference in its entirety. In one or more of those examples, processing of data may be shared with a handheld instrument with a limited processor. The surgical data system 45002 may include a situational awareness system that is described herein. Examples that are suitable for use with the surgical data system 45002 are described in U.S. Patent Application Publication No. US 2019-0206551 A1 (U.S. patent application Ser. No. 15/940,666), titled SPATIAL AWARENESS OF SURGICAL HUBS IN OPERATING ROOMS, filed Mar. 29, 2018, the disclosure of which is herein incorporated by reference in its entirety. In one or more of those examples, a surgical hub may identify the bounds of an operating space.

The surgical data system 45002 may include one or more functional modules. Each module may include hardware, software, or a combination thereof that enable functionality of the module. One or more modules, operating in concert or otherwise, may enable authentication and verification of data, data security, database integration, data classification, data processing, data removal and big data management. The modules may include hardware elements, such as a computer processing unit, a graphics processing unit, a field-programmable gate array (FPGAs), communications hardware, memory, and the like. The modules may include software elements that when executed by a processor cause the modules to perform the functionalities of the modules.

The surgical data system 45002 may include an interface module 45030. The interface module 45030 may enable communication with one or more of human interface device 45014, a surgical instrument 45016, or a surgical hub 45018. The human interface device 45014 may include a display. In some examples, the surgical hub 45018 may be the surgical hub 20006 that has a communication module 20056. The surgical data system 45002 may include, for example, on or more surgical data repositories. The surgical data system 45002 may interact with a surgical data storage 45028 through the surgical data storage interface module 45010. In an example, the surgical data storage 45028 may include the remote server 20067 of the cloud computing system 20064 in FIG. 4.

The surgical data system 45002, may obtain data, for example, from various OR equipment and sensing devices, as shown in FIG. 2. For example, the data may include any surgical data collected from the various OR equipment and sensing devices. For example, the surgical data system 45002 may receive data directly from any of the networked devices disclosed in FIGS. 1-8. Such data may include information about a live surgical procedure, for example. Such data may include information about a past surgical procedure. Such data may include information about future, scheduled surgical procedures. Examples of data this is suitable for use with the present disclosure are described in U.S. Patent Application Publication No. US 2019-0207773 A1 (U.S. patent application Ser. No. 15/940,645), titled SELF DESCRIBING DATA PACKETS GENERATED AT AN ISSUING INSTRUMENT, filed Mar. 29, 2018, the disclosure of which is herein incorporated by reference in its entirety. In one or more of those examples, self-describing data may allow a processor to interpret data without having been told in advance of its receipt.

Information about surgical procedures (e.g., surgical information) may include information about the patient, the staff, the procedure as planned, the procedure as experienced, and post-operative activity including patient outcomes. For example, the information received and used by the surgical data system 45002 may include patient records, patient imaging, models of patient anatomy, patient lab results, patient medical history, and the like. For example, the information received and used by the surgical data system 45002 may include a staff manifest for a procedure, details about the past procedures of the specific staff members, staff metrics, experience, recent scheduling and workload, and historical surgical activity, such instrument use statistics, procedure duration, and the like. For example, the information received and used by the surgical data system 45002 may include procedure plans, equipment and inventory information, pull-lists, checklists, procedure plan analysis and recommendations. For example, the information received and used by the surgical data system 45002 may include any data collected or generated during a live procedure, such as procedure progress, milestones, patient information, vitals, operating theater setup, staff movement, imaging, instrument use, surgical technique, such as that captured by video, recorded manually, and/or inferred from smart-instrument reporting for example, duration, abnormal event reporting, and the like. Any data captured during a live procedure may also be stored and made available as a past procedure. For example, the information received and used by the surgical data system 45002 may include post-operative records, patient recovery information, and patient outcome information, post-operative diagnostic information, such as labs, imaging, etc.

The surgical data system 45002 may include authentication and verification module 45020. The authentication and verification module 45020 may authenticate and/or verify surgical data that the device receives by employing the surgical data system 45002. Examples that are suitable for use with the authentication and verification module 45020 are described in in U.S. Patent Application Publication No. US 2019-0205441 A1 (U.S. patent application Ser. No. 16/182,224), titled SURGICAL NETWORK, INSTRUMENT, AND CLOUD RESPONSES BASED ON VALIDATION OF RECEIVED DATASET AND AUTHENTICATION OF ITS SOURCE AND INTEGRITY, filed Nov. 6, 2018, the disclosure of which is herein incorporated by reference in its entirety. In one or more of those examples, hub, instrument, and cloud responses may operate based on validation of a received dataset and authentication of its source and integrity. One or more of the responses may be a choice of reactions to either the data or metadata.

The surgical data system 45002 may include security module 45026. In an example, the security module 45026 may provide security of monitoring authenticity and sterility of manual device assisting in robotic case. Examples that are suitable for use with the security module 45026 are described in in U.S. Patent Application Publication No. US 2019-0207911 A1 (U.S. patent application Ser. No. 15/940,641), titled INTERACTIVE SURGICAL SYSTEMS WITH ENCRYPTED COMMUNICATIONS CAPABILITIES, filed Mar. 29, 2018, the disclosure of which is herein incorporated by reference in its entirety. In one or more of those examples, mantle generator data may be encrypted and communicated through the internet. Examples that are suitable for use with the security module 45026 are described in in U.S. Patent Application Publication No. US 2019-0206216 A1 (U.S. patent application Ser. No. 16/182,248), titled DETECTION AND ESCALATION OF SECURITY RESPONSES OF SURGICAL INSTRUMENTS TO INCREASING SEVERITY THREATS, filed Nov. 6, 2018, the disclosure of which is herein incorporated by reference in its entirety. In one or more of those examples, a wireless pair surgical instrument may detect and escalate security responses to numerous or increasing severity threats.

The surgical data system 45002 may include a data management module 45006. The data management module 45006 may provide management of a data stream, and/or an organization and structure of the data stream, for example, to facilitate an integration of the data stream into a databases or multiple databases. The data management module 45006 may provide management of a data stream, and/or an organization and structure of the data stream, for example, by selecting one or more rule sets from rule sets 45008. The rule sets 45008 may be generated via rule set creation 45012. Examples that are suitable for use with the data management module 45006 are described in in U.S. Patent Application Publication No. 2019-0200988 A1 (U.S. patent application Ser. No. 16/024,162), titled SURGICAL SYSTEMS WITH PRIORITIZED DATA TRANSMISSION CAPABILITIES, filed Jun. 29, 2018, the disclosure of which is herein incorporated by reference in its entirety. In one or more of those examples, same data from two different sources may be prioritized. Examples that are suitable for use with the security module 45026 are described in in U.S. Patent Application Publication No. US 2019-0205567 A1 (U.S. patent application Ser. No. 15/940,649), titled DATA PAIRING TO INTERCONNECT A DEVICE MEASURED PARAMETER WITH AN OUTCOME, filed Mar. 29, 2018, the disclosure of which is herein incorporated by reference in its entirety. In one or more of those examples, data pairing method may allow a surgical hub to interconnect a device measured parameter with an outcome.

Data standardization (e.g., data structure standardization) may include one or more of parsing, merging, or processing within a device. For example, the device may include the surgical data system 45002. The device may be a surgical hub, for example, the surgical hub 20006. The device may include a data management module, for example, the data management module 45006 in FIG. 39. Data standardization may enable database integration. Data streams from multiple sources may differ in resolution, sampling rate, measurement type, unit type, communication path, importance, data stream type (e.g., discrete or continuous), etc. Data streams (e.g., each data point of each data stream) and the associated metadata may be formatted and/or organized into a standard format such that the formatted data streams can be input into a data base that is in the standard format. For example, the device may adjust the format (e.g., the structure and organization) of a data stream into a standard format to enable annotation or contextual attachment to other data streams. The standard format may be a standardized and organized form.

The device may cooperate with various OR equipment and sensing devices, for example, the various OR equipment and sensing devices as shown in FIG. 2. An OR equipment (or sensing device) may provide a data stream. For example, each of the various OR equipment and sensing devices may provide a respective data stream, and each of the various OR equipment and sensing devices may function as a data source for the respective data stream. The respective data streams may include one or more surgical data streams. The respective data streams may be assimilated, displayed and recorded, for example, in the surgical system shown in FIG. 2. Examples that are suitable for use with the present disclosure are described in in U.S. Patent Application Publication No. US 2019-0206576 A1 (U.S. patent application Ser. No. 16/182,260), titled AUTOMATED DATA SCALING, ALIGNMENT, AND ORGANIZING BASED ON PREDEFINED PARAMETERS WITHIN SURGICAL NETWORKS, filed Nov. 6, 2018, the disclosure of which is herein incorporated by reference in its entirety. In one or more of those examples, automated data scaling, alignment, and organizing may be based on predefined parameters within a surgical hub before transmission.

The respective data streams from the various OR equipment and sensing devices may be in different forms and/or frequencies. For example, at least one of a resolution, a sampling rate, a measurement type, a unit of measurement, or a data stream type of a data stream may be different from that of another data stream. A data stream type may be a discrete data stream type or a continuous data stream type. For example, the device may receive data streams from two different patient monitoring devices of the patient monitoring devices 5124 in FIG. 8. One of the patient monitoring devices may be a BP monitor, and the other of the patient monitoring devices may be an EKG monitor. Depending on a patient's profile, the BP monitor may be set up to take a measurement every x minutes, and the sampling rate of EKG monitor may be set at y kHz. The data stream received from the BP monitor (the BP data stream) and the data stream received from the EKG monitor (the EKG data stream) may be transformed into a standard format, and the transformed BP data stream and the transformed EKG data stream may be input to a data base that is in the standard format.

The device may organize data streams into standardized formats and associations, for example, to allow for display of relational data with respect to an instrument, a task, and/or the device. For example, the device may process and/or organize data streams into standardized formats and/or associations using algorithms and/or transformations. The device may be a data standardization device.

Figure 40:
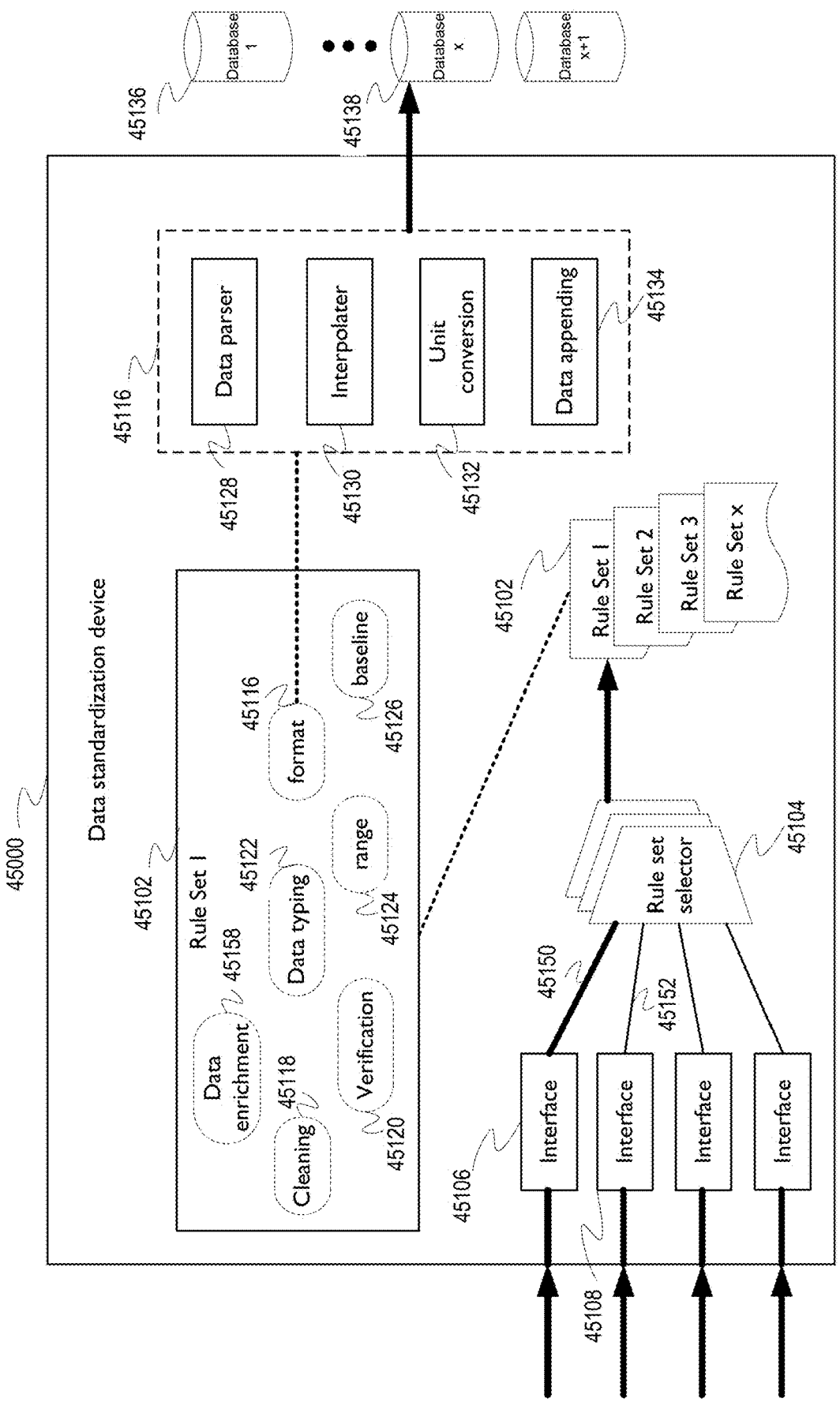
FIG. 40 shows an example data standardization device.

FIG. 40 shows an example data standardization device 45000. The data standardization device 45000 may receive surgical data stream 45150 via surgical data interface 45106. The data standardization device 45000 may receive surgical data stream 45152 via surgical data interface 45108. An interface, for example, the surgical data interfaces 45106, 45108, and 44540-44546, may include a logical entity that interfaces with a certain type of surgical instrument. The interface may be configured to receive a data stream from a surgical instrument of that type. In an example, a certain type of surgical instruments may communicate with the surgical data system 45002 via a designated surgical data interface. The designated surgical data interface used to receive a surgical data stream may indicate the surgical instrument of the type, from which the surgical data stream is received. The interface, for example, one or more of the surgical data interfaces 45106, 45108, and 44540-44546, may be provided by an interface engine or an interface module, for example, the interface module 45030 in FIG. 39. The surgical data stream 45150 may indicate surgical information (e.g., a patient's symbolic and diabolic BP are in normal ranges).

The data standardization device 45000 may include a rule set selector 45104. The rule set selector 45104 may select a rule set for a data stream based on the interface that is configured to receive the data stream. In FIG. 40, the rule set selector 45104 may select rule set 1, referred as 45102, for example, among multiple rule sets including rule set 2 to rule set x, for the surgical data stream 45150. The rule set selector 45104 may identify the surgical data interface 45106. The rule set selector 45104 may select rule set 1 based on the identified surgical data interface 45106. The surgical data stream 45150 may be transformed into the standard format using rule set 1. The transformed surgical data stream may then be input to a database. The transformed surgical data stream may include the surgical information that is indicated by the surgical data stream 45150 (e.g., a patient's symbolic and diabolic BP are in normal ranges).

The selection of rule set 1 may be further based on the database into which the transformed surgical data stream is to be input. For example, database x, referred as 45138 may be selected. Database x may be in a standard format. The data standardization device 45000 may be operatively coupled to one or more databases, for example, database 45136 and the database 45138. The database 45136 and the database 45138 may be in the same standard format or different standard formats. A standard format may be a format having one or more of a certain resolution, a certain sampling rate, a certain measurement type, a certain unit of measurement, a certain priority, or a certain type of data stream such as whether a data stream is a discrete data stream or a continuous data stream. The one or more databases may use different architectures. The different database architectures may include a hierarchical Database, a flat files database, an object database, or a relational database.

The selected rule set 1 may include, for example, data cleaning rules 45118, data verification rules 45120, rules for data typing 45122, rules 45124 for setting a data range, rules 45126 for setting a baseline, and data formatting rules 45116. The data formatting rules 45116 may include, for example, data parser rules 45128, interpolator rules 45130, unit conversion rules 45132, and data appending rules 45134. Depending on the surgical data stream which the selected rule set 1 is to be applied, rule set 1 may include some or all of the rules herein.

The selected rule set 1 may include the data cleaning rules 45118. Based on the data cleaning rules 45118, the data standardization device 45000 may detect and correct (or remove) corrupt or inaccurate records from a data stream, a record set, a table, or a database. The data standardization device 45000 may identify incomplete, inaccurate or irrelevant parts of the surgical data stream 45150. The data standardization device 45000 may replace, modify, or delete incomplete, inaccurate or irrelevant parts (e.g., dirty or coarse data) of the surgical data stream 45150. The data standardization device 45000 may determine a reference data set (e.g., similar but clean data sets). The data standardization device 45000 may determine a data cleaning target (e.g., what the data should appear like) based on the reference data set. The reference data set may be used for comparison and adaptation of the surgical data stream 45150. The data standardization device 45000 may determine how to clean the surgical data stream 45150 in consistency with the reference data set. The data standardization device 45000 may replace or supplement partial data sets (e.g., partial mating data sets) based on correlated records. The data standardization device 45000 may perform harmonization or normalization of data streams, for example, to convert varying data formats into a cohesive database.

The selected rule set 1 may include the data verification rules 45120. The data verification rules 45120 may be used to improve data integrity. The data verification rules 45120 may define which data sets or data streams a data set or a data stream is permitted to be related to. For example, a patient record or a procedure record may be permitted to link to products that are used or applied to the patient or to the procedure; the patient record or the procedure record may not be permitted to link to unrelated data such as OR equipment used.

The data verification rules 45120 may include checks for invalid data and correction for the invalid data, for example, based on a fixed schema or a predefined set of rules. Data verification rules may be used to control data integrity, produce database stability, improve database performance, improve data re-usability, improve database maintainability, improve data or transformation traceability. Data verification rules may include rules that improve one or more of entity integrity, referential integrity, domain integrity, customized parameters integrity.

The selected rule set 1 may include the data enrichment rules 45158. The data enrichment rules 45158 may include merging third-source data from related systems or merging semi-parity data from sources within an OR, OR equipment, or OR measurement systems. The data enrichment rules 45158 may be used to enhance data streams to make more informed decisions. Data enrichment rules may include data appending rules.

The selected rule set 1 may include the data formatting rules 45116. The data formatting rules 45116 may include the data parser rules 45128 for organization. To generate the transformed data stream, the data standardization device 45000 may parse a received data stream according to the organization of the database in a standard format. In FIG. 40, parsing the received data stream according to the organization of the database in the standard format may be performed according to the data parser rules 45128.

The data formatting rules 45116 may include the interpolator rules 45130. The interpolator rules 45130 may include adding and/or calculating intermediate average data points, for example, to create a complete even cadence of data points. For example, the surgical data stream 45150 may have a sampling rate that is lower than the sampling rate of the standard format. The data standardization device 45000 may determine intermediate average data points for the surgical data stream 45150 based on the data points of the surgical data stream 45150. The data standardization device 45000 may generate the transformed data stream by adding the intermediate average data points to the surgical data stream 45150. In FIG. 40, the determination of the intermediate average data points and the addition of the intermediate average data points may be performed according to the interpolator rules 45130.

The data formatting rules 45116 may include the unit conversion rules 45132. The unit conversion rules 45132 may include processing the units into common unit measures (e.g., inches to millimeters). In FIG. 40, processing the units into common unit measures may be performed according to the unit conversion rules 45132.

The data formatting rules 45116 may include the data appending rules 45134. The data appending rules 45134 may include adding tags to the data stream for one or more of integration, organization, searching, annotating, or highlighting. In FIG. 40, adding tags for integration may be performed according to the data appending rules 45134.

In an example, the data standardization device 45000 may receive patient sensor data, for example, in a patient sensor data stream. The data standardization device 45000 may select a rule set for the patient sensor data based on the surgical data interface configured to receive the patient sensor data from a wearable patient sensor system, and a relational data base to store the patient sensor data. The data standardization device 45000 may generate transformed patient sensor data based on the selected rule set such that the patient sensor data can be input into the relational data base.

The rule set selector 45104 may select a different rule set (e.g., rule set 2) for the surgical data stream 45152. For example, rule set 2 may include one or more of the data cleaning rules 45118, the data verification rules 45120, the rules for data typing 45122, the rules 45124 for setting a data range, the rules 45126 for setting a baseline, or the data formatting rules 45116. The data formatting rules of rule set 2 may include one or more of the data parser rules 45128, the interpolator rules 45130, the unit conversion rules 45132, and the data appending rules 45134.

The data standardization device 45000 may receive instrument operational data, for example, in an instrument operational data stream. The data standardization device 45000 may receive OR equipment data, for example, in an OR equipment data stream. The data standardization device 45000 may select a rule set for the instrument operational data and generate a transformed instrument operational data based on the selected rule set for the instrument operational data. The data standardization device 45000 may select a rule set for OR equipment data and generate transformed OR equipment data based on the selected rule set for the OR equipment data. The rule set selected for the patient sensor data, the rule set selected for the instrument operational data, and the rule set selected for the OR equipment data may differ. For example, the patient sensor data may need a more complex cleaning rule and a more extensive interpolation than the instrument operational data does, for example, due to irregular wearing habits of the patent that has the wearable patient sensor system. The selected rule set for the patient sensor data may include data cleaning rules that are more complex than, for example, a selected rule set for the instrument operational data. The selected rule set for the patient sensor data may include interpolation that is more extensive than, for example, the selected rule set for the instrument operational data.

By using different rule sets, the transformed patient sensor data, the transformed instrument operational data, and the transformed OR equipment data may be in a format that has common sampling, synchronization, and interactive common events linked together. The transformed patient sensor data, the transformed instrument operational data, and the transformed OR equipment data may be stored in one database. The database may include a relational database. In some examples, the transformed patient sensor data, the transformed instrument operational data, and the transformed OR equipment data may be stored in different databases of the same or different standard formats.

Transforming a data stream into a standard format or standard formats using the selected rule set may include verifying the integrity of the patient sensor data, the instrument operational data, and the OR equipment data. For example, the data standardization device 45000 may select rule set 1 for the patient sensor data. Rule set 1 may include the data cleaning rules 45118. The data standardization device 45000 may determine invalid data and invalid associations based on the data cleaning rules 45118. Transforming the patient sensor data may include excluding the invalid data and the invalid associations from the transformed patient sensor data.

Transforming a data stream into a standard format or standard formats using the selected rule set may include enhancing one data stream using a related data stream. Transforming a data stream into a standard format or standard formats may enable annotation of other related data or enable attachment of other related data to provide a context (or syntax) for the other related data. For example, the instrument operational data and the OR equipment data may be associated with a same surgical event. The data standardization device 45000 may generate one or more annotations for the instrument operational data using the OR equipment data. The generated annotations may enable the transformation of the instrument operational data into a standard format.

A rule set may be used to maintain qualities of data streams. Transforming data streams using suitable rule sets may improve the consistency or capacity of decisions or improve transformations that can result from the data streams. The data standardization device 45000 may improve data qualities of the data streams before the data streams are inputted to the databases by monitoring the data streams, adjusting the data streams, and enhancing the data streams.

Figure 41:
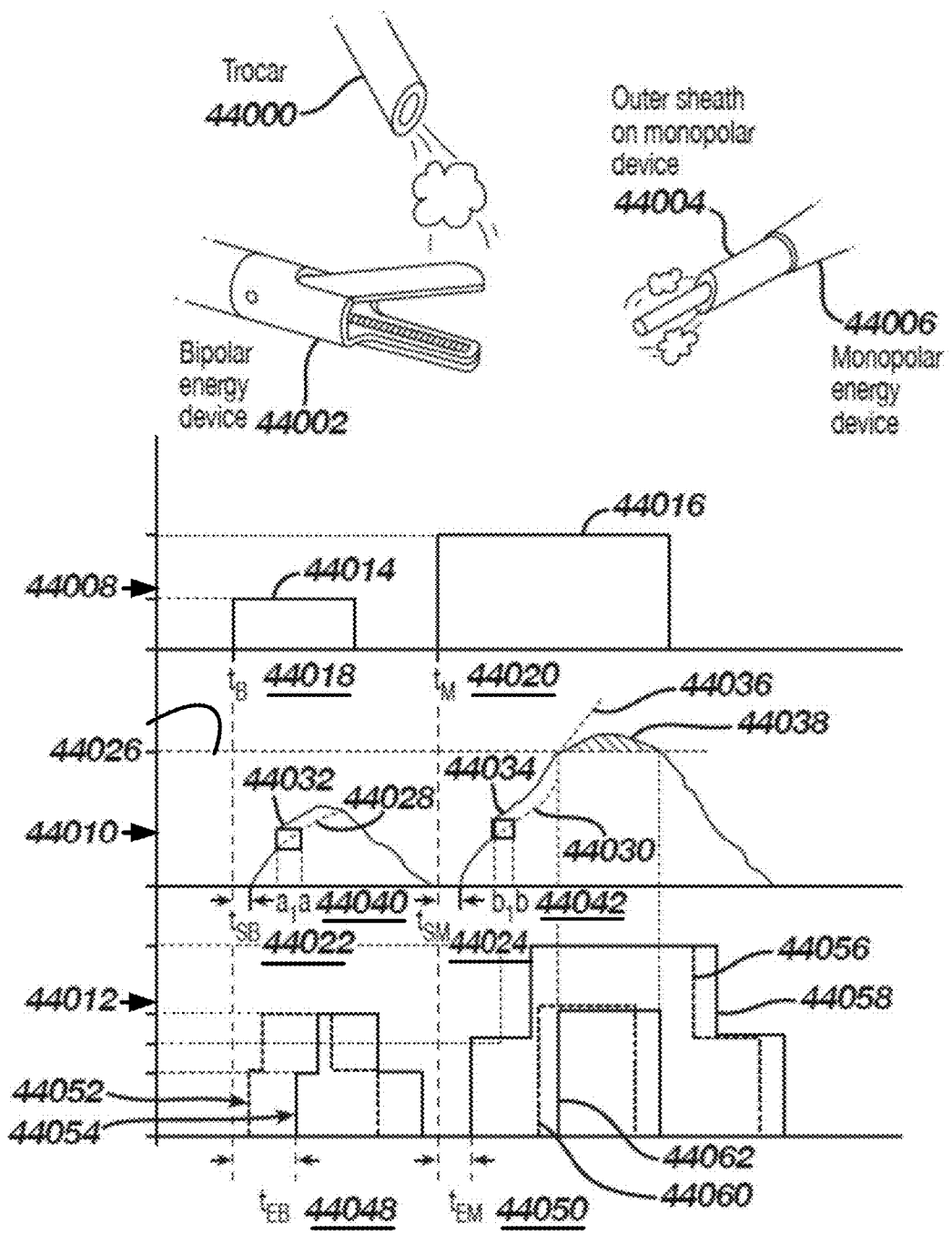
FIG. 41 shows an example data quality control.

FIG. 41 illustrates an example of data quality control. Data from an advanced energy generator may be paired with data from a monopolar generator with a tethered conventional smoke evacuator. A smoke evacuator (e.g., trocar 44000) may be used for a bipolar energy device 44002. A monopolar energy device 44006 may have an outer sheath 44004. The outer sheath 44004 may evacuate a smoke plume generated by the monopolar energy device 44006.

The graphs in FIG. 41 include a top portion 44008, a middle portion 44010, and a bottom portion 44012. The top portion 44008 shows energy activation types and amounts used by the bipolar energy device 44002 and the monopolar energy device 44006 over time. The top portion 44008 shows activation control signal. Graph 44014 shows the energy activation type and amount used by the bipolar energy device 44002 over time. Graph 44016 shows the energy activation type and amount used by the monopolar energy device 44006 over time. The middle portion 44010 shows the amounts of visual smoke plumes generated by the bipolar energy device 44002 and the monopolar energy device 44006 over time. The bottom portion 44012 shows the energy types and amounts used by the smoke evacuator for the bipolar energy device 44002 and by the smoke evacuator for the monopolar energy device 44006 over time.

The energy types and amounts used by the smoke evacuators may be plotted over time, shown in the bottom portion 44012. For example, an advanced energy generator (e.g., for the monopolar energy device 44006) may have an analog pigtail on the motor current of a smoke evacuator activation line and the power output and return path of the monopolar lines. A current monitoring device may measure the pigtail. Dotted energy graph 44052 shows the activation and energy amount used by the smoke evacuator (e.g., the trocar 44000) for the bipolar energy device 44002. Energy graph 44054 shows the activation and energy amount used for in situ smoke evacuation of the smoke plume generated by the bipolar energy device 44002. The energy graph 44054 shows a delay (e.g., 2 seconds). Dotted energy graph 44056 shows the activation and energy amount used by the smoke evacuator for the monopolar energy device 44006. Energy graph 44058 shows the activation and energy amount used for in situ smoke evacuation of the smoke plume generated by the monopolar energy device 44006. The energy graph 44058 shows a delay (e.g., 1 second). Dotted energy graph 44060 shows the activation and energy amount used by the smoke evacuator for the bipolar energy device 44002 when the smoke evacuator for the bipolar energy device 44002 is used with the smoke evacuator for the monopolar energy device 44006. Energy graph 44062 shows the activation and energy amount used for in situ smoke evacuation of the smoke plume generated by the bipolar energy device 44002 when the smoke evacuator for the bipolar energy device 44002 is used with the smoke evacuator for the monopolar energy device 44006.

The middle portion 44010 shows a resynchronized point 44032 of the amount of visual smoke plume generated by the bipolar energy device 44002 over time and lag 44028 of the amount of visual smoke plume generated by the bipolar energy device 44002 over time. The middle portion 44010 shows a resynchronized point 44034 of the amount of visual smoke plume generated by the monopolar energy device 44006 over time and lag 44030 of the amount of visual smoke plume generated by the monopolar energy device 44006 over time. (a, a1) is the estimated delay 44040. (b, b1) is the estimated delay 44042. During resynchronization of visual smoke plumes, a flag indicating a1 and b1 may be shown on a visual display. Dotted line 44036 shows the amount of visual smoke plume if only the smoke evacuator for the monopolar energy device 44006 is on. The shaded area 44038 corresponds to the amount of visual smoke plume if the smoke evacuator for the bipolar energy device 44002 and the smoke evacuator for the monopolar energy device 44006 are used together. A threshold 44026 (e.g., the maximum amount of visual smoke plume amount) may be set for visibility.

In an example, the synchronized graphs of the amount of visual smoke plume generated by the bipolar energy device 44002 over time, followed by the amount of visual smoke plume generated by the monopolar energy device 44006 over time, may show a visibility issue (e.g., caused by the smoke plume) from the scope, for example, following the activations of smoke evacuator for the monopolar energy device 44006 and the smoke evacuator for the bipolar energy device 44002. The amount of visual smoke plume generated by the monopolar energy device 44006 may be shown to be greater than the amount of visual smoke plume generated by the bipolar energy device 44002. The visual smoke plume generated by the monopolar energy device 44006 may be shown to last longer than the visual smoke plume generated by the bipolar energy device 44002. The visual smoke plume generated by the monopolar energy device 44006 may be shown to be delayed several seconds from the activation of the smoke evacuator for the monopolar energy device 44006. The visual smoke plume generated by the bipolar energy device 44002 may be shown to be delayed from the activation of the smoke evacuator for the bipolar energy device 44002.

The delays may be data artifacts because monitoring is lagging when the smoke evacuators are activated. The current monitoring device may have a low sampling rate. The current monitoring device may miss and overshoot the smoke evacuator activations and current draw levels. The delays may not be due to the application itself. Other data may be used to understand the delays, for example, using data enrichment techniques. Data cleaning techniques may be used to identify the delays and clean the data set related to the delays and/or overshooting.

The activation control signal 44008 may be used to clean the overshooting and clean the lagging data set (e.g., the lagging data set corresponding to the monitoring of the smoke evacuator motor control). The graph 44014 that shows the energy activation type and amount used by the bipolar energy device 44002 over time may be used to enrich data regarding the activation and energy amount used by the smoke evacuator for the bipolar energy device 44002, shown by the dotted energy graph 44052. The graph 44014 may be used to enrich data regarding in situ smoke evacuation of the smoke plume generated by the bipolar energy device 44002, shown in the energy graph 44054. The graph 44014 may be used to enrich data regarding the amount of visual smoke plume generated by the bipolar energy device 44002 over time and the lag 44028 of the amount of visual smoke plume generated by the bipolar energy device 44002 over time. The graph 44016 that shows the energy activation type and amount used by the monopolar energy device 44006 over time may be used to enrich the dotted energy graph 44056 that shows the activation and energy amount used by the smoke evacuator for the monopolar energy device 44006. The graph 44016 may be used to enrich the energy graph 44058 that shows in situ smoke evacuation of the smoke plume generated by the monopolar energy device 44006. The graph 44016 may be used to enrich data regarding the amount of visual smoke plume generated by the monopolar energy device 44006 over time and the lag 44030 of the amount of visual smoke plume generated by the monopolar energy device 44006 over time.

The activation timing, initiation points, deactivation points, and levels may be used to enrich the data to enhance the situational awareness of why, how and when the smoke evacuator motor control is synced or linked to the procedure and visibility data for the scope. Bipolar energy activation time point tB 44018 may be used to determine bipolar smoke plume delay tSB 44022. The bipolar energy activation time point tB 44018 may be used to determine bipolar smoke evacuation delay tEB 44048. Monopolar energy activation time point tM 44020 may be used to determine monopolar smoke plume delay tSM 44024. The monopolar energy activation time point tM 44020 may be used to determine monopolar smoke evacuation delay tEM 44050.

For example, amount of visual smoke plume generated by the monopolar energy device 44006 may be shown to be greater than the amount of visual smoke plume generated by the bipolar energy device 44002 because the monopolar energy level is higher. The visual smoke plume generated by the monopolar energy device 44006 may be shown to last longer than the visual smoke plume generated by the bipolar energy device 44002 because the on-duration for the monopolar energy is longer. The data enhancement of linking the mono-polar activation to the smoke evacuator activation corrects for the correlation and indicates that the magnitude of the motor activation may need to be changed, and the timing shifts (e.g., the delays) may be artifacts and need not be acted on.

Data streams that are in standard formats may be compared. For example, storing the transformed patient sensor data, the transformed instrument operational data, and the transformed OR equipment data in a standard format (e.g., in a cohesive database) or standard formats may enable a comparison from one surgical procedure to another surgical procedure. Surgical procedures may be compared when they share a common medical characteristic. For example, a surgical procedure for a patient may be compared with a surgical procedure for another patient, when these patients share a similar medical profile. A past surgical procedure of a patient may be compared with the current surgical procedure of the same patient. A same or similar procedures of different patients may be compared. The comparison may inform a surgeon on a likely outcome or risk of a surgical procedure.

The data standardization device 45000 may receive data streams from related equipment channeled through a primary equipment. The transformed data streams may include annotations of their relationship aspects. For example, two types of surgical instruments may both be channeled through a primary equipment such as a surgical hub. The data streams received from the two types of surgical instruments may be transformed into data streams of standard formats, and the transformed data streams may each include an annotation indicating the association with the primary equipment.

The data management module 45006 may include machine learning algorithms to adapt wearable device and/ or sensor collection, for example, to improve operability.

The surgical data system 45002 may include a data classification module 45004. The data classification module 45004 may classify a surgical data stream so that the data stream is handled in consistency with a healthcare data policy (e.g., Health Insurance Portability and Accountability Act (HIPPA)).

A device, for example, via the data classification module 45004 may determine a classification parameter for a surgical data stream. For example, the device may include the surgical data system 45002. The classification parameter may indicate a classification level for the surgical data stream. The classification parameter may indicate the classification levels for the surgical data stream if the classification parameter is multidimensional. The classification parameter may indicate a mapping between the informational content in the surgical data stream and a data handling scheme. The classification parameter may be indicated by a data tag included in the surgical data stream. The classification parameter may include a payload routing parameter and/or a payload handling parameter. The classification parameter may indicate the extent of sensitivity of the informational content in the surgical data stream. In an example, the classification level may be restricted, confidential, internal, public, or mid-classification levels, for example, a mid-classification level of the restricted classification level and the confidential classification level.

The classification parameter of the surgical data stream may be determined based on one or more of data source for the surgical data stream, a priority of the surgical data stream, a determination of whether the surgical data stream is requisite for another device's operation, a determination of whether the surgical data stream is requisite for a process, a determination of whether the surgical data stream is requisite for a task, or a determination of whether the surgical data stream is requisite for a decision making operation. A surgical data stream may be requisite when the surgical data stream is required to complete the task, process, or operation. A surgical data stream may be requisite when the surgical data stream is required to prepare the task, process, or operation. A surgical data stream may be requisite when the surgical data stream is required to follow up regarding the task, process, or operation.

The classification parameter of the surgical data stream may be determined based on the privacy of the surgical data stream. The types of data classifications, for example, the privacy-based data classifications, may include content-based classification, context-based classification, or user-based classification.

Content-based classification may include identifying sensitive information (e.g., patient specific data) by inspecting and interpreting files in the surgical data stream. The classification parameter may be determined based on whether the surgical data stream includes sensitive information. If the surgical data stream includes sensitive information, the classification parameter may be determined based on the amount of sensitive information in the surgical data stream and the nature of the sensitive information in the surgical data stream.

Context-based classification may include determining indicators (e.g., indirect indicators) of whether the surgical data stream includes sensitive information and indicators of the amount or nature of the sensitive information in the surgical data stream. The indicators of sensitive information may include one or more of an application, a location, or a creator among other variables. The classification parameter may be determined based on the indicators of sensitive information.

User-based classification may include a manual, end-user selection of surgical data or a document that includes the surgical data. The classification parameter may be determined based on user knowledge and/or discretion in creating editing, reviewing, or disseminating, for example, to flag sensitive information in the surgical data or in the document.

Two or more of content-based classification, context-based classification, and user-based classification may be combined to determine a classification parameter. Mid-classifications may be created where the surgical data stream is classified differently from a content-based-only classification, but not to the threshold of the context-based-only classification. A protected subgroup of a first group (e.g., a content-based-only classification) or a second group (e.g., context-based-only classification) may be created. The protected subgroup may share the characteristics of the first group or the second group, and may have one or more of additional limitations, protections, restrictions, or data handing requirements than the first group or the second group.

A classification parameter may be determined based on a priority of a surgical data stream. The determined classification parameter may indicate the priority of the surgical data stream. The determined classification parameter of the surgical data stream may increase in value based on the importance of the surgical data stream to a specific user utilization. For example, the determined classification parameter of the surgical data stream may increase in value if part or all of the surgical data stream is used to attach or enhance another data stream that has higher priority. In an example, the priority of the surgical data stream may be the dominant factor (e.g., relative to the privacy of the surgical data stream) used to determine the classification parameter of the surgical data stream, for example, when the surgical data stream is processed relative to other surgical data streams in a system where resources are limited.

The determination of the classification parameter for a surgical data stream may be based on the content of the surgical data stream. The content of the surgical data stream may indicate other classification-related information than the privacy of the surgical data stream. The surgical data stream may be decoded, for example, when it is received by a device having a decoder. The device, for example, via the data classification module 45004, may infer the classification parameter of the surgical data stream based on the decoded surgical data stream. For example, the device may determine the nature of the content using the decoded surgical data stream. The device may infer the classification parameter based on the nature of the content. In an example, if the nature of the content indicates that the surgical data stream is useful for a mission-critical task, the device may infer that the classification parameter of the surgical data stream is at higher priority level than a surgical data stream that is not used for a mission-critical task. The device may determine the classification parameter of the surgical data stream in a look-up table. The look-up table may correspond one or more of a nature of content, a type of content, a context of content with a certain classification parameter.

The determination of the classification parameter for a surgical data stream may be based on contextual information of the surgical data stream. The contextual information may indicate the content of the surgical data stream, the type of the surgical data stream, the source of the surgical data system, the identification of the user who collected the surgical data stream. For example, for core body temperature data stream, the contextual information may indicate abnormal temperature, characteristic fluctuations, infection, menstrual cycle, climate, physical activity, and/or sleep. The device may determine a risk factor associated with the core body temperature data stream based on the contextual information. The device may determine a classification parameter for the core body temperature data stream according to the risk factor.

The determination of the classification parameter for a surgical data stream may be based on additional factors including one or more of a determination whether an error or a fault associated with the surgical data stream has occurred, an importance of the data to other interactions of other surgical data streams, whether the users (or manufactures) of the corresponding data source have highlighted data from the data source as having a special need, or whether a patient recovery related data has resulted in undesirable outcome(s).

A classification parameter for a surgical data stream may be multidimensional. The classification parameter may indicate one of more of a privacy of the surgical data stream, a priority of the surgical data stream, a content type of the surgical data stream, a context of the surgical data stream, a retention period associated with the surgical data stream, the usage of the surgical data stream, a user preference associated with the surgical data stream, or the like. For example, data received from incidental wearable devices may have a different classification parameter from that of data received from task specific devices. The data received from the task specific devices may require a different data handling scheme from that for the data received from the incidental wearable devices. The data received from the task specific devices may require data processing to be organized into the correct dataset and/or format. In an example, the classification parameter may be an index. The index may include multiple bits. A bit of the multiple bits may be given a binary value. In some examples, the index may be a combination of numbers or symbols of different numbering system, with each symbol or number indicating a level of a certain dimension (e.g., privacy, priority, etc.).

The device, for example, via the data classification module 45004, may determine the data classification parameter for a surgical data stream based on a surgical data interface used to receive the surgical data stream. The device may receive surgical data streams via the surgical data interfaces. The device may determine one or more the source, the priority, the privacy, or the like for a surgical data stream based on which surgical data interface is used to receive the surgical data stream. The device may identify the surgical data interface via which the surgical data stream is received and determine the data classification parameter for the surgical data stream based on the surgical data interface.

The surgical data interface may be designated for a type of surgical instrument. For example, endocutter devices and smoke evacuators are different types of surgical instruments. The device may receive endocutter data via an endocutter data interface and receive smoke evacuator data from a smoke evacuator data interface. The types of surgical instruments may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. In an example, each of the types of surgical instruments may have a designated surgical data interface.

A classification parameter of a surgical data stream may be determined or adjusted based on the interaction between the surgical data stream and another surgical data stream.

A surgical data stream may interact with a different surgical data steam according to a mode of interaction. The interaction of the surgical data streams may occur pre-surgery, or post-surgery, or may be intra-operative. A mode of interaction may include one or more of an enrichment of a surgical data stream using another surgical data stream, an aggregation of a surgical data stream and another surgical data stream, or a synthesis of a surgical data stream and another surgical data stream. An enrichment of a surgical data stream using another surgical data stream may include one or more of tagging one surgical data stream using another surgical data stream, generation an annotation of one surgical data stream using another surgical data stream, generating a notification regarding one surgical data stream using another surgical data stream, generating a threshold and/or baseline regarding one surgical data stream using another surgical data stream, generating contextual information regarding one surgical data stream using another surgical data stream, or the like.

A mode of interaction may be determined based on a surgical event. The surgical event may include one or more of pre-surgical, post-surgical, or intra-operative event. For example, if the surgical event is incision line leakage, data regarding staple and patient tissue thickness may be synthesized to generate insights that otherwise would not be shown using either data regarding staple or patient tissue thickness data.

A surgical event may include any identifiable unit of a surgery. The identifiable unit may have a beginning, a duration, and an end. The identifiable unit may be identified relative to a clock (e.g., at 5 mins into the surgery). The identifiable unit may be identified relative to a procedure (e.g., the initial incision). The identifiable unit may be identified relative to a patient's response (e.g., bleeding).

Figure 42:
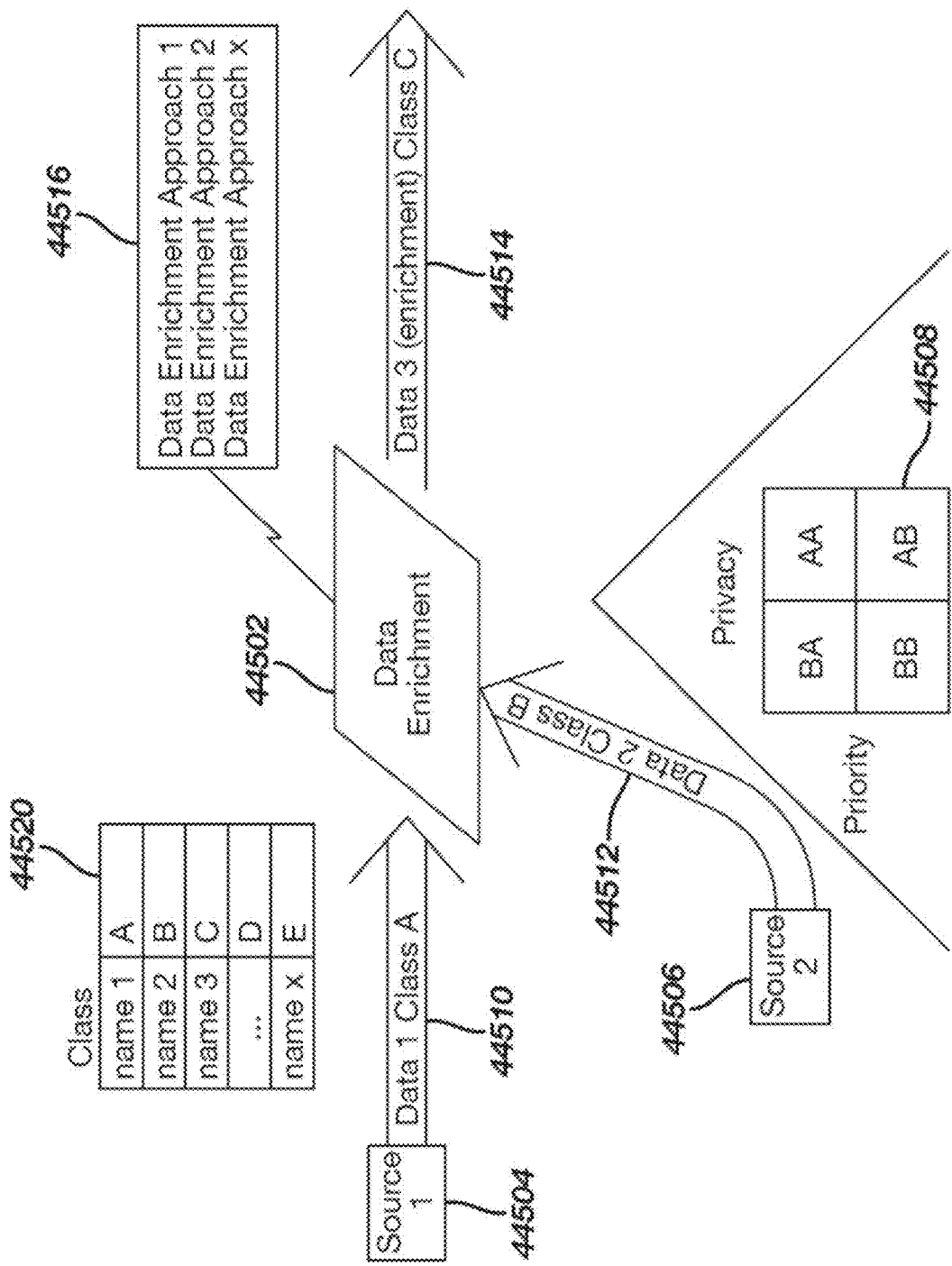
FIG. 42 shows an example data classification module.

FIG. 42 shows an example data classification module, for example, the data classification module 45004. The example data classification module may include a data enrichment function 44502. A classification for a surgical data stream may be adjusted based on an interaction of the surgical data stream with a differently classified surgical data stream. A device may receive a first surgical data stream 44510 from a data source 44504. For example, the device may include the surgical data system 45002. The device may receive a second surgical data stream 44512 from a data source 44506. The mode of interaction between the first surgical data stream 44510 and the second surgical data stream 44512 may be selected from multiple modes of interactions. The mode of interaction between the first surgical data stream 44510 and the second surgical data stream 44512 may be data enrichment. The data enrichment may be selected from multiple data enrichment approaches. For example, the data enrichment approaches may be in a list 44516 that includes multiple data enrichment rules 1, 2 . . . X. Surgical data stream 44514 may be generated by enriching the first surgical data stream 44510 using the second surgical data stream 44512.

The surgical data streams may be associated with different classification parameters. The first surgical data stream 44510 may be associated with a first classification parameter. The second surgical data stream 44512 may be associated with a second classification parameter. The first surgical data stream 44510 may be received in one or more data packets (e.g., a data packet including fields shown in FIG. 43). A data packet of the one or more data packets may include an element (e.g., a field) indicating the first classification parameter. In FIG. 42, the first classification parameter for the first surgical data stream 44510 is A, and the second classification parameter for the second surgical data stream 44512 is B. In some examples, the first surgical data stream 44510 may include a data tag indicating the first classification parameter.

A device may read the first classification parameter for the first surgical data stream 44510 or the second classification parameter for the second surgical data stream 44512 based on predetermined rules (e.g., a lookup table). In an example, table 44520 may be used for a one-dimensional classification parameter. The alphabet letters A-E may each indicate a different level of restrictions. The alphabet letters A-E may each indicate a different level of priorities. The alphabet letters A-E may each indicate a different level of privacies.

The first classification parameter for the first surgical data stream 44510 and the second classification parameter for the second surgical data stream 44512 may be multidimensional. The first classification parameter for the first surgical data stream 44510 and the second classification parameter for the second surgical data stream 44512 may have different number of dimensions, for example, depending on the nature of the respective surgical data stream. In an example, the first surgical data stream 44510 may include patient BP data, and the first classification parameter may have privacy dimension and priority dimension. The second surgical data stream 44512 may include monopolar energy data, and the second classification parameter may have a priority dimension but not a privacy dimension. When a classification parameter is multidimensional, a grid may be used to incorporate the multiple dimensions. In the example in FIG. 42, a grid 44508 may be used for a two-dimensional classification parameter. In the grid 44508, the two dimensions may be privacy and priority. "BA" may indicate low privacy and high priority, "AA" may indicate high privacy and high priority, "BB" may indicate low privacy and low priority, and "AB" may indicate high privacy and low priority. The first classification parameter for the first surgical data stream 44510 or the second classification parameter for the second surgical data stream 44512 may be any combination of numbers and symbols.

The classification parameter of the third surgical data stream 44514 may be determined based on the first classification parameter for the first surgical data stream 44510, the second classification parameter for the second surgical data stream 44512, and the data enrichment function 44502. The third surgical data stream 44514 may be generated using the data enrichment function 44502. The mode of interaction may be determined based on a surgical event. Based on the mode of interaction, the classification parameter of the third surgical data stream 44514 may be higher (e.g., AA) than both the first classification parameter (e.g., AB) for the first surgical data stream 44510 and the second classification parameter (BA) for the second surgical data stream 44512. Based on the mode of interaction, the classification parameter of the third surgical data stream 44514 may be the same (e.g., AB) as the first classification parameter (e.g., AB) for the first surgical data stream 44510 and higher than the second classification parameter (BB) for the second surgical data stream 44512. For example, if the mode of interaction is to aggregate patient BP data with endocutter data, the aggregated data stream may share the same privacy level and priority level with the patient BP data. Based on the mode of interaction, the classification parameter of the third surgical data stream 44514 may be lower (e.g., BB) than both the first classification parameter (e.g., AB) for the first surgical data stream 44510 and the second classification parameter (BA) for the second surgical data stream 44512. The classification parameter of the third surgical data stream 44514 may be determined using a surgical data classification engine tailored to solve multidimensional classification parameters.

The classification parameter of a surgical data stream may control how the surgical data stream is handled, for example, where and how the surgical data stream is stored, where and how the surgical data stream is transmitted, and how long the surgical data stream is stored locally. The communication path of the surgical data stream may be determined based on the classification parameter of the surgical data stream, for example, regarding how protected the channel used for the communication is and regarding the reliability and/or the stability of the channel used for the communication.

A device may determine a data handling scheme for a surgical data stream based on the determined classification parameter. For example, the device may include the surgical data system 45002. The data handling scheme may be consistent with the healthcare data policy (e.g., HIPPA). For example, the data handling scheme may include one or more rules that are consistent with HIIPPA. The data handling scheme may specify one or more of a type of storage location for a surgical data stream, a configuration of a data storage location, a long-term treatment for a surgical data stream, a reliability level associated with a communication path used for a surgical data stream, a security level associated with the type of storage location and/or the communication path, a retention period for a surgical data stream, an environment (e.g., HIPPA protected) where a surgical data stream may be used, or the like. In an example, the classification parameter of the third surgical data stream 44514 may be AA indicating higher privacy level and higher priority level. The device may determine that the third surgical data stream 44514 may be stored locally so it can be used to prevent an urgent, life-threatening surgical event. The device may determine that the third surgical data stream 44514 may be stored in a HIPPA protected environment to ensure that patient's identifiable information is contained in the HIPPA protected environment. The device may determine that a communication path used to transmit the third surgical data stream 44514 has a reliability level and security level to the patient's identifiable information.

The transmission priority and the retention period of the surgical data stream on a local surgical hub system may be based on the classification parameter of the surgical data stream and additional variables. In an example, whether and how long the surgical data stream is to be stored locally may be based on the magnitude of the available free storage space of the appropriate type (e.g., having appropriate security level). As the free space of the appropriate type for data having a certain classification becomes less, the device may determine a transmission priority to a larger storage location or reclassification to a higher level of security, for example, to ensure required protection and adequate retention.

In an example, based on the classification parameter of a surgical data stream, the device may determine that a surgical data stream has the highest classification level among multiple surgical data streams that are to be transmitted. The device may select a communication path having the least amount of interruption among transmission resources that are available to be used for the transmission of the surgical data streams and send the surgical data stream using the selected communication path. In an example, data that is critical to procedure may be communicated through the secured or protected communication pathway, for example, to ensure that the data stream encounters the least interruption possible.

The device may communicate redundantly through the communication path having the least amount of interruption. For example, the device may, based on the determination that the third surgical data stream has the highest classification level among surgical data streams to be transmitted, repeat the sending of the third surgical data stream using the selected communication path. In an example, the device may duplicate the surgical data stream and communicate the original surgical data stream and the duplicate surgical data stream using two independent communication bus architecture or paths, for example, to ensure that the user is not deprived of receiving or displaying the surgical data stream. The device may separate the surgical data stream into less dense but useable data streams and communicate the separate data streams, for example, using multiple independent communication bus architecture or paths, for example, to ensure that the user is not deprived of receiving or displaying the surgical data stream. In some examples, being deprived of receiving or displaying the surgical data stream may result in a delay of a procedure or an interruption of a procedure or a conversation from lap to open.

In some examples, the classification of a related and coupled data stream may change the classification of another data stream such that the interaction of the data streams has the same priority, storage requirements, retention, or communication protections or the like. In FIG. 42, the classification parameter of the third surgical data stream 44514, the first classification parameter for the first surgical data stream 44510, and the second classification parameter for the second surgical data stream 44512 may be kept the same such that a same data handling scheme may be used for the third surgical data stream 44514, the first surgical data stream 44510, and the second surgical data stream 44512.

Classification of a surgical data stream may be used to determine how secure the communication link is utilized for the surgical data stream. In an example, classification of a surgical data stream may be used as the initial determination of what pathway of communication or processing is to be used. Visualization or primary control and/or response data streams that are required for key instrument operations or baseline instrument operations may be separated from the more advanced features or advanced processing, for example, to ensure at least the baseline operation is provided even if the processing or rebooting of the system is required. Examples that are suitable for use with the present disclosure are described in in U.S. Patent Application Publication No. US 2019-0201126 A1 (U.S. patent application Ser. No. 16/182,255), titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, filed Nov. 6, 2018, the disclosure of which is herein incorporated by reference in its entirety. In one or more of those examples, usage and technique analysis of the surgeon/staff performance against a baseline may be used to optimize device utilization and performance for both current and future procedures.

The surgical data system 45002 may include a data processing module 45024 for data stream processing. Data stream processing may provide one or more real-time analytics, streaming analytics, complex event processing, real-time streaming analytics, or event processing of surgical data streams. Examples that are suitable for use with the present disclosure are described in in U.S. Patent Application Publication No. US 2019-0206556 A1 (U.S. patent application Ser. No. 16/182,242), titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES, filed Nov. 6, 2018, the disclosure of which is herein incorporated by reference in its entirety. In one or more of those examples, real-time analysis of the comprehensive cost of instrumentation used in surgery may be performed, including the cost of reusable devices, their maintenance, cleaning, and re-sterilization by utilizing data fluidity to track instruments. Examples that are suitable for use with the present disclosure are described in in U.S. Patent Application Publication No. US 2019-0201102 A1 (U.S. patent application Ser. No. 16/182,290), titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Nov. 6, 2018, the disclosure of which is herein incorporated by reference in its entirety. In one or more of those examples, hub recommendations may be based on real-time analysis of procedure variables against a baseline highlighting differences from the optimal solution.

A device, for example, a surgical hub, may receive data streams from multiple data input feeds. For example, the device may include the surgical data system 45002. The multiple data input feeds may be interrelated. For example, multiple data input feeds may be used to generate a data stream that is more actionable or more capable of forming decisions from. The device may be configured with on-the-fly processing capabilities and real-time analytics. The device may, for example, using the real-time analytics, process data streams from one or more of the visualization, biomarker, instruments, and connected capital equipment. The device may distill the streams to a more context rich and decision able form. For example, the device may enhance a primary data stream using a secondary data stream. The primary data stream and the secondary data stream may be from separate sources. The enhanced primary data stream may be in a distilled form. In examples, the device may annotate, create meta data of, or provide context for the primary data stream using the secondary data stream.

The device may be configured to describe and/or summarize what has happened during a surgical event using real-time analytics. The surgical event may be on-going. The device may be configured to diagnose one or more reasons for what has happened during the surgical event using the real-time analytics. The device may be configured to predict what might happen based on the description of what has happened and the reasons for what has happened. The device may be configured to generate rules and recommendations for the surgical event based on the prediction what might happen. For example, the device may suggest an adjustment of an operation of an instrument. Examples that are suitable for use with the present disclosure are described in in U.S. Patent Application Publication No. US 2019-0201140 A1 (U.S. patent application Ser. No. 15/940,654), titled SURGICAL HUB SITUATIONAL AWARENESS, filed Mar. 29, 2018, the disclosure of which is herein incorporated by reference in its entirety. In one or more those examples, situational awareness of collected events may be provided. Examples that are suitable for use with the present disclosure are described in in U.S. Patent Application Publication No. US 2019-0201127 A1 (U.S. patent application Ser. No. 16/182,256), titled ADJUSTMENT OF A SURGICAL DEVICE FUNCTION BASED ON SITUATIONAL AWARENESS, filed Nov. 6, 2018, the disclosure of which is herein incorporated by reference in its entirety. In one or more those examples, a control for a hub or hub connected device may be adjusted based on a sensed situation or usage. Examples that are suitable for use with the present disclosure are described in in U.S. Patent Application Publication No. US 2019-0204201 A1 (U.S. patent application Ser. No. 16/182,246), titled ADJUSTMENTS BASED ON AIRBORNE PARTICLE PROPERTIES, filed Nov. 6, 2018, the disclosure of which is herein incorporated by reference in its entirety. In one or more those examples, airborne particulates and aerosols in insufflation gases within the abdomen may be detected and a device function may be altered based on the type, concentration, and flow of the particles. Examples that are suitable for use with the present disclosure are described in in U.S. Patent Application Publication No. US 2019-0206542 A1 (U.S. patent application Ser. No. 16/182,243), titled SURGICAL HUB AND MODULAR DEVICE RESPONSE ADJUSTMENT BASED ON SITUATIONAL AWARENESS, filed Nov. 6, 2018, the disclosure of which is herein incorporated by reference in its entirety. In one or more those examples, a hub response to a sensed parameter or event may be adjusted based on a second pre-existing sensed step, situation, or parameter.

The device may receive one or more surgical data streams. For example, a surgical data stream of the one or more surgical data steams may include one or more indications. FIG. 43 shows an example data stream. The data stream may include a surgical data stream. As shown in FIG. 43, a surgical data stream may include indications of standard format ID 45206, classification parameter 45208, source 45210, payload type 45212, and timing element 45213. The surgical data stream may include the payload 45214.

The standard format ID 45206 may indicate whether the surgical data stream is in a standard format and which standard format the surgical data stream is in. For example, the surgical data stream may have been transformed based on rule set 1 in FIG. 40, and the standard format ID 45206 may indicate that the surgical data stream is in a standard format associated with the database x 45138.

The classification parameter 45208 may indicate the classification level(s) at which the surgical data stream is classified. For example, for the third surgical data stream 44514 in FIG. 42, the classification parameter 45208 may indicate that the third surgical data stream 44514 is at a high privacy level and a high priority level.

The source 45210 may indicate the data source from which the surgical data stream is received. The data source may include a surgical instrument, capital equipment, a biomarker sensing system, or a visualization device. The biomarker sensing system may include a wearable device. In FIG. 8, the data source may be a modular device 5102, a database 5122, a patient monitoring device 5124, an HCP monitoring device 35510, or an environment monitoring device 35512.

The payload type 45212 may indicate the type of the surgical data stream. For example, the type of the surgical data stream may include visualization data (e.g., an image or a frame), biomarker data (e.g., heart rate), energy level, actuation data, sensor data, tunnel, or operational status, and other type of data related to one or more surgical events.

The timing element 45213 may indicate a frame number, a time stamp (e.g., one or more of a local time, a local time offset, a global time, a global time offset, a milestone, a milestone offset, a latency, etc.). In an example, the timing element may indicate the time when the surgical data stream is collected. The timing element may indicate the time when the surgical data stream is sent. The timing element may indicate the time when the surgical data stream is used or to be used.

The indications including the standard format ID 45206, the classification parameter 45208, the source 45210, the payload type 45212, the timing element 45213 may be received via one or more data packets, for example, as elements or fields. The data packet may include the payload 45214.

The device may process the surgical data streams to generate a data stream that is more actionable or more capable of forming decisions from.

Figure 44:
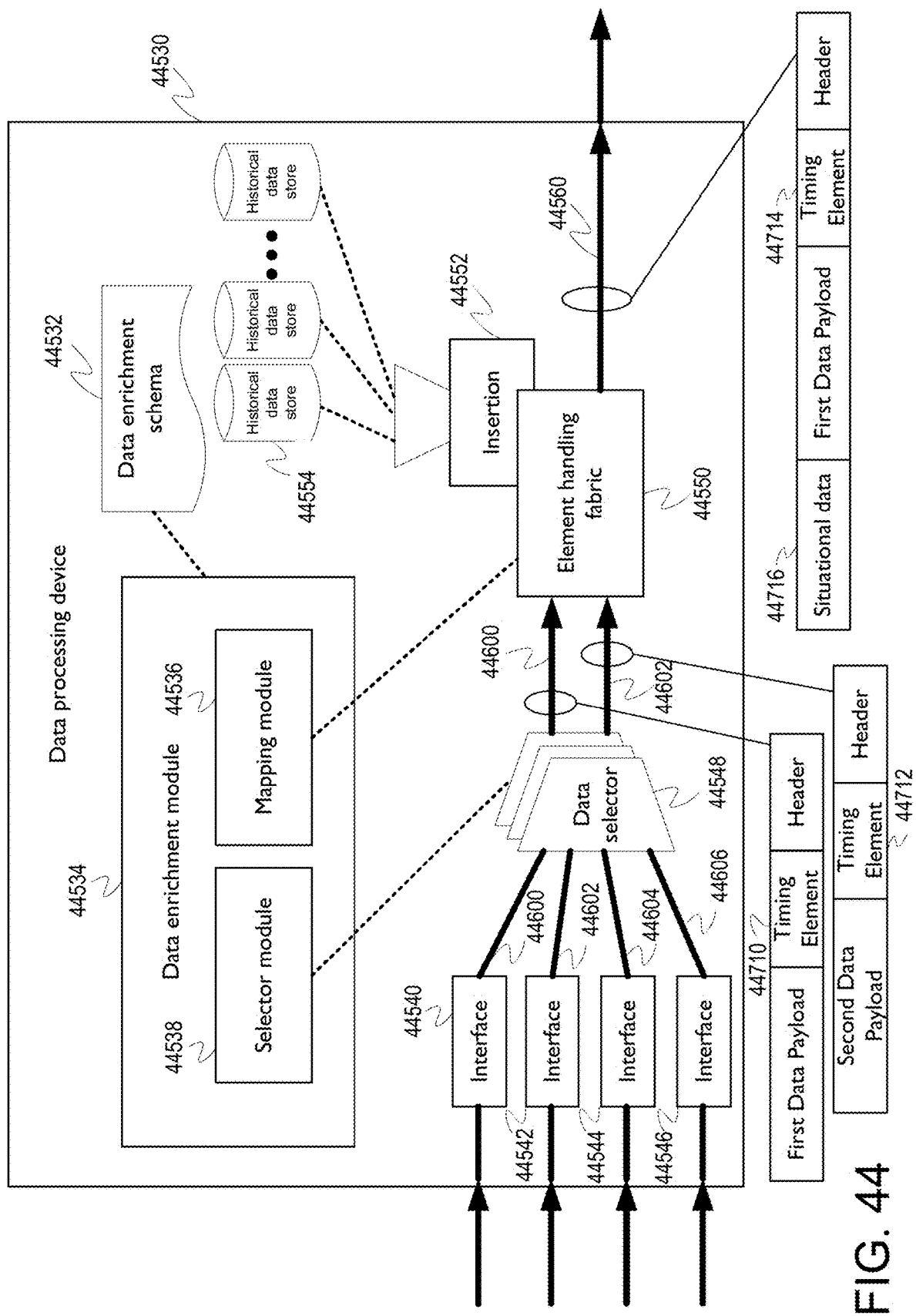
FIG. 44 shows an example data processing device.

FIG. 44 shows an example data processing device. The device in FIG. 44 may process multiple data streams. A device 44530 may include a surgical data system 45002 including the data processing module 45024. The device 44530 may be a data processing device. The device may receive surgical data streams 44600-44606 through the surgical data interfaces 44540-44546. The reception of the surgical data streams 44600-44606 may be during a surgical event (e.g., in real time while the surgical event is ongoing). The device may identify the surgical data interface from which a surgical data stream is received. In FIG. 43, the device 44530 may identify the surgical data interface 44540 via which the surgical data stream 44600 is received. The device 44530 may identify the surgical data interface 44542 via which surgical data stream 44602 is received.

Data selector 44548 may select the surgical data streams that are to be processed, based on a selector module 44538. For example, the data selector 44548 may select the surgical data stream 44600 and the surgical data stream 44602. The selection of the surgical data stream 44600 and the surgical data stream 44602 may be based on the selector module 44538. The selector module 44538 may be part of data enrichment module 44534. In an example, the data enrichment module 44534 may be part of the data processing module 45024 shown in FIG. 39. The data enrichment module 44534 may include the data enrichment function 44502. The selector module 44538 may be used to identify the surgical event and select the surgical data stream 44600 and the surgical data stream 44602 based on the surgical event. For example, the surgical data stream 44600 and the surgical data stream 44602 may include image data that needs to be inspected before an incision operation is to be performed on a patient. The selector module 44538 may identify the surgical data stream 44600 and the surgical data stream 44602 based on the incision operation. To identify the surgical data stream 44600 and the surgical data stream 44602, the selector module 44538 may identify the incision operation. The selector module 44538 may determine that the image data needs to be inspected for the incision operation. The selector module 44538 may identify the image data. The selector module 44538 may determine that surgical data stream 44600 and the surgical data stream 44602 include the image data based on the surgical data interface 44540 via which the surgical data stream 44600 is received and the surgical data interface 44542 via which the surgical data stream 44602 is received. The selector module 44538 may be used to select the surgical data stream 44600 and the surgical data stream 44602 based on the determination that the surgical data stream 44600 and the surgical data stream 44602 include the image data.

The device 44530 may include an element handing fabric 44550. The element handing fabric 44550 may include a mapping module 44536. The mapping module 44536 may be part of the data enrichment module 44534. The mapping module 44536 may be used to determine that a surgical data stream is associated with another surgical data stream. The mapping module 44536 may identify the type of association of a surgical data stream with another surgical data stream. The mapping module 44536 may select a mode of interaction between a surgical data stream and another surgical data stream based on the type of association of the surgical data stream and the other surgical data stream. For example, the mode of interaction may include data enrichment. The data enrichment may use data enrichment schema 44532. The mode of interaction may include other modes of interactions. If the mode of interaction is one other than data enrichment, other types of schemas may be used to support that mode of interaction.

The data enrichment schema 44532 may indicate a characteristic of a primary surgical data stream, a characteristic of a secondary surgical data stream, which part of the primary surgical data stream is to be enriched, in what manner the part of the primary surgical data stream is to be enriched, which part of the secondary surgical data stream is to be used to enrich the primary surgical data stream, in what manner the secondary surgical data stream is to be used to enrich the primary surgical data stream, and other rules or provisions regarding the data enrichment.

The mapping module 44536 may be used to determine that the surgical data stream 44600 is the primary surgical data stream, for example, based on the surgical data interface 44540 via which the surgical data stream 44600 is received. The mapping module 44536 may be used to determine that the surgical data stream 44602 is the secondary surgical data stream, for example, based on the surgical data interface 44542 via which the surgical data stream 44602 is received. That the surgical data stream 44600 is received via the surgical data interface 44540 may be indicative of the surgical data stream 44600 having the characteristic of the primary data stream. That the surgical data stream 44602 is received via the surgical data interface 44542 may be indicative of the surgical data stream 44602 having the characteristic of the secondary data stream. The device 44530 may determine, for example, using the mapping module 44536 and/or the data enrichment schema 44532, that the secondary surgical data stream is to be used to provide surgical information for the primary surgical data stream. For example, the data enrichment schema 44532 may provide that the secondary surgical data stream may be used to provide situational data for the primary surgical data stream.

The selector module 44538 may collaborate with the mapping module 44536 to select surgical data streams. For example, the selector module 44538 may select the surgical data streams based on the type of association of a surgical data stream with another surgical data stream, as identified by the mapping module 44536.

The primary data stream and the secondary data stream may be handled differently. The secondary surgical data stream may not be stored in its entirety, for example, after the secondary surgical data stream has been processed to provide the situational data for the primary surgical data stream. In some examples, secondary surgical data stream may not be stored locally or may be removed from storage locations after the secondary surgical data stream has been processed to provide the situational data. The device 44530 may display the primary surgical data stream and the situational data, for example, without displaying the secondary surgical data stream.

The element handing fabric 44550 may generate situational data for the primary surgical data stream based on the secondary surgical data stream and/or the data enrichment schema 44532. The situational data may include surgical information that may be used to make a medical decision about the surgical event. The medical decision may be made based on the primary surgical data stream and the surgical data for the primary surgical data stream. The situational data may indicate a medical decision-making factor of the surgical event. The medical decision-making factor may indicate the surgical information. The medical decision-making factor may indicate an interpretation of one or more of the following: a surgical procedure (e.g., a procedure step or a procedure plan), imaging data (e.g., a pre-operative scan, an intra-operative scan, a primary scope, or a flexible endoscope), patient data (e.g., co-morbidities, physiologic monitors, or anesthesia), or instrument measures (e.g., tissue impendence, seal strength, or cartridge type). The medical decision-making factor may inform a user of the primary data stream about complications or risks associated with the surgical event. One or more the following examples may illustrate the primary surgical data stream and the situational data for the primary surgical data stream: when the primary data stream includes core body temperature data, the situational data may include abnormal temperature, characteristic fluctuations, infection, menstrual cycle, climate, physical activity, and/or sleep; when the primary data stream includes behavior and psychology-related data, including sleep, circadian rhythm, physical activity, and/or mental aspects for analysis, the situational data may include behavior and psychology scores may include scores for social interaction, diet, sleep, activity, and/or psychological status; when the primary data stream is activity-related data, the situational data may include activity duration, activity intensity, activity type, activity pattern, recovery time, mental health, physical recovery, immune function, and/or inflammatory function; when the primary data stream includes lymphatic system-related data, the situational data may include fibrosis, inflammation, and/or infection; when the primary data stream includes blood vessel-related data, the situational data may include infection, anastomotic leak, septic shock and/or hypovolemic shock.

The element handing fabric 44550 may output surgical data steam 44560 during the surgical event. The surgical data stream 44560 may include the primary surgical data stream and the situational data.

One or more of the reception of the surgical data streams 44600-44606, the selections of the surgical data streams 44600 and 44602, the identification of the surgical data interfaces 44540 and 44542, the determination of the primary surgical data stream and the secondary surgical data stream, or the generation of the situational data may occur in real time (e.g., processed using real-time analytics). A predetermined value may be used to facilitate real-time processing. In FIG. 44, the surgical data stream 44600 may include a timing element 44710. The timing element 44710 may indicate a time when the surgical data stream 44600 is collected. The surgical data stream 44602 may include a timing element 44712. The timing element 44712 may indicate a time when the surgical data stream 44602 is collected.

The generation of the situation data for the primary surgical data stream may occur at a time that is the same as or similar to the time when the surgical data stream 44600 is collected, or the same as or similar to the time when the surgical data stream 44602 is collected. The primary surgical data stream and the situational data may be sent at a time that is the same as or similar to the time when the surgical data stream 44600 is collected, or the same as or similar to the time when the surgical data stream 44602 is collected. The similarity in time may be determined based on a predetermined value (e.g., a predetermined time duration value such as a threshold). In FIG. 44, the surgical data stream 44560 may include a timing element 44714. The timing element 44714 may indicate a time when the surgical data stream 44560 and situational data 44716 are sent. The timing element 44714 may indicate a time when the situational data 44716 is generated. The difference between the timing element 44714 and the timing element 44710 may be lower than a predetermined value. The difference between the timing element 44714 and the timing element 44712 may be lower than the predetermined value. The difference between the timing element 44714 and the timing element 44710, which is lower than the predetermined value, may indicate that the surgical data stream 44560 is sent in real time as the surgical data stream 44600 is collected. The difference between the timing element 44714 and the timing element 44712, which is lower than the predetermined value, may indicate that the situational data 44716 is generated in real time as the surgical data stream 44602 is collected.

A risk indicator may be generated based on the situational data and the primary surgical data stream. The risk indicator may be sent to a display device, for example, during the surgical event. The risk indicator may include one or more of actionable triggers, thresholds, or insights.

Risk assessment of patient biomarkers may be performed to determine the suitability of the surgical procedure and/or likely outcomes. A device, e.g., a surgical hub, may include an interactive hub algorithm. The device may include the surgical data system 45002. The device may analyze risk probabilities using the interactive hub algorithm. For example, the device may analyze the primary data stream and the situational data to determine risk probabilities. The device may notify users about the risk probabilities. The device may adjust coupled instrument parameters based on the risk probabilities. In an example, the device may generate control instructions based on the primary data stream and the situational data. The control instructions may be sent to adjust an operation of a surgical instrument operatively coupled to the device. The interactive hub algorithm may determine a probability of a certain surgical outcome and/or generate a notification about the probability of the surgical outcome. The notification may be sent to a wearable system. Examples that are suitable for use with the present disclosure are described in in U.S. Patent Application Publication No. US 2019-0201125 A1 (U.S. patent application Ser. No. 16/182,251), titled INTERACTIVE SURGICAL SYSTEM, filed Nov. 6, 2018, the disclosure of which is herein incorporated by reference in its entirety. In one or more those examples, interactive feedback to the user may enable adjustment of a device or display based on presence of an actionable aspect of the task at hand for the user. Examples that are suitable for use with the present disclosure are described in in U.S. Patent Application Publication No. US 2019-0201124 A1 (U.S. patent application Ser. No. 16/182,239), titled ADJUSTMENT OF DEVICE CONTROL PROGRAMS BASED ON STRATIFIED CONTEXTUAL DATA IN ADDITION TO THE DATA, filed Nov. 6, 2018, the disclosure of which is herein incorporated by reference in its entirety. In one or more those examples, device control programs may be adjusted based on stratified contextual data in addition to the data. The contextual data may represent the circumstances around data collected or related patient, procedure, surgeon, or facility information. Examples that are suitable for use with the present disclosure are described in in U.S. Patent Application Publication No. US 2019-0201123 A1 (U.S. patent application Ser. No. 16/182,233), titled SURGICAL SYSTEMS WITH AUTONOMOUSLY ADJUSTABLE CONTROL PROGRAMS, filed Nov. 6, 2018, the disclosure of which is herein incorporated by reference in its entirety. In one or more those examples, hub or instrument control programs may be modified based on machine learning that analyzes performance and outcomes recorded over more than one procedure.

The device may include algorithms for monitoring wearable streaming data from patient(s) or OR staff. The wearable streaming data may indicate measurements taken on the patient(s) or the OR staff. The measurements may include biomarker measurements. The measurements may be associated with a procedure situation. The device may compare the measurements with biomarkers indicating the risk probabilities of a procedure situation. The device may identify a procedure step that may result in a complication or issue. The device may generate a notification of intervention. If the probability of that monitored biomarker(s) at that step is above the predefined likelihood of complication, a notification(s) may be sent to the OR staff about the possible risk or complication, or a signal may be sent to a surgical instrument operatively coupled with the device or an imaging system to request a change in the control algorithm of the surgical instrument or the imaging system.

In an example, a patient undergoes a colorectal resection of the descending sigmoid colon. The resection may require a considerable amount of colon removal and mobilization of the colon. As the surgeon mobilizes the colon, an insufficient amount of the colon may be mobilized, resulting in a high tissue tension on the remnant portion. Once the surgeon reconnects the anastomosis and is preparing to close the patient, a sensor on the patient that monitors the local pH of the surgical area exceeds a threshold. That biomarker exceeding that threshold indicates a risk probability. That biomarker exceeding that threshold indicates or implies a reasonable probability of an insufficient blood flow to the region, which may result in a CO2 buildup that results in a local pH change. The surgeon may be notified (e.g., via a notification) of the possible issue or the risk probability. A request may be sent to the attached multi-spectral imaging to examine that region using a Doppler transform of the laser light through the green-red spectrums to visualize blood flow in the connective tissue and the bowel of that region. The concentrated focus area of that region along with the laser Doppler Flowmetry may show an occlusion of the blood flow, which the surgeon tracks back to the elevated macro tissue tension. The surgeon corrects the issue. If left uncorrected, the issue could have resulted in tissue necrosis and a leak forming from the colon to abdomen, which could have resulted in a hospital acquired infection or even require a re-admittance and a re-operation.

Data streams may be processed continuously to change operational tool controls and/or to change scheduling. The change of the operational tool controls and scheduling may improve outcomes.

One or more data streams (e.g., surgical data streams generated by patient sensing systems) may be processed with historical data regarding outcomes of previous surgeries. A more actionable decision point may be generated by coupling the one or more data streams with the historical data regarding the outcomes of the previous surgeries. The historical data regarding the outcomes of the previous surgeries may indicate a likelihood of a surgery operation including a surgery timing to result in a certain outcome (e.g., a desired outcome).

The element handing fabric 44550 may generate situational data for the primary surgical data stream based on historical data. An insertion operation 44552 may be performed to add historical data from a historical data store, for example, historical data store 44554. The historical data may be from a historical surgical event. The historical surgical event and the current surgical event may have a common characteristic. The common characteristic may be that the historical surgical event and the current surgical event are both for a same patient or patients with same or similar medical profiles. The common characteristic may be that the historical surgical event and the current surgical event are both for a same or similar type of surgical procedure. The common characteristic may be that the historical surgical event and the current surgical event both use a same type of surgical instrument or the same surgical instrument. The common characteristic may be that the historical surgical event and the current surgical event both use a same type of surgical equipment or same equipment. For example, if a piece of equipment has a pre-surgery history of interference or irregular sensing issues in a predictable manner, during surgery an event that could be misinterpreted as an issue may be noted as a probable equipment issue and adjusted based on pre-history data sets for that piece of equipment.

In an example, biomarker data streams may be processed over time based on comparisons with previous data sets, for example, to determine when a surgical procedure may be best run, staffed, or scheduled.

Biomarker data streams (e.g., patient biomarker data streams) and a surgical procedure (e.g., the current surgical procedure) may be processed based on historical data (e.g., historical data from the local facility's database or global network database). The local facility's database or global network database may include data collected from previous surgeries. The data collected from previous surgeries may include outcomes of surgical events that occurred during the previous surgeries. An indication or notification of one or more predicted issues may be generated by processing the biomarker data streams and the historical data. The indication or notification may be sent to the surgical team. The indication or notification may indicate one or more predicted complications. The processing of the biomarker data streams and the historical data may be based on one or more patients with similar biomarkers of the same or similar procedure. The indication or notification may better prepare the surgical team if the predicted issue(s) or predicted complication(s) occurs. The staff may be prepared for the risk(s) associated with the current patient or the current surgical procedure. A more informed staff may be prepared to react rather than being caught off guard if the predicted issue(s) or predicted complication(s) occurs. Examples that are suitable for use with the present disclosure are described in in U.S. Patent Application Publication No. US 2019-0201115 A1 (U.S. patent application Ser. No. 15/940,668), titled AGGREGATION AND REPORTING OF SURGICAL HUB DATA, filed Mar. 29, 2018, the disclosure of which is herein incorporated by reference in its entirety. In one or more those examples, surgical tool utilization and OR event(s) may be correlated with the global outcomes and efficiencies.

Biomarker data of a patient may be compared against the patient's historical biomarker data. Biomarker data that is outside of the normal range may be identified based on the comparison. A risk of certain biomarker data and the impact of the biomarker data on a surgical procedure and/or an outcome may be determined based on the comparison.

Biomarker data of a patient may be evaluated based on database that includes the patient's historical biomarker data and the historical biomarker data of the direct relatives and/or family. Hereditary deficiencies or risk may be identified based on the comparison. Suitability of a surgical procedure or outcome may be identified based on the comparison.

In an example, a certain patient has a consistent BP reading of 128/84+/−2 points in either direction. The BP reading of 128/84+/−2 points may be considered elevated (e.g., a high BP) based on the American Heart Association guidelines. A primary care physician first places this patient on BP medicine, with quarterly check-ups. When such treatment regimen does not change this patient's BP reading, the medical history of the patient is examined. The medical history shows that the patient's BP has been 128/84+/−2 since childhood. Blood work may be done for the patient after the original treatment regimen is discontinued, which concludes all markers are normal. It is further concluded that, based on the patient's body type and genetics, the patient's normal BP is higher than the standard. Utilizing the patient's historical data may provide more insights and help develop a more unique solution with surgical procedures and outcomes. The patient's historical data is tailored to the patient. The treatment regimen may be updated based on individual patients' normal ranges and not based on a standardized approach.

Instrument event data streams may be processed with patient biomarker data to produce a data output feed that may be used to adapt the instrument control program. Biomarker feedback may be used to adjust the operational parameters of the instrument, for example, by allowing the instrument event data streams and the patient biomarker data to be coupled to identify coupled relationships in their operation and outcomes.

A surgical procedure may be compared with another surgical procedure. The outcome of a surgical procedure may be used to predict the outcome of another surgical procedure based on a comparison of the surgical procedure. The current surgical procedure (e.g., the type of procedure) may be compared with previous surgical procedures. The outcomes of the previous surgical procedures may be used to predict the outcome of the current surgical procedure. Patient biomarker data during a previous surgical procedure and/or pre-operative testing of the patient who underwent the previous surgical procedure may be stored in a local facility database or global network database. In an example, the current surgical procedure type may be compared with the previous surgical procedure type. If the current surgical procedure type is same as or similar to the previous surgical procedure type, the current patient biomarker data may be compared with the previous patent biomarker data. If the current patient biomarker data is the same as or similar to the previous patent biomarker data, a probable outcome of the current surgical procedure may be determined based on the outcomes of the previous surgical and/or based on determined risks. The comparison of the current surgical procedure with the previous surgical procedures (e.g., past data sets) may facilitate an identification of a trigger that have resulted in adverse events in the previous surgical procedure, an identification of a potential risk to the current patient, an identification of a probability of an increased time for a certain procedure, or an identification of a probability of a requirement for additional staff. The current surgical procedure, for example, if it is being considered in a surgical plan, may be delayed or rescheduled until the patent's biomarker data show results in an acceptable range and/or until a pharmaceutical intervention controls biomarkers identifiers into a safe zone prior to the procedure, or until the staffing or products that need to mitigate a predicted issue are acquired. The outcomes and cost-effectiveness of care for patients undergoing surgery may be improved.

Pre-surgery biomarker data, post-surgery biomarker data, and intra-operative biomarker data (e.g., regarding surgical occurrences) may be used to adjust post-surgery monitoring.

A device, for example, a surgical hub, may identify and set post-surgery critical thresholds (e.g., post-surgery critical thresholds for wearable devices). The device may include the surgical data system 45002.

The device may identify based on the type of procedure and patient's information, pre-operative and intra-operative biomarkers, pre-operative and intra-operative test results to determine factors that should be tracked post-operation and/or determine the thresholds that should be applied. The device may communicate and/or set other systems and/or devices to continue monitoring post-surgery. For example, the thresholds may include one of more of BP thresholds, activity thresholds, step count thresholds, thresholds related to breathing, thresholds related to sleeping, and thresholds related to dehydration.

Figure 45A:
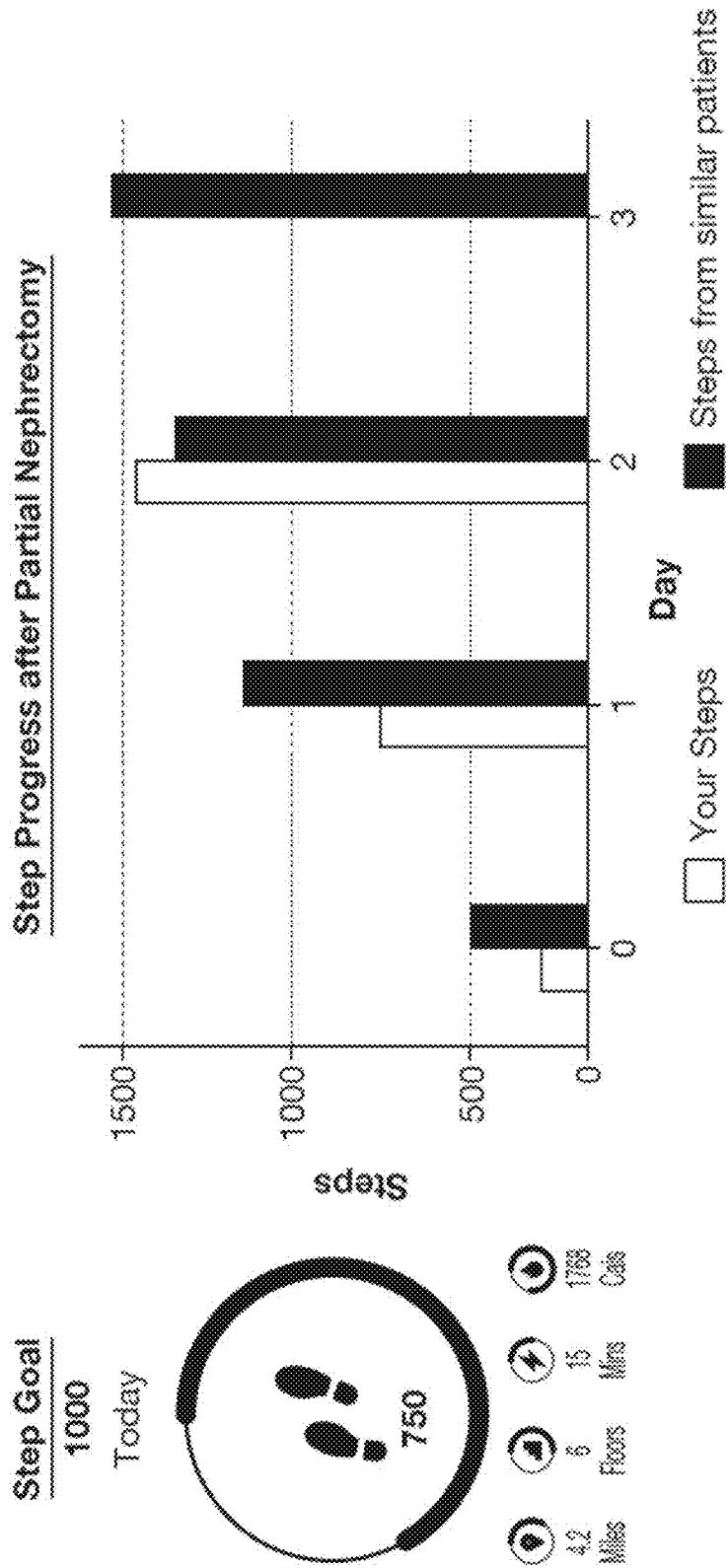
FIG. 45A shows a patient's step progress after patrial nephrectomy, compared with similar patients.
Figure 45B:
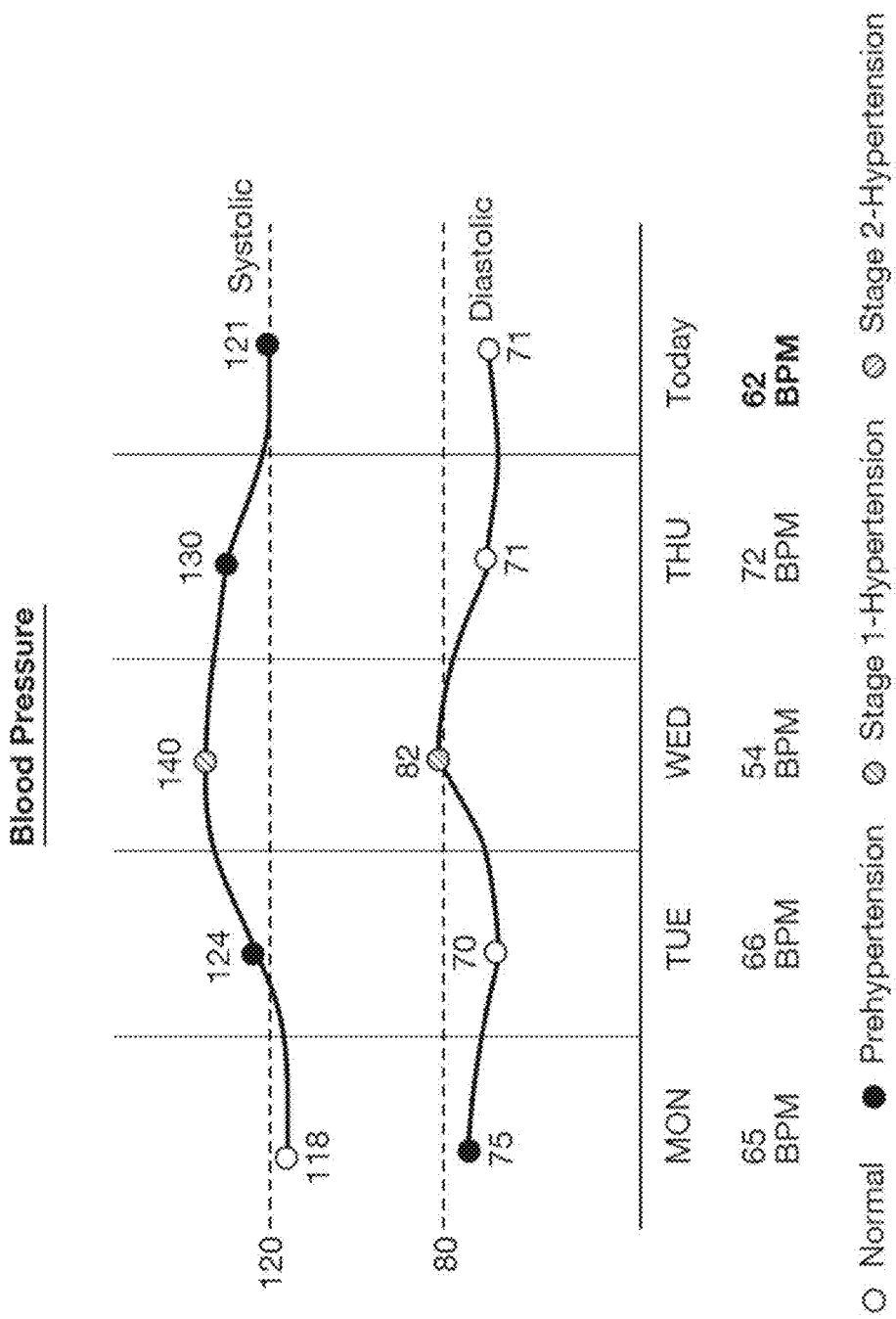
FIG. 45B shows a patient's daily systolic BP and diastolic BP over a week and assessments of a normal BP, prehypertension BP, and stage 1 hypertension BP.

The device may communicate to post-surgery room monitor(s) to provide recommended activities to the patient. The device may provide the patient's goals to achieve or compare the patient's current activity levels to the activity levels of other patients that have undergone similar procedures and share similar patient data. The device may advise the patient how the patient is doing. The comparison may motivate the patient to achieve the goals such that the patient may improve the patient's recovery and reduce the hospital stay. FIG. 45A shows a patient's step progress after patrial nephrectomy, compared with similar patients. FIG. 45B shows a patient's daily systolic BP and diastolic BP over a week and assessments of a normal BP, prehypertension BP, and stage 1 hypertension BP. The device may communicate and set the required items and thresholds on the patient's wearable devices, for example, to provide notifications to the patients and/or heath care providers.

The device may communicate to a local facility data storage or a cloud storage in which other monitoring equipment (e.g., all other monitoring equipment) may be tagged to the patient and may automatically pull the data sent from the device to the local facility data storage or the cloud storage as the monitored values or thresholds for the patient. Other monitoring equipment may be adapted to the patient based on the identity of the patient that is connected to the other monitoring equipment and may automatically set which items are monitored and thresholds for that patient. Errors caused by incorrect setting by a user may be prevented. The patient may not need to be mounted to various equipment as the patient moves through the facility. When the patient moves to a room where the equipment needed for additional testing, checks, or follow-ups is located, there is no need to reset the needed equipment. Post-operative monitoring data streams may be collected and/or processed regularly, for example, to further adjust and refine the post-surgery thresholds and targets.

The device may set and control the patient's wearables, for example, enabling an early discharge and an increased willingness of patients to be discharged early. Wearable devices may change the landscape of preoperative optimization as well as postoperative monitoring of high-risk patients or patients undergoing high-risk surgeries. For example, cystectomy has 90-day readmission rates as high as 40%. The ability to identify patients at risk for or in the early stages of serious postoperative complications, such as sepsis, may improve outcomes and save millions in health care dollars. Reliable at-home monitoring may potentially enable an early discharge and an increased willingness of patients to be discharged early. A wearable device may include a heart rate monitoring feature. Heart rate monitoring may be clinically useful. Heart rate may act as a surrogate for a number of common postoperative complications such as dehydration or infection. A wearable device designed for patient monitoring may focus on heart rate monitoring capabilities. The wearable device may be configured to identify cardiac arrhythmias in addition to a patient's respiratory rate, skin temperature, steps, and fall detection.

Batch processing may be used to process data streams. Data may build up and be processed in a batch as data streams. The amount of data may be voluminous and make it difficult to store the data in an unprocessed or uncomplied state. A batch processing system may split data into time intervals. Data streams may be processed to reduce the data intro smaller more storable or communicable paired data or streams. In some examples, events that start during a time interval but end during another time interval may not be analyzed. Continuous data streams may be queried to detect conditions.

The data processing module 45024 may include a data integration module (e.g., data input/export) and/or a data collection module. The data collection module, for example, in collaborations with other modules in the surgical data system 45002, may perform one or more of dynamic form creation, monitoring and reporting, protocol design, and patient recruitment.

The surgical data system 45002 may include a data removal module 45022. Privacy data may go through selective or controlled redaction while the privacy data is used for other control processes. Videos, data streams, and annotations may go through selective data redaction. Selectivity may be based on differing portions of the collection, compilation, and recording steps of the system. Utilization of the data for annotation, metadata tagging of other data points, or verification of data quality may be followed by redaction of the data itself for privacy. Selectivity may be based on detected predefined events. Automatic data redaction during data monitoring and collection may be performed. In an example, face identification may be used to blur the face or block the entire video until the identified face is no longer displayed. Recognizable characters or symbols may be identified. The symbols for predefined acceptable symbols (e.g., bar codes, product labels, etc) may be compared with unexpected symbols which may be redacted or blurred in the recordings. Redaction of data for privacy and data control may be predefined and constant. Data may be redacted as the surgical data system compiles and assembles the data for inputting into databases for storage. Examples that are suitable for use with the present disclosure are described in in U.S. Patent Application Publication No. US 2019-0205566 A1 (U.S. patent application Ser. No. 15/940,632), titled DATA STRIPPING METHOD TO INTERROGATE PATIENT RECORDS AND CREATE ANONYMIZED RECORD, filed Mar. 29, 2018, the disclosure of which is herein incorporated by reference in its entirety. In one or more those examples, data stripping may extract the relevant portions to configure and operate a surgical hub.

Data deletion control and documentation may be enabled. A data erasure process may be implemented, for example, to ensure complete removal of the data and the notation of the removal authorization. Annotation of when and who authorized the deletion of archived data may be removed. Erasure where the removed data is over-written may be secure, for example, to ensure non-recoverability of the removed data. The data that is selected to be erased and all linked data or metadata coupled to the selected data may be erased.

The surgical data system 45002 may include a big data storage and management module. The big data storage and management module may include one or more of containers, generation algorithms, operational parameters, analytics (e.g., algorithms, automation and real time), usage, security, privacy, compliance, data visualization, copy of raw data (e.g., cloud access to raw data and low storage costs), graphical representation of larger data sets looking for outliers, or algorithms for implementing and monitoring data flows. The generation algorithms may specify data type (e.g., structured; unstructured), data class (e.g., human; machine), and data speed (e.g., batch processing; streaming). The operational parameters may include data management and storage (e.g., store; secure; access; network), engines (e.g., visualization; cloud integration), and how to prepare data for analytics. Algorithms for implementing and monitoring data flows may include one or more of monitor version, parsing un-necessary data, quality checks or processing code.

As described herein, a device (e.g., a surgical hub) may perform one or more of a classification of a data stream (e.g., a surgical data stream), processing the data stream using at least another data stream (e.g., another surgical data stream), or generating a transformed data stream according to a rule set.

The device may determine a classification parameter for the data stream. The device may adjust the classification parameter for the data stream. The device may determine the classification parameter for the data stream based on a classification parameter for a first data stream, a classification parameter for a second data stream, and a mode of interaction between the first data stream and the second data stream, for example, if the data stream is generated using the first data stream and the second data stream. The device may select a data handling scheme for the data stream based on the determined classification parameter for the data stream.

Figure 46:
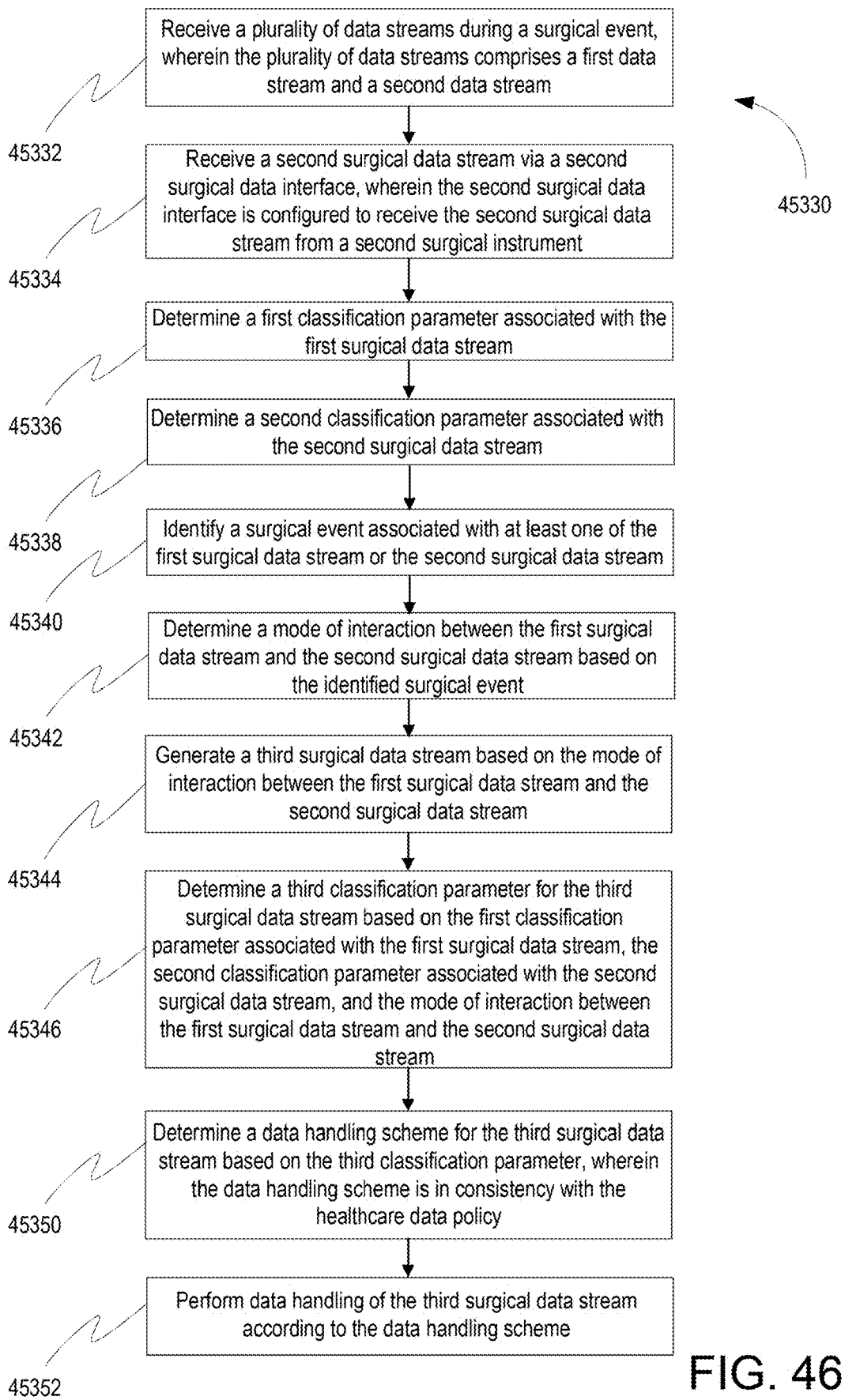
FIG. 46 shows a data classification example.

FIG. 46 shows a data classification example 45330. In FIG. 46, a first surgical data stream may be received via a first surgical data interface at 45332. The first surgical data interface may be configured to receive the first surgical data stream from a first surgical instrument. A second surgical data stream may be received via a second surgical data interface at 45334. The second surgical data interface may be configured to receive the second surgical data stream from a second surgical instrument. A first classification parameter associated with the first surgical data stream may be determined at 45336. The first surgical data interface may be identified, and the device may determine the first classification parameter based on the identified first surgical data interface. In an example, the first surgical data interface may be designated to communicate with a first type of surgical instrument. A second classification parameter associated with the second surgical data stream may be determined at 45338. The second surgical data interface may be identified. The device may determine the second classification parameter based on the identified second surgical data interface. In an example, the second surgical data interface may be designated to communicate with a second type of surgical instrument.

The device may determine the first classification parameter based on decoding the first classification parameter in the first surgical data stream. In some examples, the device may determine the first classification parameter by decoding the first surgical data stream and inferring the first classification parameter based on the decoded first surgical data stream, for example, if the first surgical data stream does not include an indication of the first classification parameter. The device may determine the second classification parameter based on decoding the second classification parameter in the second surgical data stream. In some examples, the device may determine the second classification parameter by decoding the second surgical data stream and inferring the second classification parameter based on the decoded second surgical data stream, for example, if the second surgical data stream does not include an indication of the second classification parameter.

A surgical event associated with at least one of the first surgical data stream or the second surgical data stream may be identified at 45340. At 45342, a mode of interaction between the first surgical data stream and the second surgical data stream may be determined based on the identified surgical event. At 45344, a third surgical data stream may be generated based on the mode of interaction between the first surgical data stream and the second surgical data stream. The mode of interaction may include one or more of an enrichment of the first surgical data stream using the second surgical data stream, an aggregation of the first surgical data stream and the second surgical data stream, or a synthesis of the first surgical data stream and the second surgical data stream. In an example, situational data of the identified surgical event may be generated based on the mode of interaction.

At 45346, a third classification parameter for the third surgical data stream may be determined based on the first classification parameter associated with the first surgical data stream, the second classification parameter associated with the second surgical data stream, and the mode of interaction between the first surgical data stream and the second surgical data stream. A value of the third classification parameter may indicate one or more of privacy of the third surgical data stream, a priority of the third surgical data stream, a content type of the third surgical data stream, a context of the third surgical data stream, a retention period associated with the third surgical data stream, or a user preference associated with the third surgical data stream. As an example, the graph 44014 that shows the energy activation type and amount used by the bipolar energy device 44002 over time in FIG. 41 may be received with patient tissue thickness data stream. The graph 44014 and the patient tissue thickness data stream may be synthesized to generate a threshold energy level used for a particular patient's tissue. The graph 44014 may be associated with a classification parameter that indicates a low privacy level. The patient tissue thickness data stream may be associated with a classification parameter that indicates a high privacy level. The generated threshold energy level may be associated with a classification parameter that indicates a high privacy level or a classification parameter that indicates a privacy level that is lower than the high privacy level and higher than the low privacy level.

At least one of the first classification parameter, the second classification parameter, or the third classification parameter may be multidimensional. In an example, the third classification parameter for the third surgical data stream may be determined using a surgical data classification engine tailored to solve multidimensional classification parameters.

At 45350, a data handling scheme may be determined for the third surgical data stream based on the third classification parameter. The data handling scheme may be in consistency with the healthcare data policy. At 45352, data handling of the third surgical data stream may be performed according to the data handling scheme. The data handling scheme may include one or more of a type of storage location for the third surgical data stream or a reliability level associated with a communication path used for the third surgical data stream. The data handling scheme may include data retention guidelines. The data retention guidelines may specify or guarantee the length of time surgical data can be retained in a particular database.

The communication path may indicate how reliable or secure the transmission resources used to communicate the third surgical data stream should be. In an example, the device may determine based on the third classification parameter, that the third surgical data stream has the highest classification level among a plurality of surgical data streams that are to be transmitted. The device may determine a communication path that is associated with the least amount of interruption among transmission resources that are available to be used for the transmission of the plurality of surgical data streams. The device may send the third surgical data stream using the determined communication path. The device may repeat the sending of the third surgical data stream based on the determination that the third surgical data stream has the highest classification level among the plurality of surgical data streams to be transmitted. The device may select a same data handling scheme for the second surgical data stream as the data handling scheme for the third surgical data stream based on the second classification parameter that is the same as the third classification parameter.

The first classification parameter, the second classification parameter, and the third classification parameter may be determined in consistency with a healthcare data policy (e.g., one or more rules that are consistent with HIIPPA).

Figure 47:
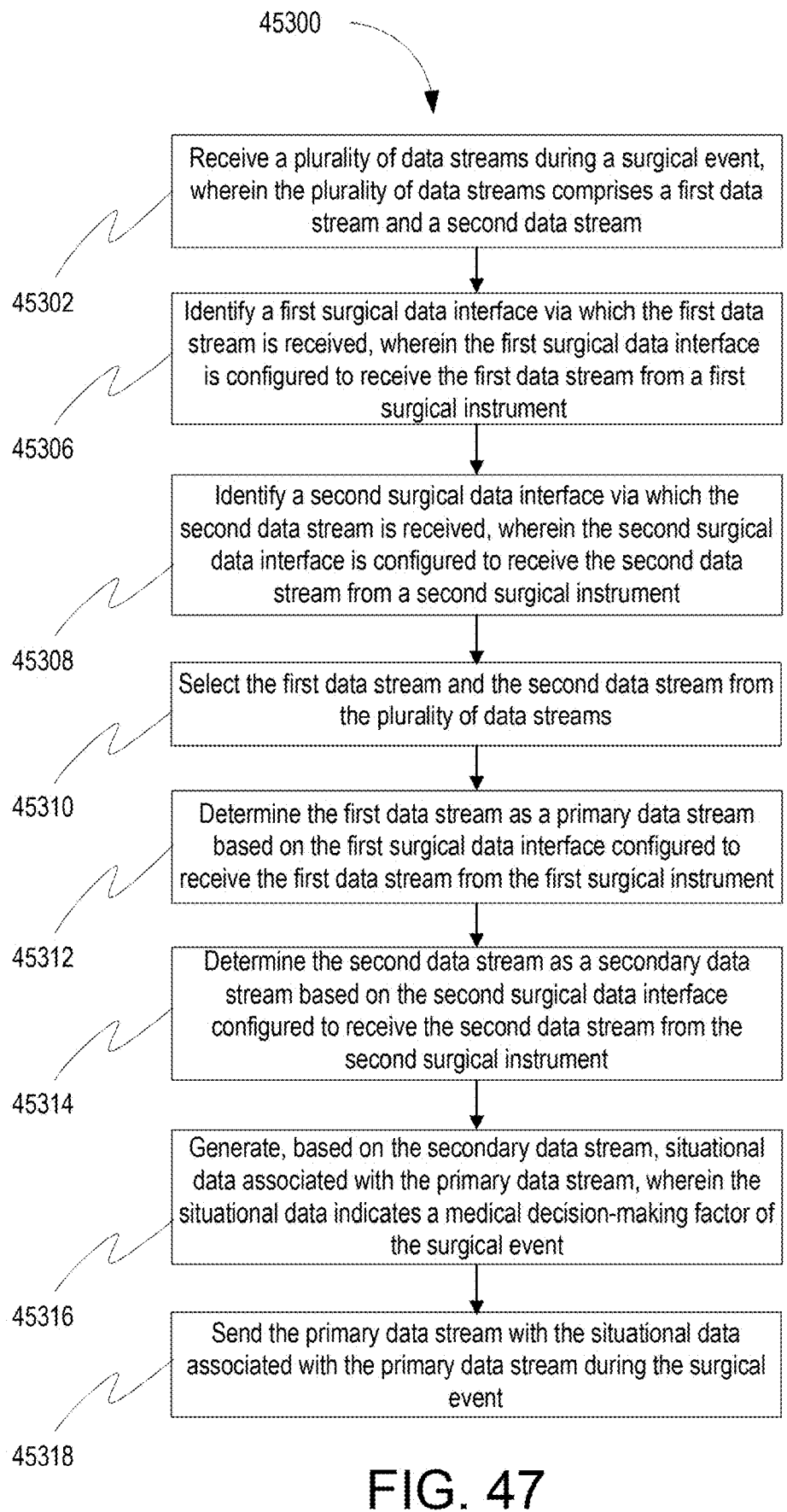
FIG. 47 shows a data processing example.

The device may generate situational data for the data stream using another data stream. The device may select two or more data streams and use one data stream to enhance or distill another data stream. The device may select the data stream as the primary data stream and select another data stream as the secondary data stream. The device may enhance or distill the primary data stream using the secondary data stream. FIG. 47 shows a data processing example 45300. For example, the surgical hub 5104 may be configured to perform one or more of 45302, 45306, 45308, 45310, 45312, 45314, 45316, or 45318 in FIG. 47. In FIG. 47, a plurality of data streams may be received during a surgical event at 45302. The plurality of data streams may comprise a first data stream and a second data stream. A first surgical data interface via which the first data stream is received may be identified at 45306. The first surgical data interface may be configured to receive the first data stream from a first surgical instrument. For example, the first surgical data interface may be designated to communicate with a first type of surgical instrument. A second surgical data interface via which the second data stream is received may be identified at 45308. The second surgical data interface may be configured to receive the second data stream from a second surgical instrument. For example, the second surgical data interface may be designated to communicate with a second type of surgical instrument. The first data stream and the second data stream may be selected from the plurality of data streams at 45310. At 45312, the first data stream may be determined as a primary data stream based on the first surgical data interface configured to receive the first data stream from the first surgical instrument. At 45314, the second data stream may be determined as a secondary data stream based on the second surgical data interface configured to receive the second data stream from the second surgical instrument. The secondary data stream may include a first portion and a second portion. The device may store the first portion of the secondary data stream and not the second portion of the secondary data stream.

Situational data associated with the primary data stream may be generated based on the secondary data stream at 45316. The situational data may indicate a medical decision-making factor of the surgical event. At 45318, the primary data stream with the situational data associated with the primary data stream may be sent during the surgical event. The situational data may be sent using at least one of an annotation for the primary data stream, a context associated with the primary data stream, or meta data that indicates the context associated with the primary data stream. For example, the graph 44014 that shows the energy activation type and amount used by the bipolar energy device 44002 over time in FIG. 41 may be used to generate situational data about the activation and energy amount used by the smoke evacuator for the bipolar energy device 44002, shown by the dotted energy graph 44052. The situational data about the activation and energy amount used by the smoke evacuator for the bipolar energy device 44002 may include one or more of the activation timing, initiation points, deactivation points, and levels.

In an example, the primary data stream may be sent via data packets. At least one of the data packets may include a field indicative of the situational data.

The device may generate a risk indicator based on the primary data stream and the situational data associated with the primary data stream and send the risk indicator. The risk indicator may indicate a probability of an outcome (e.g., an outcome that has a negative impact on the surgical event) associated with the primary data stream. The risk indicator may indicate at least one of an action trigger, a notification, or a threshold. The device may generate control instructions based on the primary data stream and the situational data associated with the primary data stream and send the control instructions to a surgical instrument in communication with the device to change an operation of the surgical instrument.

The first data stream may include a first timing element. The first timing element may indicate a first time when the first data stream is collected during the surgical event. The primary data stream may be sent with the situational data associated with the primary data stream at a second time during the surgical event. A difference between the first time and the second time may be lower than a predetermined value.

The predetermined value may be associated with real-time processing. The difference lower than the predetermined value may indicate that the collection of the first data stream and the sending of the third data stream occur in real time. The difference between the first time and the second time may be minimized to correspond with surgical practices. For example, the difference between the first time and the second time may be minimized to represent real-time processing (e.g., on-the-fly processing) or near real-time processing to enable information exchange in a timely manner for purposes of being displayed during the surgical event.

The surgical event may be an ongoing surgical event. The plurality of data streams may include a data stream associated with a historical surgical event, and the processor is further configured to determine that the ongoing surgical event and the historical surgical event have a characteristic in common. The device may generate the situational data based on the data stream associated with the historical surgical event. The characteristic in common may include at least one of a same patient, a same type of surgical procedure, a same type of surgical instrument, or a same type of surgical equipment. For example, the ongoing surgical event and the historical surgical event may use surgical equipment that has the same model number.

Temporally different data streams may be used to provide context to intra-op data streams. Aspects of multiple pre-surgery data sources may be combined to provide contextual aspects of surgical biomarkers or procedure plans, which, for example, may reduce pre-operative biomarker data streams. Reduced pre-operative biomarker data streams may be used to annotate or provide contexts to intra-operative events or biomarker stream processing. In an example, if a biomarker monitor within the OR suddenly plummets or rises outside of the normal acceptable level coincidently with another surgical event, but the pre-operative baseline shows similar events, then the correlation between the event and the biomarker may be noted as not causational. If the same event occurs and there was not history of these similar issues, the annotation may indicate a probable causational link between the event and the biomarker.

Pre-processing of data streams may enable a data stream to be combined with another data stream to provide contexts or annotations. Contextual algorithmic transformations of data streams may be used to create actionable data feeds. The transformed data may be displayed, or it may be displayed with respect to another transformed data stream, for example, to enable the surgeon to monitor the critical aspects and variables and make decisions from them. A first data stream may be combined with an understanding of a surgical procedure, imaging data, patient data, or instrument measures, etc., for example, to transform the data stream into a data stream that is more capable of making decisions from. Contextual transformation of data may be used to aggregate displayed feeds. Examples that are suitable for use with the present disclosure are described in in U.S. Patent Application Publication No. US 2019-0200980 A1 (U.S. patent application Ser. No. 16/182,230), titled SURGICAL SYSTEM FOR PRESENTING INFORMATION INTERPRETED FROM EXTERNAL DATA, filed Nov. 6, 2018, the disclosure of which is herein incorporated by reference in its entirety. In one or more those examples, interpreted information may be displayed to the user based on at least one function of a device including at least one data source not originating within the device.

Figure 48:
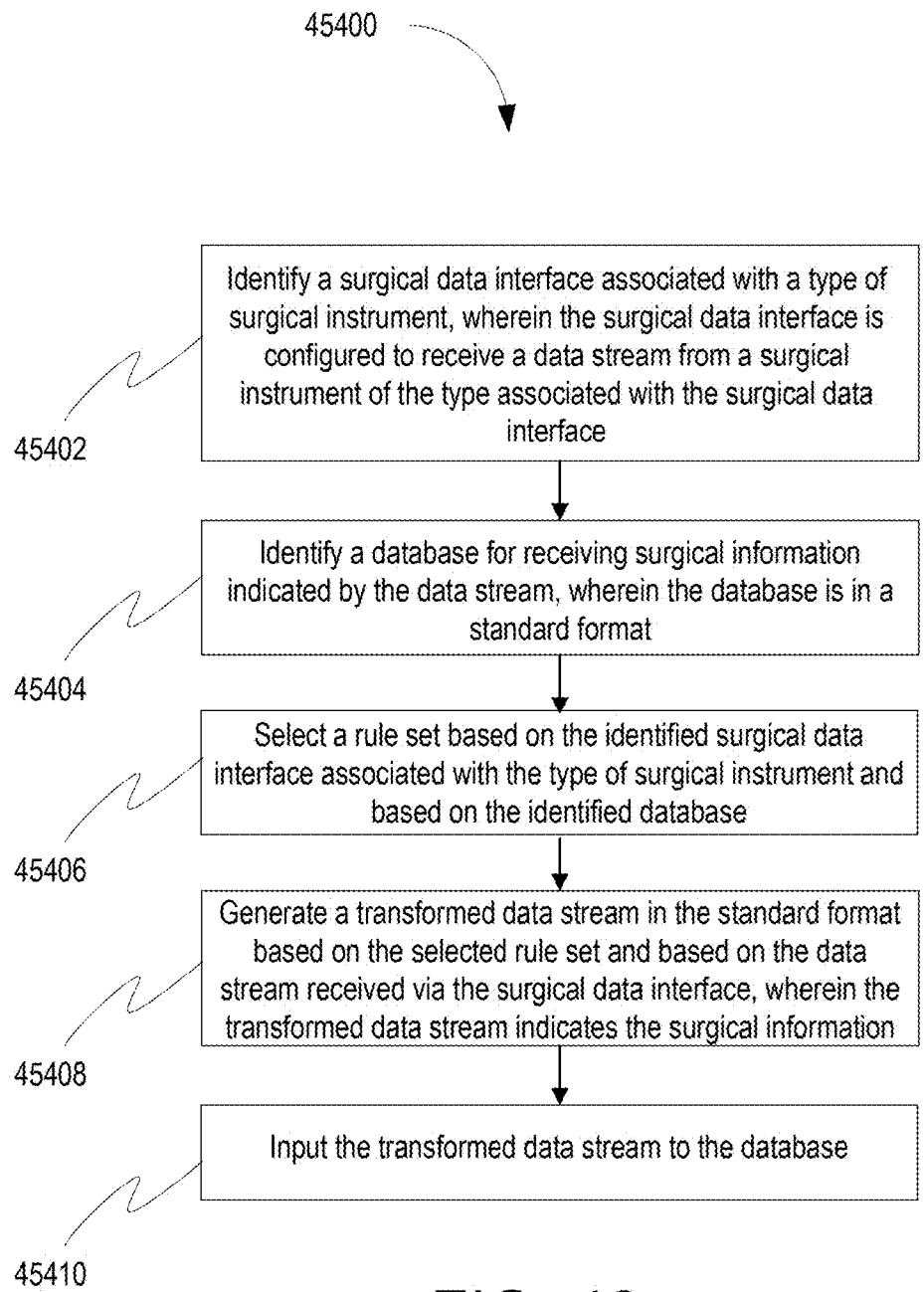
FIG. 48 shows a data standardization example.

The device may transform the data stream into a standardized data stream. The device may select a data base in a standard format for inputting the transformed data stream. The device may determine a rule set for transforming the data stream. FIG. 48 shows a data standardization example 45400.

In FIG. 48, a surgical data interface associated with a type of surgical instrument may be identified at 45402. The surgical data interface may be configured to receive a data stream from a surgical instrument of the type associated with the surgical data interface. The data stream may include visualization data, biomarker data, surgical instrument data, or surgical equipment data.

A database may be identified for receiving surgical information indicated by the data stream at 45404. The database may be in a standard format. The standard format may indicate at least one of a resolution, a sampling rate, a measurement type, a unit of measurement, or a type of data stream. The type of data stream may include a discrete data stream or a continuous data stream. In an example, the database may be a relational database.

At 45406, a rule set may be selected based on the identified surgical data interface associated with the type of surgical instrument and based on the identified database. The rule set may include one or more of a data cleaning rule, a data verification rule, or a data formatting rule. In an example, the device may determine, for a first data stream, invalid data and invalid associations based on the selected rule set. A first transformed data stream may exclude the invalid data and the invalid associations. For example, the activation control signal 44008 may be used to clean the overshooting and clean the lagging data set in FIG. 41.

The device may generate a second transformed data stream in the standard format based on a second data stream. The second transformed data stream and the first transformed data stream may be associated with a same sampling rate, a same synchronization, and a same surgical event. The second data stream may include a patient data stream, a surgical instrument data stream associated with a surgical operation, or a surgical equipment data stream. The device may generate an annotation for the first data stream based on the second data stream. The first transformed data stream may include the annotation. In an example, the device may receive a plurality of data streams from a plurality of data sources. Each data stream of the plurality of data streams may be received from a respective data source of the plurality of data sources and comprises an annotation. The annotation may indicate that the respective data source is operatively coupled with a primary surgical equipment.

At 45408, a transformed data stream in the standard format may be generated based on the selected rule set and based on the data stream received via the surgical data interface. The transformed data stream may indicate the surgical information. For example, the device may parse the data stream based on the standard format. The device may determine that a sampling rate associated with standard format is greater than a sampling rate associated with the data stream. The device may determine intermediate average data points based on the data stream and based on the sampling rate associated with the standard format. The transformed data stream may include the intermediate average data points. The transformed data stream may be input to the database at 45410.

Using the database, related surgical procedures may be compared. For example, the device may identify a first surgical data interface associated with a first type of surgical instrument. The first surgical data interface may be configured to receive a first data stream from a first surgical instrument of the first type associated with the first surgical data interface. The device may identify a second surgical data interface associated with a second type of surgical instrument. The second surgical data interface may be configured to receive a second data stream from a second surgical instrument of the second type associated with the second surgical data interface. The device may determine that the first data stream is collected from a first surgical procedure, that the second data stream is collected from a second surgical procedure, and that the first surgical procedure and the second surgical procedure are associated with a common medical characteristic (e.g., a same medical characteristic). The device may determine that a format of the first data stream and a format of the second data stream are different. The device may identify a database that is in a standard format. The device may select a first rule set based on the first surgical data interface associated with the first type of surgical instrument and based on the identified database. The device may select a second rule set based on the second surgical data interface associated with the second type of surgical instrument and based on the identified database. The device may generate a first transformed data stream in the standard format based on the first rule set and based on the first data stream received via the first surgical data interface. The device may generate a second transformed data stream in the standard format based on the second rule set and based on the second data stream received via the second surgical data interface. The device may input the first transformed data stream and the second transformed data stream to the database. The device may compare the first surgical procedure and the second surgical procedure using the database.

Challenges of data stream processing may have implications specific to medical applications. Smart patient care and monitoring may be used. Some data architectures may have a high latency. For example, results may be computed after a significant delay. Data may be received as a continuous stream. Challenges of data stream processing may include scalability, consistency and durability, fault tolerance and data guarantees. In stream computing environments, the data processors may include tens of thousands of diverse sets of computing nodes with different capabilities and interconnected with arbitrary network architectures. Failures may occur due to the inherently unreliable nature of the computing nodes and communication links. Different types of failures may be correlated with each other and have adverse effects on applications running in such environments. Algorithms for connected instruments in the OR may compile data regarding surgical instrument operations in acute outcomes and compile data regarding long term outcomes of the patient. Long streams of data may be collected although such data may not have an immediate effect on the treatment or action of a device. These long steams may include an enormous amount of data in an uncomplied state. The collection of the long streams of data may take days. Data storage may not be freed up until days of the long streams of data have been collected and the outcome has been determined and tied to the collected data.

Complied data may use less data storage. For example, an advanced energy device may record the tissue impendence over a weld, the time to accomplish the weld, the power usage, and the tissue type and combine it with advanced imaging of the tissue or an annotation of a good or bad weld based on bleeding or weeping post transection local to the event. This way, the stream of impendence data may be compiled into a series of key data points or events, a couple key parameters such as a power level, and a resulting micro-outcome of the integrity of the weld. This compiled data may be a smaller data stream than the raw data. This compiled data may need less data storage or communication bandwidth than the raw data does.

Micro-outcomes (e.g., outcomes of s single step, single task, single event, or single job) may be used to provide context and results local to a recorded data stream. The overall outcomes regarding a surgery may not be used to provide context and results. Certain surgical instruments may not have enough processing overhead (e.g., the processing overhead required to process the signals of all the inputs). A powered stapler may have a smart device running an ARM processor. The ARM processor may be linked to a communication array and may have limited storage for its own control programs and some recording of its usage profiles. A certain amount of data regarding the motor current (e.g., a proxy for a force in the end-effector), closure load, internal accelerometers, and control parameters may need to be discarded, for example, after an immediate action is taken. The force-to-fire data may be prescient to the performance of the staple line. The powered stapler may not have access of micro-outcomes and may not continually store the force-to-fire data. A compiled data stream may include identified key maximums, identified key minimums and identified key timing, for example, if events that may be identified by micro-outcomes include what portion of the staple line has an issue and what key data point that issue correlates to. This compiled stream may be tagged with metadata around the tissue thickness, tissue type, and access issues from the scope of advanced imaging system, which may then be more easily transformed to identify overarching trends and/or outcomes.

One or more of the examples shown in FIG. 46, FIG. 47, or FIG. 48 may be performed in association with a method, a process, an apparatus (e.g., an apparatus comprising one or more of antenna, a band limiter, or a display, or apparatus comprising an access unit and/or a transmitter), non-transitory computer readable medium, computer readable medium, computer program product, medium storing instructions, medium storing data, or a signal, for example, to compile surgical data and generate micro-outcomes.

A computing system may use redundant communication pathways for communicating surgical imaging feed(s). For example, surgical video feed(s) may be sent via multiple video stream pathways to improve resilience of the feed.

Figure 49A:
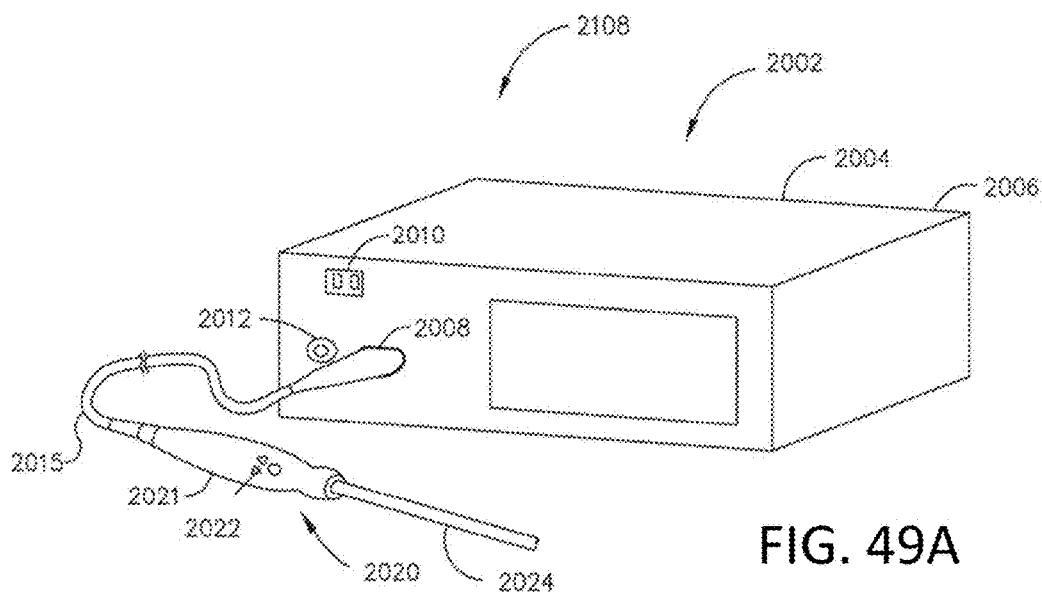
FIGS. 49A-C show an example visualization system.
Figure 49B:
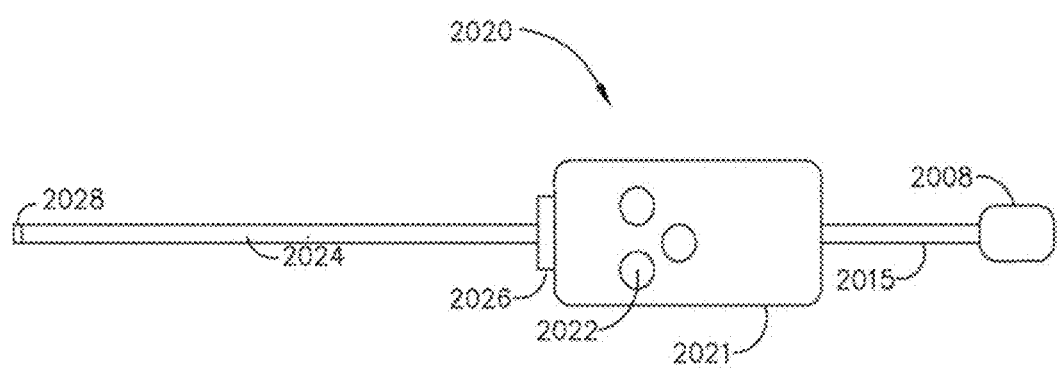
Figure 49C:
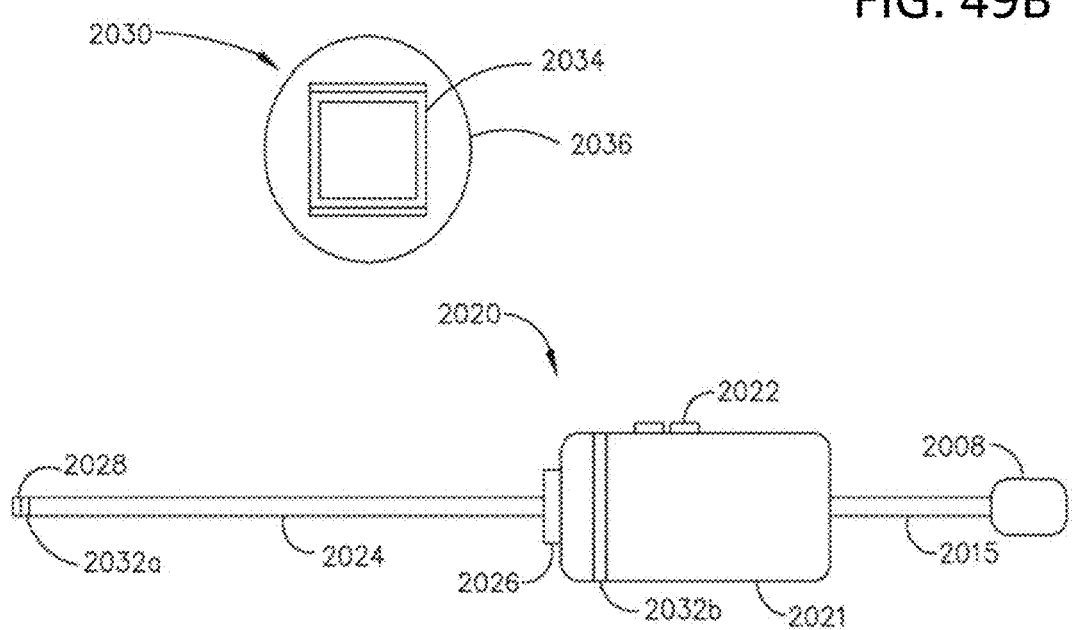

FIGS. 49A-49C show an example visualization system 2108 that may be incorporated into a surgical system. The visualization system 2108 may include an imaging control unit 2002 and a hand unit 2020. The imaging control unit 2002 may include one or more illumination sources, a power supply for the one or more illumination sources, one or more types of data communication interfaces (including USB, Ethernet, or wireless interfaces 2004), and one or more video outputs 2006. The imaging control unit 2002 may further include an interface, such as a USB interface 2010, configured to transmit integrated video and image capture data to a USB enabled device. The imaging control unit 2002 may also include one or more computational components including, without limitation, a processor unit, a transitory memory unit, a non-transitory memory unit, an image processing unit, a bus structure to form data links among the computational components, and any interface (e.g. input and/or output) devices necessary to receive information from and transmit information to components not included in the imaging control unit. The non-transitory memory may further contain instructions that when executed by the processor unit, may perform any number of manipulations of data that may be received from the hand unit 2020 and/or computational devices not included in the imaging control unit.

The illumination sources may include a white light source 2012 and one or more laser light sources. The imaging control unit 2002 may include one or more optical and/or electrical interfaces for optical and/or electrical communication with the hand unit 2020. The one or more laser light sources may include, as non-limiting examples, any one or more of a red laser light source, a green laser light source, a blue laser light source, an infrared laser light source, and an ultraviolet laser light source. In some non-limiting examples, the red laser light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some non-limiting examples, the green laser light source may source illumination having a peak wavelength that may range between 520 nm and 532 nm, inclusive. Non-limiting examples of a green laser peak wavelength may include about 520 nm, about 522 nm, about 524 nm, about 526 nm, about 528 nm, about 530 nm, about 532 nm, or any value or range of values therebetween. In some non-limiting examples, the blue laser light source may source illumination having a peak wavelength that may range between 405 nm and 445 nm, inclusive. Non-limiting examples of a blue laser peak wavelength may include about 405 nm, about 410 nm, about 415 nm, about 420 nm, about 425 nm, about 430 nm, about 435 nm, about 440 nm, about 445 nm, or any value or range of values therebetween. In some non-limiting examples, the infrared laser light source may source illumination having a peak wavelength that may range between 750 nm and 3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. In some non-limiting examples, the ultraviolet laser light source may source illumination having a peak wavelength that may range between 200 nm and 360 nm, inclusive. Non-limiting examples of an ultraviolet laser peak wavelength may include about 200 nm, about 220 nm, about 240 nm, about 260 nm, about 280 nm, about 300 nm, about 320 nm, about 340 nm, about 360 nm, or any value or range of values therebetween.

The hand unit 2020 may include a body 2021, a camera scope cable 2015 attached to the body 2021, and an elongated camera probe 2024. The body 2021 of the hand unit 2020 may include hand unit control buttons 2022 or other controls to permit a health professional using the hand unit 2020 to control the operations of the hand unit 2020 or other components of the imaging control unit 2002, including, for example, the light sources. The camera scope cable 2015 may include one or more electrical conductors and one or more optical fibers. The camera scope cable 2015 may terminate with a camera head connector 2008 at a proximal end in which the camera head connector 2008 is configured to mate with the one or more optical and/or electrical interfaces of the imaging control unit 2002. The electrical conductors may supply power to the hand unit 2020, including the body 2021 and the elongated camera probe 2024, and/or to any electrical components internal to the hand unit 2020 including the body 2021 and/or elongated camera probe 2024. The electrical conductors may also serve to provide bi-directional data communication between any one or more components the hand unit 2020 and the imaging control unit 2002. The one or more optical fibers may conduct illumination from the one or more illumination sources in the imaging control unit 2002 through the hand unit body 2021 and to a distal end of the elongated camera probe 2024. In some non-limiting aspects, the one or more optical fibers may also conduct light reflected or refracted from the surgical site to one or more optical sensors disposed in the elongated camera probe 2024, the hand unit body 2021, and/or the imaging control unit 2002.

FIG. 49B (a top plan view) depicts in more detail some aspects of a hand unit 2020 of the visualization system 2108. The hand unit body 2021 may be constructed of a plastic material. The hand unit control buttons 2022 or other controls may have a rubber overmolding to protect the controls while permitting them to be manipulated by the surgeon. The camera scope cable 2015 may have optical fibers integrated with electrical conductors, and the camera scope cable 2015 may have a protective and flexible overcoating such as PVC. In some non-limiting examples, the camera scope cable 2015 may be about 10 ft. long to permit ease of use during a surgical procedure. The length of the camera scope cable 2015 may range from about 5 ft. to about 15 ft. Non-limiting examples of a length of the camera scope cable 2015 may be about 5 ft., about 6 ft., about 7 ft., about 8 ft., about 9 ft., about 10 ft., about 11 ft., about 12 ft., about 13 ft., about 14 ft., about 15 ft., or any length or range of lengths therebetween. The elongated camera probe 2024 may be fabricated from a rigid material such as stainless steel. The elongated camera probe 2024 may be joined with the hand unit body 2021 via a rotatable collar 2026. The rotatable collar 2026 may permit the elongated camera probe 2024 to be rotated with respect to the hand unit body 2021. The elongated camera probe 2024 may terminate at a distal end with a plastic window 2028 sealed with epoxy.

The side plan view of the hand unit, depicted in FIG. 49C illustrates that a light or image sensor 2030 may be disposed at a distal end 2032*a* of the elongated camera probe or within the hand unit body 2032b. The light or image sensor 2030 may be dispose with additional optical elements in the imaging control unit 2002. FIG. 9C depicts an example of a light sensor 2030 comprising a CMOS image sensor 2034 disposed within a mount 2036 having a radius of about 4 mm. Although the CMOS image sensor in FIG. 49C is depicted to be disposed within a mount 2036 having a radius of about 4 mm, it may be recognized that such a sensor and mount combination may be of any useful size to be disposed within the elongated camera probe 2024, the hand unit body 2021, or in the image control unit 2002. Some non-limiting examples of such alternative mounts may include a 5.5 mm mount 2136, a 4 mm mount 2136, a 2.7 mm mount 2136, and a 2 mm mount 2136. It may be recognized that the image sensor may also comprise a CCD image sensor. The CMOS or CCD sensor may comprise an array of individual light sensing elements (pixels).

During a surgical procedure, a surgeon may be required to manipulate tissues to affect a desired medical outcome. The actions of the surgeon are limited by what is visually observable in the surgical site. Thus, the surgeon may not be aware, for example, of the disposition of vascular structures that underlie the tissues being manipulated during the procedure.

Since the surgeon is unable to visualize the vasculature beneath a surgical site, the surgeon may accidentally sever one or more critical blood vessels during the procedure.

Therefore, it is desirable to have a surgical visualization system that can acquire imaging data of the surgical site for presentation to a surgeon in which the presentation can include information related to the presence of vascular structures located beneath the surface of a surgical site.

Some aspects of the present disclosure further provide for a control circuit configured to control the illumination of a surgical site using one or more illumination sources such as laser light sources and to receive imaging data from one or more image sensors. In some aspects, the present disclosure provides for a non-transitory computer readable medium storing computer readable instructions that, when executed, cause a device to detect a blood vessel in a tissue and determine its depth below the surface of the tissue.

In some aspects, a surgical image acquisition system may include a plurality of illumination sources wherein each illumination source is configured to emit light having a specified central wavelength, a light sensor configured to receive a portion of the light reflected from a tissue sample when illuminated by the one or more of the plurality of illumination sources, and a computing system. The computing system may be configured to: receive data from the light sensor when the tissue sample is illuminated by each of the plurality of illumination sources; determine a depth location of a structure within the tissue sample based on the data received by the light sensor when the tissue sample is illuminated by each of the plurality of illumination sources, and calculate visualization data regarding the structure and the depth location of the structure. In some aspects, the visualization data may have a data format that may be used by a display system, and the structure may comprise one or more vascular tissues.

In an aspect, a surgical image acquisition system may include an independent color cascade of illumination sources comprising visible light and light outside of the visible range to image one or more tissues within a surgical site at different times and at different depths. The surgical image acquisition system may further detect or calculate characteristics of the light reflected and/or refracted from the surgical site. The characteristics of the light may be used to provide a composite image of the tissue within the surgical site as well as provide an analysis of underlying tissue not directly visible at the surface of the surgical site. The surgical image acquisition system may determine tissue depth location without the need for separate measurement devices.

In an aspect, the characteristic of the light reflected and/or refracted from the surgical site may be an amount of absorbance of light at one or more wavelengths. Various chemical components of individual tissues may result in specific patterns of light absorption that are wavelength dependent.

In one aspect, the illumination sources may comprise a red laser source and a near infrared laser source, wherein the one or more tissues to be imaged may include vascular tissue such as veins or arteries. In some aspects, red laser sources (in the visible range) may be used to image some aspects of underlying vascular tissue based on spectroscopy in the visible red range. In some non-limiting examples, a red laser light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some other aspects, near infrared laser sources may be used to image underlying vascular tissue based on near infrared spectroscopy. In some non-limiting examples, a near infrared laser source may emit illumination have a wavelength that may range between 750-3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. It may be recognized that underlying vascular tissue may be probed using a combination of red and infrared spectroscopy. In some examples, vascular tissue may be probed using a red laser source having a peak wavelength at about 660 nm and a near IR laser source having a peak wavelength at about 750 nm or at about 850 nm.

Near infrared spectroscopy (NIRS) is a non-invasive technique that allows determination of tissue oxygenation based on spectro-photometric quantitation of oxy- and deoxyhemoglobin within a tissue. In some aspects, NIRS can be used to image vascular tissue directly based on the difference in illumination absorbance between the vascular tissue and non-vascular tissue. Alternatively, vascular tissue can be indirectly visualized based on a difference of illumination absorbance of blood flow in the tissue before and after the application of physiological interventions, such as arterial and venous occlusions methods.

Instrumentation for near-IR (NIR) spectroscopy may be similar to instruments for the UV-visible and mid-IR ranges. Such spectroscopic instruments may include an illumination source, a detector, and a dispersive element to select a specific near-IR wavelength for illuminating the tissue sample. In some aspects, the source may comprise an incandescent light source or a quartz halogen light source. In some aspects, the detector may comprise semiconductor (for example, an InGaAs) photodiode or photo array. In some aspects, the dispersive element may comprise a prism or, more commonly, a diffraction grating. Fourier transform NIR instruments using an interferometer are also common, especially for wavelengths greater than about 1000 nm. Depending on the sample, the spectrum can be measured in either reflection or transmission mode.

Figure 49D:
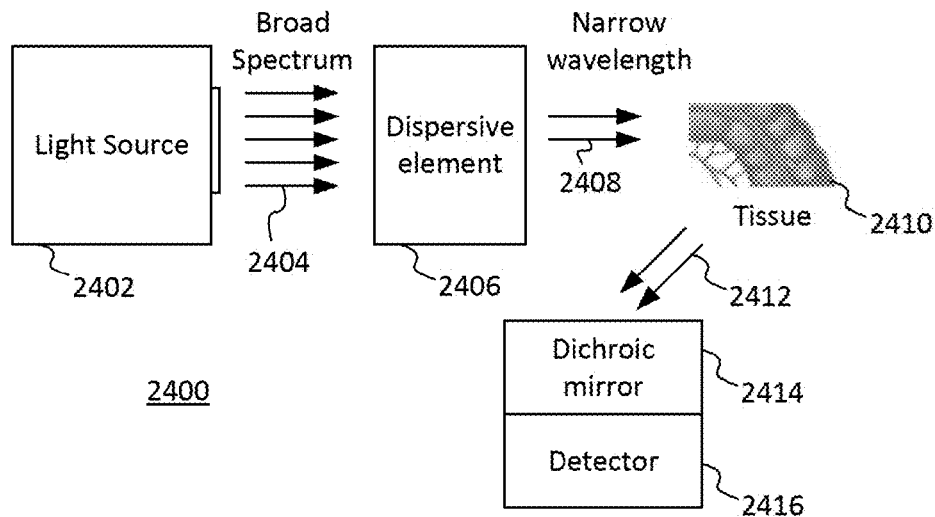
FIG. 49D illustrates example instrumentation for near infrared spectroscopy (NIRS) spectroscopy.

FIG. 49D depicts schematically one example of instrumentation 2400 similar to instruments for the UV-visible and mid-IR ranges for NIR spectroscopy. A light source 2402 may emit a broad spectral range of illumination 2404 that may impinge upon a dispersive element 2406 (such as a prism or a diffraction grating). The dispersive element 2406 may operate to select a narrow wavelength portion 2408 of the light emitted by the broad spectrum light source 2402, and the selected portion 2408 of the light may illuminate the tissue 2410. The light reflected from the tissue 2412 may be directed to a detector 2416 (for example, by means of a dichroic mirror 2414) and the intensity of the reflected light 2412 may be recorded. The wavelength of the light illuminating the tissue 2410 may be selected by the dispersive element 2406. In some aspects, the tissue 2410 may be illuminated only by a single narrow wavelength portion 2408 selected by the dispersive element 2406 form the light source 2402. In other aspects, the tissue 2410 may be scanned with a variety of narrow wavelength portions 2408 selected by the dispersive element 2406. In this manner, a spectroscopic analysis of the tissue 2410 may be obtained over a range of NIR wavelengths.

Figure 49E:
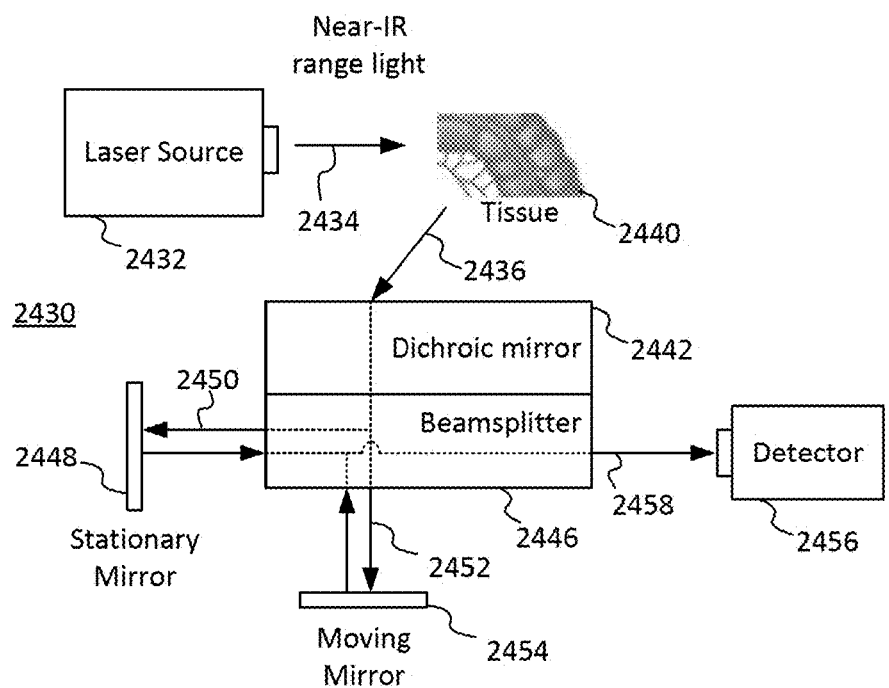
FIG. 49E illustrates example instrumentation for determining NIRS based on Fourier transform infrared imaging.

FIG. 49E depicts schematically one example of instrumentation 2430 for determining NIRS based on Fourier transform infrared imaging. In FIG. 49E, a laser source emitting 2432 light in the near IR range 2434 illuminates a tissue sample 2440. The light reflected 2436 by the tissue 2440 is reflected by a mirror, such as a dichroic mirror 2444, to a beam splitter 2446. The beam splitter 2446 directs one portion of the light 2448 reflected by the tissue 2440 to a stationary mirror 2450 and one portion of the light 2452 reflected 2436 by the tissue 2440 a moving mirror 2454. The moving mirror 2454 may oscillate in position based on an affixed piezoelectric transducer activated by a sinusoidal voltage having a voltage frequency. The position of the moving mirror 2454 in space corresponds to the frequency of the sinusoidal activation voltage of the piezoelectric transducer. The light reflected from the moving mirror and the stationary mirror may be recombined 2458 at the beam splitter 2446 and directed to a detector 2456. Computational components may receive the signal output of the detector 2456 and perform a Fourier transform (in time) of the received signal. Because the wavelength of the light received from the moving mirror 2454 varies in time with respect to the wavelength of the light received from the stationary mirror 2450, the time-based Fourier transform of the recombined light corresponds to a wavelength-based Fourier transform of the recombined light 2458. In this manner, a wavelength-based spectrum of the light reflected from the tissue 2440 may be determined and spectral characteristics of the light reflected 2436 from the tissue 2440 may be obtained. Changes in the absorbance of the illumination in spectral components from the light reflected from the tissue 2440 may thus indicate the presence or absence of tissue having specific light absorbing properties (such as hemoglobin).

An alternative to near infrared light to determine hemoglobin oxygenation would be the use of monochromatic red light to determine the red light absorbance characteristics of hemoglobin. The absorbance characteristics of red light having a central wavelength of about 660 nm by the hemoglobin may indicate if the hemoglobin is oxygenated (arterial blood) or deoxygenated (venous blood).

In some alternative surgical procedures, contrasting agents can be used to improve the data that is collected on oxygenation and tissue oxygen consumption. In one non-limiting example, NIRS techniques may be used in conjunction with a bolus injection of a near-IR contrast agent such as indocyanine green (ICG) which has a peak absorbance at about 800 nm. ICG has been used in some medical procedures to measure cerebral blood flow.

In one aspect, the characteristic of the light reflected and/or refracted from the surgical site may be a Doppler shift of the light wavelength from its illumination source.

Laser Doppler flowmetry may be used to visualize and characterized a flow of particles moving relative to an effectively stationary background. Thus, laser light scattered by moving particles, such as blood cells, may have a different wavelength than that of the original illuminating laser source. In contrast, laser light scattered by the effectively stationary background (for example, the vascular tissue) may have the same wavelength of that of the original illuminating laser source. The change in wavelength of the scattered light from the blood cells may reflect both the direction of the flow of the blood cells relative to the laser source as well as the blood cell velocity.

Figure 49F:
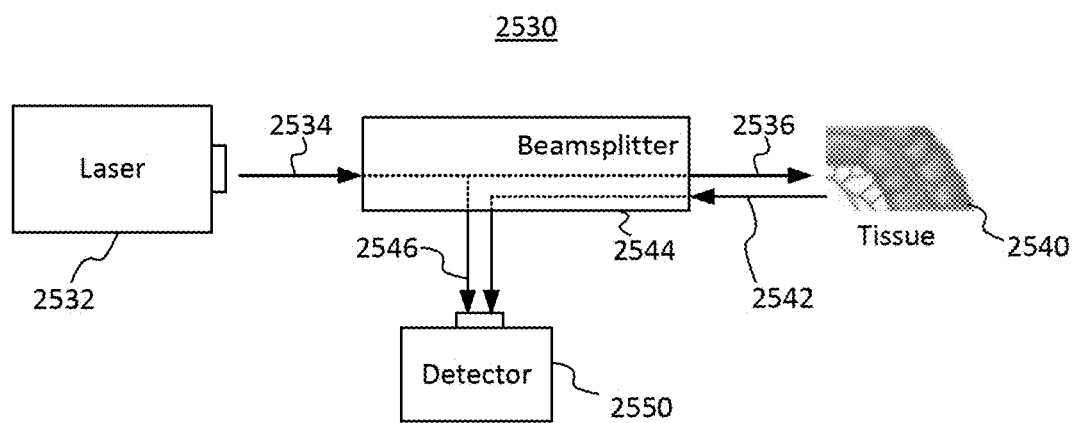
FIG. 49F illustrates example instrumentation that may be used to detect a Doppler shift in laser light scattered from portions of a tissue.

FIG. 49F depicts an aspect of instrumentation 2530 that may be used to detect a Doppler shift in laser light scattered from portions of a tissue 2540. Light 2534 originating from a laser 2532 may pass through a beam splitter 2544. Some portion of the laser light 2536 may be transmitted by the beam splitter 2544 and may illuminate tissue 2540. Another portion of the laser light may be reflected 2546 by the beam splitter 2544 to impinge on a detector 2550. The light back-scattered 2542 by the tissue 2540 may be directed by the beam splitter 2544 and also impinge on the detector 2550. The combination of the light 2534 originating from the laser 2532 with the light back-scattered 2542 by the tissue 2540 may result in an interference pattern detected by the detector 2550. The interference pattern received by the detector 2550 may include interference fringes resulting from the combination of the light 2534 originating from the laser 2532 and the Doppler shifted (and thus wavelength shifted) light back-scattered 2452 from the tissue 2540.

It may be recognized that back-scattered light 2542 from the tissue 2540 may also include back scattered light from boundary layers within the tissue 2540 and/or wavelength-specific light absorption by material within the tissue 2540. As a result, the interference pattern observed at the detector 2550 may incorporate interference fringe features from these additional optical effects and may therefore confound the calculation of the Doppler shift unless properly analyzed.

Figure 50:
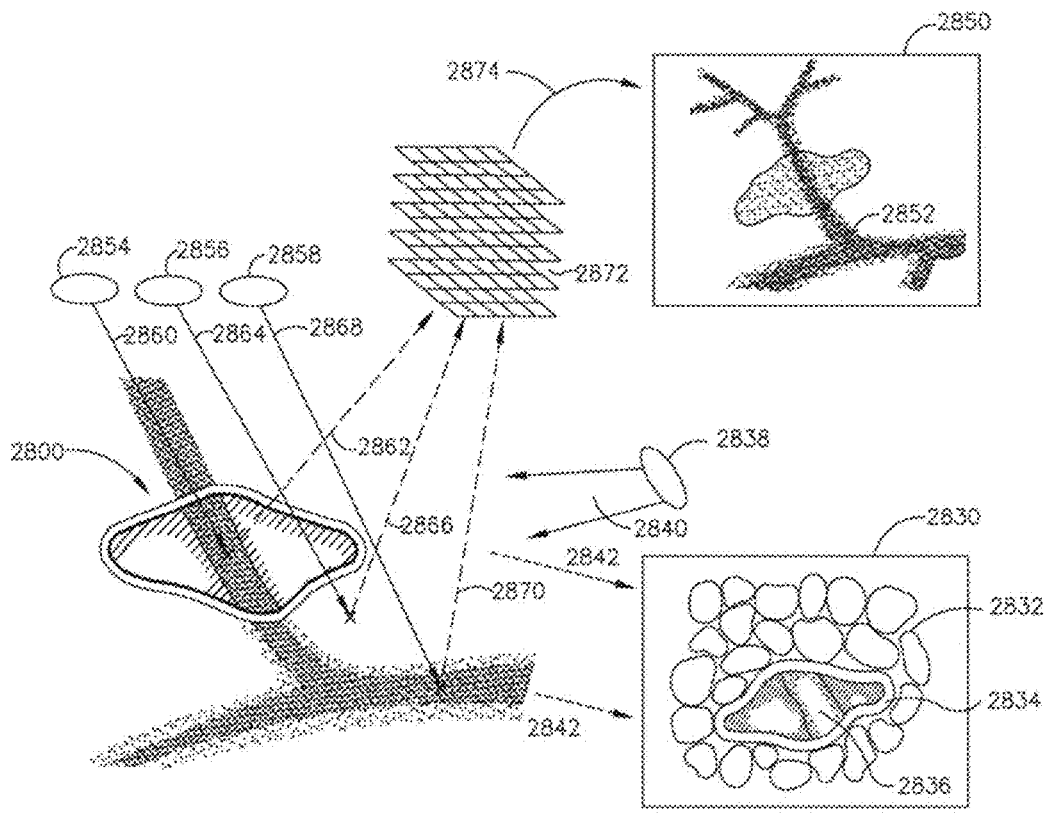
FIG. 50 illustrates an example composite image comprising a surface image and an image of a subsurface blood vessel.

FIG. 50 depicts an aspect of a composite visual display 2800 that may be presented a surgeon during a surgical procedure. The composite visual display 2800 may be constructed by overlaying a white light image 2830 of the surgical site with a Doppler analysis image 2850.

The white light image 2830 may portray the surgical site 2832, one or more surgical incisions 2834, and the tissue 2836 readily visible within the surgical incision 2834. The white light image 2830 may be generated by illuminating 2840 the surgical site 2832 with a white light source 2838 and receiving the reflected white light 2842 by an optical detector. Although a white light source 2838 may be used to illuminate the surface of the surgical site, in one aspect, the surface of the surgical site may be visualized using appropriate combinations of red 2854, green 2856, and blue 2858 laser light.

The Doppler analysis image 2850 may include blood vessel depth information along with blood flow information 2852 (from speckle analysis). Blood vessel depth and blood flow velocity may be obtained by illuminating the surgical site with laser light of multiple wavelengths, and determining the blood vessel depth and blood flow based on the known penetration depth of the light of a particular wavelength. In general, the surgical site 2832 may be illuminated by light emitted by one or more lasers such as a red leaser 2854, a green laser 2856, and a blue laser 2858. A CMOS detector 2872 may receive the light reflected back (2862, 2866, 2870) from the surgical site 2832 and its surrounding tissue. The Doppler analysis image 2850 may be constructed 2874 based on an analysis of the multiple pixel data from the CMOS detector 2872.

For example, a red laser 2854 may emit red laser illumination 2860 on the surgical site 2832 and the reflected light 2862 may reveal surface or minimally subsurface structures. In one aspect, a green laser 2856 may emit green laser illumination 2864 on the surgical site 2832 and the reflected light 2866 may reveal deeper subsurface characteristics. In another aspect, a blue laser 2858 may emit blue laser illumination 2868 on the surgical site 2832 and the reflected light 2870 may reveal, for example, blood flow within deeper vascular structures. The speckle contrast analysis my present the surgeon with information regarding the amount and velocity of blood flow through the deeper vascular structures.

Although not depicted in FIG. 50 it may be understood that the imaging system may also illuminate the surgical site with light outside of the visible range. Such light may include infra-red light and ultraviolet light. In some aspects, sources of the infra-red light or ultraviolet light may include broad-band wavelength sources (such as a tungsten source, a tungsten-halogen source, or a deuterium source). In some other aspects, the sources of the infra-red or ultraviolet light may include narrow-band wavelength sources (IR diode lasers, UV gas lasers or dye lasers).

The depth of a surface feature in a piece of tissue may be determined. An image acquisition system may illuminate a tissue with a first light beam having a first central frequency and receive a first reflected light from the tissue illuminated by the first light beam. The image acquisition system may then calculate a first Doppler shift based on the first light beam and the first reflected light. The image acquisition system may then illuminate the tissue with a second light beam having a second central frequency and receive a second reflected light from the tissue illuminated by the second light beam. The image acquisition system may then calculate a second Doppler shift based on the second light beam and the second reflected light. The image acquisition system may then calculate a depth of a tissue feature based at least in part on the first central wavelength, the first Doppler shift, the second central wavelength, and the second Doppler shift. The tissue features may include the presence of moving particles, such as blood cells moving within a blood vessel, and a direction and velocity of flow of the moving particles. It may be understood that the method may be extended to include illumination of the tissue by any one or more additional light beams. Further, the system may calculate an image comprising a combination of an image of the tissue surface and an image of the structure disposed within the tissue.

Multiple visual displays may be used. For example, a 3D display may provide a composite image displaying the combined white light (or an appropriate combination of red, green, and blue laser light) and laser Doppler image. Additional displays may provide only the white light display or a displaying showing a composite white light display and an NIRS display to visualize only the blood oxygenation response of the tissue. However, the NIRS display may not be required every cycle allowing for response of tissue.

A surgical visualization system using the imaging technologies disclosed herein may benefit from ultrahigh sampling and display frequencies. Sampling rates may be associated with the capabilities of the underlying device performing the sampling. A general-purpose computing system with software may be associated with a first range of achievable sampling rates. A pure-hardware implementation (e.g., a dedicated application specific integrated circuit, ASIC) may be associated with a second range of achievable sampling rates. The second range, associated with the pure-hardware implementation, will generally be higher (e.g., much higher) than the first range, associated with general-purpose computing software implementation.

A surgical visualization system using the imaging technologies disclosed herein may benefit from solutions that balance the higher sampling rates, associated with hardware-based implementations, with the adaptability and/or updatability of software systems. Such a surgical visualization systems may employ a mix of hardware and software solutions. For example, a surgical visualization system may employ various hardware-implemented transforms with a software selector. A surgical visualization system may also employ a field programmable gate array (FPGA). An FPGA may include a hardware device that may include one or more logic elements. These logic elements may be configured by a bitstream to implement various functions. For example, the logic elements may be configured to perform certain individual logic functions and configured to perform them with a certain order and interconnection. Once configured, the FPGA may perform its function using the hardware logic elements without further configuration. Also once configured, the FPGA may be reconfigured with a different bitstream to implement a different function. And similarly, once reconfigured, the FPGA may perform this different function using the hardware logic elements.

Figure 51:
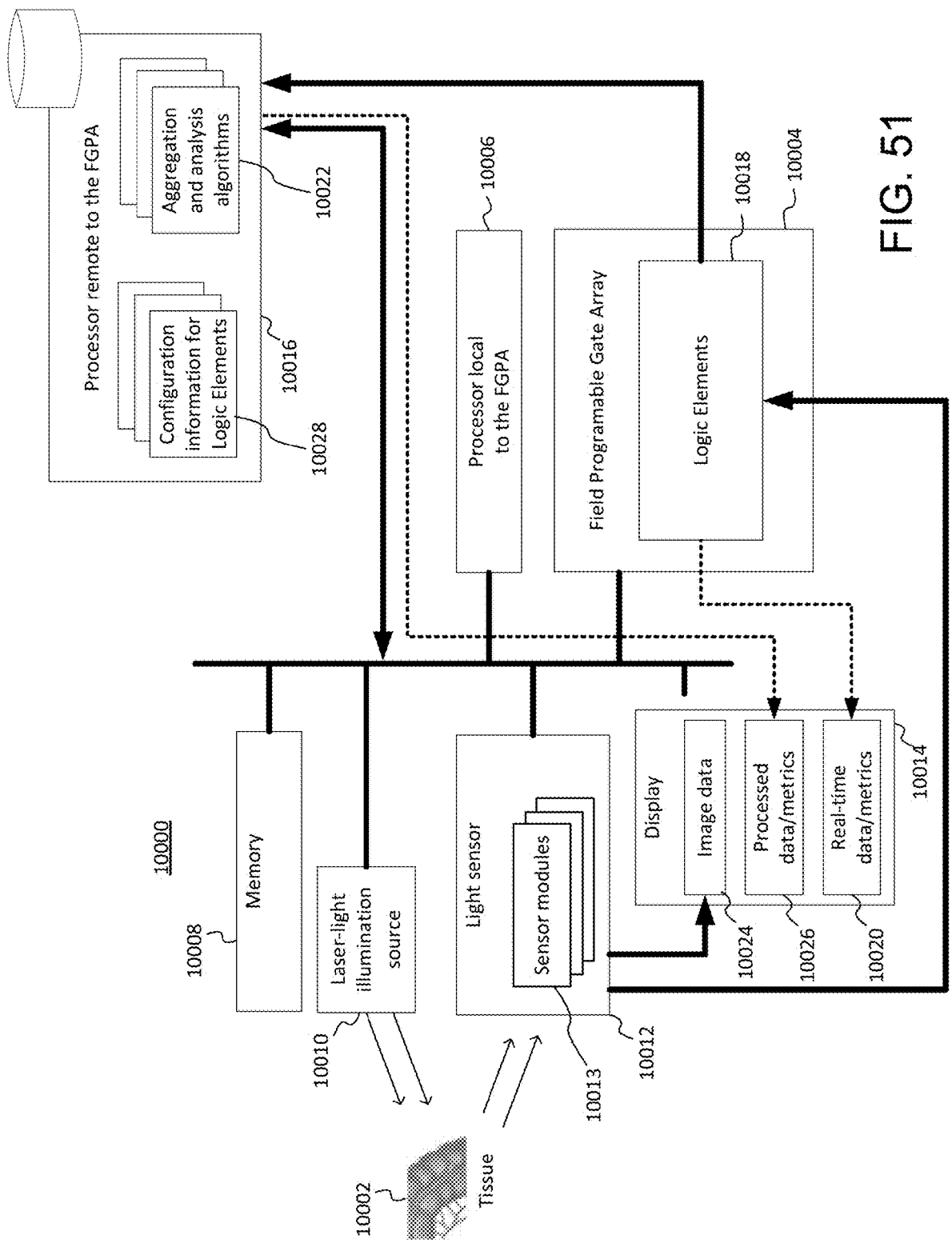
FIG. 51 illustrates an example visualization system.

FIG. 51 illustrates an example surgical visualization system 10000. The surgical visualization system 10000 may be used to analyze at least a portion of a surgical field. For example, the surgical visualization system 10000 may be used to analyze tissue 10002 within the at least a portion of the surgical field. The surgical visualization system 10000 may include an FPGA 10004, a processor (for example, a processor 10006 local to the FPGA 10004, a memory 10008, a laser-light illumination source 10010, a light sensor 10012, a display 10014, and/or a processor 10016 remote to the FGPA. The surgical visualization system 10000 may include components and functionality described in connection with FIGS. 49A-C for example.

The system 10000 may use an FPGA 10004 to convert the reflected laser light through a transform of frequency to identify a Doppler shift, for example, of the light to determine moving particles. This transformed data may be displayed (e.g., displayed in real-time). It may be displayed, for example, as a graphic and/or metric 10020, representing the number of moving particles each second. The system 10000 may include communication between the processor 10006 local to the FPGA 10004 and the processor 10016 remote to the FGPA. For example, the processor 10016 remote to the FGPA 10004 may aggregate data (e.g., multiple seconds of data). And the system may be able to display that aggregation of data. For example, it may be displayed as a graphic and/or metric 10026 representing a moving trend. This graphic and/or metric 10026 may be superimposed on the real-time data. Such trend information may be used to identify occlusions, instrument vascular sealing/clamping efficiency, vascular tree overviews, even oscillating magnitudes of motion over time. The FPGA 10004 may be configured to be on-the-fly updateable, for example, updatable with different (e.g., more sophisticated) transformations. These updates may come from local or remote communication servers. These updates may, for example, change the transform's analysis from refractivity (e.g., analysis of cellular irregularities), to blood flow, to multiple simultaneous depth analysis, and the like.

The FPGA updates may include transforms that implement a variety of imaging options for the user. These imaging options may include standard combined visual light, tissue refractivity, doppler shift, motion artifact correction, improved dynamic range, improved local clarity, super resolution, NIR florescence, multi-spectral imaging, confocal laser endomicroscopy, optical coherence tomography, raman spectroscopy, photoacoustic imaging, or any combination. The imaging options may include any of the options presented in any of the following: U.S. patent application Ser. No. 15/940,742, entitled "DUAL CMOS ARRAY IMAGING," filed Mar. 29, 2018; U.S. patent application Ser. No. 13/952,564, entitled "WIDE DYNAMIC RANGE USING MONOCHROMATIC SENSOR," FILED Jul. 26, 2013; U.S. patent application Ser. No. 14/214,311, entitled "SUPER RESOLUTION AND COLOR MOTION ARTIFACT CORRECTION IN A PULSED COLOR IMAGING SYSTEM," filed Mar. 14, 2014; U.S. patent application Ser. No. 13/952,550, entitled "CAMERA SYSTEM WITH MINIMAL AREA MONOLITIC CMOS IMAGE SENSOR," filed Jul. 26, 2013, each of which is incorporated herein by reference in its entirety. Doppler wavelength shifting may be used to identify the number, size, speed, and/or directionality of moving particles, for example. Doppler wavelength shifting may be used with multiple laser wavelengths to interrelate the tissue depth and moving particles, for example. Tissue refractivity may be used for identification of irregular or variability of tissue superficial and sub-surface aspects, for example. In surgical practice, it may benefit identifying tumor margins, infection, broken surface tissue, adhesions, changes in tissue composition, and the like. NIR Fluorescence may include techniques in which systemically-injected drugs are preferentially absorbed by targeted tissue. When illuminated with the appropriate wavelength of light, they fluoresce and can be imaged through a NIR-capable scope/camera. Hyperspectral imaging and/or multispectral imaging may include the illumination and assessment of tissue across many wavelengths throughout the electromagnetic spectrum to provide real-time images. It may be used to differentiate between target tissues. It may also enable an imaging depth of 0-10 mm for example. Confocal laser endomicroscopy (CLE) may uses light to capture high-resolution, cellular level resolution without penetrating into tissue. It may provide a real-time histopathology of tissue. Technology that uses light to capture micrometer-resolution, 3D images from within tissues. Optical coherence tomography (OCT) may employ NIR light. OCT may enable imaging of tissue at depths of 1-2 mm, for example. Raman spectroscopy may include techniques that measure photon shifts caused by monochromatic laser illumination of tissue. It may be used to identify certain molecules. Photoacoustic imaging may include subjecting tissue to laser pulses such that a portion of the energy causes thermoelastic expansion and ultrasonic emission. These resulting ultrasonic waves may be detected and analyzed to form images.

The laser-light illumination source 10010 may include any illumination source of laser light suitable for analyzing human tissue. The laser-light illumination source 10010 may include a device such as the source laser emitters. The laser light illumination source 10010 may use one or more wavelengths of laser light to illuminate the tissue 10002. For example, the laser-light illumination source 10010 may use a red-blue-green-ultraviolet 1-ultraviolet 2-infrared combination. This combination with a 360-480 Hz sampling and actuation rate, for example, would allow for each light source to have multiple frames at an end user 60 Hz combined frame rate. A laser light wavelength combination with independent sources may increase resolution from a single array and may enable various depth penetration.

The tissue 10002 may be human tissue within a portion of a surgical field, for example. The laser light may reflect from the tissue 10002, resulting in reflected laser light. The reflected laser light may be received by the light sensor 10012. The light sensor 10012 may be configured to receive reflected laser light from a least a portion of the surgical field. The light sensor 10012 may be configured to receive laser light from the entirety of the surgical field. The light sensor may be configured to receive reflected laser light from a selectable portion of the surgical field. For example, a user, such as a surgeon, may direct the light sensor and the light laser light illumination source and/or the laser light illumination source to analyze specific portions of the surgical field.

The light sensor 10012 may be any device suitable for sensing reflected laser light and outputting corresponding information. For example, the light sensor 10012 may detect one or more characteristics of the reflected laser light, such as amplitude, frequency, wavelength, doppler shift, and/or other time domain or frequency domain qualities, for example. The laser-light sensor 10012 source may include a device such as the light sensor disclosed in connection with FIGS. 49A-C for example.

The laser-light sensor 10012 may include one or more sensor modules 10013. The sensor modules 10013 may be configured to measure a wide range of wavelengths. The sensor modules 10013 may be tuned and/or filtered to measure specific wavelengths for example. The sensor modules 10013 may include discrete sensors, a collection of sensors, a sensor array, a combination of sensor arrays, or the like, for example. For example, the sensor modules 10013 may include semiconductor components such as photodiodes, CMOS (complementary metal oxide semiconductor) image sensors, CCD (charge coupled device) image sensors, or the like. The laser-light sensor 10012 may include a dual CMOS arrays. Details on using FPGA in imaging system can be found in U.S. patent application Ser. No. 17/062,521, entitled TIERED-ACCESS SURGICAL VISUALIZATION SYSTEM, filed Oct. 2, 2020, which is herein incorporated by reference in its entirety.

Figure 52:
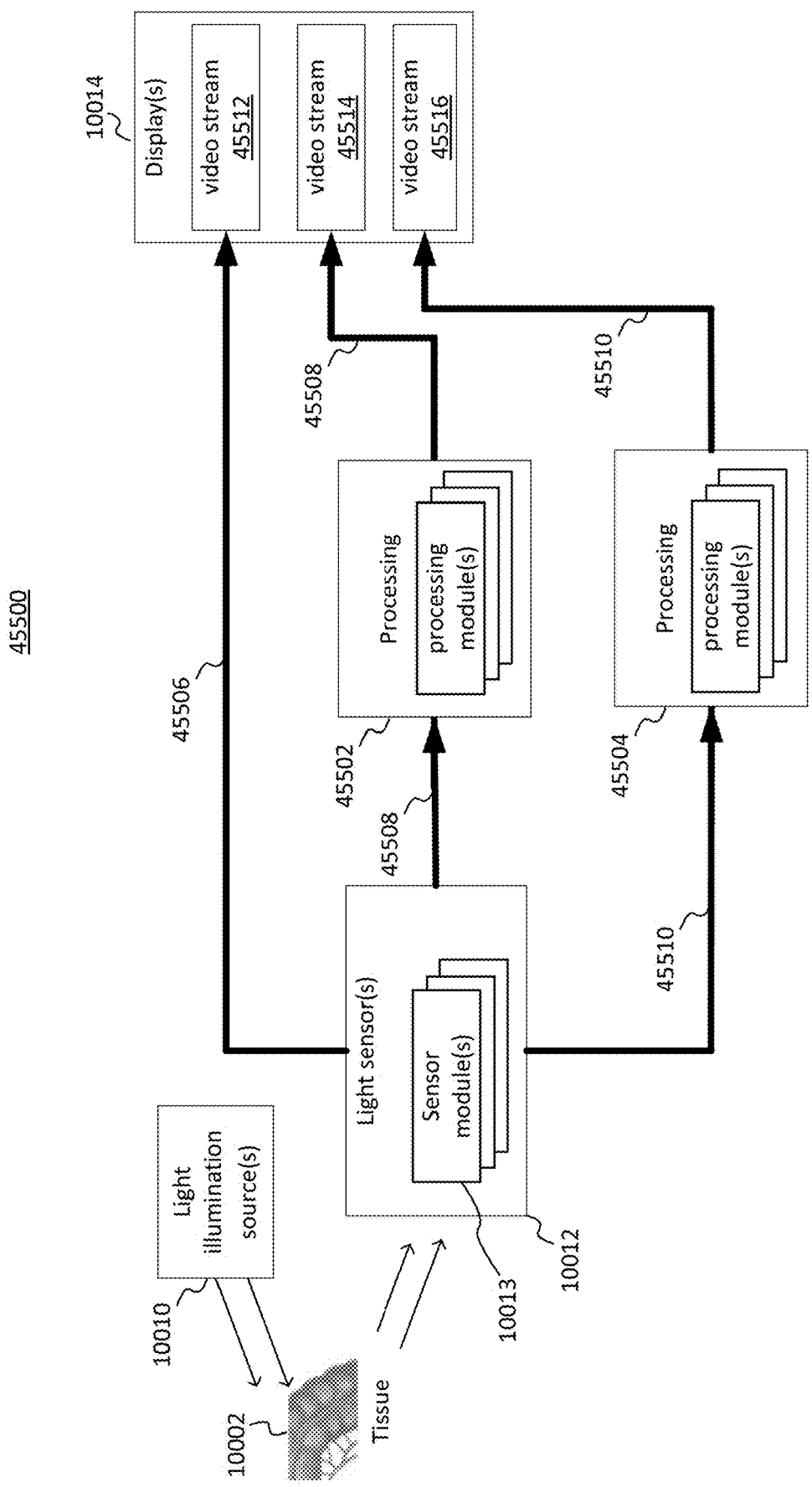
FIG. 52 illustrates an example visualization system.

FIG. 52 illustrates an example aspect of the visualization system described herein. Example surgical visualization system 45500 may be used to analyze tissue 10002 within the at least a portion of the surgical field. The surgical visualization system 45500 may include laser-light illumination source(s) 10010, light sensor(s) 10012, display(s) 10014, and/or one or more processing units 45502 and 45504. The surgical visualization system 45500 may include components and functionality described in connection with FIG. 51 for example, such as laser-light illumination source(s) 10010, light sensor(s) 10012 including sensor module(s) 10013, and/or display(s) 10014. The surgical visualization system 45500 may include components and functionality described in connection with FIGS. 49A-C for example.

As shown in FIG. 52, one or more surgical video streams generated from light sensors(s) 10012 may be transmitted via pathway 45506, pathway 45508, pathway 45510 and/or other pathways to display(s) 10014. The surgical video streams may include various video feeds described herein with reference to FIGS. 49-51. The surgical video streams may include a primary visual video feed, such as an intra-body camera feed. The surgical video streams may include one or more secondary surgical video feeds such as video streams associated with multispectral analysis, video streams associated with Doppler flowmetry, video streams of different spectral ranges, video streams captured using visible light and light outside of the visible range, video streams captured at different time intervals, and/or video stream(s) for overlaying onto another video stream.

The surgical video stream(s) may be processed via one or more processing modules. For example, video stream 45514 may be processed via processing module(s) 45502, and the video stream 45516 may be processed via processing module(s) 45504. The video streams may be multiple feeds of the same source stream being communicated and processed separately. As shown, video stream 45512 may be transmitted via a dedicated communication pipeline, bypassing processing modules, such as processing modules 45502 and 45504. For example, video stream 45512 may be an HD video feed with no processing or intermediate steps between scope and display. The video streams 45514 and 45516 may be sent through post capture processing to extract or convert the video or image(s) to supply other visualization capabilities. Video stream 45512 may be the same as the video streams 45514 and/or 45516 prior to processing via processing module(s) 45502 and/or 45504. Processing 45502 and 45504 can be the same or different.

As shown in FIG. 52, redundant surgical imaging communication pipe ways and processing may provide a fail-safe condition for the primary visual light feed. The primary video stream may be transmitted via multiple pathways. For example, the video stream may be divided into different portions for transmission via multiple pathways. A portion of the video stream, for example, every other picture frame, may be transmitted via a pathway, and the rest of the video stream or the remaining picture frames may be transmitted via another pathway. The two portions may be combined or merged prior to display. Thus, transmission speed of the video feed may be increased and may overcome the data storage and transport limits of the system architecture. For example, the two video stream portions may be encoded such that they may be independently decoded and displayed without being re-combined. Combining the two portions may result in a higher quality video feed; however, displaying a video stream portion may provide sufficient view of the surgical site for a surgeon. If an issue associated with a pathway for transmitting a portion of the video stream is detected, combining or merging of the video stream portions may be suspended, and the video stream portion that has successfully been transmitted to the display system may be displayed.

The primary video stream may be processed via multiple instances of the same processing module(s) through different pathways. If an instance of the processing modules experience latency or failure, the video stream may be processed via another instance of the processing modules may be displayed. If processing causes undue latency or experiences failure, the video stream that bypasses processing may be displayed. Utilizing multiple video stream paths may improve processing speed and reliability, as an individual pathway may be associated with isolated individual processing elements. By performing processing tasks in parallel, the failure of one video feed may not result in the loss of all feeds. Performing different processing tasks in parallel and combine the processed video streams for display may increase processing throughput and reduce latency.

For example, the computing system may control the capturing, processing, and/or communication of the visualization feed(s) to prioritize latency over reliability, or prioritize reliability over latency. The priority focus may be controlled or updated dynamically. For example, the computing system may prioritize within the FPGAs such that latency may be reduced. The visualization feed(s) may be prioritized within the FPGAs such that the reliability of the video stream may be improved. For example, the computing system may adjust the communication paths such as communication paths 45506, 45508 and 45510 to prioritize latency over reliability, or prioritize reliability over latency. For example, allocating more communication pathways to transmit the same video stream may increase reliability, and allocating communication pathways for parallel processing may reduce latency.

Thus, the redundancy allows for the advanced computational imaging processing, reduced latency, and/or allow a communication to fail while still providing an assured visual feed of the camera.

FIG. 53 illustrates example process for using redundant pipe ways for communicating surgical imaging feed(s). At 45520, multiple surgical video streams may be obtained via multiple pathways. The multiple video or imaging feeds could be copies of the same feed with different pathways to the user display. For example, a first video stream may be obtained via a communication pathway, and a second video stream may be obtained via another communication pathway. The multiple surgical video streams could be bifurcated allowing a portion of the feed to pass down one path and a different portion to pass through another pathway. For example, a surgical video stream may be an HD video feed, and a surgical video stream may be of a higher quality video stream or a video stream with added visualization capabilities. The multiple surgical video streams may be obtained from the same intra-body visual light feed, or may be obtained from different intra-body visual light feeds. At 45522, a video stream may be displayed. At 45524, whether the video stream being displayed has encountered at least one issue may be determined. Upon detecting an issue with the video stream being displayed, at 45526, another video stream may be displayed. For example, the primary video stream may be displayed initially. Upon detecting an issue associated with the primary video, the secondary video stream may be displayed. The redundant communication pathways may be used in parallel to improve reliability, communication speed, throughput, and/or to reduce latency of surgical imaging/video feeds for display.

FIG. 54 illustrates example process for using redundant processing paths for processing surgical imaging feed(s). At 45530, a source surgical imaging stream may be obtained. For example, the source surgical imaging stream may be obtained as described herein with reference to FIGS. 49-52. At 45532, the source stream may be processed using multiple processing modules. For example, at least some processing modules may be used to process the surgical imaging stream in parallel. At 45534, whether an issue has been encountered at a processing module may be determined. If no issue has been found, the processed video streams may be merged for display at 45536. Upon detecting an issue associated with a processing module, at 45540, a video stream unaffected by the detected issue may be displayed. For example, a video stream that has not been processed by the processing module associated with the detected issue may be selected for display.

For example, surgical imaging stream generated from light sensors(s) 10012 as shown in FIG. 52 may be obtained. The source surgical imaging stream may be processed using processing module(s) 45502 and processing module(s) 45504 in parallel. The processing module(s) 45502 and the processing module(s) 45504 may be different instances of the same type of processing modules. The processed video stream 45514 and the processed video stream 45516 may be merged for display.

Upon detecting an issue associated with processing module(s) 45504, the processed video stream 45516 may become unavailable, and merging of the processed video streams 45514 and 45516 may be stopped. The processed video stream 45514 may identified as a video stream unaffected by the detected issue and may be displayed. The video stream 45512 shown in FIG. 52, which bypasses the processing modules, may be identified as a video stream unaffected by the detected issue and may be displayed. For example, the unprocessed video stream may be selected for display when both processing module(s) 45502 and 45504 encounter issues. For example, the computing system may detect an issue associated with a processing module and provide an indication of the processing interruption. The computing system may provide an option to an HCP to enable the HCP to manually control the visualization system. The computing system may allow the user to select bypassing processing aspects of the visualization system. Thus, computing system may ensure that the user can display the video even if the hardware processing fails. The processing module(s) 45502 and the processing module(s) 45504 may be used in parallel to improve processing throughput, reduce latency, and/or to guarantee the availability of surgical imaging stream for display.

For example, a source video stream, such as a video stream generated from light sensors(s) 10012 as shown in FIG. 52 may be divided into different portions to be processed separately. A portion of the video stream, for example, every other picture frame, may be processed using a first processing module such as processing module(s) 45502, and the rest of the video stream or the remaining picture frames may be processed using a second processing module such as processing module(s) 45504. The two processed video portions, such as processed video streams 45514 and 45516 may be combined or merged prior to display. Thus, processing speed of the video feed may be increased and may overcome the processing limits of the system architecture. Combining the two portions may result in a higher quality video feed; however, displaying a video stream portion may provide sufficient view of the surgical site for a surgeon. If an issue associated with a processing module is detected, combining or merging of the video stream portions may be suspended, and the video stream portion that has successfully been processed may be displayed.

For example, multiple source video streams may be generated from light sensors(s) 10012 as shown in FIG. 52. The source video streams may contain images associated with different temporal aspects. The video streams, for example, after processing, may be merged for display. The video streams may be displayed on their own, without merging. For example, a video stream may serve as a redundant backup supply to ensure the user has display of the source despite of an issue with a processing module or a communication pathway.

Example processing modules may include, but not limited to, multispectral analysis module as described herein with reference to FIG. 51, Laser Doppler flowmetry analysis module as described herein with reference to FIGS. 49 and 50, field programmable arrays, a content composite module, and/or the like.

An example processing module may be configured to enhance a surgical video stream using another video stream. For example, the computing system may derive contextual information associated with the surgery by analyzing a video stream described herein. The contextual information may be used to enhance another surgical video stream. For example, the computing system may extract one or more portions (e.g., a portion that includes an area of interest) from a surgical video stream and overlay the extracted portion onto another surgical video stream, as described herein.

An example processing module may be configured to annotate the surgical video. As those skilled in the art may appreciate, a video may be annotated with metadata. Visual annotation may include denoting locations of object or people of interest in the video, describing objects in the video, describing the context of the scene, and/or providing other information. For example, the processing module may be configured to annotate the microsurgical outcomes. The processing module may be configured to analyze the video feed and identify the point(s) in time to add label(s). The processing module may receive data from surgical device(s) and may be configured to annotate data captured via device sensor(s), such as raw sensor data. The processing module may be configured to annotate scaling. The processing module may be configured to convert the video stream for use with a 3D environmental visualization tool. The annotations may be inserted on time stamp or on the video itself. The processing module may receive input from HCPs, such as resident diaries. The raw sensor data may be coupled with resident diaries when annotated into the surgical video. The video stream for use with a 3D environmental visualization tool may be annotated with resident diaries. The processing module may be configured to track an object of interest and identify the object's contour when it is obstructed or partially obstructed. The processing module may annotate the contour of the object of interest in the video. The processing module may receive surgical information such as contextual information from the situationally aware surgical hub as described herein with reference to FIG. 8 and may insert the contextual information into the video. The processing module may be configured to annotate of a process of multiple events through time.

An example processing module may be configured to derive contextual information associated with a surgery by analyzing a video stream described herein. The derived contextual information may be indicated in (e.g., inserted into) another video stream. For example, as described herein, the derived contextual information may be inserted into an overlay region described herein.

Objects may be recognized and tracked via video processing from video captured by one or more imaging systems. The video may be analyzed to identify objects. For example, a processing module may identify and highlight known objects via annotation, such that the recognized object may be recognizable with frame-to-frame outlining. The processing module may localize one or more objects of interest in the video. For example, the processing module may predict an object in an image within a boundary. Various known image or video processing technologies, such as keypoint detection and analysis, bounding box annotation, polygon mesh processing, image segmentation, facial recognition, gesture recognition, point cloud, lines and splines, and/or the like may be used to analyze the video feeds. Those skilled in the art may appreciate that various object detection and tracking technologies used in autonomous vehicle may be used in surgical video processing.

The video may be processed to identify the motion of HCP(s) and/or object(s). Based on the motion information, the surgical activities and/or actions of the HCP(s) may be determined. For example, the HCPs or objects may be tracked and categorized based on motion, function, and/or manipulation. Repeatable pattern of events may be identified.

Video may be stored during processing, as a part of the display of the video. The computing system may be configured to erase the video after processing and transferring the video, to address privacy concerns and retention aspects of in-process video.

A computing system may generate a composite video stream from multiple input feeds. The computing system may obtain a surgical video stream and overlay content associated with a surgical procedure. The computing system may determine the overlay region location for overlaying the overlay content by analyzing the content of surgical video stream. For example, based on the content of a frame of the surgical video stream, the computing system may determine an overlay region location in the frame for overlaying the overlay content; based on the content of a subsequent frame of the surgical video stream, the computing system may determine another overlay region location in the subsequent frame for overlaying the overlay content. The composite video stream may be generated based on the overlay region locations determined for different frames of the surgical video stream.

For example, the surgical video stream may be a video feed of the surgical site from a laparoscopic scope, and the composite video stream may be generated by overlaying the overlay content onto the video of the surgical site at the determined overlay region location. The location, orientation, and/or size of the overlay content may be adjusted on the surgical site in the video stream as the laparoscopic scope moves. The surgical video stream may include frames having a surgical instrument, and the composite video stream may be generated by overlaying the overlay content onto the surgical instrument at the determined overlay region location. The location, orientation, and/or size of the overlay content may be adjusted in the video stream as the surgical instrument moves.

For example, the primary imaging of the surgical site may be supplemented by overlaying or inserting secondary video feed(s) and/or data overlays. The overlay content may adjust as the primary scope image moves and may be oriented with respect to the surgical site and the surgical instrument(s). The overlay content may cover the entire primary imaging or may cover a portion of the primary imaging feed. The overlay region may coincide with a predefined location on an instrument based on one or more fiducial marker(s) on the instrument.

FIG. 55A illustrates an example process for generating a composite surgical video stream from multiple input feeds. At 45550, a surgical video stream may be obtained. For example, the computing system may obtain the surgical video stream via an imaging device such as the imaging device 20030 described herein with respect to FIG. 2. For example, the computing system may obtain the surgical video stream as described herein with reference to FIGS. 49-52. The surgical video stream may be or may include a video feed of the surgical site from a laparoscopic scope. For example, the computing system may obtain the surgical video stream via one or more cameras in the OR, such as cameras 20021 as described herein with reference to FIG. 2.

At 45552, overlay content may be obtained. Overlay content may include information associated with a device such as a surgical instrument. For example, overlay content for overlaying onto an energy device in an image or video may include an indication of the energy blade temperature, an indication of the energized state (e.g., due to capacitive coupling), and/or other information associated with the energy device. For example, the overlay content may include steps-for-use instructions associated with a surgical instrument.

For example, overlay content for overlaying onto a surgical stapling and cutting device the in an image or video may include an indication of the loading condition of the surgical instrument (e.g., whether a cartridge is loaded). The loading condition on the surgical instrument may be sensed, and the overlay content may be generated based on the sensed loading condition. This may prevent a knife blade from moving forward when cartridge is not loaded, or improperly loaded.

The overlay content can include a label for the anatomical section and a peripheral margin of at least a portion of the anatomical section. The peripheral margin can be configured to guide a surgeon to a cutting location relative to the anatomical section. The overlay content may include a supplementary image of an organ associated with the surgical procedure. The overlay content may include alternative imaging. The overlay content may include one or more of data obtained via pre-surgery tumor MRI, CT imaging, relevant pre-surgery data, ICG data, real-time doppler monitoring, procedural steps, device status, and/or other overlays customizable by the users. The overlay content may include an indication associated with previous procedure steps of the surgery, such as previous stapling(s) and/or previous weld(s).

Overlay content may include a secondary video feed or a portion of a secondary video feed. For example, the secondary video feed may be a video feed that has been processed via one or more processing modules as described herein with respect to FIG. 52. The secondary video feed may be a video associated with the current surgical procedure. The secondary video feed may be a tutorial video showing how to carry out the procedural steps. The secondary video feed may be a surgical simulation video. The secondary video feed may be a video of previous procedure steps. For example, the secondary video feed may be a video of previous stapling(s) and/or previous weld(s). This may enable the HCP to compare previous work with the current procedural step, for example, to identify the transection site more readily. The computing system may extract a portion of the secondary surgical video feed as the overlay content. For example, the portion of the secondary surgical video that includes a region of interest may be identified and extracted.

For example, the overlay content may be obtained from another video feed, a surgical hub described herein, from one or more surgical devices described herein, and/or from one or more sensors described herein. The overlay content may be updated in real time, in response to a change in a location and/or orientation of the surgical instrument within the surgical instrument frame. Various overlay content and obtaining the overlay content is further described in U.S. patent application Ser. No. 17/062,509 titled INTERACTIVE INFORMATION OVERLAY ON MULTIPLE SURGICAL DISPLAYS, filed Oct. 2, 2020, which is incorporated by reference herein in its entirety.

At 45554, the location, size and/or orientation of the overlay region may be determined. The computing system may determine the overlay region location for overlaying the overlay content by analyzing the content of surgical video stream. In examples, in-image markings may be used for insertion of data, images, and alternative imaging streams. By tracking and reading markers on instrument, the computing system may overlay information at a consistent location relative to the instrument such that the overlay content may move as the instrument moves in the video feed.

One or more overlay region(s) may be determined based on one or more fiducial marker(s). For example, a surgical instrument, such as the surgical instrument described herein with reference to FIG. 7, may include one or more fiducial markers. The fiducial markers may be placed at predetermined location(s) on the surgical instrument. The locations for placing fiducial markers may include an area on the surgical instrument suitable for overlaying overlay content. The locations for placing fiducial markers may include an area suitable for gauging the orientation of the surgical instrument and/or the distance of the instrument to the imaging system (e.g., a camera). The fiducial markers may be visible or invisible to human eyes, but recognizable via video processing. The fiducial markers may be of specific shapes, such that the computing system may identify the surgical instrument based on the fiducial marker(s).

The fiducial markers may be in a predefined pattern such that the computing system may identify the surgical instrument based on the fiducial marker. For example, the fiducial marker may include an electronic-readable code, such as QR code. The computing system may obtain a video feed that captures the fiducial marker and identify the surgical instrument based on the electronic-readable code (e.g., captured in a video feed or imaging feed). Based on the electronic-readable code, the computing system may retrieve information associated with the surgical instrument, such as the model of the surgical instrument. For example, using the electronic-readable code, the computing system may obtain the spatial property information associated with the fiducial marker(s) on the surgical instrument. The computing system may scale the overlay content based on the obtain spatial property of the marker(s) and the marker(s) in the video/imaging feed.

The size of the overlay region may be determined based on the size of an area on the surgical instrument suitable for content overlay, the size of a fiducial marker in real life, and the size of the fiducial marker in a video frame of the surgical video stream (e.g., a ratio between the real-life size and the imaged size). For example, the computing system may identify the fiducial marker in the video frames of the surgical video stream and determine the respective location, size, and/or orientation of the fiducial marker(s) in respective video frames. For a given video frame, or a group of video frames, the computing system may determine the size, location and/or orientation of the overlay region based on the location, size and/or orientation of the fiducial marker captured therein.

Details on fiducial markers and spatial awareness of surgical products and instruments can be found in application entitled HUB IDENTIFICATION AND TRACKING OF OBJECTS AND PERSONNEL WITHIN THE OR TO OVERLAY DATA THAT IS CUSTOM TO THE USER'S NEED, filed contemporaneously, the contents of which are incorporated by reference herein.

As described herein, the overlay content may include an indication of previous stapling(s) or previous weld(s). The overlay content may include alternative imaging such as CT image indicating the tumor. The overlay region may be determined such that the overlay content may be inserted next to but not interfering with the current jaw placements. This may enable the user to compare previous work with the current and/or view the alternative imaging within the jaws to identify the tumor and/or transection site more readily.

At 45556, a composite video stream may be generated by overlaying the overlay content onto the surgical video stream. A composite video stream may be generated, for example, by inserting the overlay content into the surgical video stream, such as a primary surgical video feed. For example, overlay content may be scaled, oriented and inserted onto the shaft of a surgical instrument, based on the fiducial marker(s) captured in the primary video. The location, size, shape and/or orientation of the overlay region may be adjusted dynamically, for example, as the surgical device of interest moves in the primary video. For example, when the overlay content includes a secondary video feed or a portion of a secondary video feed, the composite video may be generated using "picture-in-picture" techniques. The computing system may determine a first overlay region size for overlaying the overlay content onto the first surgical video frame based on content of the first frame, and a second overlay region size for overlaying the overlay content onto a second surgical overlay frame based on content of the second frame. The computing system may scale the secondary surgical video stream, or a portion of the secondary video stream that contains the region of interest based on the determined first overlay region size and the determined second overlay region size.

FIG. 55B shows an example process for generating a composite surgical video stream using a fiducial marker. At 45553, a surgical video stream may be obtained, for example, as described herein. At 45555, a fiducial marker may be identified in a video frame of the surgical video stream. At 45557, the overlay region location, orientation and/or size may be identified for inserting overlay content into the video frame. At 45559, the overlay content may be inserted into the overlay region. The process may be repeated for each frame, every other frame, every n frames, periodically, or aperiodically. For the example, the overlay region location, orientation and/or size may be updated upon determining that the content of the primary stream changes (e.g., the location of the surgical instrument changes significantly, the orientation of the surgical instrument changes significantly). For example, the fiducial marker may be placed on a surgical instrument. By identifying the fiducial marker in the video frames and using the identified fiducial marker to determine the overlay region, the overlay content may move in the composite video stream as the surgical instrument moves in the surgical video stream.

Figure 56A:
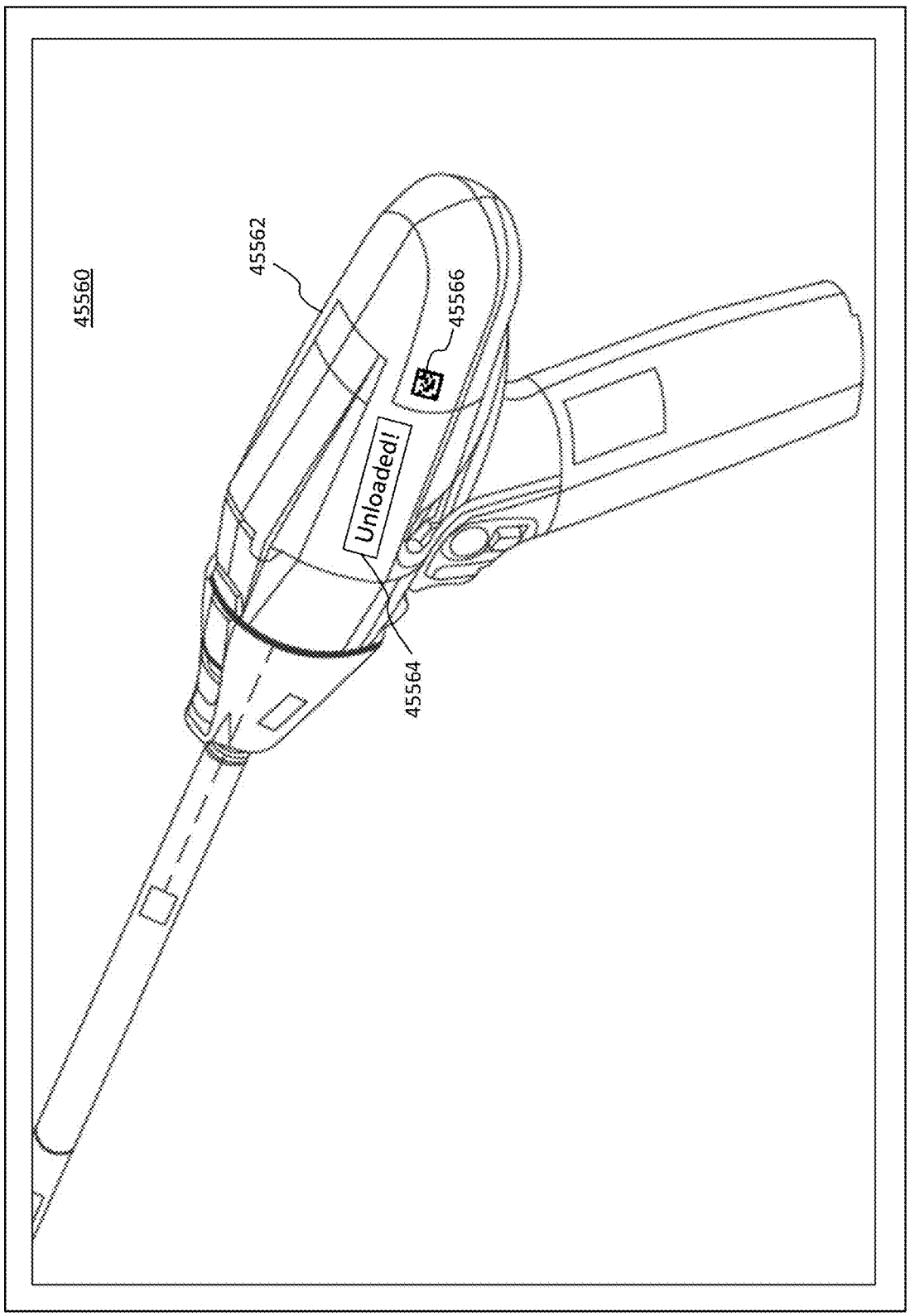
FIGS. 56A-56C illustrate example frames of a composite surgical video stream with overlay content that moves as a surgical instrument in the surgical video stream moves.
Figure 56B:
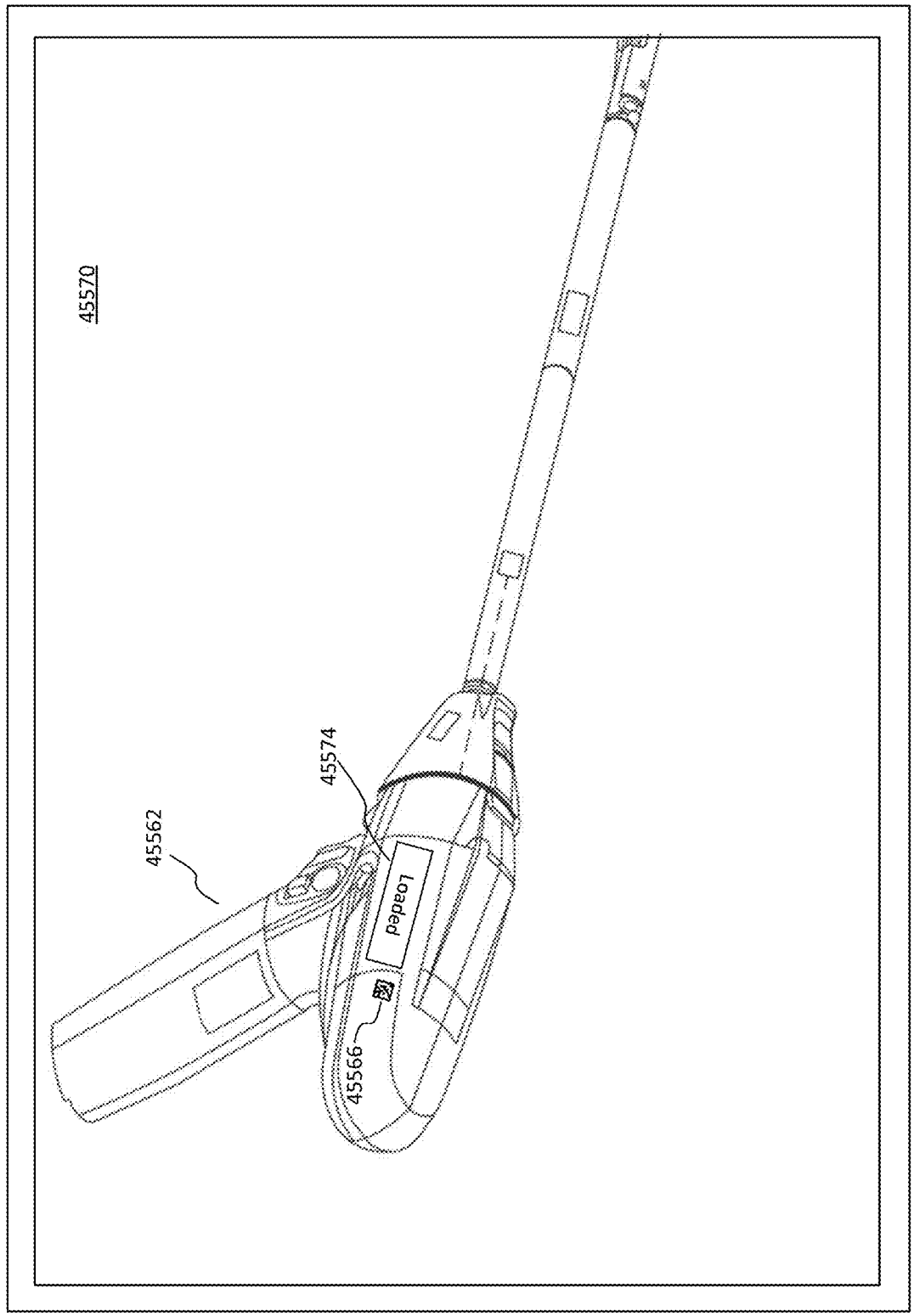
Figure 56C:
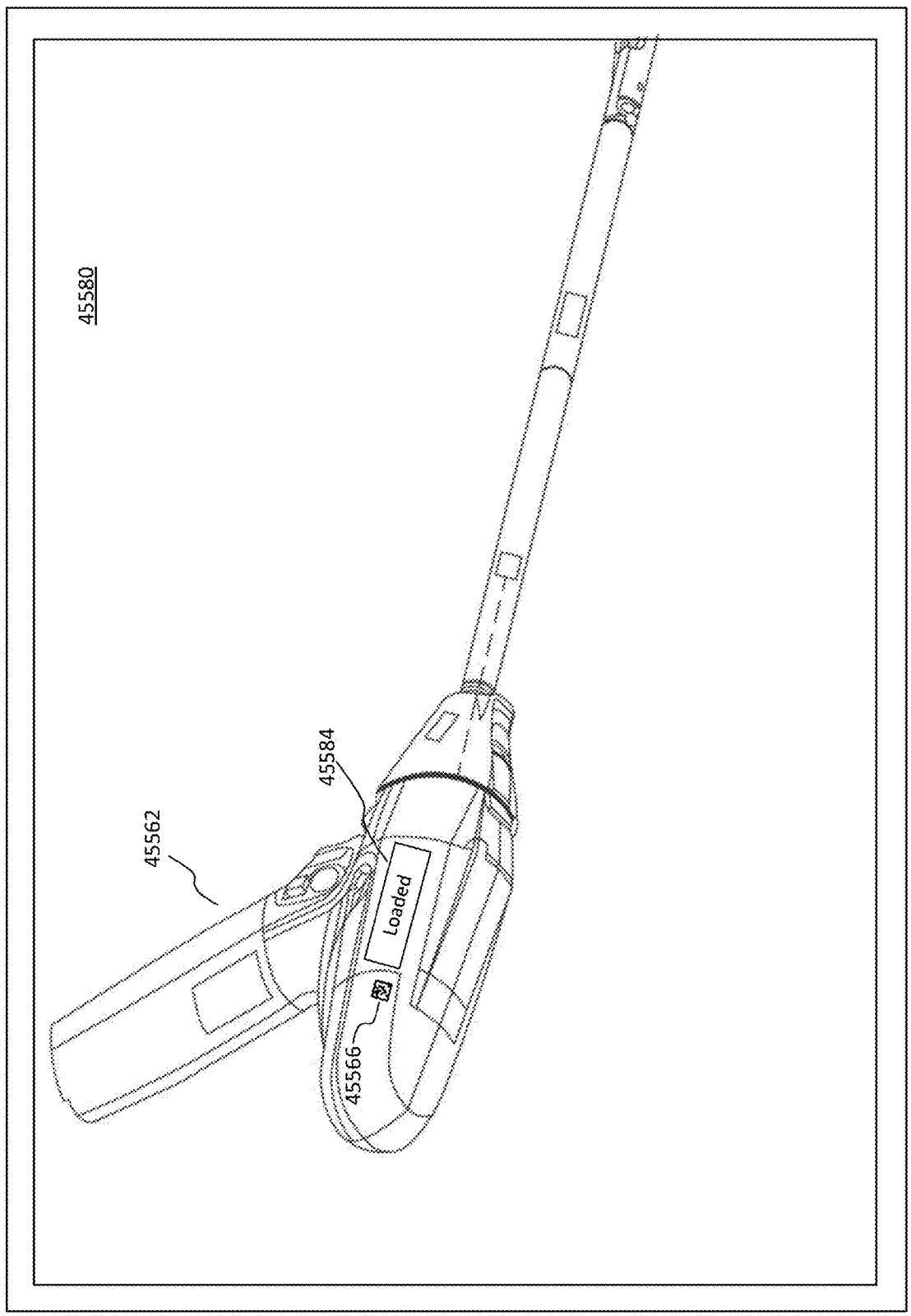

FIGS. 56A-C illustrate example video frames of a composite surgical video stream with overlay content that moves as a surgical instrument in the surgical video stream moves. As described herein, a composite surgical video stream may be generated by inserting overlay content into a surgical video feed at one or more determined overlay regions. The composite surgical video stream may include video frames with overlay content, which may be adjusted based on the content of corresponding frame from the surgical video feed. FIG. 56A shows an example video frame 45560 of an example composite surgical video stream. As shown, video frame 45560 may include an image of a surgical instrument 45562, such as the surgical instrument 20282 described herein with respect to FIG. 7. The overlay content 45564 may indicate the loading condition of the surgical instrument 45562, such as "unloaded," as shown in FIG. 56A. The overlay region for inserting the overlay content 45564 may be determined based on the fiducial marker 45566 on the surgical instrument 45562.

For example, the computing system may identify the location, size and/or orientation of the fiducial marker 45566 in a primary video frame of the primary video feed. Based on the location, size and/or orientation of the fiducial marker 45566 in the primary video frame, the computing system may determine the location, size and/or orientation of the overlay region, as described herein. As shown in FIG. 56A, the overlay region may be identified such that the overlay content is easy to read and proportional to the surgical instrument.

FIG. 56B shows an example video frame 45570 of an example composite surgical video stream. As shown in FIG. 56B, the overlay content 45574 may reflect an updated loading condition of the surgical instrument 45562, "loaded." The surgical instrument 45562 and the fiducial marker 45566 shown in video frame 45570 have moved compared to surgical instrument 45562 and the fiducial marker 45566 shown in video frame 45560. Based on the location of the fiducial marker 45566, the computing device may determine the location of the overlay content region for overlay content 45574. The surgical instrument 45562 and the fiducial marker 45566 shown in video frame 45570 is smaller compared to surgical instrument 45562 and the fiducial marker 45566 shown in video frame 45560. Based on the size of the fiducial marker 45566, the computing device may determine the size of the overlay content region for overlay content 45574. As shown in FIG. 56B, the overlay content 45574 is scaled down from the overlay content 45564 shown in FIG. 56A. The surgical instrument 45562 and the fiducial marker 45566 shown in video frame 45570 is in an "upside down" orientation compared to surgical instrument 45562 shown in video frame 45560. Based on the orientation of the fiducial marker 45566, the computing device may determine the orientation of the overlay content region for overlay content 45574. As shown in FIG. 56B, the overlay content 45574 is upside down as well. FIG. 56C shown an example video frame 45580 of an example composite surgical video stream. As shown, the overlay content 45584 may be moved and scaled based on the fiducial marker 45566 but may be kept in upright or substantially upright orientation to improve readability.

For example, de-identification may be performed for the video feed(s) described therein. De-identification process may be performed at the edge computing system, described herein with reference to FIG. 1B. For example, faces captures in the video feed(s) may be detected and blurred by the computing system. Face, silhouette, gait, and/or other characteristics may be obscured. Other person-identifying content, such as ID badges, may be detected, blurred and/or removed from the video. In some instances, a laparoscopic video, which usually contains in-body imaging may accidentally include out-of-body images. Such images may be detected by the computing system may be removed from the video.

For example, video(s) obtained via in-room cameras may be correlated with video(s) obtained via in-body cameras to identify procedural progression information. The computing system may determine the surgical task being carried out based on the video frames obtained via intra-body scope in conjunction with the video frames obtained via OR camera(s). The determination may be further based on one or more monitoring sensors described herein with reference to FIGS. 1-8. The computing system may identify an HCP (e.g., the HCP's role, present and/or pending task, and/or profession) based on the video frames obtained via intra-body scope and the video frames obtained via OR camera(s). Based on the determined procedural progression information and the identification of the HCP, the computing system may generate customized overlay content for the HCP. For example, the customized overlay content may be displayed via an augmented reality (AR) or mixed reality overlay on a user interface. The AR device may provide AR content to the HCP. For example, a visual AR device, such as safety glasses with an AR display, AR goggles, or head-mounted display (HMD), may include a graphics processor for rendering 2D or 3D video and/imaging for display. Based on the determined procedural progression information and the identification of the HCP, the computing system may generate a customized control signal to an equipment or a surgical device. For example, based on a determination that the HCP carrying an energy device is a nurse, the computing system may generate a control signal to prevent the energy device from entering the energized state. For example, based on a determination that the HCP carrying an energy device is a surgeon, the computing system may generate a control signal to allow the energy device to enter an energized state.

For example, 3D modeling may be performed by combining imaging video(s), pre-surgical imaging, and/or intraoperative imaging. For example, the computing system may analyze video frames of a primary surgical imaging or video feed to identify missing information for the primary surgical imaging or video feed. The computing system may identify region(s) of poor quality (e.g., artifacts, blurry, obstructed view, etc.) and may provide an indication to request additional imaging to supplement the primary surgical video feed.

The computing system may identify region(s) associated with incomplete or missing information in the surgical imaging or video feed based on the clarity of the region(s). The computing system may generate a notification indicating the identified region(s) associated with incomplete or missing information. For example, the notification may include an indication of the surgical imaging or video frame with the identified regions highlighted in a rendered shape and color. The computing system may interpolate the likely location and shape of the organ in the imaging or video frame.

The computing system may identify region(s) associated with potentially misleading data in the surgical imaging or video feed based on the clarity of the region(s). For example, region(s) with artifacts or defects exceeding a threshold value may be identified. The computing system may generate a notification indicating that the surgical imaging or video feed contains potentially misleading information. For example, the notification may include an indication of the surgical imaging or video frame with the identified regions marked as containing potentially misleading information.

The computing system may generate an indication with instructional information such as steps-for-use of what regions of the patient have inconclusive or insufficient imaging. The computing system may indicate information associated with access port(s) for input of the additional scan(s). The supplemental scan may be a different type of imaging/scanning from the primary image source. For example, a CT scan of the abdomen could have insufficient or inconclusive data for the inside of the liver, pancreas, or other solid organ. The computing system may provide an indication or notification of a means for scanning with an ultrasound imaging system. The computing system may obtain the imaging data from the supplemental scan and may combine the imaging data obtained from the primary imaging source with the imaging data obtained from the supplemental scan.

The computing system may fuse imagining data or videos obtained from different sources based on common anatomic landmarks. For example, the computing system may use the primary imaging as a source map for the supplementary image. The computing system, by analyzing the primary imaging, may identify the locations of content boundaries or borders, where the imaging data obtained from different sources may merge. For example, the computing system may use a third imaging source, such as imaging obtained via a laparoscope to identify linkable aspects for fusing the primary and secondary imaging data. For example, the computing system may fuse the primary and seconding imaging data based on preset imaging fiducial markers.

After performing imaging data fusing, the computing system may determine a completeness level of organ imaging for one or more portion of the fused imaging. The completeness level for a portion of the fused imaging may indicate an estimated completeness and/or accuracy of that portion of the fused image. In examples, the imaging data (e.g., still and/or video imaging data) may be generated via different energy imaging technologies. The completeness level of fused organ imaging may be determined based on the different energy imaging technologies.

The computing system may generate composite imaging data based on partial imaging data from multiple imaging feeds. The multiple imaging feeds may be received simultaneously. The composite imaging data may be generated in real-time. For example, one or more portion of the composite imaging data may include visual light imaging, while other portion(s) of the compositing imaging may include alternative source imaging as described herein. The computing system may generate the composite imaging data by replacing a portion of imaging data from one imaging feed with a corresponding portion of the imaging data from another imaging feed. The computing system may overlay a portion of imaging data from one imaging feed onto a corresponding portion of the imaging data from another imaging feed. The computing system may highlight (e.g., transparent highlight) a portion of imaging data from one imaging feed based on a corresponding portion of the imaging data from another imaging feed.

For example, one or more portion of a surgical video stream may be defined for expanded imaging overlay. The portions for expanding imaging overlay may be pre-defined or determined based on a surgeon's input during a surgical procedure. The portion(s) for expanded imaging overlay may include, but not limited to, a transection site, or a dissection site. The expanded imaging may include visualization of critical structure(s), blood supplies surrounding the transection site or the dissection site. For example, CT imaging may be superimposed on a surgical video stream (e.g., in a semi-transparent fashion). The expanded imaging overlay may enable a surgeon to select a transection or dissection path without damaging critical structure(s) of the patient's organ. The expanded imaging overlay may enable a surgeon to differentiate the vascular tree supplies blood to a tumor from blood vessels that do not supply blood to the tumor, and identify the blood vessels to be severed. Details on overlaying content on a video feed of a surgical site is further described in U.S. patent application Ser. No. 17/062,509 titled INTERACTIVE INFORMATION OVERLAY ON MULTIPLE SURGICAL DISPLAYS, filed Oct. 2, 2020), which is incorporated by reference herein in its entirety.

Machine learning is a branch of artificial intelligence that seeks to build computer systems that may learn from data without human intervention. These techniques may rely on the creation of analytical models that may be trained to recognize patterns within a dataset, such as a data collection. These models may be deployed to apply these patterns to data, such as biomarkers, to improve performance without further guidance.

Machine learning may be supervised (e.g., supervised learning). A supervised learning algorithm may create a mathematical model from training a dataset (e.g., training data). The training data may comprise a set of training examples. A training example may include one or more inputs and one or more labeled outputs. The labeled output(s) may serve as supervisory feedback. In a mathematical model, a training example may be represented by an array or a vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function may determine the output for one or more inputs that may not have been part of the training data. Example algorithms may include linear regression, logistic regression, and neutral network. Example problems solvable by supervised learning algorithms may include classification, regression problems, and the like.

Machine learning may be unsupervised (e.g., unsupervised learning). An unsupervised learning algorithm may train on a dataset that may include inputs and the unsupervised learning algorithm may find a structure in the data. The structure in the data may be similar to a grouping or clustering of data points. As such, the algorithm may learn from training data that may not have been labeled. Instead of responding to supervisory feedback, an unsupervised learning algorithm may identify commonalities in training data and may react based on the presence or absence of such commonalities in each training example. Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like.

Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of a machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal is reached, the linear prediction function with adjusted coefficients may be deemed trained and may constitute the model the training process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum is reached, the optimized hypothesis function with its layers of adjusted biases and weights may be deemed trained and may constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources comprising pre-surgical data, such as a patient's medical conditions and biomarker measurement data, may be identified. Such data sources may be a patient's electronical medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g., logically linked) and may be accessed as if they were centrally stored. Surgical data and/or post-surgical data may be similarly identified and/or collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. In an example, a patient's integrated data record of pre-surgical EMR record data and biomarker measurement data, surgical data, and post-surgical data may be in a rational database. Such data record may be converted to a flat file format for model training. In an example, the patient's pre-surgical EMR data may include medical data in text format, such as the patient's diagnoses of emphysema, pre-operative treatment (e.g., chemotherapy, radiation, blood thinner). Such data may be mapped to numeric values for model training. For example, the patient's integrated data record may include personal identifier information or other information that may identifier a patient such as an age, an employer, a body mass index (BMI), demographic information, and the like. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or scaled down, for example, to be between 0 and 1 for model training. For example, the preprocessed data may include data values that carry more meaning when aggregated. In an example, there may be multiple prior colorectal procedures a patient has had. The total count of prior colorectal procedures may be more meaningful for training a model to predict surgical complications due to adhesions. In such case, the records of prior colorectal procedures may be aggregated into a total count for model training purposes.

Model training may be another aspect of the machine learning lifecycle. The model training process as described herein may be dependent on the machine learning algorithm used. A model may be deemed suitably trained after it has been trained, cross-validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. Overfitting may be detected, for example, when the accuracy of the model may decrease when run against the validation dataset after the accuracy of the model has been increasing. The test dataset may be used to test the accuracy of the final model to determine whether the test dataset is ready for deployment or more training may be required.

Model deployment may be another aspect of the machine learning lifecycle. The model may be deployed as part of a standalone computer program. The model may be deployed as part of a larger computing system. A model may be deployed with model performance parameters(s). Such performance parameters may monitor the model accuracy as it is used for predicting on a dataset in production. For example, such parameters may keep track of false positives and false negative for a classification model. Such parameters may further store the false positives and false negatives for further processing to improve the model's accuracy.

Post-deployment model updates may be another aspect of the machine learning cycle. For example, a deployed model may be updated as false positives and/or false negatives are predicted on production data. In an example, for a deployed MLP model for classification, as false positives occur, the deployed MLP model may be updated to increase the probably cutoff for predicting a positive in order to reduce false positives. In an example, for a deployed MLP model for classification, as false negatives occur, the deployed MLP model may be updated to decrease the probably cutoff for predicting a negative to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

Figure 57:
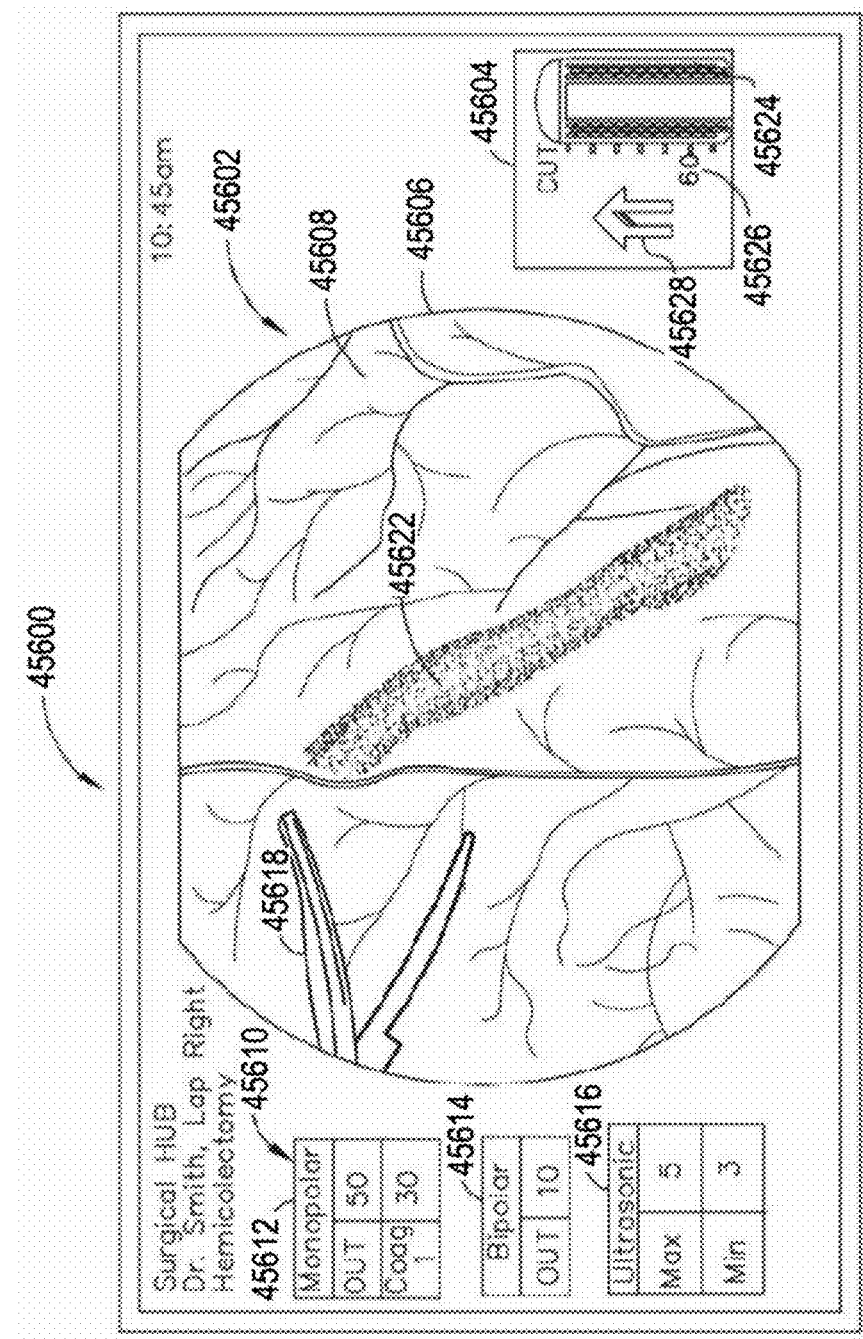
FIG. 57 illustrates a display of the surgical hub.

FIG. 57 illustrates a display of the surgical hub. For example, FIG. 57 illustrates an example primary display 45600 associated with the surgical hub 20006 comprising a global display window 45602 and a local instrument display window 45604, according to one aspect of the present disclosure. The global display window 45602 may show a field of view 45606 of a surgical site 45608, as viewed through a medical imaging device such as, for example, a laparoscope/endoscope coupled to an imaging module, at the center of a display, referred to herein also as a display and/or a monitor, for example. The end effector 45618 portion of the connected instrument may be shown in the field of view 45606 of the surgical site 45608 in the global display window 45602. The images shown on the display located on an instrument coupled to the surgical hub 20006 may be shown, or mirrored, on the local instrument display window 45604 located in the lower right corner of the monitor (e.g., primary display) 45600 as shown in FIG. 57, for example.

During operation, relevant instrument information and menus may be displayed on the display located on the instrument until the instrument senses a connection of the instrument to the surgical hub 20006 at which point all or some sub-set of the information presented on the instrument display may be displayed (e.g., only) on the local instrument display window 45604 portion of the surgical hub display (e.g., primary display) 45600 through the surgical hub 20006. The information displayed on the local instrument display window may be mirrored on the display located on the instrument or may be no longer accessible on the instrument display detonated screen. This technique frees up the instrument to show different information or to show larger font information on the surgical hub display 45600.

The primary display 45600 may provide perioperative visualization of the surgical site. Advanced imaging may identify and visually highlight 45622 critical structures such as the ureter 45620 (or nerves, etc.) and may track instrument proximity displays 45610 shown on the left side of the display 45600. In the illustrated example, the instrument proximity displays 45610 may show instrument specific settings. For example, the top instrument proximity display 45612 may show settings for a monopolar instrument, the middle instrument proximity display 45614 may show settings for a bipolar instrument, and the bottom instrument proximity display 45616 may show settings for an ultrasonic instrument.

One or more secondary displays, which may be dedicated local displays, may be linked to the surgical hub 20006 to provide both an interaction portal via a touchscreen display and/or a secondary screen that may display any number of surgical hub 20006 tracked data feeds to provide a status. The secondary screen may display force to fire (FTF), tissue gap, power level, impedance, tissue compression stability (creep), etc., while the primary screen may display key variables (e.g., only key variables) to keep the feed free of clutter. The interactive display may be used to move information that may be on the display a desired location. The interactive display may allow a user to change a character of the information, such as a size associated with the information, a color associated with the information, and/or the like. For example, a user may use the interactive display to move information to a primary display where the information may be highlighted and/or shown more prominently than other data.

As shown in FIG. 57, the secondary screen displays the instrument proximity displays 45610 on the left side of the display 45600 and the local instrument display window 45604 on the bottom right side of the display 45600. The local instrument display 45604 presented on the surgical hub display 45600 displays an icon of the end effector 45618, such as the icon of a staple cartridge 45624 currently in use, the size 45626 of the staple cartridge 45624 (e.g., 60 mm), and an icon of the current position of the knife 45628 of the end effector.

The display located on the instrument may display the wireless or wired attachment of the instrument to the surgical hub 20006 and the instrument's communication/recording on the surgical hub 20006. A setting may be provided on the instrument to enable the user to select mirroring or extending the display to both monitoring devices. The instrument controls may be used to interact with the display of information being shown on the instrument. As disclosed herein, the instrument may comprise wireless communication circuits to communicate wirelessly with the surgical hub 20006.

A first instrument coupled to the surgical hub 20006 may pair to a screen of a second instrument coupled to the surgical hub 20006. This may allow both instruments to display some hybrid combination of information from the two devices of both becoming mirrors of portions of the primary display.

The primary display 45600 of the surgical hub 20006 may provide a 360° composite top visual view of the surgical site 45608 to avoid collateral structures. For example, a secondary display of the end-effector surgical stapler may be provided within the primary display 45600 of the surgical hub 20006 or on another display in order to provide better perspective around the areas within a current field of view 45606.

Figure 58:
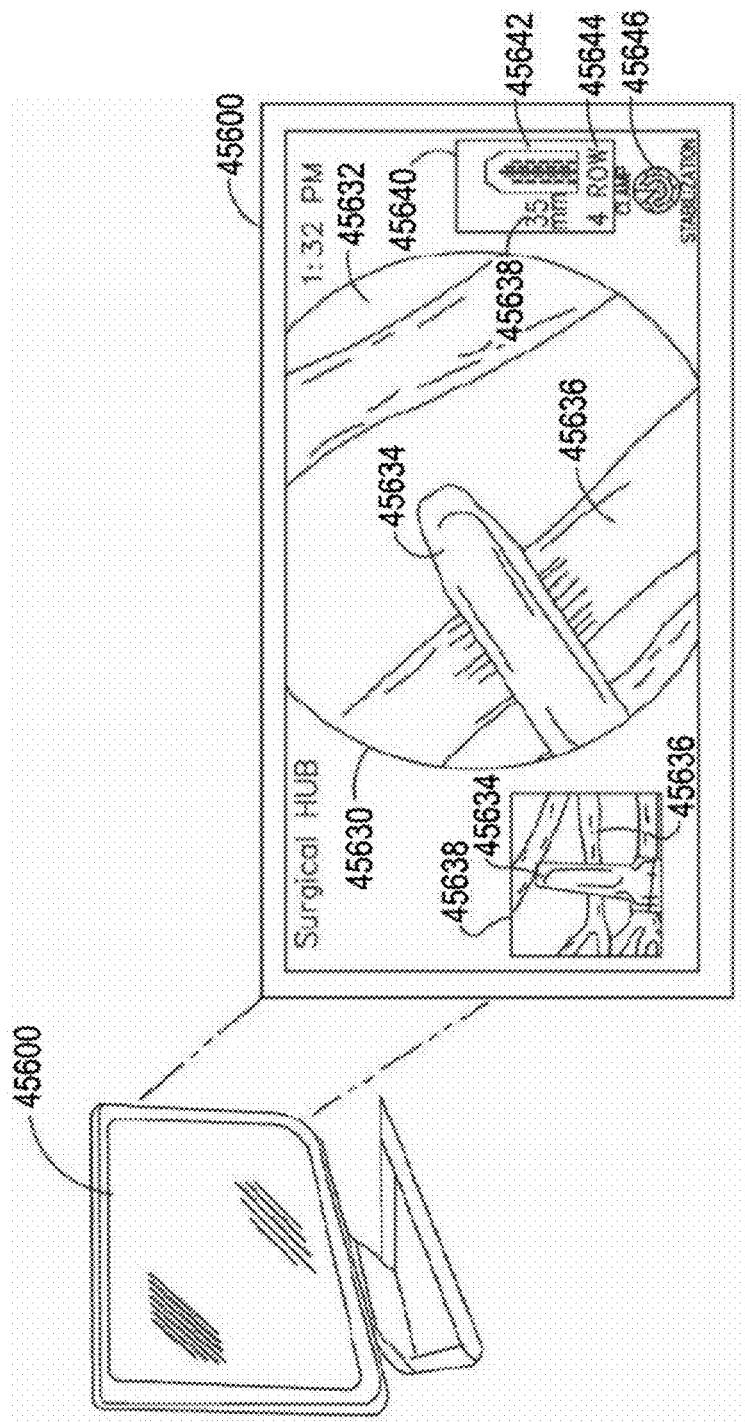
FIG. 58 illustrates an example primary display of the surgical hub.

FIG. 58 illustrates an example primary display of the surgical hub. For example, FIG. 58 may illustrate an example primary display comprising composite overhead views of an end-effector 45634 portion of a surgical stapler. The views may be mapped using two or more imaging arrays, and array and time, and/or the like to provide multiple perspective views of the end-effector 45634 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques may be performed for overlaying or augmenting images and/or text from multiple image/text sources to present composite images on a display (e.g., a single display). Further examples are disclosed in U.S. Patent. Application Publication No. 2019-0201104 A1 (U.S. patent application Ser. No. 15/940,671), titled SURGICAL HUB SPATIAL AWARENESS TO DETERMINE DEVICES IN OPERATING THEATER, filed Mar. 29, 2018, which is herein incorporated by reference in its entirety.

As shown in FIG. 58, a primary display 45600 of the surgical hub 20006 may display a primary window 45630. The primary window 45630 may be located at the center of the screen and may show a magnified or exploded narrow angle view of a surgical field of view 45632. The primary window 45630 located in the center of the screen may show a magnified or narrow angle view of an end-effector 45634 of the surgical stapler grasping a vessel 45636. The primary window 45630 may display knitted images to produce a composite image that enables visualization of structures adjacent to the surgical field of view 45632. A second window 45638 may be shown in the lower left corner of the primary display 45600. The second window 45638 may display a knitted image in a wide-angle view at standard focus of the image shown in the primary window 45630 in an overhead view. The overhead view provided in the second window 45638 may enable the viewer to easily see items that are out of the narrow field surgical field of view 45632 without moving the laparoscope, or other imaging devices coupled to the imaging module of the surgical hub 20006. A third window 45640 shown in the lower right corner of the primary display 45600 may show an icon 45642 representative of the staple cartridge of the end-effector 45634 (e.g., a staple cartridge in this instance) and additional information such as "4 Row" indicating the number of staple rows 45644 and "35 mm" indicating the distance 6248 traversed by the knife along the length of the staple cartridge. Below the third window 45640 is displayed an icon 45646 of a frame of the current state of a clamp stabilization sequence 6250 that indicates clamp stabilization.

In an example visualization control mode, display may be controlled by the user, for example, via motion tracking (e.g., head orientation relative to a monitor), hand gestures, voice activation, and other means within the sterile field. A user may use gestures, motion tracking commands, voice activation, and the like to move data from one display to another display. For example, a user may use a gesture to move data from a first display to a second display. The gesture may be detected by the hub and the hub may instruct the first display to remove the data or stop displaying the data and may instruct the second display to display the data.

Figure 59:
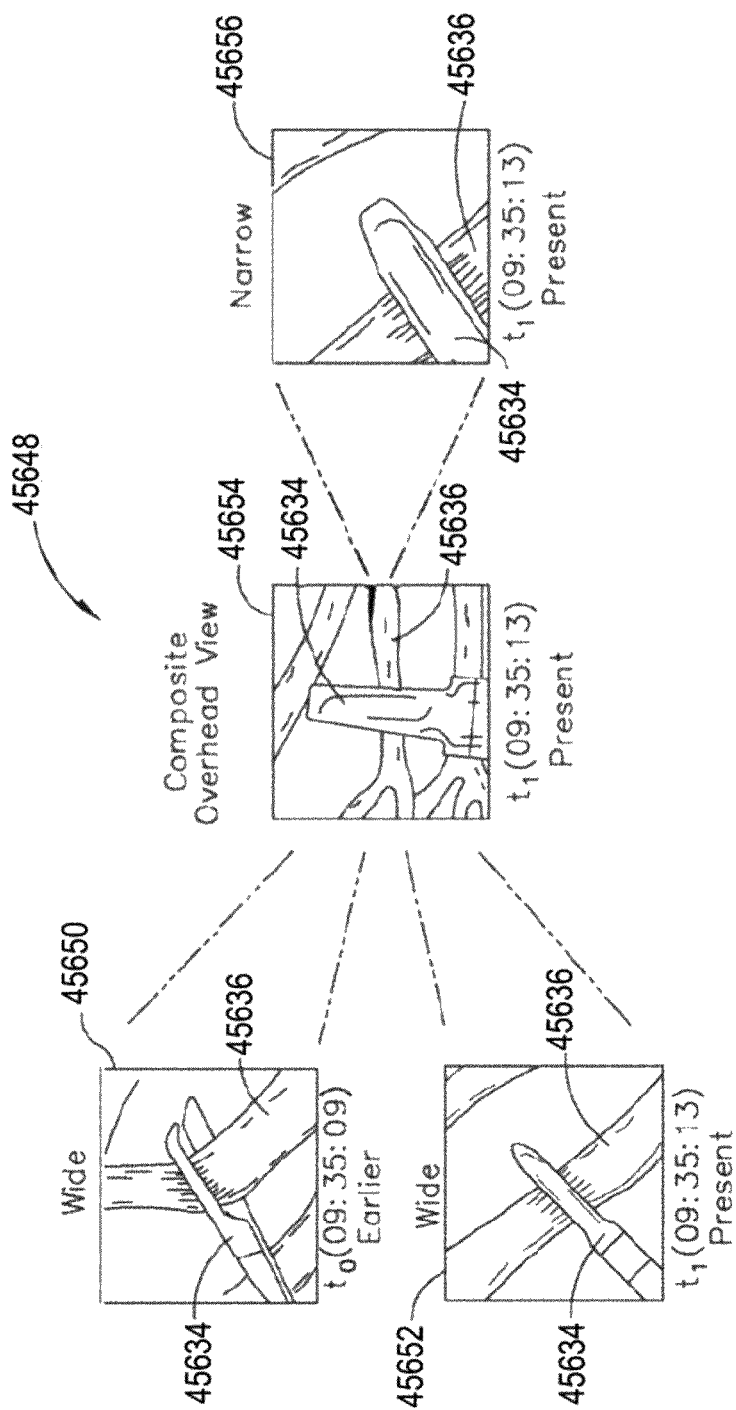
FIG. 59 illustrates a diagram of four wide angle view images of a surgical site at four separate times during the procedure.

FIG. 59 illustrates a diagram of four wide angle view images of a surgical site at four separate times during the procedure. For example, FIG. 59 illustrates a diagram 45648 of four separate wide-angle view images 45650, 45652, 45654, 45656 of a surgical site at four separate times during the procedure, according to an aspect of the present disclosure.

The sequence of images may show the creation of an overhead composite image in wide and narrow focus over time. A first image 45650 may be a wide-angle view of the end-effector 45634 clamping the vessel 45636 taken at an earlier time to (e.g., 09:35:09). A second image 45652 may be another wide-angle view of the end-effector 45634 clamping the vessel 45636 taken at the present time t1 (e.g., 09:35:13). A third image 45654 may be a composite image of an overhead view of the end-effector 45634 clamping the vessel 45636 taken at present time t1. The third image 45654 may be displayed in the second window 45638 of the primary display 45600 of the surgical hub 20006 as shown in FIG. 58. A fourth image 45656 may be a narrow angle view of the end-effector 45634 clamping the vessel 45636 at present time t1 (e.g., 09:35:13). The fourth image 45656 may be the narrow angle view of the surgical site shown in the primary window 45630 of the primary display 45600 of the surgical hub 20006 as shown in FIG. 58.

In an aspect of the present disclosure, the primary display and/or the secondary display may display one or more of the first image, the second image, the third image, and/or the fourth image. For example, the primary display may display the third image and the secondary display may display the fourth image. As another example, the primary display may display the fourth image and the second display may display the third image.

Figure 60:
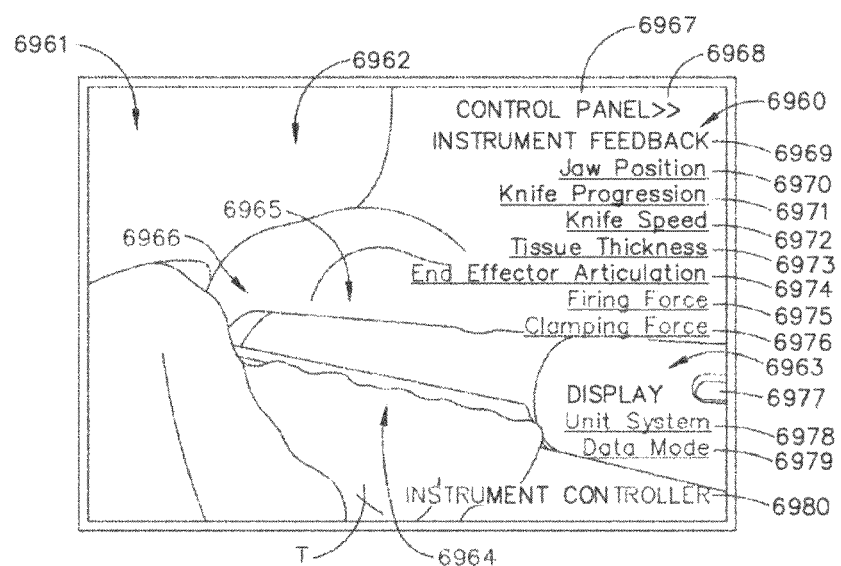
FIG. 60 illustrates a second layer of information overlaying a first layer of information, in accordance with at least one aspect of the present disclosure.

FIG. 60 illustrates a second layer of information overlaying a first layer of information, in accordance with at least one aspect of the present disclosure. For example, FIG. 60 illustrates a second layer of information overlaying a first layer of information. The second layer of information may include a symbolic representation of the knife overlapping the detected position of the knife in the disposable loading unit (DLU) depicted in the first layer of information. Further examples are disclosed in U.S. Pat. No. 9,283,054, titled SURGICAL APPARATUS WITH INDICATOR, which issued on Mar. 15, 2016, which is herein incorporated by reference in its entirety.

As described herein, a display may be referred to as a primary display, a secondary display, a monitor, a surgical hub display, an OR display, a room display, a surgical instrument display, a wearable display, and/or the like.

Referring to FIG. 60, the second layer of information 6963 may overlay at least a portion of the first layer of information 6962 on the display 6960. Furthermore, the touch screen 6961, which may be a primary display and/or a secondary display, may allow a user to manipulate the second layer of information 6963 relative to the video feedback in the underlying first layer of information 6962 on the display 6960. For example, a user may operate the touch screen 6961 to select, manipulate, reformat, resize, and/or otherwise modify the information displayed in the second layer of information 6963. In an aspect, the user may move the first layer of information and/or the second layer of information to one or more displays that may include a primary display and/or a secondary display. In an aspect, the user may use the touch screen 6961 to manipulate the second layer of information 6963 relative to the surgical instrument 6964 depicted in the first layer of information 6962 on the display 6960. A user may select a menu, category and/or classification of the control panel 6967 thereof, for example, and the second layer of information 6963 and/or the control panel 6967 may be adjusted to reflect the user's selection. In various aspects, a user may select a category from the instrument feedback menu 6969 that corresponds to a specific feature or features of the surgical instrument 6964 depicted in the first layer of information 6962. Feedback corresponding to the user-selected category may move, locate itself, and/or "snap" to a position on the display 6960 relative to the specific feature or features of the surgical instrument 6964. For example, the selected feedback may move to a position near and/or overlapping the specific feature or features of the surgical instrument 6964 depicted in the first layer of information 6962.

The instrument feedback menu 6969 may include a plurality of feedback categories, and may relate to the feedback data measured and/or detected by the surgical instrument 6964 during a surgical procedure. As described herein, the surgical instrument 6964 may detect and/or measure the position 6970 of a moveable jaw between an open orientation and a closed orientation, the thickness 6973 of clamped tissue, the clamping force 6976 on the clamped tissue, the articulation 6974 of the disposable loading unit (DLU) 6965, and/or the position 6971, velocity 6972, and/or force 6975 of the firing element, for example. Furthermore, the feedback controller in signal communication with the surgical instrument 6964 may provide the sensed feedback to the display 6960, which may display the feedback in the second layer of information 6963. As described herein, the selection, placement, and/or form of the feedback data displayed in the second layer of information 6963 may be modified based on the user's input to the touch screen 6961, for example.

When the knife of the DLU 6965 is blocked from view by the end effector jaws 6966 and/or tissue T, for example, the operator may track and/or approximate the position of the knife in the DLU 6965 based on the changing value of the feedback data and/or the shifting position of the feedback data relative to the DLU 6965 depicted in the underlying first layer of information 6962.

In various aspects, the display menu 6977 of the control panel 6967 may relate to a plurality of categories, such as unit systems (e.g., unit systems category) 6978 and/or data modes (e.g., data mode category) 6979, for example. In certain aspects, a user may select the unit systems category 6978 to switch between unit systems, such as between metric and U.S. customary units, for example. Additionally, a user may select the data mode category 6979 to switch between types of numerical representations of the feedback data and/or types of graphical representations of the feedback data, for example. The numerical representations of the feedback data may be displayed as numerical values and/or percentages, for example. Furthermore, the graphical representations of the feedback data may be displayed as a function of time and/or distance, for example. As described herein, a user may select the instrument controller menu 6980 from the control panel 6967 to input directives for the surgical instrument 6964, which may be implemented via the instrument controller and/or the microcontroller, for example. A user may minimize or collapse the control panel 6967 by selecting the minimize/maximize icon 6968, and may maximize or un-collapse the control panel 6967 by re-selecting the minimize/maximize icon 6968.

Figure 61:
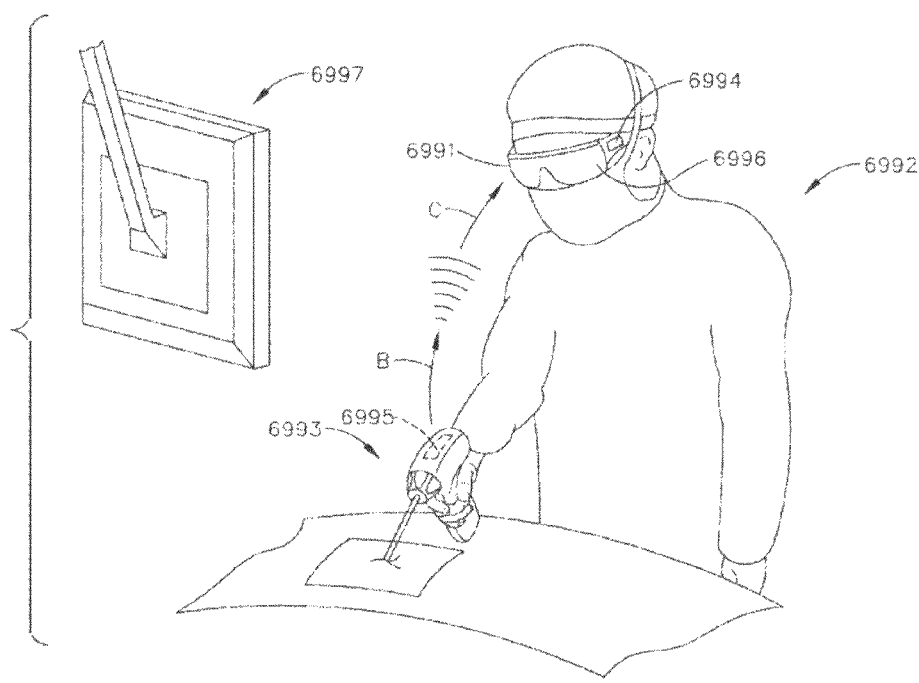
FIG. 61 depicts a perspective view of a surgeon using a surgical instrument that includes a handle assembly housing and a wireless circuit board during a surgical procedure, with the surgeon wearing a set of safety glasses, in accordance with at least one aspect of the present disclosure.

FIG. 61 depicts a perspective view of a surgeon using a surgical instrument that includes a handle assembly housing and a wireless circuit board during a surgical procedure, with the surgeon wearing a set of safety glasses, in accordance with at least one aspect of the present disclosure. The wireless circuit board may transmit a signal to a set of safety glasses worn by a surgeon using the surgical instrument during a procedure. The signal may be received by a wireless port on the safety glasses. One or more lighting devices on a front lens of the safety glasses may change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 61 shows a version of safety glasses 6991 that may be worn by a surgeon 6992 during a surgical procedure while using a medical device. The safety glasses 6991 may include a primary display and/or a secondary display. The safety glasses 6991 may be used to determine a direction in which the surgeon 6992 is looking. For example, the safety glasses 6991 may analyze the pupil movements of the surgeon 6992 (e.g., using an internal or external camera) and may determine that the surgeon is viewing the monitor 6997. As another example, the safety glasses 6991 may use one or more sensors to track the head movement of the surgeon to determine where the surgeon is viewing (e.g., the surgeon is viewing the monitor 6997).

In use, a wireless communications board housed in a surgical instrument 6993 may communicate with a wireless port 6994 on safety glasses 6991. Exemplary surgical instrument 6993 is a battery-operated device, though instrument 6993 may be powered by a cable or otherwise. Instrument 6993 includes an end effector. Particularly, wireless communications board 6995 may transmit one or more wireless signals indicated by arrows (B, C) to wireless port 6994 of safety glasses 6991. Safety glasses 6991 may receive the signal, analyze the received signal, and display indicated status information received by the signal on lenses 6996 to a user, such as surgeon 6992, wearing safety glasses 6991.

Wireless communications board 6995 may transmit a wireless signal to a surgical monitor 6997 such that the surgical monitor 6997 may display received indicated status information to a surgeon 6992, as described herein. Surgical monitor 6997 may be a primary display or a secondary display.

A version of the safety glasses 6991 may include a lighting device on peripheral edges of the safety glasses 6991. A lighting device may provide peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

LEDs may be located at edges or sides of a front lens of the safety glasses 6991 so not to distract from a user's center of vision while still being positioned within the user's field of view such that the user does not need to look away from the surgical site to see the lighting device. Displayed lights may pulse and/or change color to communicate to the wearer of the safety glasses 6991 various aspects of information retrieved from instrument 6993, such as system status information or tissue sensing information (i.e., whether the end effector has sufficiently severed and sealed tissue). Feedback from housed wireless communications board 6995 may cause a lighting device to activate, blink, or change color to indicate information about the use of instrument 6993 to a user. For example, a device may incorporate a feedback mechanism based on one or more sensed tissue parameters. In this case, a change in the device output(s) based on this feedback in sync with a tone change may submit a signal through wireless communications board 6995 to the safety glasses 6991 to trigger activation of the lighting device. Such described means of activation of the lighting device should not be considered limiting as other means of indicating status information of instrument 6993 to the user via the safety glasses 6991 are contemplated. Further, the safety glasses 6991 may be single-use or reusable eyewear. Button-cell power supplies such as button-cell batteries may be used to power wireless receivers and LEDs of versions of safety glasses 6991, which may also include a housed wireless board and tri-color LEDs. Such button-cell power supplies may provide a low-cost means of providing sensory feedback of information about instrument 6993 when in use to surgeon 6992 wearing safety glasses 6991.

A surgical hub that may provide coordination of device pairing in an operating room may be provided. One of the functions of the surgical hub 20006 is to pair (also referred to herein as "connect" or "couple") with other components of the surgical system 20002 to control, gather information from, or coordinate interactions between the components of the surgical system 20002. Since the operating rooms of a hospital are likely in close physical proximity to one another, a surgical hub 20006 of a surgical system 20002 may unknowingly pair with components of a surgical system 20002 in a neighboring operating room, which would significantly interfere with the functions of the surgical hub 20006. For example, the surgical hub 20006 may unintentionally activate a surgical instrument in a different operating room or retrieve record information from a different ongoing surgical procedure in a neighboring operating room.

Aspects of the present disclosure present a surgical hub 20006 that may pair with detected devices of the surgical system 20002 that are located within the bounds of its operating room. The surgical hub 20006 may avoid incorrectly pairing with devices in another operating room.

Furthermore, the surgical hub 20006 may rely on its knowledge of the location of other components of the surgical system 20002 within its operating room in making decisions about, for example, which surgical instruments should be paired with one another or activated. A change in the position of the surgical hub 20006 or another component of the surgical system 20002 may be problematic.

Aspects of the present disclosure further present a surgical hub 20006 that may be configured to reevaluate or redetermine the bounds of its operating room upon detecting that the surgical hub 20006 has been moved.

Aspects of the present disclosure further present a surgical hub 20006 that may be configured to redetermine the bounds of its operating room upon detection of a potential device of the surgical system 20002, which may be an indication that the surgical hub 20006 has been moved.

In various aspects, a surgical hub 20006 may be used with a surgical system 20002 in a surgical procedure performed in an operating room. The surgical hub 20006 may comprise a control circuit configured to determine the bounds of the operating room, determine devices of the surgical system 20002 located within the bounds of the operating room, and pair the surgical hub 20006 with the devices of the surgical system 20002 located within the bounds of the operating room.

In an aspect, the control circuit may be configured to determine the bounds of the operating room after activation of the surgical hub 20006. In one aspect, the surgical hub 20006 may include a communication circuit configured to detect and pair with the devices of the surgical system located within the bounds of the operating room. In an aspect, the control circuit may be configured to redetermine the bounds of the operating room after a potential device of the surgical system 20002 is detected. In one aspect, the control circuit may be configured to periodically determine the bounds of the operating room.

In an aspect, the surgical hub 20006 may comprise an operating room mapping circuit that includes a plurality of non-contact sensors configured to measure the bounds of the operating room.

In various aspects, the surgical hub 20006 may include a processor and a memory coupled to the processor. The memory may store instructions executable by the processor to pair the surgical hub with devices of the surgical system 20002 located within the bounds of the operating room, as described above. In various aspects, the present disclosure may provide a non-transitory computer-readable medium storing computer-readable instructions which, when executed, cause a machine to pair the surgical hub 20006 with devices of the surgical system 20002 located within the bounds of the operating room, as described herein.

Figure 63:
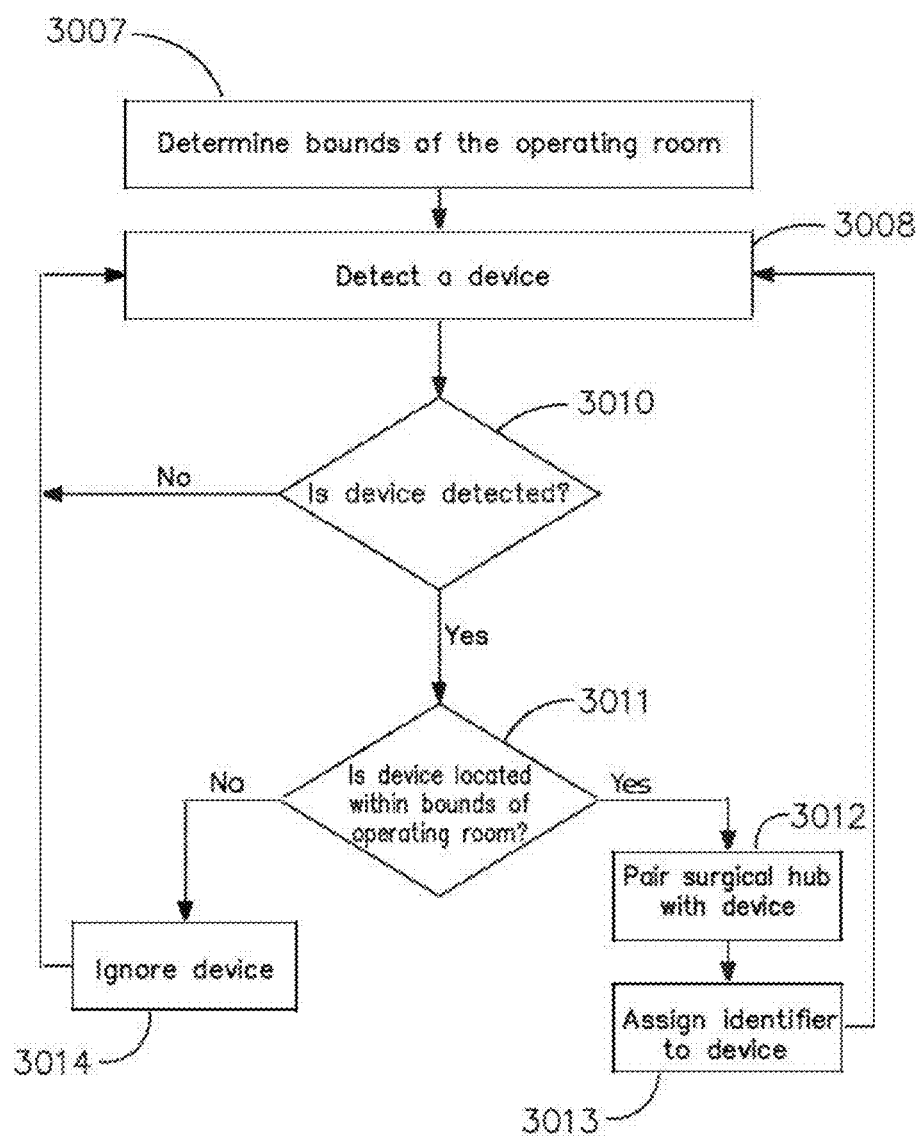
FIG. 63 is a logic flow diagram of a process depicting a control program or a logic configuration for surgical hub pairing with surgical devices of a surgical system that are located within the bounds of an operating room, in accordance with at least one aspect of the present disclosure.
Figure 64:
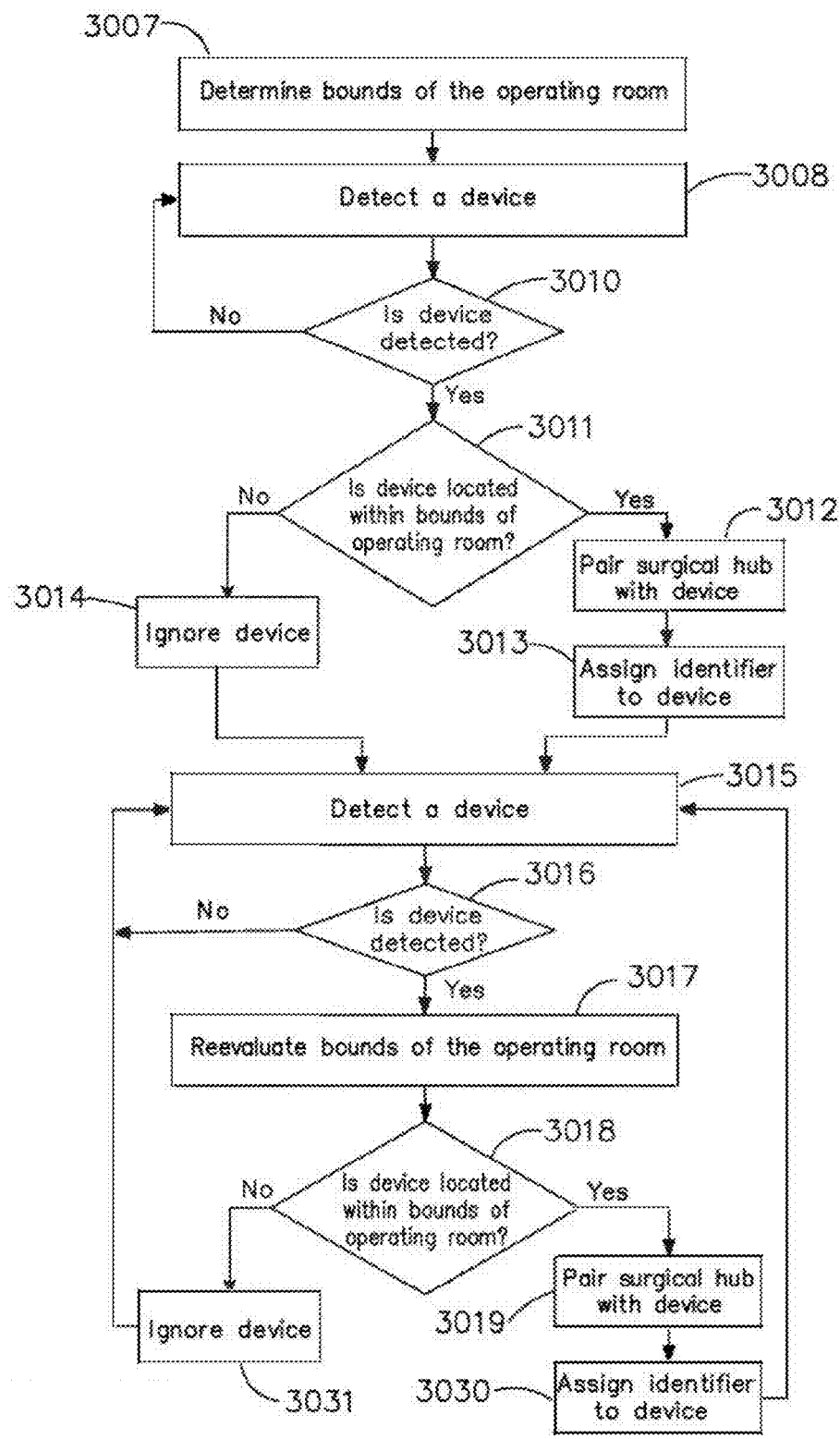
FIG. 64 is a logic flow diagram of a process depicting a control program or a logic configuration for selectively forming and severing connections between devices of a surgical system, in accordance with at least one aspect of the present disclosure.

FIGS. 63 and 64 are logic flow diagrams of processes depicting control programs or logic configurations for pairing the surgical hub 20006 with devices of the surgical system 20002 located within the bounds of the operating room, as described herein. FIG. 63 is a logic flow diagram of a process depicting a control program or a logic configuration for surgical hub pairing with surgical devices of a surgical system that are located within the bounds of an operating room, in accordance with at least one aspect of the present disclosure. FIG. 64 is a logic flow diagram of a process depicting a control program or a logic configuration for selectively forming and severing connections between devices of a surgical system, in accordance with at least one aspect of the present disclosure.

The surgical hub 20006 may perform a wide range of functions that may use short-range and long-range communication, such as assisting in a surgical procedure, coordinating between devices of the surgical system 20002, and gathering and transmitting data to the cloud. To perform its functions, the surgical hub 20006 may be equipped with a communication module capable of short-range communication with other devices of the surgical system 20002. The communication module may also be capable of long-range communication with the cloud.

The surgical hub 20006 may also be equipped with an operating room mapping module which may be capable of identifying the bounds of an operating room, and identifying devices of the surgical system 20002 within the operating room. The surgical hub 20006 may be configured to identify the bounds of an operating room, and may pair (e.g., may only pair) with or connect to potential devices of the surgical system 20002 that are detected within the operating room.

In an aspect, the pairing may comprise establishing a communication link or pathway. In another aspect, the pairing may comprise establishing a control link or pathway.

Figure 65:
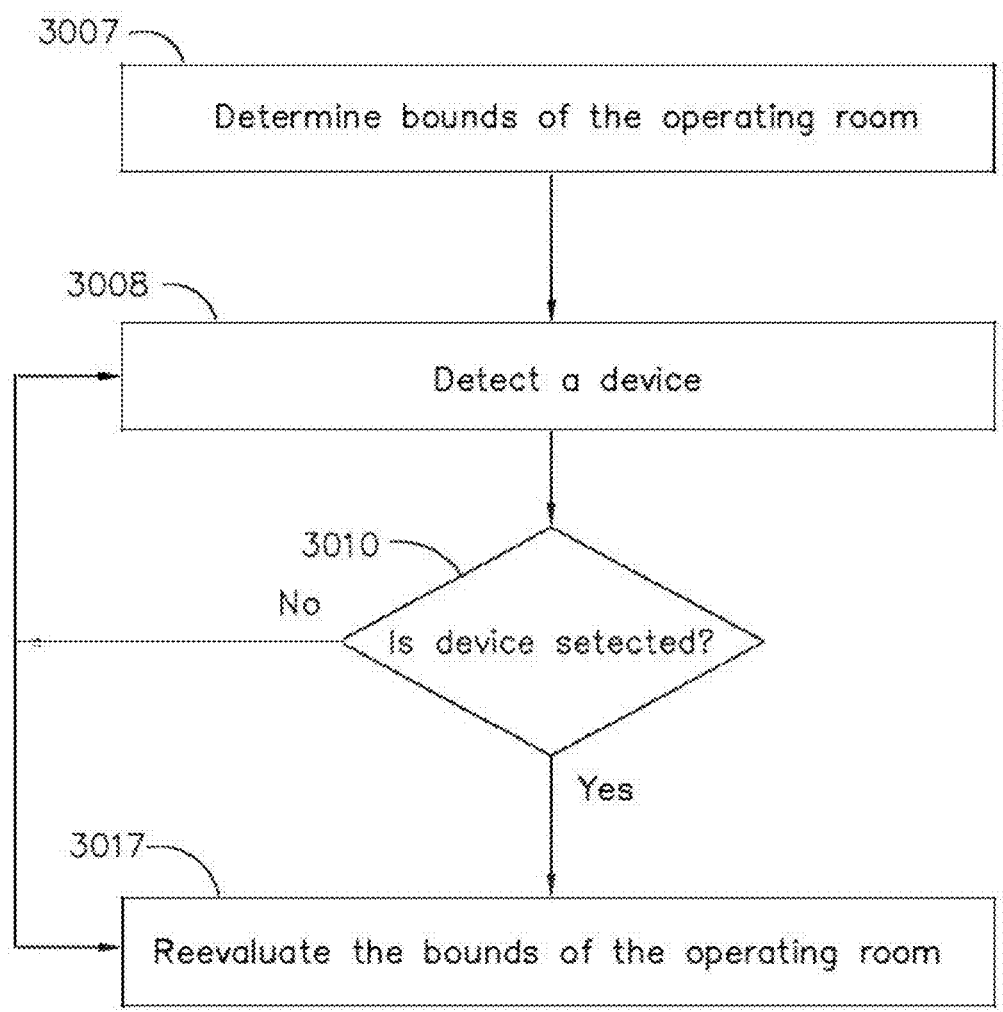
FIG. 65 is a logic flow diagram of a process depicting a control program or a logic configuration for selectively reevaluating the bounds of an operating room after detecting a new device, in accordance with at least one aspect of the present disclosure.
Figure 66:
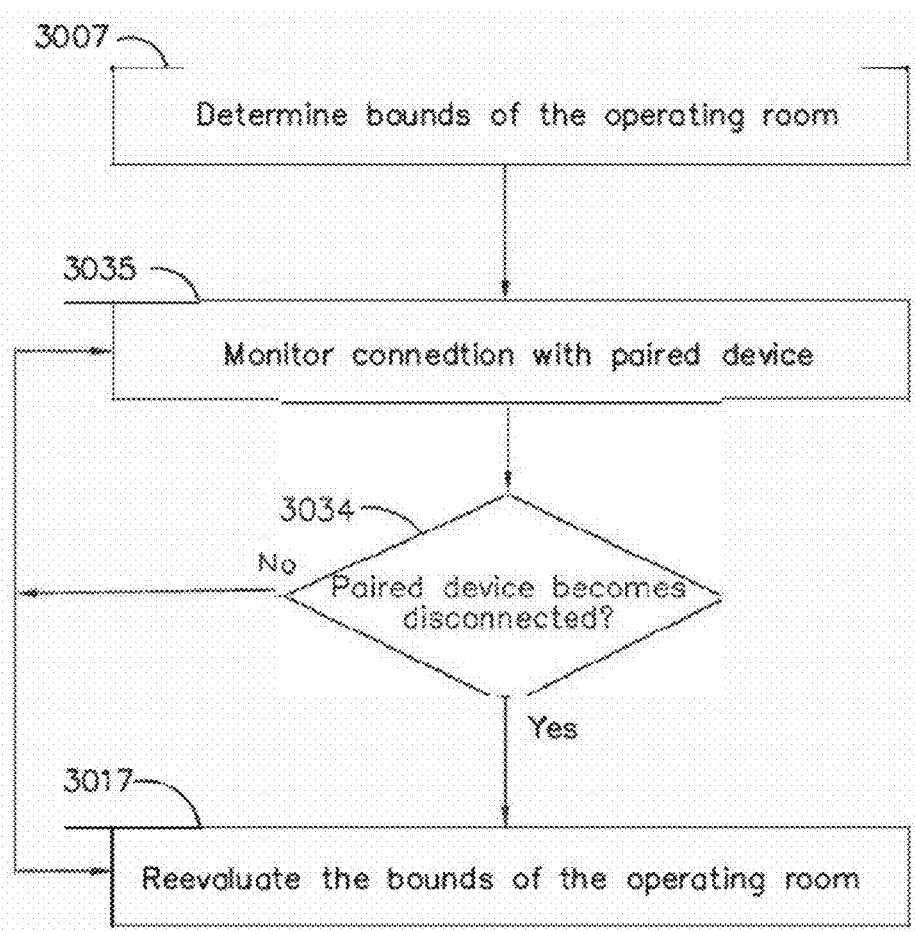
FIG. 66 is a logic flow diagram of a process depicting a control program or a logic configuration for selectively reevaluating the bounds of an operating room after disconnection of a paired device, in accordance with at least one aspect of the present disclosure.
Figure 67:
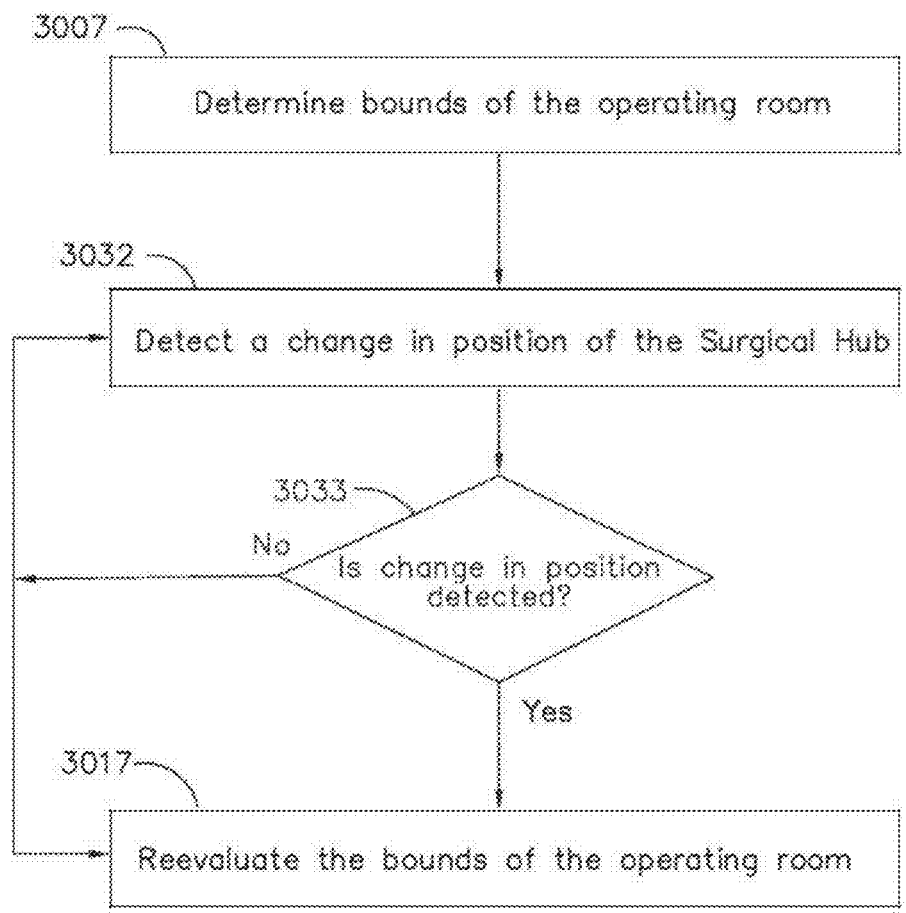
FIG. 67 is a logic flow diagram of a process depicting a control program or a logic configuration for reevaluating the bounds of an operating room by a surgical hub after detecting a change in the position of the surgical hub, in accordance with at least one aspect of the present disclosure.

A mapping or evaluation of the bounds of the operating room may take place during an activation (e.g., initial activation) of the surgical hub 20006. The surgical hub 20006 may be configured to maintain spatial awareness during operation by periodically mapping its operating room, which may be helpful in determining if the surgical hub 20006 has been moved. The reevaluation 3017 may be performed periodically or it may be triggered by an event such as observing a change in the devices of the surgical system 20002 that are deemed within the operating room. In an aspect, the change is detection 3010 of a device (e.g., a new device) that was not previously deemed as within the bounds of the operating room, as illustrated in FIG. 65. FIG. 65 is a logic flow diagram of a process depicting a control program or a logic configuration for selectively reevaluating the bounds of an operating room after detecting a new device, in accordance with at least one aspect of the present disclosure. In another aspect, the change may be a disappearance, disconnection, or un-pairing of a paired device that was previously deemed as residing within the operating room, as illustrated in FIG. 66. FIG. 66 is a logic flow diagram of a process depicting a control program or a logic configuration for selectively reevaluating the bounds of an operating room after disconnection of a paired device, in accordance with at least one aspect of the present disclosure. The surgical system 20006 may continuously monitor 3035 the connection with paired devices to detect 3034 the disappearance, disconnection, or un-pairing of a paired device.

In other aspects, reevaluation triggering events may be, for example, changes in surgeons' positions, instrument exchanges, or sensing of a new set of tasks being performed by the surgical system 20006.

In one aspect, the evaluation of the bounds of the room by the surgical system 20006 is accomplished by activation of a sensor array of the operating-room mapping module within the surgical system 20006 which enables it to detect the walls of the operating room.

Other components of the surgical system 20002 may be made to be spatially aware in the same, or a similar, manner as the surgical hub 20006. For example, a robotic hub may also be equipped with an operating room mapping module. A primary display and/or a secondary display may also be equipped with an operating room mapping module.

The spatial awareness of the surgical hub 20006 and its ability to map an operating room for potential components of the surgical system 20002 may allow the surgical hub 20006 to make autonomous decisions about whether to include or exclude such potential components as part of the surgical system 20002, which may relieve the surgical staff from dealing with such tasks. Furthermore, the surgical hub 20006 may be configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation. The spatial awareness of the surgical hub 20006 may also be used to update one of more displays within an operating room. For example, the spatial awareness of the surgical hub 20006 may display data on a primary display, may display data on a secondary display, and/or may move data between the primary display and secondary display based on at least one of a detection of an instrument, a mapping of the operating room, a detection of a user, a change in a location of the surgical hub, a disconnection of an instrument, and the like.

In one aspect, the surgical hub 20006 may employ the operating-room mapping module to determine the bounds of the surgical theater (e.g., a fixed, mobile, or temporary operating room or space) using ultrasonic or laser non-contact measurement devices.

Figure 62:
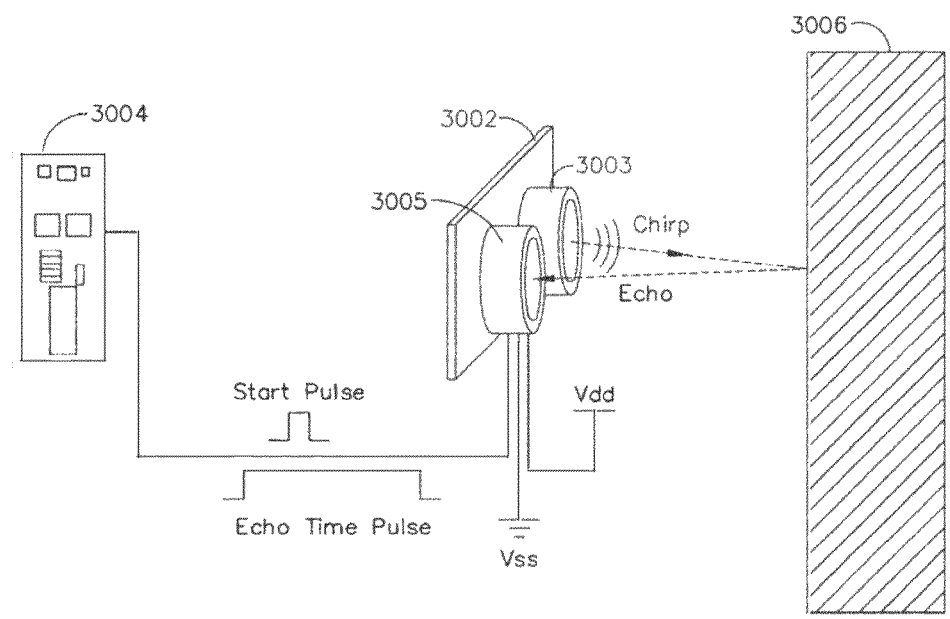
FIG. 62 illustrates ultrasonic pinging of an operating room wall to determine a distance between a surgical hub and the operating room wall, in accordance with at least one aspect of the present disclosure.

Referring to FIG. 62, ultrasound based non-contact sensors 3002 may be employed to scan the operating theater by transmitting a burst of ultrasound and receiving the echo when the ultrasound bounces off a perimeter wall 3006 of an operating theater to determine the size of the operating theater and to adjust Bluetooth pairing distance limits. In one example, the non-contact sensors (e.g., ultrasound based non-contact sensors) 3002 may be ping ultrasonic distance sensors, as illustrated in FIG. 62.

FIG. 62 illustrates ultrasonic pinging of an operating room wall to determine a distance between a surgical hub and the operating room wall, in accordance with at least one aspect of the present disclosure.

FIG. 62 shows how an ultrasonic sensor 3002 sends a brief chirp with its ultrasonic speaker 3003 and makes it possible for a micro-controller 3004 of the operating-room mapping module to measure how long the echo takes to return to the ultrasonic sensor's ultrasonic microphone 3005. The micro-controller 3004 may send the ultrasonic sensor 3002 a pulse to begin the measurement. The ultrasonic sensor 3002 then may wait long enough for the micro-controller program to start a pulse input command. Then, at about the same time the ultrasonic sensor 3002 chirps a 40 kHz tone, the ultrasonic sensor may send a high signal to the micro-controller 3004. When the ultrasonic sensor 3002 detects the echo with its ultrasonic microphone 3005, it may change that high signal back to low. The micro-controller's pulse input command may measure the time between the high and low changes and may store its measurement in a variable. This value may be used along with the speed of sound in air to calculate the distance between the surgical hub 20006 and the operating-room wall (e.g., operating room perimeter wall) 3006.

In an example, as illustrated in FIG. 62, a surgical hub 20006 may be equipped with four ultrasonic sensors 3002, wherein each of the four ultrasonic sensors is configured to assess the distance between the surgical hub 20006 and a wall of the operating room 3000. A surgical hub 20006 may be equipped with more or less than four ultrasonic sensors 3002 to determine the bounds of an operating room.

Other distance sensors may be employed by the operating-room mapping module to determine the bounds of an operating room. In an example, the operating-room mapping module may be equipped with one or more photoelectric sensors that may be employed to assess the bounds of an operating room. In one example, suitable laser distance sensors may also be employed to assess the bounds of an operating room. Laser-based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits.

Figure 70:
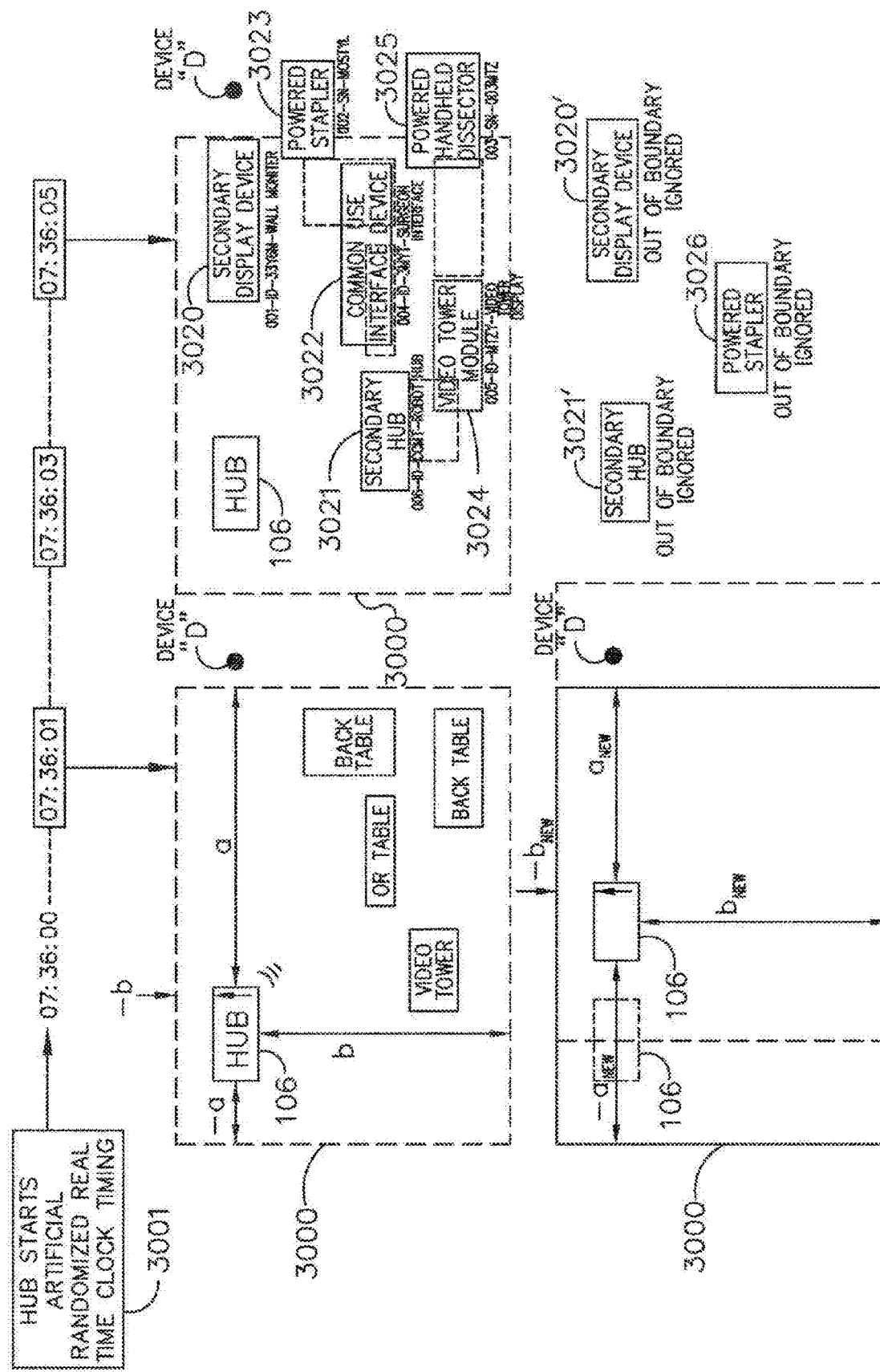
FIG. 70 illustrates a partial artificial timeline of a surgical procedure performed in an operating room via a surgical system, in accordance with at least one aspect of the present disclosure.

FIG. 70 illustrates a partial artificial timeline of a surgical procedure performed in an operating room via a surgical system, in accordance with at least one aspect of the present disclosure.

Referring to the top left corner of FIG. 70, a surgical hub 20006 may be brought into an operating room 3000. The surgical hub 20006 may be activated at the beginning of the set-up that occurs prior to the surgical procedure. In the example of FIG. 70, the set-up may start at an actual time of 11:31:14 (EST) based on a real-time clock. However, at the stated procedure set-up start time, the surgical hub 20006 may start 3001 an artificial randomized real-time clock timing scheme at artificial real time 07:36:00 to protect private patient information.

At artificial real time 07:36:01, the operating-room mapping module may employ the ultrasonic distance sensors to ultrasonically ping the room (e.g., sends out a burst of ultrasound and listens for the echo when it bounces off the perimeter walls of the operating room as described above) to verify the size of the operating room and to adjust pairing distance limits.

At artificial real time 07:36:03, the data may be stripped and time stamped. At artificial real time 07:36:05, the surgical hub 20006 may begin pairing devices located only within the operating room 3000 as verified using ultrasonic distance sensors 3002 of the operating-room mapping module. The top right corner of FIG. 70 illustrates several example devices that are within the bounds of the operating room 3000 and are paired with the surgical hub 20006, including a secondary display device 3020, a secondary hub 3021, a common interface device 3022, a powered stapler 3023, a video tower module 3024, and a powered handheld dissector 3025. On the other hand, secondary hub 3021', secondary display device 3020', and powered stapler 3026 are all outside the bounds of the operating room 3000 and, accordingly, are not paired with the surgical hub 20006.

In addition to establishing a communication link with the devices of the surgical system 20002 that are within the operating room, the surgical hub 20006 also may assign a unique identification and communication sequence or number to each of the devices. The unique sequence may include the device's name and a time stamp of when the communication was first established. Other suitable device information may also be incorporated into the unique sequence of the device.

As illustrated in the top left corner of FIG. 70, the surgical hub 20006 has determined that the operating room 3000 bounds are at distances a, −a, b, and −b from the surgical hub 20006. Since Device "D" is outside the determined bounds of its operating room 3000, the surgical hub 20006 may not pair with the Device "D."

FIG. 63 is an example algorithm illustrating how the surgical hub 20006 may pair (e.g., may only pair) with devices within the bounds of its operating room. After activation, the surgical hub 20006 may determine 3007 bounds of the operating room using the operating-room mapping module, as described herein. After the initial determination, the surgical hub 20006 may continuously search for or detect 3008 devices within a pairing range. If a device is detected 3010, the surgical hub 20006 may then determine 3011 whether the detected device is within the bounds of the operating room. The surgical hub 20006 may pair 3012 with the device if it is determined that the device is within the bounds of the operating room. The surgical hub 20006 may display data associated with the paired device on a primary display and/or a secondary display. In certain instances, the surgical hub 20006 may also assign 3013 an identifier to the device. If, however, the surgical hub 20006 determines that the detected device is outside the bounds of the operating room, the surgical hub 20006 may ignore 3014 the device.

Referring to FIG. 64, after an initial determination of the bounds of the room, and after an initial pairing of devices located within such bounds, the surgical hub 20006 may continue to detect 3015 new devices that become available for pairing. If a new device is detected 3016, the surgical hub 20006 may be configured to reevaluate 3017 the bounds of the operating room prior to pairing with the new device. If the new device is determined 3018 to be within the newly determined bounds of the operating room, then the surgical hub 20006 may pair with the device 3019 and assign 3030 a unique identifier to the new device. If, however, the surgical hub 20006 determines that the new device is outside the newly determined bounds of the operating room, the surgical hub 20006 may ignore 3031 the device.

For pairing, the operating-room mapping module may comprise a compass and integrated Bluetooth transceiver. Other communication mechanisms, which are not significantly affected by the hospital environment or geographical location, may be employed. Bluetooth Low Energy (BLE) beacon technology may currently achieve indoor distance measurements with accuracy of about 1-2 meters, with improved accuracy in closer proximities (within 0-6 meters). To improve the accuracy of the distance measurements, a compass may be used with the BLE. The operating-room mapping module may utilize the BLE and the compass to determine where modules are located in relation to the patient. For example, two modules facing each other (detected by compass) with greater than one meter distance between them may clearly indicate that the modules are on opposite sides of the patient. The more "Hub"-enabled modules that reside in the operating room, the greater the achievable accuracy may become due to triangulation techniques.

In the situations where multiple surgical hubs 20006, modules, and/or other peripherals are present in the same operating room, as illustrated in the top right corner of FIG. 70, the operating-room mapping module may be configured to map the physical location of each module that resides within the operating room. This information may be used by the user interface to display a virtual map of the room, enabling the user to more easily identify which modules are present and enabled, as well as their current status. In one aspect, the mapping data collected by surgical hubs 20006 may be uploaded to the cloud, where the data may be analyzed for identifying how an operating room is physically setup, for example.

The surgical hub 20006 may be configured to determine a device's location by assessing transmission radio signal strength and direction. For Bluetooth protocols, the Received Signal Strength Indication (RSSI) is a measurement of the received radio signal strength. In one aspect, the devices of the surgical system 20002 may be equipped with USB Bluetooth dongles. The surgical hub 20006 may scan the USB Bluetooth beacons to get distance information. In another aspect, multiple high-gain antennas on a Bluetooth access point with variable attenuators may produce more accurate results than RSSI measurements. In one aspect, the hub may be configured to determine the location of a device by measuring the signal strength from multiple antennas. Alternatively, in some examples, the surgical hub 20006 may be equipped with one or more motion sensor devices configured to detect a change in the position of the surgical hub 20006.

Referring to the bottom left corner of FIG. 70, the surgical hub 20006 has been moved from its original position, which is depicted in dashed lines, to a new position closer to the device "D," which is still outside the bounds of the operating room 3000. The surgical hub 20006 in its new position, and based on the previously determined bounds of the operating room, may naturally conclude that the device "D" is a potential component of the surgical system 20002. However, the introduction of a new device may be a triggering event for reevaluation 3017 of the bounds of the operating room, as illustrated in the example algorithm of FIGS. 63, 65. After performing the reevaluation, the surgical hub 20006 may determine that the operating room bounds have changed. Based on the new bounds, at distances anew, −a new, bnew, and −bnew, the surgical hub 20006 may conclude that it has been moved and that the Device "D" is outside the newly determined bounds of its operating room. Accordingly, the surgical hub 20006 may still not pair with the Device "D." The surgical hub 20006 may also update a primary display and/or a secondary display to reflect the change.

In one aspect, one or more of the processes depicted in FIGS. 63-67 may be executed by a control circuit of a surgical hub 20006. In another aspect, one or more of the processes depicted in FIGS. 63-67 may be executed by a cloud computing system 20008. In yet another aspect, one or more of the processes depicted in FIGS. 63-67 may be executed by at least one of the aforementioned cloud computing systems 20008 and/or a control circuit of a surgical hub 20006 in combination with a control circuit of a modular device, such as the microcontroller of a surgical instrument, the control circuit of a robotic surgical, the control circuit of the surgical instruments, and/or any other suitable microcontroller.

During a surgical procedure, a surgical instrument such as an ultrasonic or an RF surgical instrument may be coupled to a generator module 140 of the surgical hub 20006. In addition, a separate surgical instrument controller such as a controller that may be controlled by a foot, a hand, a switch, and/or another activation device may be used by an operator of the surgical instrument to activate the energy flow from the generator to the surgical instrument. Multiple surgical instrument controllers and multiple surgical instruments may be used concurrently in an operating room. Pressing or activating the wrong surgical instrument controller may lead to undesirable consequences. Aspects of the present disclosure present a solution in which the surgical hub 20006 coordinates the pairing of surgical instrument controllers and surgical instruments to ensure patient and operator safety.

Aspects of the present disclosure are presented for a surgical hub 20006 configured to establish and sever pairings between components of the surgical system 20002 within the bounds of the operating room to coordinate flow of information and control actions between such components. The surgical hub 20006 may be configured to establish a pairing between a surgical instrument controller and a surgical instrument that resides within the bounds of an operating room of surgical hub 20006.

In various aspects, the surgical hub 20006 may be configured to establish and sever pairings between components of the surgical system 20002 based on operator request(s) or situational and/or spatial awareness.

Figure 68:
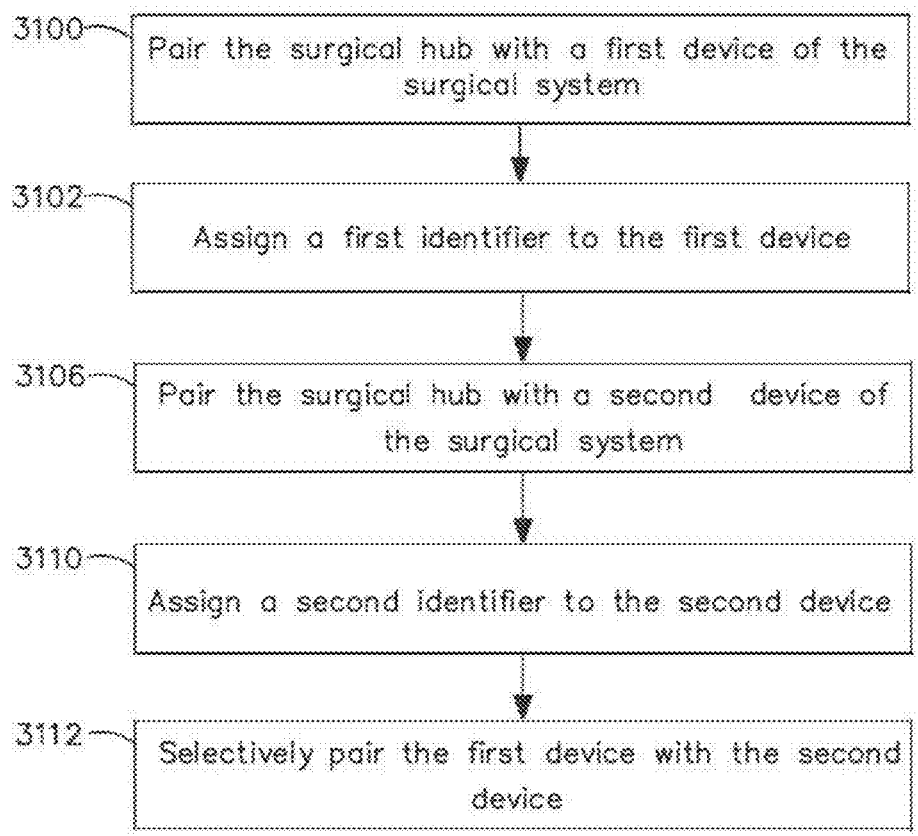
FIG. 68 is a logic flow diagram of a process depicting a control program or a logic configuration for selectively forming connections between devices of a surgical system, in accordance with at least one aspect of the present disclosure.

Aspects of the present disclosure are presented for a surgical hub for use with a surgical system in a surgical procedure performed in an operating room. The surgical hub may include a control circuit that selectively forms and severs pairings between devices of the surgical system. The surgical hub may update a primary display and/or a secondary display to reflect formed or severed pairings. In one aspect, such as shown in FIG. 68, the hub may include a control circuit that is configured to pair the hub with a first device of the surgical system at 3100, may assign a first identifier to the first device at 3102, may pair the hub with a second device of the surgical system at 3106, may assign a second identifier to the second device at 3112, and/or may selectively pair the first device with the second device at 3112. In one aspect, the surgical hub may include a storage medium, wherein the control circuit is configured to store a record indicative of the pairing between the first device and the second device in the storage medium. In one aspect, the pairing between the first device and the second device may define a communication pathway therebetween. In one aspect, the pairing between the first device and the second device may define a control pathway for transmitting control actions from the second device to the first device.

Figure 69:
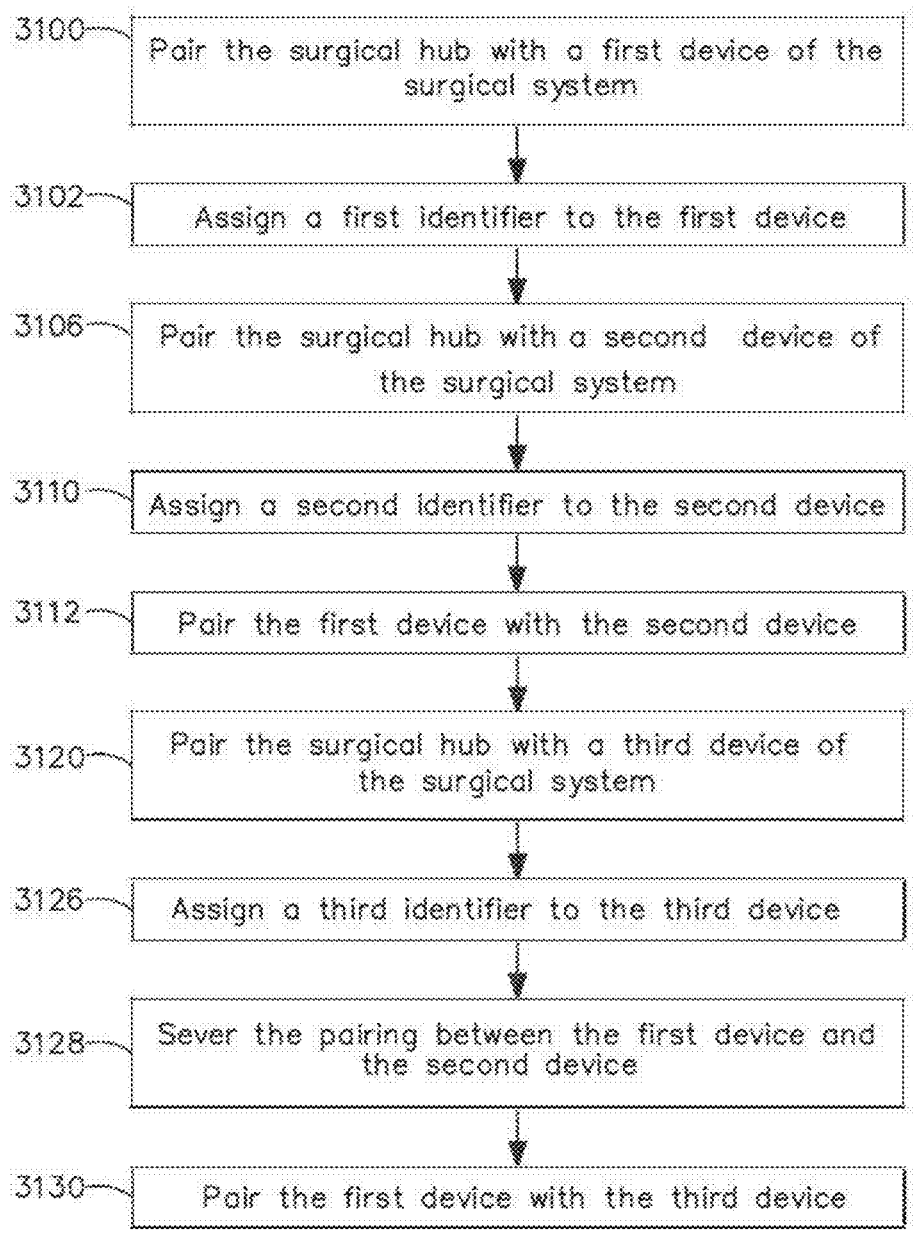
FIG. 69 is a logic flow diagram of a process depicting a control program or a logic configuration for selectively forming and severing connections between devices of a surgical system, in accordance with at least one aspect of the present disclosure.

In an aspect, such as shown in FIG. 69, the control circuit may be further configured to pair the hub with a third device of the surgical system at 3120, assign a third identifier to the third device at 3125, sever the pairing between the first device and the second device at 3128, and/or selectively pair the first device with the third device at 3130. In one aspect, the control circuit may be further configured to store a record indicative of the pairing between the first device and the third device in the storage medium. In one aspect, the pairing between the first device and the third device may define a communication pathway therebetween. In one aspect, the pairing between the first device and the third device may define a control pathway for transmitting control actions from the third device to the first device.

In various aspects, the surgical hub may include a processor and a memory coupled to the processor. The memory may store instructions executable by the processor to selectively form and sever pairings between the devices of the surgical system, as described above. In various aspects, the present disclosure may provide a non-transitory computer-readable medium storing computer-readable instructions which, when executed, cause a machine to selectively form and sever pairings between the devices of the surgical system, as described above. FIGS. 68 and 69 are logic flow diagrams of processes depicting control programs or logic configurations for selectively forming and severing pairings between the devices of the surgical system, as described herein. FIG. 62 is a logic flow diagram of a process depicting a control program or a logic configuration for selectively forming connections between devices of a surgical system, in accordance with at least one aspect of the present disclosure. FIG. 69 is a logic flow diagram of a process depicting a control program or a logic configuration for selectively forming and severing connections between devices of a surgical system, in accordance with at least one aspect of the present disclosure.

In one aspect, the surgical hub 20006 may establish a first pairing with a surgical instrument and a second pairing with the surgical instrument controller. The surgical hub 20006 may then link the pairings together, allowing the surgical instrument and the surgical instrument controller to operate with one another. The surgical hub 20006 may update the display of a primary display and/or a secondary display to reflect the linked pairings. In another aspect, the surgical hub 20006 may sever an existing communication link between a surgical instrument and a surgical instrument controller, then may link the surgical instrument to another surgical instrument controller that is linked to the surgical hub 20006. The surgical hub 20006 may update the display of a primary display and/or a secondary display to reflect the severed communication link and/or the link to another surgical instrument controller.

In one aspect, the surgical instrument controller may be paired to two sources. The surgical instrument controller may be paired to the surgical hub 20006, which includes the generator module, for control of its activation. The surgical instrument controller may also be paired to a specific surgical instrument to prevent inadvertent activation of the wrong surgical instrument.

Referring to FIG. 68, the surgical hub 20006 may cause the communication module to pair 3100 or establish a first communication link 3101 with a first device 3102 of the surgical system 20002, which may be a first surgical instrument. Then, the hub may assign 3104 a first identification number to the first device 3102. This may be a unique identification and communication sequence or number that may include the device's name and a timestamp of when the communication was first established.

In addition, the surgical hub 20006 may then cause the communication module to pair 3106 or establish a second communication link 3107 with a second device 3108 of the surgical system 20002, which may be a surgical instrument controller. The surgical hub 20006 may then assign 3110 a second identification number to the second device 3108.

In various aspects, pairing a surgical hub 20006 with a device may include detecting the presence of a new device, determining that the new device is within bounds of the operating room, as described herein, and pairing (e.g., only pairing) with the new device if the new device is located within the bounds of the operating room.

Referring to FIG. 69, the surgical hub 20006 may detect and pair 3120 or establish a third communication link 3124 with a third device 3116 of the surgical system 20002, which may be another surgical instrument controller, for example. The surgical hub 20006 may then assign 3126 a third identification number to the third device 3116. The surgical hub 20006 may update a primary display and/or a secondary display to indicate that the third device has been detected and/or paired.

In one aspect, the computer systems may utilize video/images of the OR that are external to a surgical site (e.g., an abdomen of a patient undergoing a laparoscopic procedure).

In this aspect, the camera assembly capturing the images for analysis by the computer system described herein may exclude or include images from a laparoscope, thoracoscope, or another such endoscope and/or video camera utilized for visualizing the interior of a patient's body. Rather, the camera assembly may include cameras positioned about the OR to visualize how the surgical devices are being utilized and how the surgical staff is interacting with each other and the surgical devices to provide a broader context for the actions that are occurring within the OR. In another aspect, the externally captured video/images may be utilized in conjunction with video/images from endoscopes for analysis and/or to improve the control of the surgical devices in use. Further examples are disclosed in U.S. Patent. Application Publication No. 2019-0201129 A1 (U.S. patent application Ser. No. 16/182,269), titled IMAGE CAPTURING OF THE AREAS OUTSIDE THE ABDOMEN TO IMPROVE PLACEMENT AND CONTROL OF A SURGICAL DEVICE IN USE, filed Nov. 6, 2018, which is herein incorporated by reference in its entirety.

Figure 71:
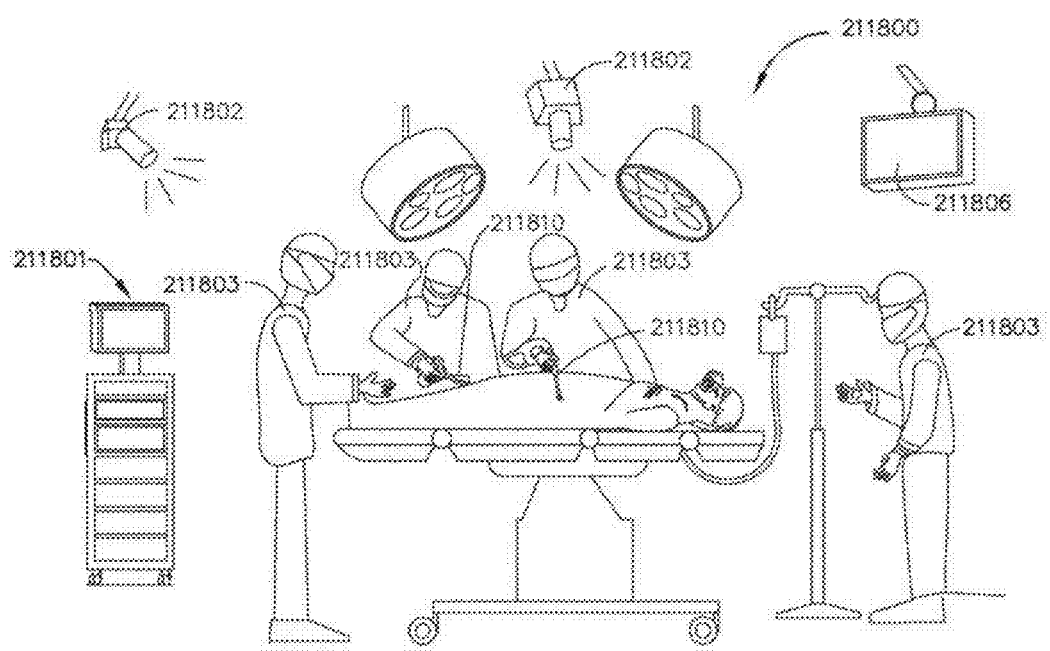
FIG. 71 is a diagram of an illustrative operating room (OR) setup, in accordance with at least one aspect of the present disclosure.

FIG. 71 is a diagram of an illustrative OR setup, in accordance with at least one aspect of the present disclosure. In various implementations, a surgical hub 211801 may be connected to one or more cameras 211802, surgical instruments 211810, displays 211806, overheard lights 211808, and other surgical devices within the OR 211800 via a communications protocol (e.g., Bluetooth), as described above under the heading SURGICAL HUBS. The cameras 211802 may be oriented in order to capture images and/or video of the surgical staff members 211803 and/or surgical instruments 211810 (or other surgical devices) within the OR 211800 during the course of a surgical procedure. The captured image(s) may include static images or moving images (i.e., video). The images of the surgical staff members 211803 and/or surgical instruments 211810 may be captured at a variety of angles and magnifications, utilize different filters, and so on. In one implementation, the cameras 211802 may be arranged within the OR 211800 so that they may collectively visualize each surgical staff member performing the procedure. Accordingly, the surgical hub 211801 may receive the captured image and/or video data from the cameras 211802 to visually analyze the surgical staff members 211803 and/or the surgical instruments 211810 during the surgical procedure. The image and/or video data may be processed utilizing a variety of machine vision, image processing, object recognition, and optical tracking techniques to track characteristics, properties, actions, and movements of the surgical staff members 211803 and/or the surgical instruments 211810.

An HCP may be a nurse, doctor, surgeon, medical technician, physician, and/or the like.

An augmented reality display may be a display that may be capable of overlaying one or more images. for example, a display may overlay a medical image over an image of a patient. In an example, a display may overlay a medical image over a video of a patient. In an example, display may overlay an indicator and or one or more instructions over an image. An augmented reality display may be a wearable device.

In examples, one or more surgical hubs may determine if an object is located (e.g., present) in the surgical operating room (OR). In examples, the surgical hub(s) may determine if an object is absent from the surgical OR. In examples, the surgical hub(s) may determine if the object is located in a room, such as a room that may be adjacent to the surgical OR. The surgical hubs may operate in concert or may operate independently. An object may be a smart device such as a smart medical instrument.

The surgical hub may use a ping (e.g., an ultrasonic ping), for example, to define the boundaries (e.g., walls) of the surgical OR. The surgical hub may be aware when objects enter or leave the surgical OR.

The surgical hub may be included in a tiered software system. The surgical hub may use spatial awareness, for example, when determining if objects are located in the surgical OR. Objects may register to the surgical hub. For example, objects may send respective identifications and/or serial numbers to the surgical hub. In examples, the surgical hub may track the objects' respective positions within the surgical OR. In examples, one or more cameras may be used to track the objects. The cameras may be in communication with the surgical hub.

In examples, the surgical hub may determine if an object is inside a patient and may indicate to remove the object. For example, a surgical hub may send a notification to a surgeon that the object is inside a patient and that the object may need to be removed. In examples, the surgical hub may track a spatial temporal component associated with each object. For example, the surgical hub may track which device is in a medical staff member's hand, for example, at a given time.

The surgical hub may overlay data on the object. For example, the object may be a medical instrument. A display may be configured for the overlaid data. The display may be included on the medical instrument. The display may be attachable to the medical instrument. The data may be depicted on the screen for a user to see. The cameras as described herein may observe a change in the surgical OR and may overlay data associated with the change to a medical instrument display.

The surgical hub may be aware of secondary objects located in a storage destination. The storage destination may be located outside the surgical OR. The surgical hub may determine when one or more secondary objects are involved in a surgery. In examples, the surgical hub may communicate to a medical staff member (e.g., a rotating nurse) to retrieve the secondary objects involved in the surgery.

The surgical hub may pinpoint an object (e.g., each object) located in the surgical OR. In examples, the surgical hub may be aware of an instrument involved in a surgery. For example, the instrument may be involved in an upcoming surgical task of the surgery. A display may be accessible to a table nurse and may be in communication with the surgical hub. The surgical hub may indicate the instrument involved in the surgery on the display. For example, the surgical hub may highlight the instrument on the display. The instrument involved in the surgery may be located in a storage destination as described herein. The surgical hub may indicate the storage destination that the instrument is located at.

Augmented reality may be used by the surgical hub to indicate the instrument. For example, the augmented reality may be associated with a secondary display overlay on another display. The surgical hub may use augmented reality to highlight the instrument involved in the surgery. The cameras as described herein may record data (e.g., metadata) associated with orientations and/or configurations of instruments. An augmented reality display may show information related to the metadata associated with each instrument. For example, an augmented reality display may be a pair of visualization glasses. The augmented reality display may show steps for a medical staff to perform. Each medical staff member may access an individual augmented reality display, for example, to see personalized steps that the medical staff has to perform. The surgical hub may determine when a medical staff member is unsure about what the next step for the surgery is and may output the step to a display accessible to the medical staff member.

In examples, the surgical hub may be aware of which instruments are sterile or not sterile. For example, the surgical hub may track whether the instrument has been touched by a non-sterile medical staff and may determine that the instrument is not sterile. The surgical hub may indicate whether the instrument is located in a sterile or a non-sterile field.

Spatial temporal data associated with an object (e.g., each object) may be collected by the surgical hub. For example, the spatial temporal data may be the number of times an instrument was exchanged. The surgical hub may analyze the spatial temporal data. For example, the spatial temporal data may indicate that the instrument was exchanged many times during a surgery. In such a case, the surgical hub may assess that the instrument is significantly involved in the surgery. The surgical hub may use the spatial temporal data to optimize the surgical OR setup.

The surgical hub may coordinate the data being exchanged between objects in the surgical OR. For example, an instrument may try to send information to a wrong display screen. In such a case, the surgical hub may identify that the display screen does not want the information and may prevent the instrument from sending the information.

An object (e.g., each object) may be associated with a power signature. The power signature may be sent to the surgical hub. The surgical hub may use the power signature to determine whether the object is powered on. The power structure signature may be used by the surgical hub to determine the identity of an object. For example, the surgical hub may identify an object based on its power signature.

The surgical hub may identify and/or verify instruments by using data clusters and/or nexuses of data points. In examples, instrument orientations and/or ergonomic information related to the instruments may be determined using data clusters and/or nexuses of data points. The surgical hub may receive data associated with a display (e.g., each display) in the surgical OR. For example, the surgical hub may receive data from a data source that may be associated with the display, such as a medical instrument.

As another example, the surgical hub may determine the data that is displayed on the screen and may modify the data on the screen, augment the data on the screen, remove data from the screen, and/or add data to the screen. For example, a display associated with a generator located in the surgical OR may send data to the surgical hub. In examples, one or more cameras may monitor the display and send data associated with the monitoring to the surgical hub. For example, the cameras may see the power levels on the generator and send data associated with the power levels to the surgical hub. For example, the cameras may see error codes on the generator and may send data associated with the error codes to the surgical hub.

The instrument may send a message to the surgical hub that notifies the hub that the instrument is located in the surgical OR. The message may include the instrument's serial number. The surgical hub may record the serial number when the hub receives the message. The instrument may include the serial number when it sends data to the surgical hub. The surgical hub may use the serial number in order to identify which instrument sent the data. The surgical hub may send a response message that indicates to the instrument that the surgical hub received the message.

In examples, boundaries of the surgical OR may be determined by camera information sent to the surgical hub. A surgical hub may identify when an object in the surgical OR moved, for example, based on the camera information. For example, the surgical OR may identify that a medical staff member bumped into a surgical robot arm based on camera information that tracked the medical staff member's movement and the surgical robot arm's movement.

The surgical hub may generate information related to the change in camera information over a period of time. The surgical hub may send the information to one or more displays accessible to the medical staff. In examples, the surgical hub may determine when a medical staff member is confused based on the camera information. In such a case, the surgical hub may determine an instrument being used by the medical staff member and, based on the instrument, the surgical hub may output a next step to a display accessible to the medical staff member.

In examples, the surgical hub may receive information associated with the patient. For example, a surgeon may be firing an energy beam on an area of the patient's body. In such a case, the surgical hub may overlay the firing location onto the monitor of the firing device being used by the surgeon. The firing information may be outputted on secondary displays accessible to the medical staff supporting the surgeon. In such a case, the medical staff may know which instrument is being fired.

The surgical hub may be aware of an indicator on each medical instrument. The camera may identify the indicator and send the indicator to the surgical hub along with the medical instrument's location (e.g., via coordinate points). In examples, the indicator may include indexing ports and/or fiducial markers. The indicator may include qualities about the instrument such as the length and thickness of the instrument shaft. The surgical hub may scale the data sent to the instrument based on the qualifies. The cameras may identify indexing coordination and/or registration points of the one or more instruments.

In examples, the camera may identify the instruments based on the characteristics of the instrument. For example, the camera may use spatial recognition to model the shape of the instrument. In such a case, the camera may identify the instrument based on the shape. For example, the camera may identify a handle resembling an endocutter handle and may determine that the instrument is an endo cutter.

The camera may generate data based on a display in the surgical OR. The camera may overlay information onto the display. The information may include information from another display. For example, a surgeon may request information related to a generator power level, EKG measurements, and instrument firing status. In such a case, the instrument may include a display that shows all three of these values. A surgical hub may port the information to the display the surgeon looks at from a laparoscopic point of view.

The surgical hub may identify and/or recognize one or more devices that may not be compatible with each other. The surgical hub may standardize the data into a form that may allow data to be exchanged between the devices.

The surgical hub may include machine learning that analyzes the metadata as described herein over time. The metadata may be based on camera information sent to the surgical hub. For example, the camera may read information on a display and send the information to the surgical hub over a duration of time. The surgical hub may input the information into a machine learning model to determine, for example, what the surgeon may be doing. The machine learning model may determine suggestions for the surgeon and the surgeon may send the suggestions to the display accessible by the surgeon. The machine learning module may determine when and/or where the surgical hub should send the information. For example, the machine learning model may tell the surgical hub to send information related to ligating the IMA when the surgeon performs mobilization.

The machine learning as described herein may allow the surgical hub to customize the data exchanged based on the medical staff. For example, the surgical hub may retrieve the identity of the surgeon performing the surgery and input the identity into the machine learning model. The machine learning model may adjust the suggestions based on the identity.

The surgical hub may filter and/or coordinate the data based on what the medical staff needs at a given time. For example, the surgical hub may comprise data related to the battery level of a harmonic scalpel. The surgeon may be performing a surgical task that does not involve the harmonic scalpel. In such a case, the surgical hub may filter out the harmonic scalpel data. The surgical hub may send the filtered data to a display accessible by the surgeon.

The surgical hub may determine the amount of data that may be sent to a display screen based on what the medical staff is doing. For example, the surgeon may be performing a critical task of the surgery. The surgical hub may determine not to send a visual graph to the display screen, for example, as it may distract the surgeon.

One or more monitoring systems may be provided. Hub adaptation and/or hub control may change based on spatial awareness of objects and personnel within the surgical OR.

Hub identification and/or tracking of objects and/or tracking of personnel within the surgical OR may be used to overlay data that is custom to a user's need. A surgical hub may include a system for monitoring one or more users within the surgical OR and/or the surgical instruments entering or leaving different predefined spaces within the surgical OR, for example, throughout tasks related to the procedure being conducted. The spaces may include the stock area, the mayo stand, and/or the surgical site. Tracking of the instrument may include ensuring that the instrument is ready for use in the procedural tasks needed and/or is in a state to operate correctly. The surgical hub may attach data to the instruments based on the surgical step and/or based on the user and/or monitor viewing the device. The attached data may be via built-in displays, displays of the room and/or tablets, and/or AR gear (e.g., glasses, personal displays, and/or audible instructions.) A step for tracking may be a final step and may include cleanup that ensures there are no retained objects in the patient and the product (e.g., all the product) is disposed of properly.

Hub spatial awareness and/or surgical suite monitoring and tracking of objects and/or people may be provided. Spatial awareness of surgical product and/or instruments may include their movement, positions, and/or orientations within the surgical OR. Instrument identification, spatial registration, and/or tracking within the OR may be provided.

The location where the product came from and/or the location of where the product is detected may trigger different interactions with the HCPs. The HCP may be alerted, for example, if the device has entered the OR. In such a case, the device may be added to inventory control.

In examples, tracking if a packaging has been opened may be provided. A surgical hub may use a camera, a sensor, and/or the like to determine if a package is present in an area, such as an area of an operating room. The surgical hub may determine if the package has been opened. For example, the surgical hub may receive a signal from a sensor associated with the package indicating that the package has been opened. As another example, the surgical hub may determine using a camera that the package has been opened. When it is determined that the package has been opened, the surgical hub may lock a time associated with the package being opened. The surgical hub may note in an inventory database that the package has been opened, such that the inventory may reflect that the object has been used.

Orientation and/or environmental parameters of the products may be used to trigger interactions and/or notifications to the HCP, for example, for actions and/or cautions. For example, Gyroscope and/or 3-axis accelerometers may be used to determine device orientation and/or position.

A surgical hub may alert a device of special environmental conditions to be aware of. For example, current OR atmospheric pressure may impact device performance. In such a case, the device may be alerted of potential adjustments it may need to make for optimal performance. Hub may inform devices of special internal conditions (e.g., any special internal conditions) that the patient presents.

The instruments may comprise spatial registration markers and/or visible fiducial markers on the devices that are monitorable by the hub and/or is the hub's sensor arrays. The marks may be in a predefined pattern and the hub may use an index of the devices for their markers and/or instrument configurations. In examples, the hub may be able to use the marks to identify and/or model the instrument with the 3D computer environment the hub creates and/or records.

The marks may allow a hub to adjust images and/or projections of an instrument for translation, rotation, scale, skew, and/or perspective. For example, a hub may present an augmented reality image that may show a portion of a medical instrument that may be scaled. The hub may be enabled to detect and/or monitor the instruments, for example, if a portion of the instrument is obscured.

For visible monitoring there may be a camera calibration that may be automatically conducted, for example, when the system starts up. There may be a predefined set of markers associated with the hub camera that may be fixed and may allow the hub to calibrate the camera for distance and/or focal length. In examples, the hub may determine the exact length from the hub or another calibration preset scale, for example, that may be within the OR. The hub may use the measure and/or the scale to calibrate the camera and/or focal distance.

The hub may determine the exact distance via another measurement system integral to the hub, such as laser doppler, ultrasonic pinging, RF, and/or other energy digital communication. Distance may be inferred from active or passive electronic signal processing. By monitoring the signal strength and compensating for emission power, emitting device antenna path, fight path, receiving device antenna path, and receiver sensitivity the communication between two Bluetooth paired systems may be used to determine the distance within the room Bluetooth paired systems are apart.

UHF or HF RFID tagged object tracking may involve a combination of predefined tag and/or distances in combination with unknown tags. The tags may identify the product in question and may provide information about the product. The tags may allow the product to be tracked within the room, for example, once identified.

RFID map made from passive or active references tags with known location (e.g., landmarks) may locate an unknown tag detected by the RFID reader antennas.

The system may measure one or more distances between readers and common detected tags, for example, using a large scale path loss propagation model. In examples, the system may calculate the distance between the unknown tag and the detected landmarks (e.g., inter-tags distance).

Use of millimeter-wave radar and/or tracking of objects may be provided. Millimeter-wave radar with a micrometer accuracy may be provided. A radar operating using frequency-modulated continuous waves (FMCW) may show how frequency and/or a phase of radar beat signal may be used to determine the distance between the radar sensor and the object from which the radar signal is reflected.

Instrument identification, spatial registration, and/or tracking within the OR may be provided. Instrument tracking spatially within the OR and/or through utilization may provide guidance on steps and/or supplementation of other collected and/or streamed data. Instruments may be tracked by cameras within the OR and/or cameras inside the patient.

The hub may monitor the connectivity of attached wired and/or wireless devices, detection of the room, and/or location of the devices and/or people within the OR (e.g., via ultrasound and/or visual cameras and customization of data on the displays for the user viewing the display). In examples, room displays may be used to look at the OR and/or to look at the OR through a picture-in-picture view. The display the surgeon sees may be allowed to show the same room and scope view. In examples, the display may be allowed to show differing information respective to the scrub nurse and assistant surgeon. The differing information may allow the scrub nurse and the assistant surgeon to see their job and how the devices being used relate to their specific tasks.

Setup and cleanup instrument counting may be provided. For example, the surgical hub may track an instrument. The surgical hub may determine that the instrument may need to be set up and may send a notification and/or instructions to an HCP. The surgical hub may determine that the instrument may need to be cleaned. The surgical hub may send a notification and order instructions to the HCP.

Utilization of an HCP worn or concentric camera may monitor what devices have been brought into the OR and/or may leave the OR. For example, the HCP may be wearing a camera. The camera may be within safety glasses that may be worn by the HCP. The camera may view what the HCP may be viewing. The camera may detect that an instrument may have entered the view of the HCP. The camera may identify the instrument. The camera may determine that the instrument may have been brought into the OR.

Cameras on HCP augmented reality gear may see what instruments are being handled. It may be determined, for example, using the augmented reality gear, that an instrument may comprise a label that may provide an identity. In examples, the cameras may scan bar codes and/or QR codes, for example, to identify serial numbers and/or product specifications.

The AR device may highlight viable reloads, for example, if an instrument has been specified for a procedure through the procedure plan or having been unpackaged within the OR as the HCP looks over stock room storage of reloads. The AR device may highlight via multiple levels competitive verse recommended for the patient and/or procedure.

Product scanning devices (e.g., barcode scanning laser, radio frequency identification (RFID) handheld scanner, RFID doorway scanner, optical QR code reader or camera, and/or another inventory scanning system) may be used to track and/or tag what products have been used in an OR. These scanners may ensure that the products brought into the OR are removed.

As two items that are related are scanned in, the hub may identify the compatibility of the items and may highlight discrepancies. As the scanning system scans a reload or instrument that is not compatible, the hub, scanner, and/or other user interaction device may highlight the discrepancy before the products are removed from their sterile packaging. As the products are scanned for removal, the device may highlight the acceptable disposable and/or recovery methods for the device. The hub may update the scanners with regional information, for example, based on where the hub knows the procedure is being conducted.

In examples, the hub may communicate with the facility to determine the disposal vendors and/or the methods and/or locations the vendors for that facility want the systems to be discarded. The hub may notify the edge processing system, for example, to tabulate and/or notify the disposal. The hub may reclaim vendors, for example, if sufficient product is ready for removal.

The hub may analyze the quantity of devices, for example, which may be re-sterilized. The hub may analyze what methods are involved for a given device, for example, in order to assist hospital cleaning and/or sterilization departments with predicting capacity and/or anticipating workload.

Monitoring instruments entering or leaving the patient treatment site may be provided. For example, as sponges, sutures, instruments, etc. are moved from the Mayo cart to the surgical site, the items may be individually identified and/or monitored via optical, RFID, electromagnetic, and/or ultrasonic sensing systems. This may provide the hub situational awareness of the step or task that is underway. The hub may notify the supporting HCPs for next steps and/or anticipate participation. In examples, the hub may ensure that there are no retained surgical instruments in the patient.

The hub may track the instruments used in the surgery and may track how long the instrument may be used during the surgery, for example, to determine if the product was involved in the procedure or ended up being wasted product. Monitoring and/or annotation of other data monitoring systems with instrument proximity and usage may be provided. Instruments may be tracked by cameras within the OR and/or inside the patient.

HCPs interactions may be identified, for example, for annotating event and situational awareness. HCP tracking within the OR and/or monitoring interactions may be provided.

The hub, scanners, and/or monitoring systems may track the instruments and the users and HCPs interacting with them. In examples, the hub may track which HCP brought the inventory to the room and at what time. In examples, the hub may record the HCP that opened the sterile packaging and at what time. In examples, the hub may track how long the product has been open and under what environmental conditions.

In examples, the hub may track when the product is reliable and/or when the product effectiveness is beginning to be effected. The hub may provide one or more instructions to be taken to minimize the effect. In examples, the hub may track the HCP or surgeon that used the product.

Recorded metadata may include usage characteristics. Usage characteristics may include one or more of the following: patient, procedure, procedure step, usage amount, preference data, orientation, location, and/or the like relative to the surgical site, HCP tracking within the OR and monitoring interactions, or spatial and/or temporal tracking and recording of instrument and equipment operations and usage.

Monitoring and recording of time, position, and orientation recording of instruments during usage may be provided.

The detection, monitoring, and/or recording of the instruments with respect to each other, the surgical staff, the room equipment, furniture, and the patient may enable the data analysis of usage, ease of use, common usage grips, and/or handling, as well as the amount of time the instruments are in differing orientations.

Tracking of the instrument and the instrument's orientation and which cameras may visualize the instrument may allow the hub to overlay data and/or secondary imaging indicating a status, highlight, and/or instruction onto the instrument, for example, to assist the user of the instrument.

Overlay of data onto instrument aspects may be different for different views and/or viewers. In examples, the overlay may be changed by the system based on the user interacting with the device. In examples, the overlay may be different for different monitors of the device.

For example, a surgeon may perform a thoracic lobectomy and may be approaching the vascular transection step. The vascular endocutter may be missing from the OR mayo cart and may be present in the stock area within the cabinets at the perimeter of the room. In such a case, the space on the mayo cart may be highlighted by the hub and the hub may monitor the space and/or may display an image indicating that that the device is missing at the space. The hub may indicate to the circulation nurse where the vascular endocutter is located. The nurse may bring the device into the area and may open and drop it sterilely onto the mayo stand and the camera may automatically identify the device and may identify that the device is unloaded. The monitor for the nurse may overlay the unloaded status and the controls to actuate, for example, to begin the loading steps. In such a case, the monitor for the surgeon may show the devices and instead of loading highlight the monitor may show the tissue type compatibility, reload need, and/or the status of the device. In such a case, the overlay of data and the highlighted data may be different for different users and may be different for the different displays looking at the device. The hub may record all of the operations and tasks in time for compilation (e.g., later compilation). The displays may be personal displays such as wearables, local displays on the device, and/or AR glasses or equipment.

In examples, overlay of data onto instrument aspects may be different for different views or viewers.

Image capturing of the areas outside the abdomen (e.g., device orientation, position, and status as well as user body position, staff activities, and other actions within the OR, etc.) may improve the placement, and/or control of the surgical device in use.

Spatial awareness of system integration and connections may be provided.

Adaptive control of interactions may be based on distance, wiring linkages, and/or port attachments.

Detection of the OR room and the hub(s) within the OR may allow the systems to define the room boundaries, to know which hubs to communicate to, and/or to know what list and/or procedure needs to compare the product for authentication and/or compatibility issues.

In examples, the camera(s) may be utilized within the OR to determine the setup, location, interconnection, and/or orientation of the equipment connected to the hub, robot, or room to configure the setup of the systems.

OR cameras and displays may identify equipment. OR cameras and display may be used to setup and initiation the equipment.

In examples, the camera may guide the user in reconfiguration and/or trouble shooting of the system layout, for example, to reconfigure the interconnections of the coupling of multiple systems to achieve inter-connectivity.

Equipment that is close to each other and may interfere or inhibit function of one or more of the equipment may be identified.

Patient attached leads and/or other incorrect setup and connections may be identified and the user may be instructed on how to correct the issue.

In examples, one or more display in the room may be configured to help a health care professional. For example, one display may be configured to help a first HCP and a second display may be configured to a second HCP. In an example, a display may be configured to provide steps-for-use for a medical instrument, a procedure task, and/or the like. Information displayed based on the user. For example, a first display may display a first set of information for a first HCP based on the task and/or job performed by the second HCP, and a second display may display second set of information for a second HCP based on the task and/or job performed by the second HCP. A display or a first portion of a display may show tasks and/or locations of a surgery while another display, or a second portion of the display may show a surgical view.

Displayed information based on the user and/or the user's location within the OR may be customized.

During surgery an OR team may perform function in coordination with one another, for example, to create an atmosphere that benefits the patient. Personnel inside the OR may comprise the operating surgeon, assistants to the surgeon, a scrub person, an anesthesiologist, and/or a circulating nurse. Each member of the team may comprise different responsibilities throughout the procedure and may interact amongst each other and may be in sync with each other in order for efficiency and successful outcomes. In examples, OR rooms may be intense, high stress, and challenging environments in which a medical staff member may get distracted and/or forget important steps that may cause delays and/or disruptions in focus with individuals and/or other team members. Utilization of the OR room displays and/or tablets may be customized to help each of the healthcare providers to know which action to do (e.g., based on monitoring the viewing user), steps-for-use, procedure step that are needed, or to predict steps to optimize the efficiency and/or focus of the team. The OR displays may be unique to each staff member and each staff member's responsibilities. In such a case, the individual looking at a monitor may be identified and the monitor may display that individual's task details.

An example of an individual involved in the surgical OR may be the surgeon.

For example, during the procedure, the display or a corner of the display to not occlude the surgeons view may identify which instrument and/or device was in his hand and may provide a steps for use (e.g., either text or visual image highlight the buttons to a user). If a step is detected that the step was pressed in a wrong sequence, the display may highlight the step and may alert the user.

In examples, prior to the start of surgery, the display that the surgeon and/or assistant are looking at may show a snapshot of the gold standard and/or watch-outs for risks for that patient based on patients bio markers.

In examples, during surgery the surgeon may be picking-up or putting-down instruments on the operating table or instrument table and the screen may provide indication(s) in the corner of the screen of where the instrument is located (e.g., prior to him needing the instrument) and the surgeon may keep focus on the screen and reach for the instrument with his hands. In examples, the hub knowing the procedure steps and knowing what instruments are plugged into it may know when instruments are needed prior to use. The monitoring system may verify that a task is completed and may know which step is needed next. The notification of what instrument is needed and when it is needed may be notified to the scrub nurse and/or assistant and they may be prepared to hand to the surgeon prior to him requesting or needing the instrument, e.g., which may improve efficiency within the OR and allow the surgeon to maintain focus.

An example of an individual involved in the surgical OR may be the scrub nurse.

For example, during surgery, the scrub nurse, circulating nurse, and/or assistant may be responsible for altering the settings of the equipment for the surgeon. In such a case, the display may provide an overview of the OR room layout and may highlight the location of the piece of equipment that requires modification. The display may show a visual image of the piece of equipment and may show steps for use on how to adjunct the setting. In examples, the monitor, hub, and/or display may confirm that the correct setting is adjusted to the correct value, for example, as a verification.

For example, a scrub nurse may be responsible for ensuring tools and the field are sterile. In such a case, the display may be set up as a checklist, for example, to indicate items needed and confirm that the items are sterile. The display may provide an indication based on the procedure type, equipment required, and/or room layout. The display may indicate how the sterile field should be and may confirm that the sterile field is ready.

An example of an individual involved in the surgical OR may be the circulating nurse.

For example, a responsibility of the circulating nurse may be the accountability of the quantity of surgical items, for example, prior to the operation and after the operation to ensure no surgical items are retained in the patient. In such a case, the display may be used as a checklist and the hub knowing the procedure may create a checklist of the items involved in the surgery and may track as the surgery is performed and after the surgery is performed to ensure the items are collected. The display may highlight, for example, if there are discrepancies and may alert the team prior to starting the procedure or closing the site.

For example, a responsibility of the circulating nurse may be preparing and positing of the patient on the table. In such a case, the display may be used to indicate how the patient should be positioned on the table and the system may verify prior to starting the surgery. In examples, the patient placement may be based on surgeon preference and/or gold standard procedure data.

For example, a responsibility of the circulating nurse may be ensuring the correct site and procedure is completed on the patient. In such a case, the display may be used as guidance in preparation and/or verification of site and procedure completed.

An approach may be based on jobs and/or locations within the OR (e.g., geographically). In examples, the team may be divided into divisions according to the function of its members. One team may be a sterile OR team and may include operating surgeon, assistants to the surgeon, and scrub person(s). One team may be an Unsterile OR team and may include anesthesiologist or nurse anesthetist, circulator, and other OR members that may be needed in operating specialized machine or devices.

In examples, the sterile OR team may perform surgical hand washing (e.g., arms are included) and may prepare sterile gowns and gloves. In such a case, the displays within the OR may identify the items needed for each of the assigned staff and may use the monitoring system to confirm the task are completed, for example, before allowing the screens to go into the procedure mode. The display may highlight and notify, for example, if a staff member missed a step. The surgical OR team may enter the sterile field. In such a case, the display may show a layout of the OR room and may highlight the different sections or boundary of the sterile field to the staff. Operating rooms may differ in layout and/or boundaries or new staff members in which the monitor may be used to inform and/or remind of sterile field boundary for the OR room. The surgical OR team may handle sterile items. In such a case, the hub may monitor and provide notification on the display on who has authorization to use and/or pass a sterile instrument and if a non-sterile team member attempted to use and/or pass, the hub may provide on the display a warning and/or notification directed at that staff member.

In examples, the unsterile OR team may include an anesthesiologist, circulator, biomedical technicians, radiology technicians, and/or other staff that may set up and/or operate specialized equipment and/or devices essential in monitoring the patient during a surgical operation.

The displayed information may be customized based on the user and/or the user's location within the OR. In examples, spatial awareness may be supplemented with temporal awareness. For example, when a task is needed relative to the procedure, the supplementation may include where the hub is and how the hub is connected to other systems within the OR. Temporal as well as spatial awareness of module and system connection to the hub may be provided. Hub may track OR staff locations within the OR suite. For example, the primary and/or secondary tasks may be displayed on the monitor closest to the staffs' current position. Additional tasks may be visually shown in a list. For example, the current task may be highlighted and/or bolded. In examples, the hub may show the current instructions and may show if the staff is not following the current procedural steps.

Sub-system self-identification, indexing, and/or integration may be provided. The hub or a higher level hierarchical system may automatically identify attached devices based on the devices' ID, signature of the devices' power usage or provided data streams, and/or by visually or electronically viewing the attached devices. Automatic identification and setup of attached devices based on their data or power signatures may be provided.

In examples, the data stream being communicated from the device to the hub may be used to identify the device, the device's setup configuration, and the device's operating program by comparing the data stream with previous summaries of data streams provided by the device. The signature of the metadata, organization of the data, and/or organization of the communication packets may be specific to the function, make, and model of the device and may be used to track and automatically setup the system, for example, when the device is attached to a higher level system.

The headers, data packet details, metadata, transmission frequency, and/or hand-shake may be used to ID a specific piece of equipment relative to other similar equipment. Errors, consistence noise, and/or other individualized additive elements may create a trackable signature of data transmission and/or power usage to ID a unit.

Automatic identification and/or setup of attached devices based on their data or power signatures may be provided.

Hub identification and/or tracking of objects and/or personnel within the OR to overlay data that is custom to the users need may be provided. For example, a surgical hub may include a system for monitoring the users within the room and the surgical instruments entering or leaving different predefined spaces within the OR throughout specific steps and/or tasks related to the procedure being conducted. The spaces may include the stock area, the mayo stand, and/or the surgical site. Tracking of the instrument may include ensuring the instrument is ready for use in the procedural steps needed and is in a state to operate correctly. In examples, the hub may attach data to the instruments based on the surgical step and/or the user or monitor viewing the device. For example, the attached data may be via the built-in displays, displays of the room and/or tablets, and/or AR gear (e.g., glasses, personal displays, or audible instructions.) One of the tasks for tracking may the finals step and cleanup insuring there are no retained objects in the patient and the product is disposed of properly.

Interaction with other facility systems and servers may be provided. OR inventory management system may be included in the hub. For example, the OR inventory management system may include billing and/or reimbursement authorization of treatment adjustments.

For example, the OR inventory management system may include adjustment of the procedure approach, instruments used, and/or medicant adjuncts based on the pre-authorization or procedure classifications.

Advanced imaging may be provided. Monitoring systems may be provided.

Hub adaptive control and/or operation of display and display interactions may be based on recognition of users, equipment, and/or usage, and user or equipment needs.

In examples, configuration of the display settings and/or displayed information may be based on the recognition of the user(s), and/or awareness of procedure, location, or usage. In examples, a surgical hub may be interconnected to display devices within the OR and may monitor and track the personnel, the procedure, and/or the patient. The hub may comprise the capability of communicating changes in each of the displays based on the situation at hand and/or the user or viewer of the display. The hub may be monitoring the procedure and/or patient, may be tracking personnel within the OR, and may be capable of relating position and/or direction of a display with the user of the display. In examples, the hub may comprise recognition algorithms that enable the hub to differentiate between users, equipment, and/or instruments within view of the hub's sensors within the OR. The hub may customize the display setting, the displayed information, and/or the instructions for the user and the step or task at hand. For example, the displays may be personal display units such as AR devices, surgical interface tables, equipment displays, local instrument displays, and/or room monitors positioned and aimed towards certain user locations.

Smart display system interaction and control may be provided. Cameras and/or sensors on one display may be used to monitor other display systems within the OR. Monitoring of one display with a camera may be used for display control and/or data collection.

In examples, a system may be used to monitor utilization, setup parameters, and/or determine which users are viewing and/or interacting with displays in the OR. A display may be monitoring information on another display for control cues and may be able to repeat or redisplay information from the other display.

In examples, the surgeon interaction display (e.g., main surgeon interaction display) may be watching patient monitoring systems such as EKG, blood pressure, sedation levels, O2 levels, etc. and may add information related to the patient monitoring system to its primary display. In such a case, the surgeon may look in one location for the compiled data (e.g., all the compiled data).

Displays may be broadcasting information in light bands outside the visual range or audible levels outside of the hearing range, for example, in order to coordinate information between displays for the users, which may be HCPs.

In examples, monitoring of multiple displays may be used as a level of confirmation of the procedure step, patient vitals, instruments in use, and/or the like. Multiple cameras may feed information into the hub system and the cameras may derive different information and may be used to confirm one another.

Assisted and/or expanded control of displays via interaction with the system verbally, visually, or physically may provide deep context to the display interaction. Assisted AI control of the display via variable inputs from the user may be provided.

Smart device control and/or interaction with smart displays may be used in order to allow the users within the room to control the displays with the devices in the users' control. For example, AR gear, smart watches, surgeon tables, and/or other instruments may be used to create individual links and/or pairing to some or all the displays in the OR, for example, in order to control what is displayed, and the parameters of the display.

Procedure, HCPs, and/or patient data may be used to determine default interaction controls for the display to allow the users intuitive interaction and control of the display and the display's data.

Voice-controlled displays may be used for changing display parameters or what is displayed or connected to the display.

AI interaction and/or direction of control parameters of the displays may be provided, for example, which may include predefined control words and/or gestures as well as ability search behavior and/or systems to interpolate commands between the predefined variables.

In examples, individualized experiences and/or responses may be used as the system may differentiate between individuals based on voice recognition, imaging of the users, and/or other electronic identification of the individuals.

Touch display supplementation of the display settings and control may enable navigation through options and may explore aspects of the displayed imaging and analyses. Assisted AI control of the display via variable inputs from the user may be provided.

A communication portal may be used by an HCP to communicate with another HCP. In examples, the verbal inputs may be utilized by the smart display to control communication outside of the OR.

The display may transcribe the spoke request and/or information and may send (e.g., digitally send) the message and/or request via SMS, email, and/or other electronic means.

Requesting a skill set and/or person may allow the display and/or hub to identify and locate the individual involved in assisting in the requested task and may send a notification to the person indicating the need for help and where the help is needed.

In examples, the system may segment the requested help or step into the system's needed tasks and may identify the available personnel (e.g., the most available personnel) with the needed skill set and notify the personnel of the need for help.

The system may make skill set and/or person recommendations to the surgeon and may highlight, rank, specify strengths or weaknesses, and/or the like of the recommendations and may allow the surgeon to choose. In such a case, the surgeon may be informed (e.g., significantly informed).

Smart display setup configurations may be based on identification of the users and/or staff, previous usage, and/or procedure or patient parameters.

Smart setup, configuration, and/or orientation control of the display may be based on user ID. In examples, previous uses may be used for improving the location, orientation, and/or displayed information.

Internal display setting may be adjusted based on the sensed users, procedure, and/or patient configuration, for example, which may increase contrast, may make the color saturation greater or less, and/or may change the background or base coloration to improve visibility and/or interpretation of the data being displayed by a user.

User interaction and utilization may include which HCPs use the displayed information, how often is the system or display used, what is the display information used for, which HCPs interact the most with the system, the orientation, utilization timing and amount, and where within the room the users are located.

Smart setup, configuration, and/or orientation control of the display may be based on user ID. Control of collected and/or communicated data by which systems may be known and the communication through which means and pipe ways may be known.

Circumstances regarding the monitored product and monitored by what object may be recorded, for example, to understand workflow and product flow through the facility.

In examples, the monitored data may include what system(s) have detected the item and where, when, and in what state the item may be in when detected.

Metadata identification of a source of the monitored data may be tied to the data. Metadata identification may include one or more of the following: measures and/or tracking, orientation, distance and/or location, height differentiation, time monitoring systems, NFC ultra-wideband (UWB) bluetooth visual visible light spectrum, multi-spectral aspects, passive thermography, surgical staff stressors, and illness task criticality.

Interaction with other facility systems and servers may be provided. OR inventory management system may be included in the hub. For example, the OR inventory management system may include billing and/or reimbursement authorization of treatment adjustments. For example, the OR inventory management system may include adjustment of the procedure approach, instruments used, and/or medicant adjuncts based on the pre-authorization or procedure classifications.

Figure 72:
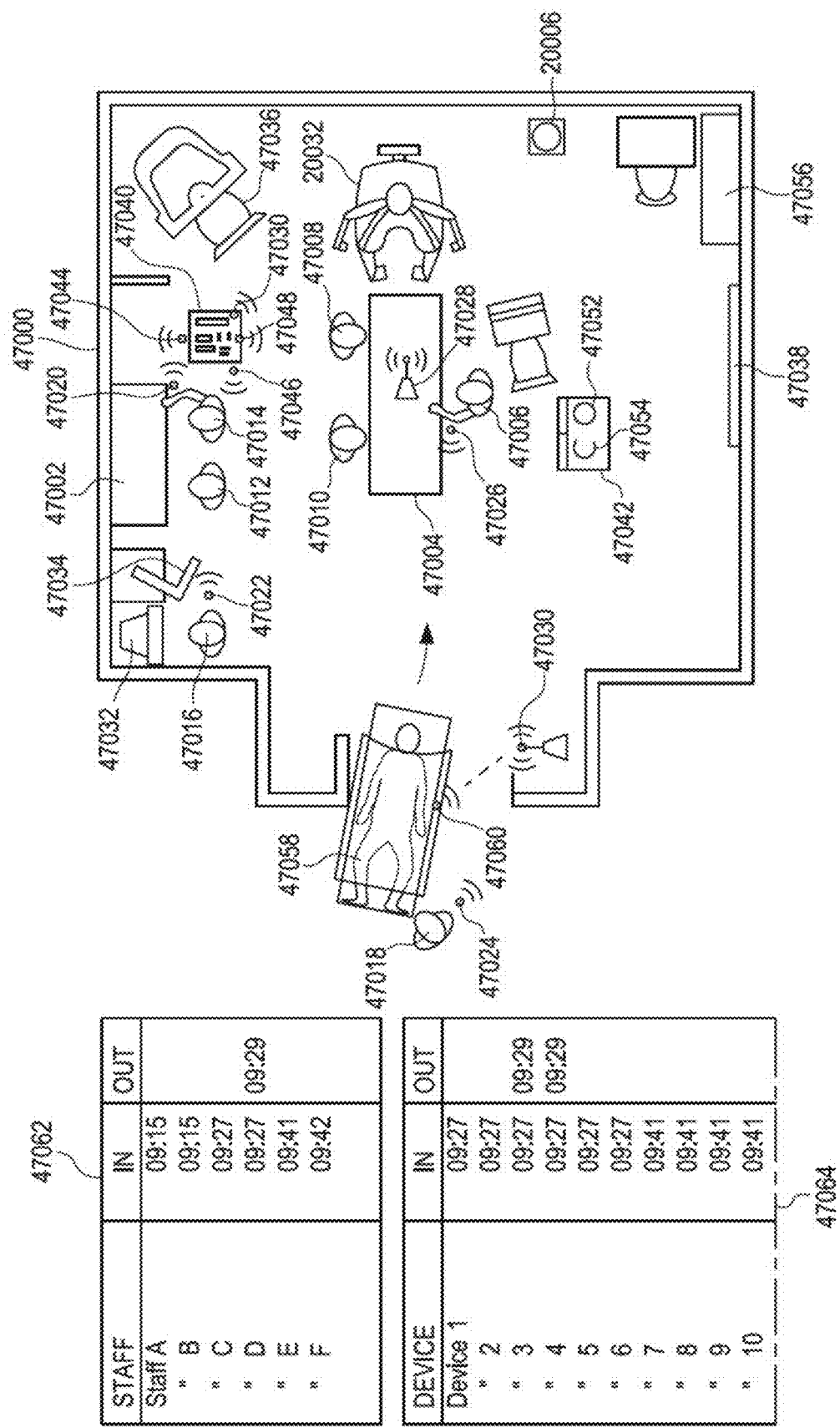
FIG. 72 depicts a diagram of an OR that may include a surgical hub for tracking patients, health care providers, surgical objects, surgical projects, and/or surgical instruments.

FIG. 72 depicts a diagram of an OR that may include a surgical hub for tracking patients, health care providers, surgical objects, surgical projects, and/or surgical instruments. As described herein, a sensor may send or receive a signal that may be used by the surgical hub 20006. For example, a sensor may be an RFID, a Bluetooth device, a computer, a wearable device, a smartphone, a smartwatch, a radio transmitter dash receiver, and/or the like.

In examples, one or more surgical hubs may determine if an object is located in the surgical OR. In examples, the surgical hub(s) may determine if an object is absent from the surgical OR. In examples, the surgical hub(s) may determine if the object is located in a room adjacent to the surgical OR. The surgical hub(s) may operate in concert or may operate independently. An object may be a smart device such as a smart medical instrument.

The operating room 47000 may include a surgical hub, such as surgical hub 20006. The surgical hub 20006 may use a ping (e.g., an ultrasonic ping), for example, to define the boundaries (e.g., walls) of the surgical OR. The surgical hub 20006 may be aware when objects enter or leave the surgical OR. The surgical hub 20006 may be connected to a number of sensors that may be used to detect the presence, absence, and/or movement of a patient, an HCP, a surgical product, a surgical instrument, and/or the like. As used herein, a surgical instrument may be referred to as a medical instrument or vice versa.

The surgical hub 20006 may include a number of sensors and/or may communicate with a number of sensors to determine one or more areas and/or spaces of the operating room. For example, the surgical hub 20006 may determine that the operating room 47000 may include a sterile field and a non-sterile field. The surgical hub 20006 may determine that the operating room 47000 may include a back table 47002 that may be used by an HCP to prepare medical instruments and/or products for surgery. The surgical hub 20006 may determine that the operating room 47000 may include an operating table 47004. The surgical hub 2006 may also determine other areas that may be associated with the operating room 47000, such as an area occupied by a patient, an area occupied by an HCP, an area outside the operating room 47000, an operating room adjacent to the operating room 47000, and/or the like. The areas may include the stock area, the mayo stand, and/or the surgical site.

The operating room 47000 may include a patient side cart 20032. The patient side cart 20032 may also be referred to as a surgical robot. The surgical hub 20006 may monitor the surgical robot 20032. The surgical hub 20006 may determine the location of the surgical robot 20032. The surgical hub 20006 may determine whether the surgical robot 20032 may be within an area that may include a sterile field. The surgical hub 20006 may determine whether the surgical robot 20032 may be within an area that may include a non-sterile field. In an example, when the surgical robot 20032 may have been in a non-sterile field and the surgical hub 20006 determines that the surgical robot 20032 may not have been prepared for surgery, the surgical hub 20006 may notify the HCP that the surgical robot 20032 is to be cleaned and/or prepared for surgery before use.

The operating room 47000 may include one or more HCPs, such as HCP 47006, HCP 47008, HCP 470010, HCP 47012, HCP 47014, HCP 47016, and/or HCP 47018. The surgical hub 20006 may use one or more sensors and/or one or more cameras within the operating room 47000 to monitor, track, and/or detect the one or more HCPS. For example, HCP 47014, HCP 47016, and/or HCP 47006 may be wearing a wearable sensor which may be detected by the surgical hub 20006. The wearable sensors may include sensor 47020 which may be associated with the HCP 47014, sensor 47022 which may be associated with the HCP 47016, sensor 47024 which may be associated with the HCP 47018, and/or sensor 47026 which may be associated with the HCP 47006. The wearable sensors may be any suitable sensor for tracking a person, such as an RFID tag, a smartwatch, a smartphone, a computer, a Bluetooth device, and/or the like.

The surgical hub 20006 may monitor and/or track HCP using a wearable device. For example, the surgical hub 20006 may receive a signal from the wearable device that may indicate the presence of the device in the room period by associating the wearable device with a person. The surgical hub 20006 may estimate and/or determine where that person may be within the OR. The surgical hub 20006 may use a location determined from a wearable device to determine an area where the associated person may be within the OR. For example, the surgical hub 20006 may determine that the HCP 47014 may be at a back table. Using contextual information, the surgical hub 2006 may determine a task that may be performed during a surgery and may associate the location of an HCP with that task. For example, the surgical hub 20006 may determine that the HCP 47014 is at the back table 47002 to prepare a medical instrument to be used in current surgical task.

The operating room may include one or more cameras. The one or more cameras may include cameras that may be on a wearable device that may be worn by an HCP. For example, the HCP may be wearing safety glasses that may include a camera. The surgical hub 20006 may utilize data from one or more cameras within the OR to determine a location of a person, such as an HCP. For example, the surgical hub 20006 may use a camera within the operating room to determine the location of the HCP 47010. As another example, the surgical hub 2006 may use a camera associated with safety glasses worn by the HCP 47010 to determine the location of the HCP 47008.

The operating room 47000 may include sensors that are associated with areas of the operating room. For example, the sensor 47028 may be placed on or near the operating table 47004 such that the surgical hub 2006 may associate the sensor 47028 with the operating table 47004. As another example, sensor 47030 may be near the entrance of the operating room 47000 such that the surgical hub 20006 may associate the sensor 47030 with the entrance of the operating room 47000.

The operating room 47000 may include one or more displays such as display 47032, display 47034, display 47036, and/or display 47038. The surgical hub 20006 may determine the presence of a display, may determine the capability of the display, and may determine what may be displayed on a display. For example, surgical hub 20006 may determine that display 47038 may be a primary display that may be used for displaying X-rays of the patient during a surgical task of the surgical procedure. The surgical hub 20006 may determine that the display 47038 is a display that may be capable of super imposing one or more images. The surgical hub 20006 may instruct display 47038 to display the X-rays of the patient along with a video stream taken from a medical instrument that is being used by HCP 47008 during a surgery. As another example, surgical hub 20006 may determine that display 47036 may be used by HCP 47014. The surgical hub 20006 may determine data that may be relevant to HCP 47014 and may send an instruction 247036 to display the data that is relevant to HCP 47014.

Operating room 47000 may include Mayo stand 47040 and Mayo stand 47042. The surgical hub 20006 may determine a terminal location of Mayo stand 47040 and/or Mayo stand 47042. For example, the surgical hub 20006 may use a camera located within the operating room 47000 to determine the location of Mayo stand 7040 and/or Mayo stand 47042. The surgical hub 20006 may determine that Mayo stand 47040 and/or Mayo stand 7042 may be located within a sterile field. Surgical hub 20006 may determine that Mayo stand 47040 may be associated with a number of medical instruments. For example, surgical hub 20006 may determine that medical instrument 47044, medical instrument 47046, medical instrument 47048, and medical instrument for 47050 may be on top of Mayo stand 47040. Surgical hub 20006 may determine that Mayo stand 47042 may be associated with a number of medical products. For example, medical product (e.g., surgical product) 47052 and medical product 47054 may be located on top of Mayo stand for 47042. Surgical hub 20006 may determine that surgical product 47054 may have entered the surgical room at a first time and may have been opened at a second time. Surgical hub 20006 may determine the surgical product 47052 may have entered the surgical room at a time and may not have been opened. Surgical hub 20006 may determine that surgical product 47052 may be associated with another surgical product which may be stored at storage 47056, and surgical hub 20006 may notify HCP that the surgical product associated with surgical product 47052 may be located at storage 47056.

Surgical hub 20006 may determine a location of a patient. For example, patient 47058 may be associated with a sensor 47060. Sensor 47060 may be a wearable device. Surgical hub 2006 may determine that patient 47058 may have entered the operating room 47000 at a time. Surgical hub 20006 may record that patient 4705 having entered the operating room 4700 at the time. Surgical hub 20006 may determine that patient 47058 may have been prepared for surgery, may be moving through a non-sterile field, and may be moving toward operating table 47004. Surgical hub 20006 may identify individuals and their objects that may come in contact with patient 47058. For example, surgical hub 20006 may log a list of medical instruments that may have been used on patient 47058; medical instruments that may be used on patient 47058; surgical products that may be used during the surgical procedure to be performed on patient 47058; HCPs that may be involved with the surgical procedure to be performed on patient 47058; HCPs that may have come in contact with patient 4705 before, during, or after the surgical procedure, and/or the like.

Surgical hub 20006 may keep a log of surgical staff that may be involved with the surgical procedure to be performed on patient 47058. For example, as shown at 47062, surgical hub 20006 may record when an HCP enters the operating room 47000 and may record when an HCP exits the operating room 47000. The surgical hub 20006 may record when patient 47058 enters or exits operating room 47000.

Surgical hub 20006 may keep a log of medical instruments, devices, and/or medical objects (e.g., medical products) that may be involved with the surgical procedure to be performed on patient 47058. For example, as shown at 47064, surgical hub 20006 may record when a medical device, such as a medical instrument, enters the operating room 47000 and may record when the medical device exits the operating room 47000.

The surgical hub 20006 may be included in a tiered software system. The surgical hub 20006 may use spatial awareness, for example, when determining if surgical objects are located in the surgical OR. As disclosed herein, a surgical object may be one or more of a surgical instrument, a surgical product, a medical device, a surgical device, a medical instrument, and/or the like. A medical object may register to the surgical hub 20006. For example, medical instrument 47046 may send a respective identification and/or serial numbers to the surgical hub 20006. The surgical hub 20006 may track medical instrument 47046 respective positions within the operating room 47000. In examples, one or more cameras may be used to track the objects. The cameras may be in communication with the surgical hub 27000.

The surgical hub 20006 may determine if an object is inside a patient and may indicate to remove the object. For example, the surgical hub 20006 may determine that surgical product 47054 has been opened and may have been placed inside patient 47058 during a surgical procedure. The surgical hub 20006 may determine and/or track a spatial temporal component associated with surgical product 47054. For example, the surgical hub 20006 may track when surgical product 47054 may have been opened and when surgical product 47054 may have been placed inside patient 47058. In an example, surgical hub 20006 may determine that surgical product 47054 is to be removed from patient 47058.

The surgical hub 20006 may determine and/or track a spatial temporal component associated with medical instrument 47044, medical instrument 47046, medical instrument 47048, and/or medical instrument 47050. The surgical hub may overlay data on medical instrument 47044, medical instrument 47046, medical instrument 47048, and/or medical instrument 47050. For example, the object may be the medical instrument 47044. A display may be configured for the overlaid data. The display may be included on the medical instrument 47044. The display may be attachable to the medical instrument 47044. The data may be depicted on the screen for a user to see. The cameras as described herein may observe a change in the surgical OR and may overlay data associated with the change to a medical instrument display.

The surgical hub 20006 may be aware of secondary objects located in a storage destination, such as storage 47056. The surgical hub may determine when one or more secondary objects are involved in a surgery. In examples, the surgical hub may communicate to an HCP (e.g., a rotating nurse) to retrieve the secondary objects from storage 47056 at a time for a surgical task to be performed.

The surgical hub 20006 may be aware of a medical instrument that may be involved in a surgery. For example, medical instrument 47044, medical instrument 47046, medical instrument 47048, and/or medical instrument 47050 may be involved in an upcoming surgical task of the surgery. The display 47034 may be accessible to a table nurse, such as HCP 47016, and may be in communication with the surgical hub 27000. The surgical hub may indicate the instrument involved in the surgery on the display. For example, the surgical hub 20006 may highlight the medical instrument 47046 on the display 47034. The instrument involved in the surgery may be located in a storage destination as described herein. The surgical hub may indicate the storage destination that the instrument is located at.

Augmented reality may be used by the surgical hub 20006 to indicate a medical instrument being used. For example, the augmented reality may be associated with a secondary display overlaid on another display. The surgical hub 20006 may use augmented reality to highlight the instrument involved in the surgery. For example, surgical hub 20006 may determine that medical instrument 47050 may be used by HCP 47008. The surgical hub 20006 may determine that HCP 47008 is wearing safety goggles that include a display. The surgical hub 20006 may send data associated with the medical instrument 450502 to the safety goggles associated with HCP 47008 such that data is overlaid over the view as HCP 47008 looks through the safety goggles.

The surgical hub 20006 may use one or more cameras within OR 47000 to analyze HCP, such as HCP 47008. Surgical hub 20006 may determine that HCP 47008 may be using medical instrument 47046. Surgical hub 20006 may determine that HCP 47008 maybe unsure about the current surgical test that involves HCP 47008. For example, surgical hub 20006 may analyze HCP 47008 gestures and/or posture and may determine that HCP 47008 may be confused or may be using medical instrument 47046 inefficiently. Surgical hub 20006 may send a notification to HCP 47008 using display 47038. The notification may indicate instructions regarding the surgical task to be performed using medical instrument 47046. The surgical hub 20006 may continue to monitor HCP 47008 to determine if the instructions assisted HCP 47008.

The surgical hub 20006 may customize and/or personalize one or more displays for an HCP. For example, surgical hub 20006 may customize display 47032 for HCP 47016. As another example, surgical hub 20006 may customize display 47038 for HCP 47008.

In examples, the surgical hub 20006 may be aware of which instruments are sterile or not sterile. For example, the surgical hub 20006 may track whether an instrument has been touched by a non-sterile medical staff and may determine that the instrument is not sterile. The surgical hub may indicate whether the instrument is located in a sterile or a non-sterile field. For example, the surgical hub 20006 may determine that medical instrument 47046 was sterile, may determine that HCP 47018 has come in contact with the medical instrument 7046, and may determine that medical instrument 47046 is no longer sterile. As another example, surgical hub 20006 may determine that medical instrument 47048 may have been dropped on the floor of operating room 47000 and may no longer be sterile. As another example, surgical hub 20006 may determine that surgical product 47054 may have been opened and may no longer be sterile.

Spatial temporal data associated with a medical object may be collected by the surgical hub 20006. The spatial temporal data may be the number of times an instrument was exchanged. For example, the spatial temporal data may indicate that the medical instrument 47044 was exchanged between HCP 47008 and HCP 47014 five times. The surgical hub may analyze the spatial temporal data. For example, the surgical hub 20006 may determine that medical instrument 47044 may be involved in the surgery based on a number of exchanges between HCP 47008 and HCP 47014. The surgical hub may analyze the spatial temporal data to optimize the surgical OR setup.

The surgical hub may coordinate the data being exchanged between medical objects in the surgical OR. For example, medical instrument 47046 may try to send information to display 47038, which may be an incorrect display. In such a case, the surgical hub 20006 may identify that display 47036 may be a suitable display. The surgical hub 20006 may send data to display 47036. The surgical hub 20006 may prevent medical instrument 47046 from sending information to display 47038.

A medical instrument and/or medical product may be associated with a power signature. The surgical hub 20006 may determine the power signature and may determine that a medical instrument and/or medical product has been powered on based on the power signature.

The surgical hub 20006 may identify and/or verify medical instruments by using data clusters and/or nexuses of data points. In examples, instrument orientations and/or ergonomic information related to the instruments may be determined using data clusters and/or nexuses of data points. For example, the surgical hub 20006 may receive data associated with display 47038 and display 47036, which may be associated with a generator located in the OR 47000. The generator may not be able send data directly to the surgical hub 20006. The surgical hub 20006 may use one or more cameras to monitor the display 47036 such that the surgical hub 20006 may have an ability to read the display 47036. For example the surgical hub 20006 may determine the power level of the generator from the display 47036 and may adjust one or more medical instruments in the OR 47000 based on the determined power level of the generator. As another example, surgical hub 20006 may determine a setting of the generator and may display the setting of the generator on display 47038. As another example, surgical hub 20006 may determine that there is an error code on display 47036 and may send notification to HCP 47008 regarding the error.

The surgical hub 20006 may receive a message from a medical instrument that indicates identifying information for the medical instrument. For example, medical instrument 47046 may send a message to surgical hub 20006 that may include a serial number for the medical instrument 47046. The surgical hub 27006 may log the serial number of the medical instrument 47046. The surgical hub 27006 may identify the medical instrument 47046 using the serial number and may customize one or more settings for the medical instrument 47046 based on the identification. The surgical hub 27006 may use the serial number to determine one or more capabilities of the medical device (e.g., medical instrument) 47046.

In examples, boundaries of the surgical OR may be determined by camera information sent to the surgical hub. A surgical hub may identify when an object in the surgical OR moved, for example, based on the camera information. For example, the surgical OR may identify that a medical staff member bumped into a surgical robot arm based on camera information that tracked the medical staff member's movement and the surgical robot arm's movement. For example, surgical hub 20006 may use a camera in OR 47000 to determine that HCP 47012 may have come in contact with surgical robot 20032. Surgical hub 20006 may send a notification to HCP 47008 that indicates contact occurred between surgical robot 20032 and HCP 47012.

In examples, the surgical hub may receive information associated with the patient 47058. For example, HCP 47010 may be firing an energy beam on an area of the body of patient 47058 using medical instrument 47048. In such a case, the surgical hub 20006 may overlay the firing location onto display 47038 which may be used by HCP 47010 during the firing of medical instrument. The firing information may be outputted on secondary display, such as display 47032, which may be accessible to the HCP 47016 that may be supporting HCP 47010.

The surgical hub 20006 may identify an indicator on a medical instrument, such as medical instrument 47050. For example, the surgical hub 20006 may use a camera within OR 47000 to identify medical instrument 47050. The surgical hub 20006 may retrieve information associated with the indicator. The indicator may include indexing ports and/or fiducial markers. The indicator may include qualities about medical instrument 47050 such as the length and thickness of the instrument shaft. The surgical hub 20006 may scale the data sent to the medical instrument 47050 based on the qualities. For example, the surgical hub 20006 may determine that medical instrument 47050 may not comprise a fast processor and may reduce amount of data sent to medical device 47050 to prevent the medical device 47050 from becoming less responsive. The cameras that may be used by surgical hub 20006 may identify indexing coordination and/or registration points of the one or more instruments.

The surgical hub 20006 may use a camera to identify a medical instrument based on a characteristic of the medical instrument. For example, surgical hub 20006 may use spatial recognition, via a camera for example, to model the shape of the instrument. In such a case, the camera may identify the instrument based on the shape. For example, surgical hub 20006 may identify medical instrument 47044 as an endo cutter based on an image captured by a camera that includes a shape that resembles an endo cutter.

The surgical hub 20006 may use one or more cameras in the operation room 47000 to generate data based on a display in the operation room 47000. For example, the surgical hub 20006 may use a camera to monitor medical instrument 47046 to determine a setting being displayed on a display that is part of medical instrument 47046. The surgical hub 20006 may read the setting from medical instrument 47046 and may display the setting on display 47038. The surgical hub 20006 may overlay information onto a display. The information may include information from another display. For example, HCP 47008 may request information related to a generator power level, EKG measurements, and instrument firing status. In such a case, the surgical hub 20006 may configure a display associated with medical instrument 47048 such that the display associated with medical instrument 47048 may show the generator power level, the EKG measurement, and the instrument firing status. The instrument may include a display that shows all three of these values. The surgical hub 20006 may port the information to the display that the HCP 47008 may be viewing from a laparoscopic point of view.

The surgical hub 20006 may recognize one or more devices that may not be compatible with each other. For example, surgical hub 20006 may determine that medical instrument 47046 may not be compatible with medical product 47052.

The surgical hub 20006 may take one or more actions to allow one device to be compatible with another device. For example, the surgical hub 20006 may standardize data from medical instrument 47046 such that medical instrument 47050 may be able to exchange data with the medical instrument for 47046.

The surgical hub 20006 may include machine learning that analyzes the metadata as described herein over time. The metadata may be based on camera information sent to the surgical hub 20006. For example, the camera may read information on a display and send the information to the surgical hub 20006 over a duration of time. The surgical hub may input the information into a machine learning model to determine, for example, what an HCP, such as HCP 47010 is doing. The machine learning model may determine suggestions for the HCP 47010 and the HCP 47010 may send the suggestions to the display accessible by the HCP 47010, such as display 47038. The machine learning module may determine when and/or where the surgical hub 20006 may send the information.

The surgical hub 20006 may filter and/or coordinate the data based on what the medical staff needs at a given time. For example, the surgical hub 20006 may comprise data related to the battery level of a harmonic scalpel. The HCP 47008 may be performing a surgical task that does not involve the harmonic scalpel. In such a case, the surgical hub 20006 may filter out the harmonic scalpel data. The surgical hub 20006 may send the filtered data to a display accessible by the surgeon.

Figure 73:
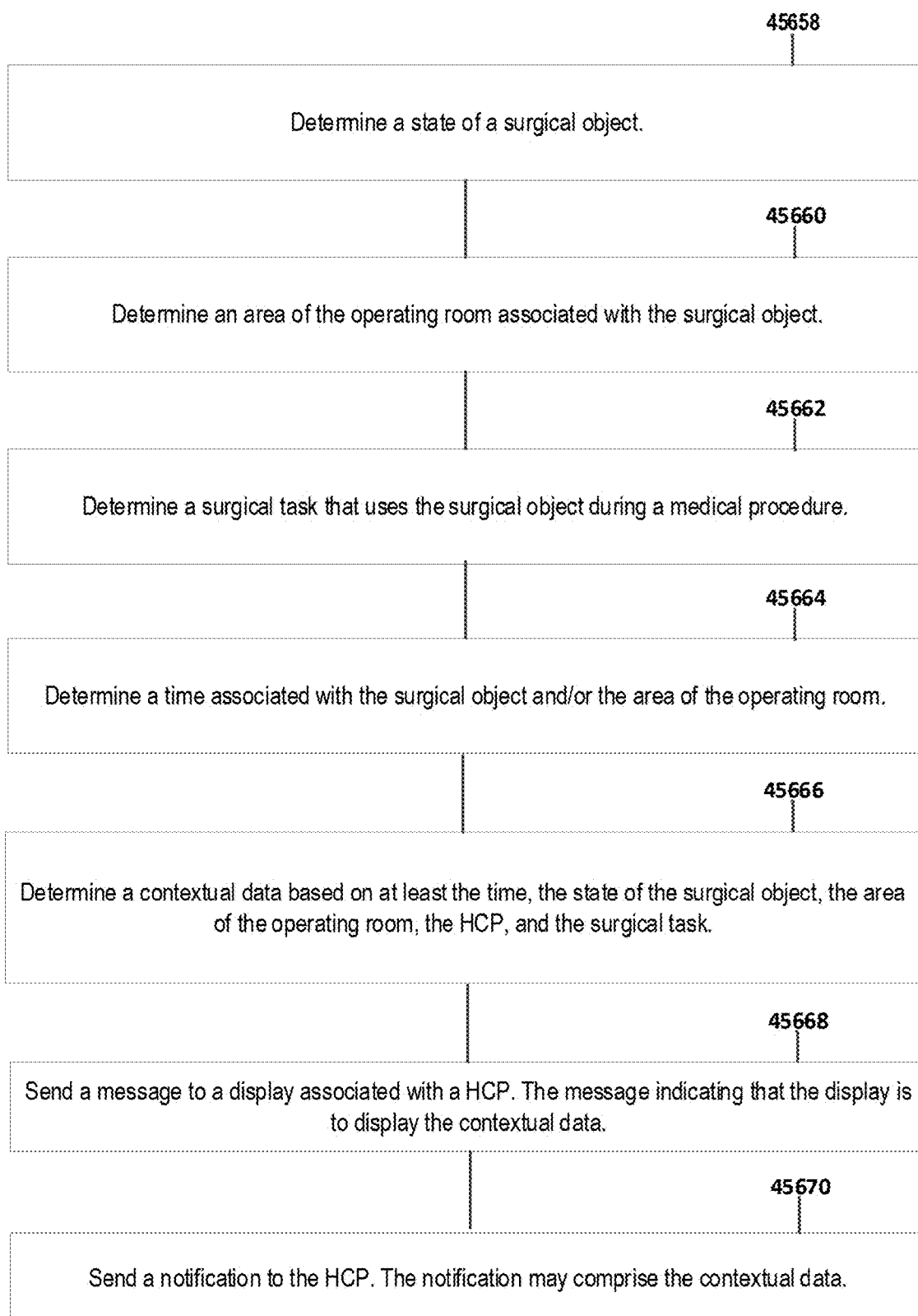

FIG. 73 depicts a method that may be performed by a surgical hub for providing adaptations and/or controls that may change based on spatial awareness of objects and personnel within the surgical OR.

In examples, the surgical hub may determine if an object is inside a patient and may indicate to remove the object. In examples, the surgical hub may track a spatial temporal component associated with each object. For example, the surgical hub may track which device is in a medical staff member's hand, for example, at a given time.

The surgical hub may overlay data on the object. For example, the object may be a medical instrument. A display may be configured for the overlaid data. The display may be included on the medical instrument. The display may be attachable to the medical instrument. The data may be depicted on the screen for a user to see. The cameras as described herein may observe a change in the surgical OR and may overlay data associated with the change to a medical instrument display.

The surgical hub may be aware of secondary objects located in a storage destination. The storage destination may be located outside the surgical OR. The surgical hub may determine when one or more secondary objects are involved in a surgery. In examples, the surgical hub may communicate to a medical staff member (e.g., a rotating nurse) to retrieve the secondary objects involved in the surgery.

The surgical hub may pinpoint each object located in the surgical OR. In examples, the surgical hub may be aware of an instrument involved in a surgery. For example, the instrument may be involved in an upcoming surgical task of the surgery. A display may be accessible to a table nurse and may be in communication with the surgical hub. The surgical hub may indicate the instrument involved in the surgery on the display. For example, the surgical hub may highlight the instrument on the display. The instrument involved in the surgery may be located in a storage destination as described herein. The surgical hub may indicate the storage destination that the instrument is located at.

As shown in FIG. 73, a method may be provided. The method may be performed by a surgical hub for providing adaptations and/or controls that may change based on spatial awareness of objects and personnel within the surgical OR. The method may comprise a number of processes that may be performed in any order. The processes may include 45658, 45660, 45662, 45664, 45666, 45668, and/or 45670.

At 45658, the state of a surgical object may be determined. For example, a surgical hub may detect a surgical object and may determine the state of the surgical object. The surgical object may be a medical instrument, a common surgical instrument, a surgical product, a medical product, a medical equipment, an object in the operation room, and/or the like. The state of a surgical object may indicate that the surgical product may be new, may be unopen, may be opened, may be used, may need to be discarded, and the like, or any combination thereof. The state of the surgical object may indicate that the surgical instrument may be ready to be used, that the surgical instrument may need to be cleaned, that the surgical instrument may not be ready, that the surgical instrument is being used, and/or the like.

At 45660, an area of the operating room may be determined. The area of the operating room may be associated with the surgical object. The area of the operating room may be associated with a medical instrument and/or a medical equipment. The area of the operating room may be a storage area, a shelf, a surgical table, an area associated with HCP, an area associated with the patient, a Mayo cart, a surgical back table, an area for preparation of medical instruments, an area for cleaning medical instruments, a sterile field, a non-sterile field, and/or the like.

In an example, a surgical hub may determine that a Mayo cart may be present in the operating room. The surgical hub may determine that one or more medical instruments may be present on the Mayo cart. The surgical hub may determine that one or more HCPs may be near the Mayo cart.

In an example, the surgical hub may determine that a portion of the operating room may be a sterile field. The sterile field may be an area that is sterile. The surgical hub may determine that one or more objects within the sterile field are sterile. The surgical hub may determine that a medical instrument may pass from a non-sterile field to the sterile field and may determine that the medical instrument may have been cleaned and may be sterile, and that the medical instrument may be allowed in the sterile field. The surgical hub may determine that a medical instrument may not be allowed to pass from a non-sterile field to a sterile field. The medical hub may determine that the non-sterile medical instrument may have entered into the sterile field. The medical hub may notify one or more HCP's that the non-sterile medical instrument may be in the sterile field and the medical hub may indicate that an individual that may have contacted the non-sterile medical instrument may also be non-sterile.

In an example, the surgical hub may determine that a portion of the operating room may be associated with the floor of the operating room. The surgical hub may monitor the floor of the operating room to determine if an object may come in contact with the floor. For example, the surgical hub may identify a medical instrument that may have been dropped by an HCP onto the floor. The surgical hub may notify one or more HCPs that the medical instrument may be on the floor and may not be sterile. The surgical hub may indicate to an HCP to retrieve the medical instrument on the floor and may provide instructions to the HCPs on how to clean the medical instrument.

In an example, the surgical hub may have determined that a portion of the operating room may be associated with a storage area. The surgical hub may monitor the storage area. The surgical hub may determine that one or more medical instruments and/or medical products may be located within the storage area. The surgical hub may keep an inventory of the one or more medical instruments and/or medical products that may be located within the storage area. For example, the surgical hub may remove a medical instrument from the inventory when the HCP retrieves the medical instrument from the storage area.

The surgical hub may determine an area of the operating room in any one of the ways described herein. For example, the surgical hub may use an ultrasonic ping to determine one or more areas of the operating room. As another example, the surgical hub may use laser radar (lidar). The surgical hub may use electrical signals, Wi-Fi signals, wireless signals, the determination of signal strength, a determination of distances between devices, ultrasonic measurements, sensors, indicators, RFID's, and/or the like to determine one or more areas of the operating room. The surgical hub may use one or more cameras to determine areas of the operating room. For example, the surgical hub may analyze video and/or images retrieved from a camera to determine one or more areas of the operating room.

The surgical hub may determine a surgical object and may determine an area associated with the surgical object. For example, the surgical hub may use one or more sensors and/or one or more cameras to determine a surgical object, such as a medical instrument. In an example, the surgical hub may use a camera to identify a Mayo cart and may identify one or more medical instruments on the Mayo cart. In an example, the surgical hub may identify an area of the operating room that may be occupied by an HCP and may identify a medical instrument that may be held by the HCP.

The surgical hub may identify one or more objects that may be on, near, and/or in a patient. For example, the surgical hub may identify a medical instrument that may be used to perform a procedure on a patient. The surgical hub may identify that the medical instrument may have contacted the patient. The surgical hub may identify that the medical instrument may be inserted into the patient. The surgical hub may track that the medical instrument may be in the patient and may notify an HCP if the medical instrument may be left inside the patient. The surgical hub may identify a medical product that may be applied on the patient. The surgical hub may identify a medical device that may be placed inside the patient.

At 45662, a surgical task that may use the surgical object may be determined. For example, a surgical task that may use the surgical object during a medical procedure may be determined. In an example, the surgical hub may determine a surgical procedure and may determine one or more surgical tasks that may be associated with the surgical procedure. The surgical task may indicate that an HCP is to use a medical instrument to perform a task on a patient. For example, the surgical task may indicate that an HCP is to use a medical stapler to staple the patient's tissue together during a surgery. In an example, the surgical task may indicate that an HCP is to clean a medical instrument before the medical instrument may be used on a patient. In an example, the surgical task may indicate one or more instructions for an HCP to clean the medical instrument and/or prepare the medical instrument to be used.

At 45664, a time associated with the surgical object and/or the area of the operating room may be determined. For example, the time may be associated with a surgical object, such as a medical instrument and/or a medical product. The time may indicate when a medical instrument may have entered the operating room, may have been cleaned, may have been made sterile, may have been used, may have been made non sterile, may have come in contact with a patient, may have come in contact with an HCP, may have left the operating room, may have entered a patient, may have left the patient, and/or the like. The time may indicate when a medical product may have been used, may have been opened, how long the medical product has been opened, when the medical product entered the operating room, when the medical product came into contact with a patient, when the medical product may have been made sterile, when the medical product was sterile, when the medical product may not have been sterile, when the medical product became non sterile, when the medical product may have been placed inside the patient, when the medical product may have been removed from a patient, when the medical product may have come in contact with an HCP, and/or the like.

The time may be associated with an area of the operating room. For example, the time may indicate when an HCP may have entered the operating room, may have entered an area of the operating room, may have left an area of the operating room, may have exited the operating room, and/or the like. The time may indicate when a patient may have entered the operating room, may have entered an area of the operating room, may have left an area of the operating room, may have exited the operating room, and/or the like.

At 45666, contextual data may be determined. The contextual data may be based on the time, the state of the surgical object, the area of the operating room, the HCP, the surgical task, and/or the like. The contextual data may be any contextual data described herein. For example, the contextual data may indicate that a medical instrument may have come in contact with an HCP in an area of the operating room and may indicate one or more settings of the medical instrument. In an example, the contextual data may indicate one or more vital signs of a patient that may be located in an area of the operating room.

At 45668, a message may be sent to a display associated with an HCP. In an example, the display may be determined and the message may be sent to the determined display. The message may indicate that the display is to display the contextual data. The contextual data may be any contextual data described herein.

At 45670, a notification may be sent to an HCP. The notification may comprise the contextual data. A notification may be sent to an HCP to provide the HCP with instructions on how to use a medical instrument. The notification may be sent to an HCP to provide the HCP with an indication as to what settings may be applied to a medical instrument and/or what settings have been applied to a medical instrument. The notification may be sent to an HCP to provide the HCP with the contextual data, such as a vital sign of a patient and/or a suggested setting for a medical instrument.

Systems, methods, and/or instrumentalities for a surgical hub providing a health care provider (HCP) with a data overlay may be provided. A state of a surgical object and/or an area of the operating room where the surgical object is located may be determined. Determining an area of the operating room where the surgical object is located may comprise using a sensor data associated with the area, a wearable device data, sensor data associated with the HCP, an image from a camera within the operating room, an ultrasonic sensor, a laser sensor, a laser doppler sensor, a radio frequency sensor, and/or a video from the camera within the operating room. A time associated with the surgical object and/or the area of the operating room may be determined. The state of the surgical object may be determined to indicate that the surgical object is ready for use in the surgical task.

A surgical task that uses the surgical object during a medical procedure may be determined. The surgical object entering the area of the operating room during the task and/or medical procedure may be determined. In examples, determining that the surgical object has entered the operating room may be based on the area of the operating room where the surgical object is located. The time may indicate when the surgical object entered the operating room. In examples, it may be determined that the surgical object has left the area of the operating room. The time may indicate when the surgical object has left the area.

In examples, contextual data may be determined based on the state of the object, the area of the operating room, and/or the surgical task. In examples, the contextual data may be determined based on the time associated with the surgical object and/or the area of the operating room. In examples, the state of the surgical object may be determined to indicate that the surgical object has not been prepared for use in the surgical task. For example, the contextual data may comprise one or more instructions for preparing the surgical object in the surgical task. It may be determined that the surgical object has not been retained in a patient. For example, the contextual data may comprise an indication that the surgical object has not been retained in the patient.

The contextual data may comprise an indication that the surgical object has been used. For example, the contextual data may comprise an instruction for cleaning the surgical object and/or an instruction for disposing of the surgical object. In examples, the surgical object may comprise a package. The package may be determined to have been opened in the area at the time. In examples, the area of the operating room may be a stock area, a mayo stand, a surgical site, a sterile field, and/or a non-sterile field.

A message may be sent to a display associated with the HCP. In examples, the message may indicate that the display is to display the contextual data. The message may be sent to a database. The message may indicate that the package has been opened. The message may comprise the contextual data. The message may indicate that the surgical object is to be removed from an inventory. In examples, it may be determined that the display is within a distance of the location of the HCP. In examples, the display may include a wearable display, a tablet, an augmented reality device, and/or a smart phone. A notification may be sent to the HCP. For example, the notification may comprise the contextual data.

In examples, a surgical instrument that is to be used to perform a surgical task during a medical procedure may be determined. An area of the operating room associated with the surgical instrument may be determined. The area of the operating room may be a stock area. The message sent to the display may comprise a notification to the HCP that guides the HCP to the surgical instrument in the stock area. An orientation of the surgical instrument may be determined. In examples, a display associated with the HCP may be determined. Contextual data may be determined based on the surgical task, the area of the surgical room, and/or the orientation of the surgical instrument. The contextual data may comprise an image and/or a status of the instrument. The message sent to the display may indicate the image and/or the status of the instrument to be overlaid on a display data being shown on the display.

The surgical instrument may comprise a fiducial marker. For example, it may be determined that the surgical instrument is using the fiducial marker. It may be determined that contextual data may comprise an orientation of the surgical instrument that may be improved. For example, the contextual data may comprise an instruction to the HCP to improve the orientation of the surgical instrument. The capability of the display associated with the HCP may be determined. For example, the contextual data may be modified based on the capability of the display.

Figure 74:
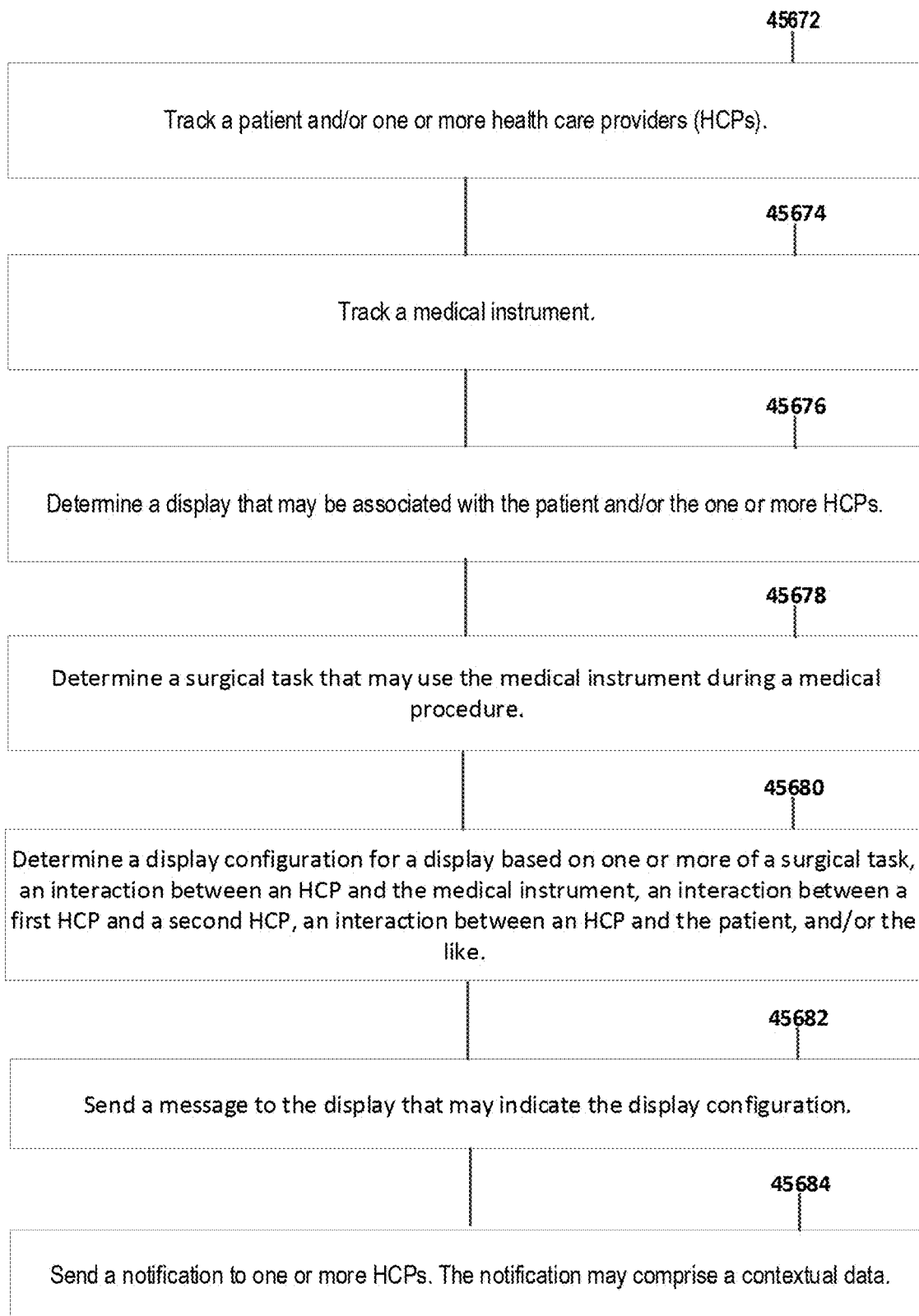
FIG. 74 depicts a method that may be performed by a surgical hub for providing adaptive control, operation of display, and/or display interactions that may be based on recognition of users, equipment, and/or usage and user or equipment needs.

FIG. 74 depicts a method that may be performed by a surgical hub for providing adaptive control, operation of display, and/or display interactions that may be based on recognition of users, equipment, and/or usage and user or equipment needs.

The surgical hub may be aware of an indicator on each medical instrument. The camera may identify the indicator and send the indicator to the surgical hub along with the medical instrument's location (e.g., via coordinate points). In examples, the indicator may include indexing points and/or fiducial markers. The indicator may include qualities about the instrument such as the length and thickness of the instrument shaft. The surgical hub may scale the data sent to the instrument based on the qualities. The cameras may identify indexing coordination and/or registration points of the one or more instruments.

In examples, the camera may identify the instruments based on the characteristics of the instrument. For example, the camera may use spatial recognition to model the shape of the instrument. In such a case, the camera may identify the instrument based on the shape. For example, the camera may identify a handle resembling an endo cutter handle and may determine that the instrument is an endo cutter.

The camera may generate data based on a display in the surgical OR. The camera may overlay information onto the display. The information may include information from another display. For example, a surgeon may request information related to a generator power level, EKG measurements, and instrument firing status. In such a case, the instrument may include a display that shows all three of these values. A surgical hub may port the information to the display the surgeon looks at from a laparoscopic point of view.

The surgical hub may identify and/or recognize that one or more devices are not compatible with each other. The surgical hub may standardize the data into a form to allow data to be exchanged between the devices.

The surgical hub may include machine learning that analyzes the metadata as described herein over time. The metadata may be based on camera information sent to the surgical hub. For example, the camera may read information on a display and send the information to the surgical hub over a duration of time. The surgical hub may input the information into a machine learning model to determine, for example, what the surgeon is doing. The machine learning model may determine suggestions for the surgeon and may send the suggestions to the display accessible by the surgeon. The machine learning module may determine when and/or where the surgical hub should send the information. For example, the machine learning model may tell the surgical hub to send information related to ligating the IMA when the surgeon performs mobilization.

As shown in FIG. 74, a method may be provided. The method may be performed by a surgical hub for providing adaptations and/or controls that may change based one or more interactions, a recognition of users, recognition of equipment, usage, a user request, an equipment request, and/or the like. The one or more interactions may include a display interaction, an interaction with a patient, an interaction with an HCP, an interaction between one or more HCPs, an interaction between an HCP and the patient, and/or the like. The method may comprise a number of processes that may be performed in any order. The processes may include 45672, 45674, 45676, 45678, 45680, 45682, and/or 45684.

At 45672, a patient and/or one or more HCPs may be tracked. For example, a surgical hub may track a patient, a first HCP, and a second HCP. The patient, the first HCP, and the second HCP may be located within an operating room. The surgical hub may track the patient, the first HCP, and the second HCP using any of the methods described herein. For example, the surgical hub may track the patient using a camera, a RFID, an ultrasonic device, a tracking device, a sensor, and/or the like. In an example, the surgical hub may track the first HCP using a device that may be associated with the HCP, such as a smart watch.

At 45674, a medical object, which may be a medical instrument and/or a medical product, may be tracked. For example, the surgical hub may track a medical instrument that may be located within the operating room. As another example, the surgical hub may track a medical instrument that may not be located within the operating room. The surgical hub may notify a user, such as an HCP, of the location of the medical product, such as the medical instrument. For example, the surgical hub may notify a user that the medical instrument may be located within the operating room, such as an area that indicates a Mayo cart, and may indicate a status of the medical instrument, such as that the medical instrument may need to be cleaned in order to be used.

At 45676, a display that may be associated with the patient and/or the one or more HCP's may be determined. For example, the surgical hub may determine that an HCP is near a display. The surgical hub may determine the identity of the display and may send data to be viewed by the HCP to the display associated with the HCP. In an example, the surgical hub may determine that the patient may be near a display that is likely to be viewed by an HCP. The surgical hub may determine data that may be sent to the display that may be near the patient such that an HCP may be able to view the data.

At 45678, a surgical task that may use a medical object during a medical procedure may be determined. The medical object may be a medical instrument and/or a medical product. The surgical task may be a task that may be part of the medical procedure that may be performed by an HCP. For example, the task may indicate that a surgeon may use a stapler on the patient. In an example, the task may indicate that a nurse may need to clean a medical instrument before the medical instrument may be provided to a surgeon. In an example, the task may indicate that a medical instrument may need to be retrieved from an area outside the operating room by a first HCP, that the medical instrument may need to be provided to a second HCP that may prepare and clean the medical instrument, and that a third HCP may use the medical instrument to perform the medical procedure on the patient.

At 45680, a display configuration for a display may be determined. For example, the display configuration for the display may be determined based on one or more of a surgical task, an interaction between an HCP and the medical object, an interaction between a first HCP and a second HCP, an interaction between an HCP and the patient, an interaction between the patient and a medical object, and/or the like. A medical object may be a medical instrument, a medical product, a surgical instrument, a surgical product, a medical equipment, and/or the like.

The configuration may be customized for an HCP. For example, the surgical hub may have determined that the surgical task may require the HCP to use the medical instrument on the patient. The surgical hub may determine that the medical instrument may comprise one or more settings. The surgical hub may determine that the HCP may prefer to view a portion of the one or more settings. The surgical hub may determine that the HCP may have one or more preferred settings for the medical instrument. The surgical hub may determine a configuration for the display such that the display may display the HCP's preferred settings for the medical instrument and the surgical hub may configure the medical instrument according to the HCP preferred settings.

The surgical hub may determine one or more settings based on an analysis of patient outcome. For example, the surgical hub may analyze the history of surgeries performed and may determine that display settings and/or medical instrument settings may result in improved outcomes. The surgical hub may use these display settings and/or medical instrument settings to determine the display configuration and may provide that display configuration to a display and/or a medical instrument.

At 45682, a message may be sent to a display that may indicate the display configuration. The message may include an indication and/or instruction for the display. For example, the message may indicate that the display is to display data according to the display configuration. In an example, the message may indicate that the display is to display data that may be included in the display configuration. In an example, the message may indicate that the display is to coordinate with another device, such as another display or a medical instrument, in accordance with the display configuration.

In an example, the message may be sent to an augmented reality display. For example, an HCP may be wearing safety glasses that may include a device that is able to provide an augmented display to the HCP. The message may indicate to the augmented safety glasses that data may be overlaid on the view that the HCP is viewing. For example, the HCP may be viewing the patient through the safety glasses and the safety glasses may overlay vital signs for the patient on or near the patient. In an example, the HCP may be viewing the patient through the safety glasses and the safety glasses may overlay a medical image of the patient on or over the patient.

At 45684, a notification may be sent to one or more HCP's. The notification may comprise contextual data. The contextual data may be the contextual data described herein. For example, the contextual data may include data that may be associated with the surgical task, the patient, a setting for the medical instrument, a vital sign for the patient, a medical image, and/or the like. The notification may be sent to the HCP via a display, a speaker, an email, a message, and/or the like. For example, the notification may be sent to a smartwatch that may be worn by the HCP. In an example, the notification may be sent to a speaker such that the HCP may be able to listen to a voice that speaks the data to the HCP.

Systems, methods, and/or instrumentalities for a surgical hub configuring a display may be provided. In examples, a health care provider (HCP) and/or a medical instrument may be tracked within an operating room. In examples, a first HCP and a second HCP may be tracked within an operating room. In examples, an HCP and/or a patient may be tracked within an operating room. A surgical task that uses the medical instrument during a medical procedure may be determined.

A display configuration for the display may be determined, for example, based on the surgical task and/or an interaction between the HCP and the medical instrument. In examples, a first display configuration may be determined based on a first interaction between the HCP and the medical instrument. For example, a second interaction may be determined between the HCP and the medical instrument, the HCP and the display, and/or the HCP and the patient. The display configuration may be modified based on the second interaction. The display configuration for the display may be determined based on the surgical task and an interaction between a first HCP and a second HCP. For example, the interaction between the first HCP and the second HCP may be a verbal communication. The verbal communication may be determined to be a request from the first HCP for assistance from the second HCP in performing the surgical task. The display configuration may be modified such that the display configuration may configure the display with one or more preferences that are relevant to the second HCP.

In examples, a third HCP that is able to assist in performing the surgical task may be determined. The third HCP may be outside the operating room. In examples, the interaction between the HCP and the patient may be determined to indicate that the surgical task is being performed. A notification may be sent to the third HCP. For example, the notification may indicate that the third HCP has been requested to assist in the operating room with the surgical task. In examples, determining the interaction between the first HCP and the second HCP may comprise the first HCP providing the medical instrument to the second HCP. For example, the display may include an augmented reality display, a personal display, a display associated with a surgical interface table, an equipment display, a medical instrument display, a room monitor, a primary monitor, and/or a secondary monitor. In examples, the display configuration may comprise contextual data, medical instrument data, patent data, an instruction associated with the surgical task, a notification for the HCP regarding the patient, a notification for the HCP regarding the medical instrument, a notification for the HCP regarding the surgical task, and/or a status of the medical instrument. The display configuration may comprise one more preferences for the second HCP.

In examples, the orientation of the display in relation to the HCP may be determined. For example, the orientation may comprise a position of the display in relation to the HCP, a direction of the display in relation to the HCP, and/or a distance between the display and the HCP. A position and/or orientation of the HCP may be determined. The display configuration may be modified, for example, based on the orientation and/or position of the HCP. In examples, a message may be sent to the display. The message may comprise the display configuration. The message to the display may comprise an instruction associated with the surgical task, patient data, a status of the medical instrument, and/or a parameter associated with the medical instrument. In examples, a first message may be sent to a first display. For example, it may be determined that an HCP has viewed a second display. Displayed data being displayed on the second display may be determined. A second message may be sent to the first display. For example, the second message may instruct the first display to display the displayed data.

A location of the operating room where the display is positioned may be determined. A direction between the display and the HCP may be determined. In examples, the display configuration may be modified based on the location of the operating room and/or the direction between the display and the HCP. In examples, a capability of the display may be determined using a camera within the operating room. The display configuration may be modified based on the capability of the display.

In examples, patient data associated with the surgical task may be determined. The display configuration may be modified based on the patient data. A voice command provided by the HCP may be received. For example, the voice command may indicate that a setting of the display is to be changed. The display configuration may be modified, for example, based on the voice command.

The invention claimed is:

1. A method, comprising:
   determining a present network locus, wherein the present network locus is associated with a first surgical network, and wherein the first surgical network is associated with a first operating room;
   determining a previous network locus, wherein the previous network locus is associated with a second surgical network, and wherein the second surgical network is associated with a second operating room, wherein the previous network locus is different than the present network locus;
   identifying a first data communication session and a second data communication session;
   determining a first surgical data type and a second surgical data type, wherein the first surgical data type is associated with the first data communication session and the second surgical data type is associated with the second data communication session, wherein the first surgical data type is of a first type of surgical data and the second surgical data type is of a second type of surgical data;
   directing the first data communication session to the first surgical network based on the determination that the first surgical data type is the first type of surgical data; and
   directing the second data communication session to the second surgical network based on the determination that the second surgical data type is the second type of surgical data.

2. The method of claim 1, wherein the first surgical network is a primary surgical network and the second surgical network is a secondary surgical network.

3. The method of claim 1, further comprising:
   determining that the first surgical data type is of the first type of surgical data or based on connectivity adjustments of the first surgical network; and
   determining that the second surgical data type is of the second type of surgical data based on connectivity adjustments of the second surgical network.

4. The method of claim 3, further comprising:
   determining the connectivity adjustments of the first surgical network based on at least one of: latency, data transfer parameters, bandwidth, message handling, service available, or service reliability; and
   determining the connectivity adjustments of the second surgical network based on at least one of: latency, data transfer parameters, bandwidth, message handling, service available, or service reliability.

5. The method of claim 1, wherein the method is performed at a surgical computing device, and the method further comprises: when the surgical computing device is moved from the first operating room to the second operating room, determining that the surgical computing device is moved from the previous network locus to the present network locus.

6. The method of claim 1, wherein the first surgical network and the second surgical network are configured in a bus topology, a ring or dual ring topology, a mesh topology, a star topology, or a hybrid tree topology.

7. The method of claim 1, wherein directing the first data communication session to the first surgical network comprises directing a first surgical data of the first surgical data type to the first surgical network, and wherein directing the second data communication session to the second surgical network comprises directing a second surgical data of the second surgical data type to the second surgical network.

8. A method comprising, comprising:
   determining a present network locus of a processor, wherein the present network locus is associated with a first surgical network, and wherein the first surgical network is associated with a first operating room;
   determining a previous network locus, wherein the previous network locus is associated with a second surgical network, and wherein the second surgical network is associated with a second operating room, wherein the previous network locus is different than the present network locus;
   identifying a first data communication session and a second data communication session;
   determining a first surgical data type and a second surgical data type, wherein the first surgical data type is associated with the first data communication session and the second surgical data type is associated with the second data communication session;

directing the first data communication session to the first surgical network based on a determination that the first surgical data type is a first type of surgical data; and directing the second data communication session to the second surgical network based on a determination that the second surgical data type is a second type of surgical data.

9. The method of claim 8, wherein the first surgical network is a primary surgical network and the second surgical network is a secondary surgical network.

10. The method of claim 8, wherein the first surgical network and the second surgical network are configured in a bus topology, a ring or dual ring topology, a mesh topology, a star topology, or a hybrid tree topology.

11. The method of claim 8, wherein the first surgical data type is determined to be of the first type of surgical data based on connectivity adjustments of the first surgical network; and wherein the second surgical data type is determined to be of the second type of surgical data based on connectivity adjustments of the second surgical network.

12. The method of claim 11, further comprising:

determining the connectivity adjustments of the first surgical network based on at least one of: latency, data transfer parameters, bandwidth, message handling, service available, or service reliability; and determining the connectivity adjustments of the second surgical network based on at least one of: latency, data transfer parameters, bandwidth, message handling, service available, or service reliability.

13. The method of claim 8, wherein the method is performed at a surgical computing device, and the method further comprises:

when the surgical computing device has been moved from the first operating room to the second operating room, determining that the surgical computing device is moved from the previous network locus to the present network locus.

14. The method of claim 8, wherein directing the first data communication session to the first surgical network comprises directing a first surgical data of the first surgical data type to the first surgical network, and wherein directing the second data communication session to the second surgical network comprises directing a second surgical data of the second surgical data type to the second surgical network.

15. A method comprising:

combining at least one of a first plurality of functions within a first surgical network with at least one of a second plurality of functions within a second surgical network to create a third surgical network, wherein the first surgical network is associated with a first type of surgical data, the second surgical network is associated with a second type of surgical data, and the third surgical network is associated with a third type of surgical data, and wherein the first surgical network is present in a first operating room, the second surgical network is present in a second operating room, and the third surgical network is present in a third operating room;

determining a present network locus, wherein the present network locus is the third surgical network;

determining a previous network locus, wherein the previous network locus is any of the first surgical network or the second surgical network, wherein the previous network locus is different than the present network locus;

identifying a data communication session;

determining a first surgical data type and a second surgical data type, wherein the first surgical data type is associated with a first data communication session and the second surgical data type is associated with a second data communication session; and directing the first data communication session to the first surgical network based on a determination that the first surgical data type is of the first type of surgical data; and directing the second data communication session to the second surgical network based on a determination that the second surgical data type is of the second type of surgical data.

16. The method of claim 15, wherein the first surgical network is a primary surgical network, and the second surgical network is a secondary surgical network.

17. The method of claim 15, further comprising:

determining whether the surgical data is the third type of surgical data based on connectivity adjustments of the third surgical network.

18. The method of claim 17, further comprising:

determining the connectivity adjustments of the third surgical network based on at least one of: latency, data transfer parameters, bandwidth, message handling, service available, or service reliability.

19. The method of claim 15, wherein the first surgical network, the second surgical network, and the third surgical network are connected to at least one edge server.

20. The method of claim 15, wherein directing the first data communication session to the first surgical network comprises directing a first surgical data of the first surgical data type to the first surgical network, and wherein directing the second data communication session to the second surgical network comprises directing a second surgical data of the second surgical data type to the second surgical network.

* * * * *